US010036019B2

(12) United States Patent
Seth et al.

(10) Patent No.: US 10,036,019 B2
(45) Date of Patent: Jul. 31, 2018

(54) BICYCLIC CARBOCYCLIC NUCLEOSIDES AND OLIGOMERIC COMPOUNDS PREPARED THEREFROM

(71) Applicant: Ionis Pharmaceuticals, Inc., Carlsbad, CA (US)

(72) Inventors: Punit P. Seth, Carlsbad, CA (US); Eric E. Swayze, Encinitas, CA (US)

(73) Assignee: Ionis Pharmaceuticals, Inc., Carlsbad, CA (US)

(*) Notice: Subject to any disclaimer, the term of this patent is extended or adjusted under 35 U.S.C. 154(b) by 0 days.

(21) Appl. No.: 15/125,634

(22) PCT Filed: Mar. 17, 2015

(86) PCT No.: PCT/US2015/021050
§ 371 (c)(1),
(2) Date: Sep. 13, 2016

(87) PCT Pub. No.: WO2015/142910
PCT Pub. Date: Sep. 24, 2015

(65) Prior Publication Data
US 2017/0145409 A1    May 25, 2017

Related U.S. Application Data

(60) Provisional application No. 62/013,101, filed on Jun. 17, 2014, provisional application No. 61/980,967, filed on Apr. 17, 2014, provisional application No. 61/954,435, filed on Mar. 17, 2014.

(51) Int. Cl.
C12N 15/113    (2010.01)
C07F 9/6512    (2006.01)

(52) U.S. Cl.
CPC .......... C12N 15/113 (2013.01); C07F 9/6512 (2013.01); C12N 2310/11 (2013.01); C12N 2310/315 (2013.01); C12N 2310/321 (2013.01); C12N 2310/3231 (2013.01); C12N 2310/3235 (2013.01); C12N 2310/3341 (2013.01); C12N 2310/341 (2013.01); C12N 2310/346 (2013.01); C12N 2310/351 (2013.01); C12N 2320/52 (2013.01)

(58) Field of Classification Search
CPC combination set(s) only.
See application file for complete search history.

(56) References Cited

U.S. PATENT DOCUMENTS

| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lableu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,069 E | 9/1992 | Koster et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |

(Continued)

FOREIGN PATENT DOCUMENTS

| WO | WO 1994/002499 | 2/1994 |
| WO | WO 1994/017093 | 8/1994 |

(Continued)

OTHER PUBLICATIONS

Agrawal et al., Protocols for Oligonucleotide Conjugates (1994) 26: 1-72.

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

Altmann et al., "Second Generation Antisense Oligonucleotides—Inhibition of PKC-α and c-raf Kinase Expression by Chimeric Oligonucleotides Incorporating 6"-Substituted Carbocyclic Nucleosides and 2"-O-Ethylene Glycol Substituted Ribonucleosides" Nucleosides & Nucleotides. (1997) 16:917-926.

(Continued)

Primary Examiner — Joseph R Kosack
(74) Attorney, Agent, or Firm — McNeill Baur PLLC

(57) ABSTRACT

The present invention provides novel bicyclic carbocyclic nucleosides and oligomeric compounds prepared therefrom. Incorporation of one or more of the bicyclic carbocyclic nucleosides into an oligomeric compound is expected to enhance one or more properties of the oligomeric compound. In certain embodiments, the oligomeric compounds provided herein hybridize to a portion of a target RNA resulting in modulation of normal function of the target RNA. In certain embodiments, bicyclic carbocyclic nucleosides are provided as monomers for use as antivirals.

28 Claims, No Drawings

(56) References Cited

U.S. PATENT DOCUMENTS

| | | |
|---|---|---|
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Buhr et al. |
| 5,830,653 A | 11/1998 | Froehler et al. |
| 6,005,096 A | 12/1999 | Matteucci et al. |
| 6,268,490 B1 | 7/2001 | Imanishi et al. |
| 6,525,191 B1 | 2/2003 | Ramasamy |
| 6,600,032 B1 | 7/2003 | Manoharan et al. |
| 6,670,461 B1 | 12/2003 | Wengel et al. |
| 6,770,748 B2 | 8/2004 | Imanishi et al. |
| 6,794,499 B2 | 9/2004 | Wengel et al. |
| 6,867,294 B1 | 3/2005 | Sanghvi et al. |
| 7,034,133 B2 | 4/2006 | Wengel et al. |
| 7,053,207 B2 | 5/2006 | Wengel |
| 7,399,845 B2 | 7/2008 | Seth et al. |
| 7,427,672 B2 | 9/2008 | Imanishi et al. |
| 7,547,684 B2 | 6/2009 | Seth et al. |
| 7,696,345 B2 | 4/2010 | Allerson et al. |
| 7,741,457 B2 | 6/2010 | Seth et al. |
| 8,501,805 B2 | 8/2013 | Seth et al. |
| 8,530,640 B2 | 9/2013 | Seth et al. |
| 8,546,556 B2 | 10/2013 | Seth et al. |
| 9,012,421 B2 | 4/2015 | Migawa et al. |
| 2003/0158403 A1 | 8/2003 | Manoharan et al. |
| 2004/0033973 A1 | 2/2004 | Manoharan et al. |
| 2005/0130923 A1 | 6/2005 | Bhat et al. |
| 2008/0039618 A1 | 2/2008 | Allerson et al. |

FOREIGN PATENT DOCUMENTS

| | | |
|---|---|---|
| WO | WO 1995/008541 | 3/1995 |
| WO | WO 1998/039352 | 9/1998 |
| WO | WO 1999/014226 | 3/1999 |
| WO | WO 2001/049687 | 7/2001 |
| WO | WO 2001/051490 | 7/2001 |
| WO | WO 2002/008204 | 1/2002 |
| WO | WO 2004/106356 | 12/2004 |
| WO | WO 2005/021570 | 3/2005 |
| WO | WO 2005/121371 | 12/2005 |
| WO | WO 2005/121372 | 12/2005 |
| WO | WO 2006/047842 | 5/2006 |
| WO | WO 2006/091905 | 8/2006 |
| WO | WO 2006/128159 | 11/2006 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2010/036696 | 4/2010 |

OTHER PUBLICATIONS

Altmann et al., "Second Generation of Antisense Oligonucleotides: From Nuclease Resistance to Biological Efficacy in Animals" Chimia. (1996) 50(4):168-176.

Altmann et al., "Second-generation antisense oligonucleotides: structure-activity relationships and the design of improved signal-transduction inhibitors" Biochem. Soc. Trans. (1996) 24:630-637.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.

Beaucage et al., "Advances in the Synthesis of Oligonucleotides by the Phosphoramidite Approach" Tetrahedron (1992) 48(12):2223-2311.

Beaucage et al., "The Functionalization of Oligonucleotides Via Phosphoramidite Derivatives" Tetrahedron (1993) 49(10):1925-1963.

(56) References Cited

OTHER PUBLICATIONS

Beaucage et al., "The Synthesis of Specific Ribonucleotides and Unrelated Phosphorylated Biomolecules by the Phosphoramidite Method" Tetrahedron (1993) 49(46):10441-10488.
Braasch et al., "Locked nucleic acid (LNA): fine-tuning the recognition of DNA and RNA" Chem. Biol. (2001) 8:1-7.
Brazma et al., "Gene expression data analysis" FEBS Letters (2000) 480:17-24.
Carulli et al., "High Throughput Analysis of Differential Gene Expression" J. Cell. Biochem. Suppl. (1998) 30:286-296.
Celis et al., "Gene expression profiling monitoring transcription and translation products using DNA microarrays and proteomics" FEBS Lett (2000) 480:2-16.
Chiang et al., "Antisense Oligonucleotides Inhibit Intercellular Adhesion Molecule 1 Expression by Two Distinct Mechanisms" J. Biol. Chem. (1991) 266:18162-18171.
Conte et al., "Conformational properties and thermodynamics of the RNA duplex r(CGCAAAUUUGCG)2: comparison with the DNA analogue d(CGCAAATTTGCG)2" Nucleic Acids Res. (1997) 25(13):2627-2634.
Eckstein, "Oligonucleotides Attached to Intercalators, Photoreactive & Cleavage Agents" Oligonucleotides and Analogues, a Practical Approach, Ed., Oxford University Press, New York (1991) 283-306.
Egli et al., "RNA Hydration: A Detailed Look" Biochemistry (1996) 35:8489-8494.
Elayadi et al., "Application of PNA and LNA oligomers to chemotherapy" Curr. Opinion Invens. Drugs (2001) 2:558-561.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Fuchs et al., "Identification of Differentially Expressed Genes by Mutually Subtracted RNA Fingerprinting" Anal. Biochem. (2000) 286:91-98.
Going et al., "Molecular Pathology and Future Developments" Eur. J. Cancer (1999) 35:1895-1904.
Gu et al., "Base Pairing Properties of D- & L-Cyclohexene Nucleic Acids (CeNA)" Oligonucleotides, (2003) 13(6): 479-489.
Gu et al., "Enzymatic resolution and base pairing properties of D- and L-cyclohexenyl nucleic acids (CeNA)." Nucleosides, Nucleotides & Nucleic Acids (2005) 24(5-7), 993-998.
Gu et al., "Synthesis of enantiomeric-pure cyclohexenyl nucleoside building blocks for oligonucleotide synthesis" Tetrahedron (2004) 60(9): 2111-2123.
Horvath et al., "Seteroselective synthesis of (−)-ara-cyclohexenyl-adenine." Tetrahedron Letters (2007) 48:3621-3623.
Jin et al., "Stereoselective Synthesis of Dithymidine Phosphorothioates Using Xylose Derivatives as Chiral Auxiliaries" J. Org. Chem. (1997) 63:3647-3654.
Jung et al., "Synthesis and Duplex-Stabilizing Properties of Fluorinated N-Methanocarbathymidine Analogues Locked in the C3'-endo conformation." Angew. Chem. Int. (Jul. 15, 2014) 53:9893-9897.
Jungblut et al., "Proteomics in human disease: Cancer, heart and infections diseases" Electrophoresis (1999) 20:2100-2110.
Jurecic et al., "Long-distance DD-PCR and cDNA microarrays" Curr. Opin. Microbiol. (2000) 3:316-321.
Kim et al., "2-Substitution of adenine nucleotide analogues containing a bicyclo[3.1.0]hexane ring system locked in a northern conformation: enhanced potency as P2Y1 receptor antagonists." J. Med. Chem. (2003) 46:4974-4987.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kumar et al., "The first analogues of LNA (locked nucleic acids): phosphorothioate-LNA and 2'-thio-LNA" Bioorg Med Chem Lett. (1998) 8:2219-2222.
Larson et al., "Rapid DNA Fingerprinting of Pathogens by Flow Cytometry" Cytometry (2000) 41:203-208.
Larsson et al., "High-throughput protein expression of cDNA products as a tool in functional genomics" J. Biotech. (2000) 80:143-157.
Lesnik et al., "Relative Thermodynamic Stability of DNA, RNA, and DNA:RNA Hybried Duplexes: Relationship with Base Composition and Structure" Biochemistry (1995) 34:10807-10815.
Leumann et al., "DNA Analogues: From Supramolecular Principles to Biological Properties" Bioorganic & Medicinal Chemistry (2002) 10:841-854.
Madden et al., "Serial analysis of gene expression: from gene discovery to target identification" DDT (2000) 5:415-425.
Maier et al., "Synthesis and characterization of oligonucleotides containing conformationally constrained bicyclo[3.1.0]hexane pseudosugar analogs." Nucleic Acids Research (2004) 32(12):3642-3650.
Martin, "New acces to 2'-O-alkylated ribonucleosides and properties of 2'-O-alkylated oligoribonucleotides" Helv. Chim. Acta. (1995) 78:486-504.
Nauwelaerts et al., "Cyclohexenyl Nucleic Acids: Conformationally Flexible Oligonucleotides" Nucleic Acids Research (2005) 33(8): 2452-2463.
Nauwelaerts et al., "Structural Characterization & Biological Evaluation of Small Interfering RNAs Containing Cyclohexenyl Nucleosides" Journal of American Chemical Society (2007) 129(30): 9340-9348.
Orum et al., "Locked nucleic acids: A promising molecular family for gene-function analysis and antisense drug development" Curr. Opinion Mol. Ther. (2001) 3:239-243.
Prashar et al., "READS: A Method for Display of 3'-End Fragment of Restriction Enzyme-Digested cDNAs for Analysis of Differential Gene Expression" Methods Enzymol. (1999) 303:258-272.
Robeyns et al., "Oligonucleotides with cyclohexene-nucleoside building blocks: crystallization & preliminary X-ray studies of left-handed sequence GTGTACAC" Acta Oystallographica, Section F: Structural Biology and Crystallization Communications (2005) F61(6): 585-586.
Robeyns et al., "Structure of the Fully Modified Left-Handed Cyclohexene Nucleic Acid Sequence GTGTACAC" Journal of American Chemical Society (2008) 130(6): 1979-1984.
Sanghvi et al., "Heterocyclic Base Modifications in Nucleic Acids & Their Applications in Antisense Oligonucleotides" Chapter 15, Antisense Research and Applications, Eds., CRC Press (1993) 273-288.
Scaringe, "RNA Oligonucleotide Synthesis via 5'-Silyl-2'Orthoester Chemistry" Methods (2001) 23: 206-217.
Searle et al., "On the stability of nucleic acid structures in solution: enthalpy-entropy compensations, internal rotations and reversibility" Nucleic Acids Res. (1993) 21:2051-2056.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Sofia et al., "Discovery of a β-d-2'-deoxy-2'-α-fluoro-2'β-C-methyluridine nucleotide prodrug (PSI-7977) for the treatment of hepatitis C virus." J. Med. Chem. (2010) 53:7202-7218.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Sutcliffe et al., "TOGA: An automated parsing technology for analyzing expression of nearly all genes" PNAS (2000) 97:1976-1981.
Terrazas et al., "A Direct, Efficient Method for the Preparation of siRNAs Containing Ribo-like North Bicyclo[3.1.0]hexane Pseudosugars" Organic Letters, 2011, 13(11), 2888-2891.

(56) References Cited

OTHER PUBLICATIONS

To, "Identification of Differential Gene Expression by High Throughput Analysis" Comb. Chem. High Throughput Screen (2000) 3:235-241.

Verbeure et al.,"Rnase H Mediated cleavage of RNA by cyclohexene nucleic acid (CeNA)" Nucleic Acids Research (2001) 29(24): 4941-4947.

Wahlestedt et al., "Potent and nontoxic antisense oligonucleotide containing locked nucleic acids" Proc. Natl. Acad. Sci. USA (2000) 97: 5633-5638.

Wang et al., "A stereoselective synthesis of dinucleotide phosphorothioate triesters through a chiral indol-oxazaphosphorine intermediate" Tetrahedron Letters (1997) 38(5):705-708.

Wang et al., "A stereoselective synthesis of dinucleotide phosphorothioates, using chiral indol-oxazaphosphorine intermediates" Tetrahedron Letters (1997) 38(22):3797-3800.

Wang et al., "A Straightforward Steroselective Synthesis of D- & L-5-Hydroxy-4-hydroxymethyl-2-cyclohexenylguanine" Journal of Organic Chemistry (2001) 66: 8478-82.

Wang et al., "Cyclohexene Nucleic Acids (CeNA) Form Stable Duplexes with RNA & Induce RNASE H Activity" Nucleosides, Nucleotides & Nucleic Acids (2001) 20(4-7): 785-788.

Wang et al., "Cyclohexene Nucleic Acids (CeNA): Serum Stable Oligonucleotides that Activate RNase H & Increase Duplex Stability with Complementary RNA" Journal of American Chemistry (2000) 122: 8595-8602.

Wang et al., "Stereocontrolled Synthesis of Ara-Type Cyclohexenyl Nucleosides" Journal of Organic Chemistry (2003) 68, 4499-4505.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

BICYCLIC CARBOCYCLIC NUCLEOSIDES AND OLIGOMERIC COMPOUNDS PREPARED THEREFROM

FIELD OF THE INVENTION

Provided herein are novel bicyclic carbocyclic nucleosides and oligomeric compounds prepared therefrom. In certain embodiments, the bicyclic carbocyclic nucleosides are provided as monomers for use as antivirals. Incorporation of one or more of the bicyclic carbocyclic nucleosides herein into an oligomeric compound is expected to enhance one or more properties of the oligomeric compound such as nuclease stability. In certain embodiments, the oligomeric compounds provided herein are expected to hybridize to a portion of a target RNA resulting loss of normal function of the target RNA. In certain embodiments, hybridization of an oligomeric compound as provided herein to a target pre-mRNA alters its splicing to provide a splice variant. The oligomeric compounds provided herein are also expected to be useful as primers and probes in diagnostic applications.

SEQUENCE LISTING

The present application is being filed along with a Sequence Listing in electronic format. The Sequence Listing is provided as a file entitled CHEM0090USASEQ_ST25.txt, created Aug. 25, 2016, which is 264 Kb in size. The information in the electronic format of the sequence listing is incorporated herein by reference in its entirety.

BACKGROUND OF THE INVENTION

Targeting disease-causing gene sequences was first suggested more than thirty years ago (Belikova et al., Tet. Lett., 1967, 37, 3557-3562), and antisense activity was demonstrated in cell culture more than a decade later (Zamecnik et al., Proc. Natl. Acad. Sci. U.S.A., 1978, 75, 280-284). One advantage of antisense technology in the treatment of a disease or condition that stems from a disease-causing gene is that it is a direct genetic approach that has the ability to modulate (increase or decrease) the expression of specific disease-causing genes. Another advantage is that validation of a therapeutic target using antisense compounds results in direct and immediate discovery of the drug candidate; the antisense compound is the potential therapeutic agent.

Generally, the principle behind antisense technology is that an antisense compound hybridizes to a target nucleic acid and modulates gene expression activities or function, such as transcription and/or translation. The modulation of gene expression can be achieved by, for example, target degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi generally refers to antisense-mediated gene silencing involving the introduction of dsRNA leading to the sequence-specific reduction of targeted endogenous mRNA levels.

An additional example of modulation of RNA target function by an occupancy-based mechanism is modulation of microRNA function. MicroRNAs are small non-coding RNAs that regulate the expression of protein-coding RNAs. The binding of an antisense compound to a microRNA prevents the microRNA from binding to its messenger RNA target, and thus interferes with the function of the microRNA. Regardless of the specific mechanism, this sequence-specificity makes antisense compounds extremely attractive as tools for target validation and gene functionalization, as well as therapeutics to selectively modulate the expression of genes involved in the pathogenesis of malignancies and other diseases.

Antisense technology is an effective means for reducing the expression of one or more specific gene products and can therefore prove to be uniquely useful in a number of therapeutic, diagnostic, and research applications. Chemically modified nucleosides are routinely incorporated into antisense compounds to enhance one or more properties, such as nuclease resistance, pharmacokinetics or affinity for a target RNA. In 1998, the antisense compound, Vitravene® (fomivirsen; developed by Isis Pharmaceuticals Inc., Carlsbad, Calif.) was the first antisense drug to achieve marketing clearance from the U.S. Food and Drug Administration (FDA), and is currently a treatment of cytomegalovirus (CMV)-induced retinitis in AIDS patients.

New chemical modifications have improved the potency and efficacy of antisense compounds, uncovering the potential for oral delivery as well as enhancing subcutaneous administration, decreasing potential for side effects, and leading to improvements in patient convenience. Chemical modifications increasing potency of antisense compounds allow administration of lower doses, which reduces the potential for toxicity, as well as decreasing overall cost of therapy. Modifications increasing the resistance to degradation result in slower clearance from the body, allowing for less frequent dosing. Different types of chemical modifications can be combined in one compound to further optimize the compound's efficacy.

Various antiviral monomers based on the bicyclo[3.1.0] hexane pseudo-sugar analog scaffold have been reported (see PCT International Application WO 2006/128159, published on Nov. 30, 2006; PCT International Application WO 2006/091905, published on Aug. 31, 2006; PCT International Application WO 01/51490, published on Jul. 19, 2001; PCT International Application WO 95/08541, published on Mar. 30, 1995; PCT International Application WO 02/08204, published on Jan. 31, 2002; and Kim et al., *J. Med. Chem.*, 2003, 46, 4974-4987).

siRNAs with one or two ribo-like north bicyclo[3.1.0] hexane pseudosugars (2'-OH) have been prepared (see Terrazas et al., *Organic Letters*, 2011, 13(11), 2888-2891). The Tms of the resulting oligos was lowered by addition of the modified pseudo-sugar analogs (−1.6° C./modification). In vitro studies using the siRNA with one or two modifications compared to wild type guide strand showed that one incorporation had comparable results to wild type and two modifications was less active.

Oligonucleotides have been prepared with one or two ribo-like north bicyclo[3.1.0]hexane pseudosugars (2'-H) (see Maier et al., *Nucleic Acids Research*, 2004, 32(12), 3642-3650).

BRIEF SUMMARY OF THE INVENTION

Provided herein are novel bicyclic carbocyclic nucleosides and oligomeric compounds prepared therefrom. More particularly, the bicyclic carbocyclic nucleosides provided herein, comprise a cyclopropanated cyclopentane ring in place of the naturally occurring furanose ring which further includes at least one stereospecific 2'-substituent group. The bicyclic carbocyclic nucleosides can also include further substituent groups in place of one or more hydrogen atoms. The bicyclic carbocyclic nucleosides provided herein are expected to be useful for enhancing one or more properties of the oligomeric compounds they are incorporated into. In certain embodiments, the oligomeric compounds provided herein are expected to hybridize to a portion of a target RNA resulting in loss of normal function of the target RNA. In certain embodiments, oligomeric compounds are provided as antisense compounds that alter splicing of a target pre-mRNA resulting in a different splice variant. In certain embodiments, the novel bicyclic carbocyclic nucleosides are provided as monomers for use as antivirals.

In certain embodiments, bicyclic carbocyclic nucleosides are provided having Formula Ia:

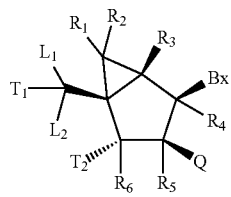

Ia wherein:

Bx is an optionally protected heterocyclic base moiety;

$T_1$ is a protected hydroxyl;

$T_2$ is a reactive phosphorus group capable of forming an internucleoside linkage;

Q is halogen or $O$—$[C(A_1)(A_2)]_n$-$[(C=O)_m$—$X]_j$—$Z$ wherein Q is other than a protected hydroxyl group;

$A_1$ and $A_2$ are each, independently, H, halogen, $C_1$-$C_6$ alkyl or substituted $C_1$-$C_6$ alkyl;

X is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

when j is 1 then Z is other than halogen and when X is $N(E_1)$ then Z is other than $N(E_2)(E_3)$;

$L_1$ and $L_2$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy or substituted $C_1$-$C_6$ alkoxy;

$R_1$, $R_2$, $R_3$, $R_4$, $R_5$ and $R_6$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy or substituted $C_1$-$C_6$ alkoxy;

each substituted group comprises one or more optionally protected substituent groups independently selected from halogen, $OJ_1$, $N(J_1)(J_2)$, $=NJ_1$, $SJ_1$, $N_3$, $OC(=G)J_1$, $OC(=G)N(J_1)(J_2)$ and $C(=G)N(J_1)(J_2)$;

G is O, S or $NJ_3$; and each $J_1$, $J_2$ and $J_3$ is, independently, H or $C_1$-$C_6$ alkyl.

In certain embodiments, bicyclic carbocyclic nucleosides are provided having Formula I:

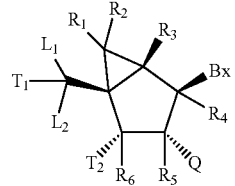

I wherein:

Bx is an optionally protected heterocyclic base moiety;

$T_1$ is a protected hydroxyl;

$T_2$ is a reactive phosphorus group capable of forming an internucleoside linkage;

Q is halogen or $O$—$[C(A_1)(A_2)]_n$-$[(C=O)_m$—$X]_j$—$Z$ wherein Q is other than a protected hydroxyl group;

$A_1$ and $A_2$ are each, independently, H, halogen, $C_1$-$C_6$ alkyl or substituted $C_1$-$C_6$ alkyl;

X is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

when j is 1 then Z is other than halogen and when X is $N(E_1)$ then Z is other than $N(E_2)(E_3)$;

$L_1$ and $L_2$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy or substituted $C_1$-$C_6$ alkoxy;

$R_1$, $R_2$, $R_3$, $R_4$, $R_5$ and $R_6$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy or substituted $C_1$-$C_6$ alkoxy;

each substituted group comprises one or more optionally protected substituent groups independently selected from halogen, $OJ_1$, $N(J_1)(J_2)$, $=NJ_1$, $SJ_1$, $N_3$, $OC(=G)J_1$, $OC(=G)N(J_1)(J_2)$ and $C(=G)N(J_1)(J_2)$;

G is O, S or $NJ_3$; and each $J_1$, $J_2$ and $J_3$ is, independently, H or $C_1$-$C_6$ alkyl.

In certain embodiments, when j is 1 then Z is other than halogen or $N(E_2)(E_3)$.

In certain embodiments, one of $L_1$ and $L_2$ is H and the other of $L_1$ and $L_2$ is $C_1$-$C_6$ alkyl, substituted $C_1$-$C_6$ alkyl or $C_1$-$C_6$ alkoxy. In certain embodiments, one of $L_1$ and $L_2$ is H and the other of $L_1$ and $L_2$ is O—$CH_3$ or O—$CH_2CH_3$. In certain embodiments, one of $L_1$ and $L_2$ is H and the other of $L_1$ and $L_2$ is $C_1$-$C_6$ alkyl or $C_1$-$C_6$ alkoxy. In certain embodiments, one of $L_1$ and $L_2$ is H and the other of $L_1$ and $L_2$ is $CH_3$ or $OCH_3$. In certain embodiments, $L_1$ and $L_2$ are each H. In certain embodiments, one of $L_1$ and $L_2$ is H and the other of $L_1$ and $L_2$ is $C_1$-$C_6$ alkyl or substituted alkyl. In certain embodiments, one of $L_1$ and $L_2$ is H and the other of $L_1$ and $L_2$ is $CH_3$.

In certain embodiments, at least one of $R_1$, $R_2$, $R_3$, $R_4$, $R_5$ and $R_6$ is halogen, $C_1$-$C_6$ alkyl, substituted $C_1$-$C_6$ alkyl, $C_1$-$C_6$ alkoxy or substituted $C_1$-$C_6$ alkoxy. In certain embodiments, at least one of $R_1$, $R_2$, $R_3$, $R_4$, $R_5$ and $R_6$ is F, $CH_3$ or $OCH_3$. In certain embodiments, $R_1$, $R_2$, $R_3$, $R_4$, $R_5$ and $R_6$ are each H. In certain embodiments, $L_1$, $L_2$, $R_1$, $R_2$, $R_3$, $R_4$, $R_5$ and $R_6$ are each H. In certain embodiments, one of $R_1$, $R_2$, $R_3$, $R_4$, $R_5$ and $R_6$ is F, $CH_3$ or $OCH_3$ and the remaining of $R_1$, $R_2$, $R_3$, $R_4$, $R_5$ and $R_6$ are each H.

In certain embodiments, Q is F, $OCH_3$, $OCF_3$, $OCH_2CH_3$, $OCH_2CF_3$, $OCH_2$—$CH$=$CH_2$, $O(CH_2)_2$—$OCH_3$, $O(CH_2)_2$—$O(CH_2)_2$—$N(CH_3)_2$, $OCH_2C$(=O)—$N(H)CH_3$, $OCH_2C$(=O)—$N(H)$—$(CH_2)_2$—$N(CH_3)_2$ or $OCH_2$—$N(H)$—$C$(=$NH$)$NH_2$. In certain embodiments, Q is F, $OCH_3$, $OCH_2C$(=O)—$N(H)$—$CH_3$ or $O(CH_2)_2$—$OCH_3$. In certain embodiments, Q is F. In certain embodiments, Q is $O(CH_2)_2$—$OCH_3$.

In certain embodiments, Bx is a pyrimidine, substituted pyrimidine, purine or substituted purine. In certain embodiments, Bx is uracil, thymine, cytosine, 4-N-benzoylcytosine, 5-methyl-cytosine, 4-N-benzoyl-5-methylcytosine, adenine, 6-N-benzoyladenine, guanine or 2-N-isobutyrylguanine.

In certain embodiments, $T_1$ is O-acetyl, O-benzyl, O-trimethylsilyl, O-t-butyldimethylsilyl, O-t-butyldiphenylsilyl or O-dimethoxytrityl. In certain embodiments, $T_2$ is H-phosphonate or a phosphoramidite. In certain embodiments, $T_1$ is O-4,4'-dimethoxytrityl and $T_2$ is diisopropylcyanoethoxy phosphoramidite.

In certain embodiments, oligomeric compounds are provided comprising at least one bicyclic carbocyclic nucleoside having Formula IIa:

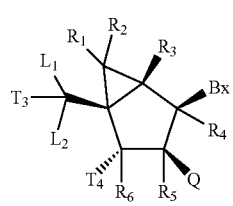

IIa wherein independently for each bicyclic carbocyclic nucleoside of Formula IIa:

Bx is an optionally protected heterocyclic base moiety;

one of $T_3$ and $T_4$ is an internucleoside linking group attaching the bicyclic nucleoside to the remainder of one of the 5' or 3' end of the oligomeric compound and the other of $T_3$ and $T_4$ is hydroxyl, a protected hydroxyl, a 5' or 3' terminal group or an internucleoside linking group attaching the bicyclic nucleoside to the remainder of the other of the 5' or 3' end of the oligomeric compound;

Q is halogen or O—$[C(A_1)(A_2)]_n$-$[(C$=$O)_m$—$X]_j$—Z wherein Q is other than a protected hydroxyl group;

$A_1$ and $A_2$ are each, independently, H, halogen, $C_1$-$C_6$ alkyl or substituted $C_1$-$C_6$ alkyl;

X is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

wherein when j is 1 then Z is other than halogen and when X is $N(E_1)$ then Z is other than $N(E_2)(E_3)$;

$L_1$ and $L_2$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy or substituted $C_1$-$C_6$ alkoxy;

$R_1$, $R_2$, $R_3$, $R_4$, $R_5$ and $R_6$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy or substituted $C_1$-$C_6$ alkoxy;

each substituted group comprises one or more optionally protected substituent groups independently selected from halogen, $OJ_1$, $N(J_1)(J_2)$, =$NJ_1$, $SJ_1$, $N_3$, OC(=G)$J_1$, OC(=G)$N(J_1)(J_2)$ and C(=G)$N(J_1)(J_2)$;

G is O, S or $NJ_3$;

each $J_1$, $J_2$ and $J_3$ is, independently, H or $C_1$-$C_6$ alkyl; and wherein said oligomeric compound comprises from 8 to 40 monomeric subunits linked by internucleoside linking groups and wherein at least some of the heterocyclic base moieties are capable of hybridizing to a nucleic acid molecule.

In certain embodiments, when j is 1 then Z is other than halogen or $N(E_2)(E_3)$.

In certain embodiments, oligomeric compounds are provided comprising at least one bicyclic carbocyclic nucleoside having Formula II:

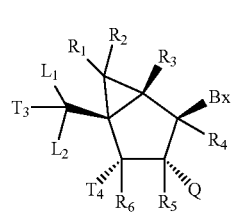

II wherein independently for each bicyclic carbocyclic nucleoside of Formula II:

Bx is an optionally protected heterocyclic base moiety;

one of $T_3$ and $T_4$ is an internucleoside linking group attaching the bicyclic nucleoside to the remainder of one of the 5' or 3' end of the oligomeric compound and the other of $T_3$ and $T_4$ is hydroxyl, a protected hydroxyl, a 5' or 3' terminal group or an internucleoside linking group attaching the bicyclic nucleoside to the remainder of the other of the 5' or 3' end of the oligomeric compound;

Q is halogen or O—$[C(A_1)(A_2)]_n$-$[(C$=$O)_m$—$X]_j$—Z wherein Q is other than a protected hydroxyl group;

$A_1$ and $A_2$ are each, independently, H, halogen, $C_1$-$C_6$ alkyl or substituted $C_1$-$C_6$ alkyl;

X is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

wherein when j is 1 then Z is other than halogen and when X is $N(E_1)$ then Z is other than $N(E_2)(E_3)$;

$L_1$ and $L_2$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy or substituted $C_1$-$C_6$ alkoxy;

$R_1$, $R_2$, $R_3$, $R_4$, $R_5$ and $R_6$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy or substituted $C_1$-$C_6$ alkoxy;

each substituted group comprises one or more optionally protected substituent groups independently selected from halogen, $OJ_1$, $N(J_1)(J_2)$, $=NJ_1$, $SJ_1$, $N_3$, $OC(=G)J_1$, $OC(=G)N(J_1)(J_2)$ and $C(=G)N(J_1)(J_2)$;

G is O, S or $NJ_3$;

each $J_1$, $J_2$ and $J_3$ is, independently, H or $C_1$-$C_6$ alkyl; and wherein said oligomeric compound comprises from 8 to 40 monomeric subunits linked by internucleoside linking groups and wherein at least some of the heterocyclic base moieties are capable of hybridizing to a nucleic acid molecule.

In certain embodiments, one of $L_1$ and $L_2$ is H and the other of $L_1$ and $L_2$ is $C_1$-$C_6$ alkyl or $C_1$-$C_6$ alkoxy for each bicyclic carbocyclic nucleoside having Formula IIa. In certain embodiments, one of $L_1$ and $L_2$ is H and the other of $L_1$ and $L_2$ is $CH_3$ or $OCH_3$ for each bicyclic carbocyclic nucleoside having Formula IIa. In certain embodiments, $L_1$ and $L_2$ are each H for each bicyclic carbocyclic nucleoside having Formula IIa. In certain embodiments, one of $L_1$ and $L_2$ is H and the other of $L_1$ and $L_2$ is $C_1$-$C_6$ alkyl or substituted $C_1$-$C_6$ alkyl for each bicyclic carbocyclic nucleoside having Formula IIa. In certain embodiments, one of $L_1$ and $L_2$ is H and the other of $L_1$ and $L_2$ is $CH_3$ for each bicyclic carbocyclic nucleoside having Formula IIa.

In certain embodiments, one of $L_1$ and $L_2$ is H and the other of $L_1$ and $L_2$ is $C_1$-$C_6$ alkyl or $C_1$-$C_6$ alkoxy for each bicyclic carbocyclic nucleoside having Formula II. In certain embodiments, one of $L_1$ and $L_2$ is H and the other of $L_1$ and $L_2$ is $CH_3$ or $OCH_3$ for each bicyclic carbocyclic nucleoside having Formula II. In certain embodiments, $L_1$ and $L_2$ are each H for each bicyclic carbocyclic nucleoside having Formula II. In certain embodiments, one of $L_1$ and $L_2$ is H and the other of $L_1$ and $L_2$ is $C_1$-$C_6$ alkyl or substituted $C_1$-$C_6$ alkyl for each bicyclic carbocyclic nucleoside having Formula II. In certain embodiments, one of $L_1$ and $L_2$ is H and the other of $L_1$ and $L_2$ is $CH_3$ for each bicyclic carbocyclic nucleoside having Formula II.

In certain embodiments, at least one of $R_1$, $R_2$, $R_3$, $R_4$, $R_5$ and $R_6$ is halogen, $C_1$-$C_6$ alkyl, substituted $C_1$-$C_6$ alkyl, $C_1$-$C_6$ alkoxy or substituted $C_1$-$C_6$ alkoxy for each bicyclic carbocyclic nucleoside having Formula IIa. In certain embodiments, at least one of $R_1$, $R_2$, $R_3$, $R_4$, $R_5$ and $R_6$ is F, $CH_3$ or $OCH_3$ for each bicyclic carbocyclic nucleoside having Formula IIa. In certain embodiments, $R_1$, $R_2$, $R_3$, $R_4$, $R_5$ and $R_6$ are each H for each bicyclic carbocyclic nucleoside having Formula IIa. In certain embodiments, $L_1$, $L_2$, $R_1$, $R_2$, $R_3$, $R_4$, $R_5$ and $R_6$ are each H for each bicyclic carbocyclic nucleoside having Formula IIa. In certain embodiments, one of $R_1$, $R_2$, $R_3$, $R_4$, $R_5$ and $R_6$ is F, $CH_3$ or $OCH_3$ and the remaining of $R_1$, $R_2$, $R_3$, $R_4$, $R_5$ and $R_6$ are each H for each bicyclic carbocyclic nucleoside having Formula IIa.

In certain embodiments, at least one of $R_1$, $R_2$, $R_3$, $R_4$, $R_5$ and $R_6$ is halogen, $C_1$-$C_6$ alkyl, substituted $C_1$-$C_6$ alkyl, $C_1$-$C_6$ alkoxy or substituted $C_1$-$C_6$ alkoxy for each bicyclic carbocyclic nucleoside having Formula II. In certain embodiments, at least one of $R_1$, $R_2$, $R_3$, $R_4$, $R_5$ and $R_6$ is F, $CH_3$ or $OCH_3$ for each bicyclic carbocyclic nucleoside having Formula II. In certain embodiments, $R_1$, $R_2$, $R_3$, $R_4$, $R_5$ and $R_6$ are each H for each bicyclic carbocyclic nucleoside having Formula II. In certain embodiments, $L_1$, $L_2$, $R_1$, $R_2$, $R_3$, $R_4$, $R_5$ and $R_6$ are each H for each bicyclic carbocyclic nucleoside having Formula II. In certain embodiments, one of $R_1$, $R_2$, $R_3$, $R_4$, $R_5$ and $R_6$ is F, $CH_3$ or $OCH_3$ and the remaining of $R_1$, $R_2$, $R_3$, $R_4$, $R_5$ and $R_6$ are each H for each bicyclic carbocyclic nucleoside having Formula II.

In certain embodiments, Q is F, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C(=O)$—$N(H)CH_3$, $OCH_2C(=O)$—$N(H)$—$(CH_2)_2$—$N(CH_3)_2$ or $OCH_2$—N(H)—$C(=NH)NH_2$ for each bicyclic carbocyclic nucleoside having Formula IIa.

In certain embodiments, Q is F, $OCH_3$, $OCH_2C(=O)$—$N(H)CH_3$ or $O(CH_2)_2$—$OCH_3$ for each bicyclic carbocyclic nucleoside having Formula IIa. In certain embodiments, Q is F for each bicyclic carbocyclic nucleoside having Formula IIa. In certain embodiments, Q is $O(CH_2)_2$—$OCH_3$ for each bicyclic carbocyclic nucleoside having Formula IIa.

In certain embodiments, Q is F, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C(=O)$—$N(H)CH_3$, $OCH_2C(=O)$—$N(H)$—$(CH_2)_2$—$N(CH_3)_2$ or $OCH_2$—N(H)—$C(=NH)NH_2$ for each bicyclic carbocyclic nucleoside having Formula II.

In certain embodiments, Q is F, $OCH_3$, $OCH_2C(=O)$—$N(H)CH_3$ or $O(CH_2)_2$—$OCH_3$ for each bicyclic carbocyclic nucleoside having Formula II. In certain embodiments, Q is F for each bicyclic carbocyclic nucleoside having Formula II. In certain embodiments, Q is $O(CH_2)_2$—$OCH_3$ for each bicyclic carbocyclic nucleoside having Formula II.

In certain embodiments, each Bx is, independently, a pyrimidine, substituted pyrimidine, purine or substituted purine. In certain embodiments, each Bx is, independently, uracil, thymine, cytosine, 4-N-benzoylcytosine, 5-methylcytosine, 4-N-benzoyl-5-methylcytosine, adenine, 6-N-benzoyladenine, guanine or 2-N-isobutyrylguanine.

In certain embodiments, each substituent group is, independently, F or $C_1$-$C_6$ alkyl for each bicyclic carbocyclic nucleoside having Formula IIa.

In certain embodiments, each substituent group is, independently, F or $C_1$-$C_6$ alkyl for each bicyclic carbocyclic nucleoside having Formula II.

In certain embodiments, one $T_3$ and or one $T_4$ is a terminal group. In certain embodiments, one $T_3$ or one $T_4$ is a conjugate group that may include a bifunctional linking moiety.

In certain embodiments, oligomeric compounds are provided comprising a first region consisting of from two to 5 modified nucleosides, a second region consisting of from two to 5 modified nucleosides and a gap region consisting of from 6 to 14 monomer subunits located between the first and second region wherein at least one of the monomer subunits in the gap region is a bicyclic carbocyclic nucleoside having Formula IIa. In certain embodiments, each monomer subunit in the gap region is independently, a nucleoside or a modified nucleoside that is different from each of the modified nucleosides in the first and second region.

In certain embodiments, oligomeric compounds are provided comprising a first region consisting of from two to 5 modified nucleosides, a second region consisting of from two to 5 modified nucleosides and a gap region consisting of from 6 to 14 monomer subunits located between the first and second region wherein at least one of the monomer subunits in the gap region is a bicyclic carbocyclic nucleoside having Formula II. In certain embodiments, each monomer subunit in the gap region is independently, a nucleoside or a modified nucleoside that is different from each of the modified nucleosides in the first and second region.

In certain embodiments, at least two of the monomer subunits in the gap region are bicyclic carbocyclic nucleosides having Formula IIa. In certain embodiments, oligomeric compounds are provided comprising a single bicyclic carbocyclic nucleoside having Formula IIa in the gap region.

In certain embodiments, at least two of the monomer subunits in the gap region are bicyclic carbocyclic nucleosides having Formula II. In certain embodiments, oligomeric compounds are provided comprising a single bicyclic carbocyclic nucleoside having Formula II in the gap region.

In certain embodiments, the gap region comprises from about 8 to about 12 monomer subunits. In certain embodiments, the gap region comprises from about 8 to about 10 monomer subunits. In certain embodiments, each monomer subunit in the gap region other than bicyclic carbocyclic nucleosides of Formula IIa is a β-D-2'-deoxyribonucleoside.

In certain embodiments, the gap region comprises from about 8 to about 12 monomer subunits. In certain embodiments, the gap region comprises from about 8 to about 10 monomer subunits. In certain embodiments, each monomer subunit in the gap region other than bicyclic carbocyclic nucleosides of Formula II is a β-D-2'-deoxyribonucleoside.

In certain embodiments, each modified nucleoside in the first and second region comprises a modified sugar moiety. In certain embodiments, oligomeric compounds are provided wherein each modified nucleoside in the first and second region is, independently, a bicyclic nucleoside comprising a bicyclic furanosyl sugar moiety or a modified nucleoside comprising a furanosyl sugar moiety having at least one substituent group. In certain embodiments, each modified nucleoside in the first and second region is, independently, a bicyclic nucleoside comprising a 4'-CH((S)—CH$_3$)—O-2' bridge or a 2'-O-methoxyethyl substituted nucleoside.

In certain embodiments, oligomeric compounds are provided comprising a first region consisting of from two to 5 modified nucleosides, wherein at least one of the modified nucleosides of the first region is a bicyclic carbocyclic nucleoside having Formula IIa. In certain embodiments, oligomeric compounds are provided comprising a first region consisting of from two to 5 modified nucleosides and a second region consisting of from two to 5 modified nucleosides wherein at least one of the modified nucleosides of the first region is a bicyclic carbocyclic nucleoside having Formula IIa. In certain embodiments, oligomeric compounds are provided comprising a first region consisting of from two to 5 modified nucleosides and a second region consisting of from two to 5 modified nucleosides wherein at least one of the modified nucleosides of the first region and at least one of the modified nucleosides of the second region is a bicyclic carbocyclic nucleoside having Formula IIa.

In certain embodiments, oligomeric compounds are provided comprising a first region consisting of from two to 5 modified nucleosides, wherein at least one of the modified nucleosides of the first region is a bicyclic carbocyclic nucleoside having Formula II. In certain embodiments, oligomeric compounds are provided comprising a first region consisting of from two to 5 modified nucleosides and a second region consisting of from two to 5 modified nucleosides wherein at least one of the modified nucleosides of the first region is a bicyclic carbocyclic nucleoside having Formula II. In certain embodiments, oligomeric compounds are provided comprising a first region consisting of from two to 5 modified nucleosides and a second region consisting of from two to 5 modified nucleosides wherein at least one of the modified nucleosides of the first region and at least one of the modified nucleosides of the second region is a bicyclic carbocyclic nucleoside having Formula II.

In certain embodiments, oligomeric compounds are provided comprising a first region consisting of from two to 5 modified nucleosides, a second region consisting of from two to 5 modified nucleosides and a gap region consisting of from 6 to 14 monomer subunits located between the first and second region wherein at least one of the modified nucleosides of the first region is a bicyclic carbocyclic nucleoside having Formula IIa. In certain embodiments, oligomeric compounds are provided comprising a first region consisting of from two to 5 modified nucleosides, a second region consisting of from two to 5 modified nucleosides and a gap region consisting of from 6 to 14 monomer subunits located between the first and second region wherein at least one of the modified nucleosides of the first region and at least one of the modified nucleosides of the second region is a bicyclic carbocyclic nucleoside having Formula IIa. In certain embodiments, each monomer subunit in the gap region is independently, a nucleoside or a modified nucleoside that is different from each of the modified nucleosides in the first and second region. In certain embodiments, the gap region comprises from about 8 to about 12 monomer subunits. In certain embodiments, the gap region comprises from about 8 to about 10 monomer subunits. In certain embodiments, each monomer subunit in the gap region is a β-D-2'-deoxyribonucleoside.

In certain embodiments, oligomeric compounds are provided comprising a first region consisting of from two to 5 modified nucleosides, a second region consisting of from two to 5 modified nucleosides and a gap region consisting of from 6 to 14 monomer subunits located between the first and second region wherein at least one of the modified nucleosides of the first region is a bicyclic carbocyclic nucleoside having Formula II. In certain embodiments, oligomeric compounds are provided comprising a first region consisting of from two to 5 modified nucleosides, a second region consisting of from two to 5 modified nucleosides and a gap region consisting of from 6 to 14 monomer subunits located between the first and second region wherein at least one of the modified nucleosides of the first region and at least one of the modified nucleosides of the second region is a bicyclic carbocyclic nucleoside having Formula II. In certain embodiments, each monomer subunit in the gap region is independently, a nucleoside or a modified nucleoside that is different from each of the modified nucleosides in the first and second region. In certain embodiments, the gap region comprises from about 8 to about 12 monomer subunits. In certain embodiments, the gap region comprises from about 8 to about 10 monomer subunits. In certain embodiments, each monomer subunit in the gap region is a β-D-2'-deoxyribonucleoside.

In certain embodiments, each modified nucleoside in the first and second region other than bicyclic carbocyclic nucleosides of Formula IIa comprises a modified sugar moiety. In certain embodiments, each modified nucleoside in the first and second region other than bicyclic carbocyclic nucleosides of Formula IIa is, independently, a bicyclic nucleoside comprising a bicyclic furanosyl sugar moiety or a modified nucleoside comprising a furanosyl sugar moiety having at least one substituent group. In certain embodiments, each modified nucleoside in the first and second region other than bicyclic carbocyclic nucleosides of Formula IIa is, independently, a bicyclic nucleoside comprising a 4'-CH((S)—CH$_3$)—O-2' bridge or a 2'-O-methoxyethyl substituted nucleoside. In certain embodiments, essentially each modified nucleoside of the first region is a bicyclic carbocyclic nucleoside having Formula IIa. In certain embodiments, essentially each modified nucleoside of the first and second region is a bicyclic carbocyclic nucleoside having Formula IIa.

In certain embodiments, each modified nucleoside in the first and second region other than bicyclic carbocyclic nucleosides of Formula II comprises a modified sugar moiety. In certain embodiments, each modified nucleoside in the first and second region other than bicyclic carbocyclic nucleosides of Formula II is, independently, a bicyclic nucleoside comprising a bicyclic furanosyl sugar moiety or a modified nucleoside comprising a furanosyl sugar moiety having at least one substituent group. In certain embodiments, each modified nucleoside in the first and second region other than bicyclic carbocyclic nucleosides of Formula II is, independently, a bicyclic nucleoside comprising a 4'-CH((S)—CH$_3$)—O-2' bridge or a 2'-O-methoxyethyl substituted nucleoside.

In certain embodiments, essentially each modified nucleoside of the first region is a bicyclic carbocyclic nucleoside having Formula II. In certain embodiments, essentially each modified nucleoside of the first and second region is a bicyclic carbocyclic nucleoside having Formula II.

In certain embodiments, each internucleoside linking group is, independently, a phosphodiester internucleoside linking group or a phosphorothioate internucleoside linking group.

In certain embodiments, essentially each internucleoside linking group is a phosphorothioate internucleoside linking group.

In certain embodiments, methods of inhibiting gene expression are provided comprising contacting a cell with an oligomeric as provided herein wherein said oligomeric compound is complementary to a target RNA. In certain embodiments, the cell is in an animal. In certain embodiments, the cell is in a human. In certain embodiments, the target RNA is selected from mRNA, pre-mRNA and micro RNA. In certain embodiments, the target RNA is mRNA. In certain embodiments, the target RNA is human mRNA. In certain embodiments, the target RNA is cleaved thereby inhibiting its function. In certain embodiments, the method further comprises detecting the levels of target RNA.

In certain embodiments, in vitro methods of inhibiting gene expression are provided comprising contacting one or more cells or a tissue with an oligomeric compound as provided herein.

In certain embodiments, oligomeric compounds are provided for therapeutic use in an in vivo method of inhibiting gene expression said method comprising contacting an animal with an oligomeric compound as provided herein.

In certain embodiments, oligomeric compounds are provided for use in medical therapy.

In certain embodiments, bicyclic carbocyclic nucleosides are provided having Formula IIIa:

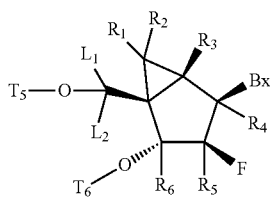

IIIa wherein:
Bx is an optionally protected heterocyclic base moiety;
$T_5$ and $T_6$ are each, independently, H, $C_2$-$C_6$ alkylcarbonyl, $C_1$-$C_6$ alkoxycarbonyl, $C_1$-$C_6$ aminoalkylcarbonyl, $P_3O_9H_4$, $P_2O_6H_3$, $P(O)R_9R_{10}$, a prodrug group or a pharmaceutically acceptable salt thereof;
$L_1$ and $L_2$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy or substituted $C_1$-$C_6$ alkoxy;

$R_1$, $R_2$, $R_3$, $R_4$, $R_5$ and $R_6$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy or substituted $C_1$-$C_6$ alkoxy;

each substituted group comprises one or more optionally protected substituent groups independently selected from halogen, $OJ_1$, $N(J_1)(J_2)$, =$NJ_1$, $SJ_1$, $N_3$, $OC(=G)J_1$, $OC(=G)N(J)(J_2)$ and $C(=G)N(J_1)(J_2)$;

G is O, S or $NJ_3$; and each $J_1$, $J_2$ and $J_3$ is, independently, H or $C_1$-$C_6$ alkyl.

In certain embodiments, bicyclic carbocyclic nucleosides are provided having Formula III:

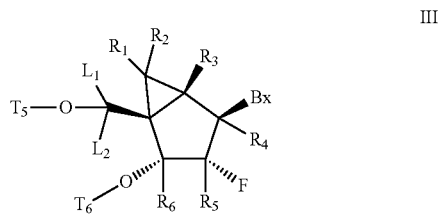

III wherein:
Bx is an optionally protected heterocyclic base moiety;
$T_5$ and $T_6$ are each, independently, H, $C_2$-$C_6$ alkylcarbonyl, $C_1$-$C_6$ alkoxycarbonyl, $C_1$-$C_6$ aminoalkylcarbonyl, $P_3O_9H_4$, $P_2O_6H_3$, $P(O)R_9R_{10}$, a prodrug group or a pharmaceutically acceptable salt thereof;
$L_1$ and $L_2$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy or substituted $C_1$-$C_6$ alkoxy;
$R_1$, $R_2$, $R_3$, $R_4$, $R_5$ and $R_6$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy or substituted $C_1$-$C_6$ alkoxy;
each substituted group comprises one or more optionally protected substituent groups independently selected from halogen, $OJ_1$, $N(J_1)(J_2)$, =$NJ_1$, $SJ_1$, $N_3$, $OC(=G)J_1$, $OC(=G)N(J_1)(J_2)$ and $C(=G)N(J_1)(J_2)$;
G is O, S or $NJ_3$; and
each $J_1$, $J_2$ and $J_3$ is, independently, H or $C_1$-$C_6$ alkyl.

In certain embodiments, one of $L_1$ and $L_2$ is H and the other of $L_1$ and $L_2$ is $C_1$-$C_6$ alkyl or substituted alkyl. In certain embodiments, one of $L_1$ and $L_2$ is H and the other of $L_1$ and $L_2$ is $CH_3$. In certain embodiments, $L_1$ and $L_2$ are each H.

In certain embodiments, at least one of $R_1$, $R_2$, $R_3$, $R_4$, $R_5$ and $R_6$ is halogen, $C_1$-$C_6$ alkyl, substituted $C_1$-$C_6$ alkyl, $C_1$-$C_6$ alkoxy or substituted $C_1$-$C_6$ alkoxy. In certain embodiments, one of $R_1$, $R_2$, $R_3$, $R_4$, $R_5$ and $R_6$ is F, $CH_3$ or $OCH_3$ and the remaining of $R_1$, $R_2$, $R_3$, $R_4$, $R_5$ and $R_6$ are each H. In certain embodiments, $R_1$, $R_2$, $R_3$, $R_4$, $R_5$ and $R_6$ are each H. In certain embodiments, $L_1$, $L_2$, $R_1$, $R_2$, $R_3$, $R_4$, $R_5$ and $R_6$ are each H.

In certain embodiments, Bx is a pyrimidine or substituted pyrimidine. In certain embodiments, Bx is uracil, thymine, cytosine, 4-N-benzoylcytosine, 5-methylcytosine or 4-N-benzoyl-5-methylcytosine. In certain embodiments, Bx is a purine or substituted purine. In certain embodiments, Bx is adenine, 6-N-benzoyladenine, guanine or 2-N-isobutyrylguanine.

In certain embodiments, $T_5$ and $T_6$ are each, independently, a prodrug group. In certain embodiments, $T_5$ is $P_3O_9H_4$, $P_2O_6H_3$ or $P(O)R_9R_{10}$ and $T_6$ is H. In certain embodiments, $T_5$ and $T_6$ are each H.

In certain embodiments, methods of treating a subject infected by a virus are provided which comprise administering to the subject a therapeutically effective amount of a bicyclic carbocyclic nucleoside as provided herein. In certain embodiments, the methods further comprise administering at least one immune system modulator and/or at least one further antiviral agent.

In certain embodiments, a pharmaceutical composition is provided comprising a therapeutically effective quantity of a bicyclic carbocyclic nucleoside as provided herein admixed with at least one pharmaceutically acceptable carriers, diluent or excipient. In certain embodiments, the pharmaceutical composition further comprises a pharmaceutically acceptable medium.

DETAILED DESCRIPTION OF THE INVENTION

Provided herein are novel bicyclic carbocyclic nucleosides and oligomeric compounds prepared therefrom. More particularly, the bicyclic carbocyclic nucleosides provided herein, comprise a cyclopropanated cyclopentane ring in place of the naturally occurring furanose ring which further includes at least one stereospecific 2'-substituent group. The bicyclic carbocyclic nucleosides can also be described as substituted bicyclo[3.1.0]hexane sugar surrogates. The bicyclic carbocyclic nucleosides can also include further substituent groups in place of one or more hydrogen atoms. The bicyclic carbocyclic nucleosides are expected to be useful for enhancing one or more properties of the oligomeric compounds they are incorporated into. In certain embodiments, the oligomeric compounds provided herein are expected to hybridize to a portion of a target RNA resulting in loss of normal function of the target RNA. In certain embodiments, oligomeric compounds are provided that are antisense compounds that are expected to alter splicing of a target pre-mRNA resulting in a different splice variant. In certain embodiments, the novel bicyclic carbocyclic nucleosides are provided as monomers for use as antivirals.

In certain embodiments, the bicyclic carbocyclic nucleosides provided herein are incorporated into antisense oligomeric compounds which are used to reduce target RNA, such as messenger RNA, in vitro and in vivo. The reduction of target RNA can be effected via numerous pathways with a resultant modulation of gene expression. Such modulation can provide direct or indirect increase or decrease in a particular target (nucleic acid or protein). Such pathways include for example the steric blocking of transcription or translation and cleavage of mRNA using either single or double stranded oligomeric compounds. The oligomeric compounds provided herein are also expected to be useful as primers and probes in diagnostic applications. In certain embodiments, oligomeric compounds comprising at least one of the bicyclic carbocyclic nucleosides provided herein are expected to be useful as aptamers which are oligomeric compounds capable of binding to aberrant proteins in an in vivo setting.

In certain embodiments, the bicyclic carbocyclic nucleosides provided herein are modified following standard protocols known in the art for use as antivirals such as polymerase inhibitors (see for example Sofia et al., *J. Med. Chem.*, 2010, 53, 7202-7218 and *Antiviral Drugs, From Basic Discovery Through Clinical Trials*, Kazmierski, Wieslaw M., Ed., John Wiley & Sons, 2011, 287-315). In certain embodiments, the modified bicyclic carbocyclic nucleosides are expected to mimic natural polymerase substrates, resulting in chain termination and/or an increased error frequency when they are incorporated into a growing RNA chain. Various nucleoside analogs have entered clinical trials with some of these showing very good activity against viruses such as for example HCV and HIV (see for example, Delang et al., *Viruses*, 2010, 2, 862-866; and *Antiviral Drugs From Basic Discovery Through Clinical Trials*, William M. Kazmierski., ed., Wiley, 2011). In certain embodiments, methods of treating viral infections in a mammal in need thereof are provided comprising administering to the mammal a therapeutically effective amount of one or more modified bicyclic carbocyclic nucleosides as provided herein.

In certain embodiments, bicyclic carbocyclic nucleosides are provided having Formula I:

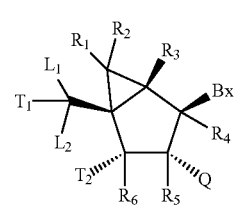

wherein:

Bx is an optionally protected heterocyclic base moiety;

$T_1$ is a protected hydroxyl;

$T_2$ is a reactive phosphorus group capable of forming an internucleoside linkage;

Q is halogen or O—$[C(A_1)(A_2)]_n$-$[(C{=}O)_m$—$X]_j$—Z wherein Q is other than a protected hydroxyl group;

$A_1$ and $A_2$ are each, independently, H, halogen, $C_1$-$C_6$ alkyl or substituted $C_1$-$C_6$ alkyl;

X is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

when j is 1 then Z is other than halogen and when X is $N(E_1)$ then Z is other than $N(E_2)(E_3)$;

$L_1$ and $L_2$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy or substituted $C_1$-$C_6$ alkoxy;

$R_1$, $R_2$, $R_3$, $R_4$, $R_5$ and $R_6$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy or substituted $C_1$-$C_6$ alkoxy;

each substituted group comprises one or more optionally protected substituent groups independently selected from halogen, $OJ_1$, $N(J_1)(J_2)$, $=NJ_1$, $SJ_1$, $N_3$, $OC({=}G)J_1$, $OC({=}G)N(J)(J_2)$ and $C({=}G)N(J_1)(J_2)$;

G is O, S or $NJ_3$; and each $J_1$, $J_2$ and $J_3$ is, independently, H or $C_1$-$C_6$ alkyl.

In certain embodiments, oligomeric compounds are provided comprising at least one bicyclic carbocyclic nucleoside having Formula II:

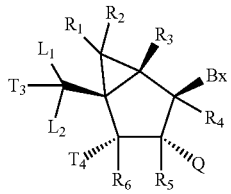

II

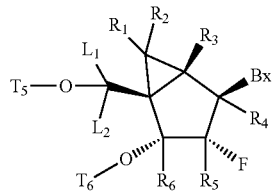

III wherein independently for each bicyclic carbocyclic nucleoside of Formula II:
Bx is an optionally protected heterocyclic base moiety;
one of $T_3$ and $T_4$ is an internucleoside linking group attaching the bicyclic nucleoside to the remainder of one of the 5' or 3' end of the oligomeric compound and the other of $T_3$ and $T_4$ is hydroxyl, a protected hydroxyl, a 5' or 3' terminal group or an internucleoside linking group attaching the bicyclic nucleoside to the remainder of the other of the 5' or 3' end of the oligomeric compound;
Q is halogen or O—$[C(A_1)(A_2)]_n$-$[(C\!=\!O)_m$—$X]_j$—Z wherein Q is other than a protected hydroxyl group;
$A_1$ and $A_2$ are each, independently, H, halogen, $C_1$-$C_6$ alkyl or substituted $C_1$-$C_6$ alkyl;
X is O, S or N($E_1$);
Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or N($E_2$)($E_3$);
$E_1$, $E_2$ and $E_3$ are each, independently, H, $C_1$-$C_6$ alkyl or substituted $C_1$-$C_6$ alkyl;
n is from 1 to about 6;
m is 0 or 1;
j is 0 or 1;
wherein when j is 1 then Z is other than halogen and when X is N($E_1$) then Z is other than N($E_2$)($E_3$);
$L_1$ and $L_2$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy or substituted $C_1$-$C_6$ alkoxy;
$R_1$, $R_2$, $R_3$, $R_4$, $R_5$ and $R_6$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy or substituted $C_1$-$C_6$ alkoxy;
each substituted group comprises one or more optionally protected substituent groups independently selected from halogen, $OJ_1$, $N(J_1)(J_2)$, $=\!NJ_1$, $SJ_1$, $N_3$, $OC(\!=\!G)J_1$, $OC(\!=\!G)N(J_1)(J_2)$ and $C(\!=\!G)N(J_1)(J_2)$;
G is O, S or $NJ_3$;
each $J_1$, $J_2$ and $J_3$ is, independently, H or $C_1$-$C_6$ alkyl; and
wherein said oligomeric compound comprises from 8 to 40 monomeric subunits linked by internucleoside linking groups and wherein at least some of the heterocyclic base moieties are capable of hybridizing to a nucleic acid molecule.

Incorporation of one or more of the bicyclic carbocyclic nucleosides, as provided herein, into an oligomeric compound is expected to enhance one or more desired properties of the resulting oligomeric compound. Such properties include without limitation stability, nuclease resistance, binding affinity, specificity, absorption, cellular distribution, cellular uptake, charge, pharmacodynamics and pharmacokinetics.

In certain embodiments, bicyclic carbocyclic nucleosides are provided having Formula III:

wherein:
Bx is an optionally protected heterocyclic base moiety;
$T_5$ and $T_6$ are each, independently, H, $C_2$-$C_6$ alkylcarbonyl, $C_1$-$C_6$ alkoxycarbonyl, $C_1$-$C_6$ aminoalkylcarbonyl, $P_3O_9H_4$, $P_2O_6H_3$, $P(O)R_9R_{10}$, a prodrug group or a pharmaceutically acceptable salt thereof;
$L_1$ and $L_2$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy or substituted $C_1$-$C_6$ alkoxy;
$R_1$, $R_2$, $R_3$, $R_4$, $R_5$ and $R_6$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy or substituted $C_1$-$C_6$ alkoxy;
each substituted group comprises one or more optionally protected substituent groups independently selected from halogen, $OJ_1$, $N(J_1)(J_2)$, $=\!NJ_1$, $SJ_1$, $N_3$, $OC(\!=\!G)J_1$, $OC(\!=\!G)N(J_1)(J_2)$ and $C(\!=\!G)N(J_1)(J_2)$;
G is O, S or $NJ_3$; and
each $J_1$, $J_2$ and $J_3$ is, independently, H or $C_1$-$C_6$ alkyl.

In certain embodiments, bicyclic carbocyclic nucleosides having Formula III are provided for use as antiviral nucleoside monomers. Nucleoside monomers have been used in antiviral applications including but not limited to reverse transcriptase and polymerase inhibitors. In certain embodiments, bicyclic carbocyclic nucleosides having Formula III are provided, modified as per standard protocols known in the art for use as polymerase inhibitors. The bicyclic carbocyclic nucleosides having Formula III are expected to mimic natural polymerase substrates, resulting in chain termination and/or an increased error frequency when they are incorporated into a growing RNA chain. Various nucleoside analogs have entered clinical trials with some of these showing very good activity against viruses such as for example HCV and HIV (see for example, Delang et al., *Viruses*, 2010, 2, 862-866; and *Antiviral Drugs From Basic Discovery Through Clinical Trials*, William M. Kazmierski., ed., Wiley, 2011). In certain embodiments, methods of treating viral infections in a mammal in need thereof comprising administering to the mammal a therapeutically effective amount of one or more bicyclic carbocyclic nucleosides having Formula III are provided.

While nucleosides often are potent antiviral and chemotherapeutic agents, their practical utility is often limited by two factors. Firstly, poor pharmacokinetic properties frequently limit the absorption of the nucleoside from the gut and; secondly, suboptimal physical properties restrict formulation options which could be employed to enhance delivery of the active ingredient. One strategy for increasing the efficiency of nucleoside antivirals is to modify the nucleoside such that it is delivered as a prodrug.

Albert introduced the term prodrug to describe a compound which lacks intrinsic biological activity but which is capable of metabolic transformation to the active drug substance (A. Albert, Selective Toxicity, Chapman and Hall, London, 1951). Prodrugs have been recently reviewed (P.

Ettmayer et al., J. Med Chem. 2004 47(10):2393-2404; K. Beaumont et al., Curr. Drug Metab. 2003 4:461-485; H. Bundgaard, Design of Prodrugs: Bioreversible derivatives for various functional groups and chemical entities in Design of Prodrugs, H. Bundgaard (ed) Elsevier Science Publishers, Amersterdam 1985; G. M. Pauletti et al. Adv. Drug Deliv. Rev. 1997 27:235-256; R. J. Jones and N. Bischofberger, Antiviral Res. 1995 27; 1-15 and C. R. Wagner et al., Med. Res. Rev. 2000 20:417-45). While the metabolic transformation can be catalyzed by specific enzymes, often hydrolases, the active compound can also be regenerated by non-specific chemical processes. The term "prodrug group" as used herein refers to groups that can be placed on at least the 5' and or 3' oxygen atoms, of the bicyclic carbocyclic nucleoside having Formula III, that are ultimately metabolized thereby providing the active drug substance.

Pharmaceutically acceptable prodrugs refer to compounds that are metabolized, for example hydrolyzed or oxidized, in the host to form the compounds of the present invention. The bioconversion should avoid formation fragments with toxicological liabilities. Typical examples of prodrugs include compounds that have biologically labile protecting groups linked to a functional moiety of the active compound. Alkylation, acylation or other lipophilic modification of the hydroxyl group(s) on the sugar moiety have been utilized in the design of pronucleosides. These pronucleosides can be hydrolyzed or dealkylated in vivo to generate the active compound.

The obligatory requirement for in vivo phosphorylation has recently led to interest in nucleoside monophosphate prodrugs containing a masked phosphate moiety which is susceptible to intracellular enzymatic activation leading to a nucleoside monophosphate. Since the rate limiting step in the formation of nucleoside triphosphates is the first step leading to a monophosphate, subsequent addition of the second and third phosphates form facilely from the monophosphate. (see, e.g., P. Perrone et al., J. Med. Chem., 2007, 50(8):1840; S. J. Hecker and M. D. Erion, J. Med Chem. 2008 51(8):2328) As used herein the term "motif" refers to the pattern created by the relative positioning of monomer subunits within an oligomeric compound wherein the pattern is determined by comparing the sugar moieties of the linked monomer subunits. The only determinant for the motif of an oligomeric compound is the differences or lack of differences between the sugar moieties. The internucleoside linkages, heterocyclic bases and further groups such as terminal groups are not considered when determining the motif of an oligomeric compound.

The preparation of motifs has been disclosed in various publications including without limitation, representative U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922; and published international applications WO 2005/121371 and WO 2005/121372 (both published on Dec. 22, 2005), certain of which are commonly owned with the instant application, and each of which is herein incorporated by reference in its entirety.

In certain embodiments, the bicyclic carbocyclic nucleosides provided herein are incorporated into oligomeric compounds such that a motif results. The placement of bicyclic carbocyclic nucleosides into oligomeric compounds to provide particular motifs can enhance the desired properties of the resulting oligomeric compounds for activity using various mechanisms such as for example RNaseH or RNAi. Such motifs include without limitation, gapmer motifs, hemimer motifs, blockmer motifs, uniformly fully modified motifs, positionally modified motifs and alternating motifs. In conjunction with these motifs a wide variety of internucleoside linkages can also be used including but not limited to phosphodiester and phosphorothioate internucleoside linkages which can be incorporated uniformly or in various combinations. The oligomeric compounds can further include terminal groups at one or both of the 5' and or 3' terminals such as a conjugate or reporter group. The positioning of the bicyclic carbocyclic nucleosides provided herein, the use of linkage strategies and terminal groups can be easily optimized to enhance a desired activity for a selected target.

As used herein the term "alternating motif" refers to an oligomeric compound comprising a contiguous sequence of linked monomer subunits wherein the monomer subunits have two different types of sugar moieties that alternate for essentially the entire sequence of the oligomeric compound. Oligomeric compounds having an alternating motif can be described by the formula: 5'-A(-L-B-L-A)$_n$(-L-B)$_{nn}$-3' where A and B are monomer subunits that have different sugar moieties, each L is, independently, an internucleoside linking group, n is from about 4 to about 12 and nn is 0 or 1. The heterocyclic base and internucleoside linkage is independently variable at each position. The motif further optionally includes the use of one or more other groups including but not limited to capping groups, conjugate groups and other 5' and or 3'-terminal groups. This permits alternating oligomeric compounds from about 9 to about 26 monomer subunits in length. This length range is not meant to be limiting as longer and shorter oligomeric compounds are also amenable to oligomeric compounds provided herein. In certain embodiments, each A or each B comprise bicyclic carbocyclic nucleosides as provided herein.

As used herein the term "uniformly fully modified motif" refers to an oligomeric compound comprising a contiguous sequence of linked monomer subunits that each have the same type of sugar moiety. The heterocyclic base and internucleoside linkage is independently variable at each position. The motif further optionally includes the use of one or more other groups including but not limited to capping groups, conjugate groups and other 5' and or 3'-terminal groups. In certain embodiments, the uniformly fully modified motif includes a contiguous sequence of bicyclic carbocyclic nucleosides. In certain embodiments, one or both of the 5' and 3'-ends of the contiguous sequence of bicyclic carbocyclic nucleosides, comprise 5' and or 3'-terminal groups such as one or more unmodified nucleosides.

As used herein the term "hemimer motif" refers to an oligomeric compound comprising a contiguous sequence of monomer subunits that each have the same type of sugar moiety with a further short contiguous sequence of monomer subunits located at the 5' or the 3' end that have a different type of sugar moiety. The heterocyclic base and internucleoside linkage is independently variable at each position. The motif further optionally includes the use of one or more other groups including but not limited to capping groups, conjugate groups and other 5' and or 3'-terminal groups. In general, a hemimer is an oligomeric compound of uniform sugar moieties further comprising a short region (1, 2, 3, 4 or about 5 monomer subunits) having uniform but different sugar moieties located on either the 3' or the 5' end of the oligomeric compound.

In certain embodiments, the hemimer motif comprises a contiguous sequence of from about 10 to about 28 monomer subunits having one type of sugar moiety with from 1 to 5 or from 2 to about 5 monomer subunits having a second type of sugar moiety located at one of the termini. In certain embodiments, the hemimer is a contiguous sequence of from about 8 to about 20 β-D-2'-deoxyribonucleosides having from 1-12 contiguous bicyclic carbocyclic nucleosides located at one of the termini. In certain embodiments, the hemimer is a contiguous sequence of from about 8 to about 20 β-D-2'-deoxyribonucleosides having from 1-5 contiguous bicyclic carbocyclic nucleosides located at one of the termini. In certain embodiments, the hemimer is a contiguous sequence of from about 12 to about 18 β-D-2'-deoxyribonucleosides having from 1-3 contiguous bicyclic carbocyclic nucleosides located at one of the termini. In certain embodiments, the hemimer is a contiguous sequence of from about 10 to about 14 β-D-2'-deoxyribonucleosides having from 1-3 contiguous bicyclic carbocyclic nucleosides located at one of the termini.

As used herein the terms "blockmer motif" and "blockmer" refer to an oligomeric compound comprising an otherwise contiguous sequence of monomer subunits wherein the sugar moieties of each monomer subunit is the same except for an interrupting internal block of contiguous monomer subunits having a different type of sugar moiety. The heterocyclic base and internucleoside linkage is independently variable at each position of a blockmer. The motif further optionally includes the use of one or more other groups including but not limited to capping groups, conjugate groups and other 5' or 3'-terminal groups. A blockmer overlaps somewhat with a gapmer in the definition but typically only the monomer subunits in the block have non-naturally occurring sugar moieties in a blockmer and only the monomer subunits in the external regions have non-naturally occurring sugar moieties in a gapmer with the remainder of monomer subunits in the blockmer or gapmer being β-D-2'-deoxyribonucleosides or β-D-ribonucleosides. In certain embodiments, blockmers are provided herein wherein all of the monomer subunits comprise non-naturally occurring sugar moieties.

As used herein the term "positionally modified motif" is meant to include an otherwise contiguous sequence of monomer subunits having one type of sugar moiety that is interrupted with two or more regions of from 1 to about 5 contiguous monomer subunits having another type of sugar moiety. Each of the two or more regions of from 1 to about 5 contiguous monomer subunits are independently uniformly modified with respect to the type of sugar moiety. In certain embodiments, each of the two or more regions have the same type of sugar moiety. In certain embodiments, each of the two or more regions have a different type of sugar moiety. In certain embodiments, each of the two or more regions, independently, have the same or a different type of sugar moiety. The heterocyclic base and internucleoside linkage is independently variable at each position of a positionally modified oligomeric compound. The motif further optionally includes the use of one or more other groups including but not limited to capping groups, conjugate groups and other 5' or 3'-terminal groups. In certain embodiments, positionally modified oligomeric compounds are provided comprising a sequence of from 8 to 20 β-D-2'-deoxyribonucleosides that further includes two or three regions of from 2 to about 5 contiguous bicyclic carbocyclic nucleosides each. Positionally modified oligomeric compounds are distinguished from gapped motifs, hemimer motifs, blockmer motifs and alternating motifs because the pattern of regional substitution defined by any positional motif does not fit into the definition provided herein for one of these other motifs. The term positionally modified oligomeric compound includes many different specific substitution patterns.

As used herein the term "gapmer" or "gapped oligomeric compound" refers to an oligomeric compound having two external regions or wings and an internal region or gap. The three regions form a contiguous sequence of monomer subunits with the sugar moieties of the external regions being different than the sugar moieties of the internal region and wherein the sugar moiety of each monomer subunit within a particular region is essentially the same. In certain embodiments, each monomer subunit within a particular region has the same sugar moiety. When the sugar moieties of the external regions are the same the gapmer is a symmetric gapmer and when the sugar moiety used in the 5'-external region is different from the sugar moiety used in the 3'-external region, the gapmer is an asymmetric gapmer. In certain embodiments, the external regions are small (each independently 1, 2, 3, 4 or about 5 monomer subunits) and the monomer subunits comprise non-naturally occurring sugar moieties with the internal region comprising β-D-2'-deoxyribonucleosides.

In certain embodiments, the external regions each, independently, comprise from 1 to about 5 monomer subunits having non-naturally occurring sugar moieties and the internal region comprises from 6 to 18 unmodified nucleosides. The internal region or the gap generally comprises β-D-2'-deoxyribonucleosides but can comprise non-naturally occurring sugar moieties. The heterocyclic base and internucleoside linkage is independently variable at each position of a gapped oligomeric compound. The motif further optionally includes the use of one or more other groups including but not limited to capping groups, conjugate groups and other 5' or 3'-terminal groups.

In certain embodiments, the gapped oligomeric compounds comprise an internal region of β-D-2'-deoxyribonucleosides with one of the external regions comprising bicyclic carbocyclic nucleosides as disclosed herein. In certain embodiments, the gapped oligomeric compounds comprise an internal region of β-D-2'-deoxyribonucleosides with one of the external regions comprising bicyclic carbocyclic nucleosides as disclosed herein and the other external region comprising modified nucleosides different than the bicyclic carbocyclic nucleosides as disclosed herein. In certain embodiments, the gapped oligomeric compounds comprise an internal region of β-D-2'-deoxyribonucleosides with both of the external regions comprising bicyclic carbocyclic nucleosides as provided herein. In certain embodiments, gapped oligomeric compounds are provided herein wherein all of the monomer subunits comprise non-naturally occurring sugar moieties.

In certain embodiments, gapped oligomeric compounds are provided comprising one or two bicyclic carbocyclic nucleosides at the 5'-end, two or three bicyclic carbocyclic nucleosides at the 3'-end and an internal region of from 8 to 16 β-D-2'-deoxyribonucleosides. In certain embodiments, gapped oligomeric compounds are provided comprising one of the bicyclic carbocyclic nucleosides at the 5'-end, two bicyclic carbocyclic nucleosides at the 3'-end and an internal region of from 8 to 16 β-D-2'-deoxyribonucleosides. In certain embodiments, gapped oligomeric compounds are provided comprising one bicyclic carbocyclic nucleosides at the 5'-end, two bicyclic carbocyclic nucleosides at the 3'-end and an internal region of from 8 to 14 β-D-2'-deoxyribonucleosides. In certain embodiments, gapped oligomeric compounds are provided comprising one or more bicyclic carbocyclic nucleosides at the 5'-end, one or more bicyclic carbocyclic nucleosides at the 3'-end and an internal region of from 8 to 14 β-D-2'-deoxyribonucleosides wherein each of the 3'-end and 5'-end further include from 1 to 3 modified nucleosides different from the bicyclic carbocyclic nucleosides. In certain embodiments, gapped oligomeric compounds are provided comprising one or more bicyclic carbocyclic nucleosides at the 5'-end, one or more bicyclic carbocyclic nucleosides at the 3'-end and an internal region of from 8 to 14 β-D-2'-deoxyribonucleosides wherein each of the 3'-end and 5'-end further include from 1 to 3 2'-O—$(CH_2)_2$—$OCH_3$ (MOE) modified nucleosides.

In certain embodiments, gapped oligomeric compounds are provided comprising one or two modified nucleosides at the 5'-end, two or three modified nucleosides at the 3'-end and an internal region of from 8 to 16 β-D-2'-deoxyribonucleosides wherein the internal region further includes one or two bicyclic carbocyclic nucleosides as provided herein. In certain embodiments, gapped oligomeric compounds are provided comprising two to five modified nucleosides at the 5'-end, two to five modified nucleosides at the 3'-end and an internal region of from 8 to 12 β-D-2'-deoxyribonucleosides wherein the internal region further includes one or two of the bicyclic carbocyclic nucleosides as provided herein. In certain embodiments, gapped oligomeric compounds are provided comprising three to five modified nucleosides at the 5'-end, three to five modified nucleosides at the 3'-end and an internal region of from 8 to 12 β-D-2'-deoxyribonucleosides wherein the internal region further includes one or two of the bicyclic carbocyclic nucleosides as provided herein. In certain embodiments, each of the modified nucleosides in the 5' and 3'-ends comprises a modified sugar moiety. In certain embodiments, each of the modified nucleosides in the 5' and 3'-ends is, independently, a bicyclic nucleoside comprising a bicyclic furanosyl sugar moiety or a modified nucleoside comprising a furanosyl sugar moiety having at least one substituent group. In certain embodiments, each of the modified nucleosides in the 5' and 3'-ends is, independently, a bicyclic nucleoside comprising a 4'-CH((S)—$CH_3$)—O-2' bridge or a 2'-O-methoxyethyl substituted nucleoside.

In certain embodiments, gapped oligomeric compounds are provided that are from about 18 to about 21 monomer subunits in length. In certain embodiments, gapped oligomeric compounds are provided that are from about 16 to about 21 monomer subunits in length. In certain embodiments, gapped oligomeric compounds are provided that are from about 10 to about 21 monomer subunits in length. In certain embodiments, gapped oligomeric compounds are provided that are from about 12 to about 16 monomer subunits in length. In certain embodiments, gapped oligomeric compounds are provided that are from about 12 to about 14 monomer subunits in length. In certain embodiments, gapped oligomeric compounds are provided that are from about 14 to about 16 monomer subunits in length.

As used herein the term "alkyl," refers to a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups.

As used herein the term "alkenyl," refers to a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein the term "alkynyl," refers to a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein the term "aliphatic," refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein the term "alicyclic" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein the term "alkoxy," refers to a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein the term "aminoalkyl" refers to an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein the term "alkylcarbonyl" refers to a —C(=O)—$R_a$ group wherein R is an alkyl group.

As used herein the term "alkoxycarbonyl" refers to a —C(=O)—O—$R_a$ group wherein R is an alkyl group.

The term "aminoalkylcarbonyl" as used herein refers to an alkylcarbonyl moiety as defined herein wherein one hydrogen atom is replaced by an amino group. Examples of aminoalkylcarbonyl groups include, but are not limited to, glycyl (—$COCH_2NH_2$), alanyl (—COCH($NH_2$)$CH_3$), valinyl (—COCH($NH_2$)CH($CH_3$)$_2$), leucinyl (—COCH($NH_2$)$CH_2$CH($CH_3$)$_2$), isoleucinyl (—COCH—($NH_2$)CH($CH_3$)($CH_2CH_3$)) and norleucinyl (—COCH($NH_2$)($CH_2$)$_3CH_3$).

As used herein the terms "aryl" and "aromatic," refer to a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein the terms "aralkyl" and "arylalkyl," refer to an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein the term "heterocyclic radical" refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic radical typically includes at least one atom selected from sulfur, nitrogen or oxygen. Examples of heterocyclic radicals include, [1,3]dioxolanyl, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

As used herein the terms "heteroaryl," and "heteroaromatic," refer to a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein the term "heteroarylalkyl," refers to a heteroaryl group as previously defined that further includes a covalently attached $C_1$-$C_{12}$ alkyl radical. The alkyl radical portion of the resulting heteroarylalkyl group is capable of forming a covalent bond with a parent molecule. Examples include without limitation, pyridinylmethylene, pyrimidinylethylene, napthyridinylpropylene and the like. Heteroarylalkyl groups as used herein may optionally include further substituent groups on one or both of the heteroaryl or alkyl portions.

As used herein the term "acyl," refers to a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein the term "hydrocarbyl" includes radical groups that comprise C, O and H. Included are straight, branched and cyclic groups having any degree of saturation. Such hydrocarbyl groups can include one or more additional heteroatoms selected from N and S and can be further mono or poly substituted with one or more substituent groups.

As used herein the term "mono or polycyclic ring system" is meant to include all ring systems selected from single or polycyclic radical ring systems wherein the rings are fused or linked and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and poly cyclic structures can contain rings that each have the same level of saturation or each, independently, have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or polycyclic ring system can be further substituted with substituent groups such as for example phthalimide which has two =O groups attached to one of the rings. Mono or polycyclic ring systems can be attached to parent molecules using various strategies such as directly through a ring atom, fused through multiple ring atoms, through a substituent group or through a bifunctional linking moiety.

As used herein the terms "halo" and "halogen," refer to an atom selected from fluorine, chlorine, bromine and iodine.

As used herein the term "oxo" refers to the group (=O).

As used herein the term "protecting group," refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene's Protective Groups in Organic Synthesis, 4th edition, John Wiley & Sons, New York, 2007.

Groups can be selectively incorporated into oligomeric compounds as provided herein as precursors. For example an amino group can be placed into a compound as provided herein as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal et al., *Protocols for Oligonucleotide Conjugates*, Humana Press; New Jersey, 1994, 26, 1-72.

The term "orthogonally protected" refers to functional groups which are protected with different classes of protecting groups, wherein each class of protecting group can be removed in any order and in the presence of all other classes (see, Barany et al., *J. Am. Chem. Soc.,* 1977, 99, 7363-7365; Barany et al., *J. Am. Chem. Soc.,* 1980, 102, 3084-3095). Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

Examples of hydroxyl protecting groups include without limitation, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy)methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoroacetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1 (2-fluorophenyl)-4-methoxypiperidin-4-yl (FPMP), 9-phenylxanthine-9-yl (Pixyl) and 9-(p-methoxyphenyl)xanthine-9-yl (MOX). Wherein more commonly used hydroxyl protecting groups include without limitation, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include without limitation, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include without limitation, triphenylmethyl (trityl), benzyl (Bn), and the like.

The compounds described herein contain one or more asymmetric centers and thus give rise to enantiomers, diastereomers, and other stereoisomeric forms that may be defined, in terms of absolute stereochemistry, as (R)- or (S)-, α or β, or as (D)- or (L)- such as for amino acids. Included herein are all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions*, John Wiley & Sons, 1981. When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to limit a particular configuration unless the text so states.

The terms "substituent" and "substituent group," as used herein, are meant to include groups that are typically added to a parent compounds or to further substituted substituent groups to enhance one or more desired properties or provide other desired effects. Substituent groups can be protected or unprotected and can be added to one available site or many available sites on a parent compound. As an example if a benzene is substituted with a substituted alkyl it will not have any overlap with a benzene that is substituted with substituted hydroxyl. In such an example the alkyl portion of the substituted alkyl is covalently linked by one of its carbon atoms to one of the benzene carbon atoms. If the alky is $C_1$ and it is substituted with a hydroxyl substituent group (substituted alkyl) then the resultant compound is benzyl alcohol ($C_6H_5CH_2OH$). If the benzene were substituted with a substituted hydroxyl group and the hydroxyl was substituted with a $C_1$ alkyl group then the resultant compound would be anisole ($C_6H_5OCH_3$).

Substituent groups amenable herein include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=N$R_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)—N($R_{bb}$)($R_{cc}$)), thioureido (—N($R_{bb}$)C(S)N($R_{bb}$)($R_{cc}$)), guanidinyl (—N($R_{bb}$)C(=N$R_{bb}$)N($R_{bb}$)($R_{cc}$)), amidinyl (—C(=N$R_{bb}$)N($R_{bb}$)($R_{cc}$) or —N($R_{bb}$)C(=N$R_{bb}$)($R_{aa}$)), thiol (—S$R_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S(O)$_2R_{bb}$). Wherein each $R_{aa}$, $R_{bb}$ and $R_{cc}$ is, independently, H, an optionally linked chemical functional group or a further substituent group with a preferred list including without limitation, H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The terms "stable compound" and "stable structure" as used herein are meant to indicate a compound that is sufficiently robust to survive isolation to a useful degree of purity from a reaction mixture, and formulation into an efficacious therapeutic agent. Only stable compounds are contemplated herein.

As used herein the term "nucleobase" generally refers to the nucleobase of a nucleoside or modified nucleoside. The term "heterocyclic base moiety" is broader than the term nucleobase in that it includes any heterocyclic base that can be attached to a sugar to prepare a nucleoside or modified nucleoside. Such heterocyclic base moieties include but are not limited to naturally occurring nucleobases (adenine, guanine, thymine, cytosine and uracil) and protected forms of unmodified nucleobases (4-N-benzoylcytosine, 6-N-benzoyladenine and 2-N-isobutyrylguanine) as well as modified (5-methyl cytosine) or non-naturally occurring heterocyclic base moieties and synthetic mimetics thereof (such as for example phenoxazines).

In one embodiment, a heterocyclic base moiety is any heterocyclic system that contains one or more atoms or groups of atoms capable of hydrogen bonding to a heterocyclic base of a nucleic acid. In certain embodiments, nucleobase refers to purines, modified purines, pyrimidines and modified pyrimidines. In certain embodiments, nucleobase refers to unmodified or naturally occurring nucleobases which include, but are not limited to, the purine bases adenine (A) and guanine (G), and the pyrimidine bases thymine (T), cytosine (C) and uracil (U) and analogs thereof such as 5-methyl cytosine. The terms nucleobase and heterocyclic base moiety also include optional protection for any reactive functional groups such as 4-N-benzoylcytosine, 4-N-benzoyl-5-methyl-cytosine, 6-N-benzoyladenine or 2-N-isobutyrylguanine.

In certain embodiments, heterocyclic base moieties include without limitation modified nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein.

In certain embodiments, heterocyclic base moieties include without limitation tricyclic pyrimidines such as 1,3-diazaphenoxazine-2-one, 1,3-diazaphenothiazine-2-one and 9-(2-aminoethoxy)-1,3-diazaphenoxazine-2-one (G-clamp). Heterocyclic base moieties also include those in which the purine or pyrimidine base is replaced with other heterocycles, for example 7-deaza-adenine, 7-deazaguanosine, 2-aminopyridine and 2-pyridone. Further heterocyclic base moieties include without limitation those known to the art skilled (see for example: U.S. Pat. No. 3,687,808; Swayze et al., *The Medicinal Chemistry of Oligonucleotides in Antisense a Drug Technology*, Chapter 6, pages 143-182, Crooke, S. T., ed., 2008); *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-302). Modified polycyclic heterocyclic compounds useful as heterocyclic base moieties are disclosed in the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,681,941; 5,750,692; 5,763,588; 5,830,653; 6,005,096; and U.S. Patent Application Publication 20030158403, each of which is incorporated herein by reference in its entirety.

As used herein the term "sugar moiety" refers to naturally occurring sugars having a furanose ring system (ribose and 2'-deoxyribose), synthetic and/or non-naturally occurring sugars having a modified furanose ring system and sugar surrogates wherein the furanose ring has been replaced with a mono or polycyclic ring system such as for example a morpholino or hexitol ring system or a non-cyclic sugar surrogate such as that used in peptide nucleic acids. The sugar moiety of a monomer subunit provides the reactive groups that enable the linking of adjacent monomer subunits into an oligomeric compound. Illustrative examples of sugar moieties useful in the preparation of oligomeric compounds include without limitation, β-D-ribose, β-D-2'-deoxyribose, substituted sugars (such as 2', 5' and bis substituted sugars), 4'-S-sugars (such as 4'-S-ribose, 4'-S-2'-deoxyribose and 4'-S-2'-substituted ribose wherein the ring oxygen atom has been replaced with a sulfur atom), bicyclic modified sugars (such as the 2'-O—CH(CH$_3$)-4', 2'-O—CH$_2$-4' or 2'-O—(CH$_2$)$_2$-4' bridged ribose derived bicyclic sugars) and sugar surrogates (such as for example when the ribose ring has been replaced with a morpholino, a hexitol ring system or an open non-cyclic system).

As used herein the term "sugar surrogate" refers to replacement of the nucleoside furanose ring with a non-furanose (or 4'-substituted furanose) group with another structure such as another ring system or open system. Such structures can be as simple as a six membered ring as opposed to the five membered furanose ring or can be more complicated such as a bicyclic or tricyclic ring system or a non-ring system such as that used in peptide nucleic acid. In certain embodiments, sugar surrogates include without limitation sugar surrogate groups such as morpholinos, cyclohexenyls and cyclohexitols. In general the heterocyclic base is maintained even when the sugar moiety is a sugar surrogate so that the resulting monomer subunit will be able to hybridize.

As used herein the term "sugar substituent group" refers to a group that is covalently attached to a sugar moiety. In certain embodiments, examples of sugar substituent groups include without limitation halogen, alkyl, substituted alkyl, alkoxy, substituted alkoxy, alkenyl, substituted alkenyl, alkynyl, substituted alkynyl, amino, substituted amino, thio, substituted thio and azido. In certain embodiments the alkyl and alkoxy groups are $C_1$ to $C_6$. In certain embodiments, the alkenyl and alkynyl groups are $C_2$ to $C_6$. In certain embodiments, examples of sugar substituent groups include without limitation 2'-F, 2'-allyl, 2'-amino, 2'-azido, 2'-thio, 2'-O-allyl, 2'-OCF$_3$, 2'-O—C$_1$-C$_{10}$ alkyl, 2'-OCH$_3$, 2'-O(CH$_2$)$_n$CH$_3$, 2'-OCH$_2$CH$_3$, 2'-O—(CH$_2$)$_2$CH$_3$, 2'-O—(CH$_2$)$_2$—O—CH$_3$ (MOE), 2'-O[(CH$_2$)$_n$O]$_m$CH$_3$, 2'-O(CH$_2$)$_2$SCH$_3$, 2'-O—(CH$_2$)$_3$—N(R$_p$)(R$_q$), 2'-O(CH$_2$)$_n$NH$_2$, 2'-O—(CH$_2$)$_2$—O—N(R$_p$)(R$_q$), O(CH$_2$)$_n$ON[(CH$_2$)$_n$CH$_3$]2, 2'-O(CH$_2$)$_n$ONH$_2$, 2'-O—(CH$_2$)$_2$—O—(CH$_2$)$_2$—N(R$_p$)(R$_q$), 2'-O—CH$_2$C(=O)—N(R$_p$)(R$_q$), 2'-OCH$_2$C(=O)N(H)CH$_3$, 2'-O—CH$_2$C(=O)—N(H)—(CH$_2$)$_2$—N(R$_p$)(R$_q$) and 2'-O—CH$_2$—N(H)—C(=NR$_r$)[N(R$_p$)(R$_q$)], wherein each R$_p$, R$_q$ and R$_r$ is, independently, H, substituted or unsubstituted C$_1$-C$_{10}$ alkyl or a protecting group and where n and m are from 1 to about 10.

In certain embodiments, examples of sugar substituent groups include without limitation 2'-F, 2'-allyl, 2'-amino, 2'-azido, 2'-thio, 2'-O-allyl, 2'-OCF$_3$, 2'-O—C$_1$-C$_{10}$ alkyl, 2'-O—CH$_3$, OCF$_3$, 2'-O—CH$_2$CH$_3$, 2'-O—(CH$_2$)$_2$CH$_3$, 2'-O—(CH$_2$)$_2$—O—CH$_3$ (MOE), 2'-O(CH$_2$)$_2$SCH$_3$, 2'-O—CH$_2$—CH=CH$_2$, 2'-O—(CH$_2$)$_3$—N(R$_m$)(R$_n$), 2'-O—(CH$_2$)$_2$—O—N(R$_m$)(R$_n$), 2'-O—(CH$_2$)$_2$—O—(CH$_2$)$_2$—N(R$_m$)(R$_n$), 2'-O—CH$_2$C(=O)—N(R$_m$)(R$_n$), 2'-O—CH$_2$C(=O)—N(H)—(CH$_2$)$_2$—N(R$_m$)(R$_n$) and 2'-O—CH$_2$—N(H)—C(=NR$_m$)[N(R$_m$)(R$_n$)] wherein each R$_m$ and R$_n$ is, independently, H, substituted or unsubstituted C$_1$-C$_{10}$ alkyl or a protecting group. In certain embodiments, examples of 2,-sugar substituent groups include without limitation fluoro, —O—CH$_3$, —O—CH$_2$CH$_3$, —O—(CH$_2$)$_2$CH$_3$, —O—(CH$_2$)$_2$—O—CH$_3$, —O—CH$_2$—CH=CH$_2$, —O—

(CH$_2$)$_3$—N(R$_1$)(R$_2$), O—(CH$_2$)$_2$—O—N(R$_1$)(R$_2$), —O—(CH$_2$)$_2$—O—(CH$_2$)$_2$—N(R$_1$)(R$_2$), —O—CH$_2$C(=O)—N(R$_1$)(R$_2$), —O—CH$_2$C(=O)—N(H)—(CH$_2$)$_2$—N(R$_1$)(R$_2$) and —O—CH$_2$—N(H)—C(=NR)[N(R$_1$)(R$_2$)] wherein R$_1$ and R$_2$ are each independently, H or C$_1$-C$_2$ alkyl. In certain embodiments, examples of sugar substituent groups include without limitation fluoro, —O—CH$_3$, —O—(CH$_2$)$_2$—O—CH$_3$, —O—CH$_2$C(=O)—N(H)(CH$_3$), —O—CH$_2$C(=O)—N(H)—(CH$_2$)$_2$—N(CH$_3$)$_2$ and —O—CH$_2$—N(H)—C(=NCH$_3$)[N(CH$_3$)$_2$]. In certain embodiments, examples of sugar substituent groups include without limitation fluoro, —O—CH$_3$, —O—(CH$_2$)$_2$—O—CH$_3$, —O—CH$_2$C(=O)—N(H)(CH$_3$) and —O—CH$_2$C(=O)—N(H)—(CH$_2$)$_2$—N(CH$_3$)$_2$. Further examples of modified sugar moieties include without limitation bicyclic sugars (e.g. bicyclic nucleic acids or bicyclic nucleosides discussed below).

In certain embodiments, examples of "sugar substituent group" or more generally "substituent group" include without limitation one or two 5'-sugar substituent groups independently selected from C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl and halogen. In certain embodiments, examples of sugar substituent groups include without limitation one or two 5'-sugar substituent groups independently selected from vinyl, 5'-methyl, 5'-(S)-methyl and 5'-(R)-methyl. In certain embodiments, examples of sugar substituent groups include without limitation one 5'-sugar substituent group selected from vinyl, 5'-(S)-methyl and 5'-(R)-methyl.

In certain embodiments, examples of sugar substituent groups include without limitation substituted silyl, an RNA cleaving group, a reporter group, an intercalator, a group for improving pharmacokinetic properties, or a group for improving the pharmacodynamic properties of an oligomeric compound, and other substituents having similar properties. In certain embodiments, oligomeric compounds include modified nucleosides comprising 2'-MOE substituent groups (Baker et al., *J. Biol. Chem.*, 1997, 272, 11944-12000). Such 2'-MOE substitution has been described as having improved binding affinity compared to unmodified nucleosides and to other modified nucleosides, such as 2'-O-methyl, 2'-O-propyl, and 2'-O-aminopropyl. Oligonucleotides having the 2'-MOE substituent also have been shown to be antisense inhibitors of gene expression with promising features for in vivo use (Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

Sugar moieties can be substituted with more than one sugar substituent group including without limitation 2'-F-5'-methyl substituted nucleosides (see PCT International Application WO 2008/101157, published on Aug. 21, 2008 for other disclosed 5', 2'-bis substituted nucleosides). Other combinations are also possible, including without limitation, replacement of the ribosyl ring oxygen atom with S and further substitution at the 2'-position (see published U.S. Patent Application US2005-0130923, published on Jun. 16, 2005) and 5'-substitution of a bicyclic nucleoside (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group).

As used herein the term "monomer subunit" is meant to include all manner of monomers that are amenable to oligomer synthesis. In general a monomer subunit includes at least a sugar moiety having at least two reactive sites that can form linkages to further monomer subunits. Essentially all monomer subunits include a heterocyclic base moiety that is hybridizable to a complementary site on a nucleic acid target. Reactive sites on monomer subunits located on the termini of an oligomeric compound can be protected or unprotected (generally OH) or can form an attachment to a terminal group (conjugate or other group). Monomer subunits include, without limitation, nucleosides and modified nucleosides. In certain embodiments, monomer subunits include nucleosides such as β-D-ribonucleosides and β-D-2'-deoxyribnucleosides and modified nucleosides including but not limited to substituted nucleosides (such as 2', 5' and bis substituted nucleosides), 4'-S-modified nucleosides (such as 4'-S-ribonucleosides, 4'-S-2'-deoxyribonucleosides and 4'-S-2'-substituted ribonucleosides), bicyclic modified nucleosides (such as bicyclic nucleosides wherein the sugar moiety has a 2'-O—CHR$_a$-4' bridging group, wherein R$_a$ is H, alkyl or substituted alkyl), other modified nucleosides and nucleosides having sugar surrogates. As used herein, the term "nucleoside" refers to a nucleobase-sugar combination. The two most common classes of such nucleobases are purines and pyrimidines. The term nucleoside includes β-D-ribonucleosides and β-D-2'-deoxyribonucleosides.

As used herein, the term "nucleotide" refers to a nucleoside further comprising a modified or unmodified phosphate internucleoside linking group or a non-phosphate internucleoside linking group. For nucleotides that include a pentofuranosyl sugar, the internucleoside linking group can be linked to either the 2', 3' or 5' hydroxyl moiety of the sugar. The phosphate and or a non-phosphate internucleoside linking groups are routinely used to covalently link adjacent nucleosides to one another to form a linear polymeric compound.

As used herein the term "modified nucleoside" refers to a nucleoside comprising a modified heterocyclic base and or a sugar moiety other than ribose and 2'-deoxyribose. In certain embodiments, a modified nucleoside comprises a modified heterocyclic base moiety. In certain embodiments, a modified nucleoside comprises a sugar moiety other than ribose and 2'-deoxyribose. In certain embodiments, a modified nucleoside comprises a modified heterocyclic base moiety and a sugar moiety other than ribose and 2'-deoxyribose. The term "modified nucleoside" is intended to include all manner of modified nucleosides that can be incorporated into an oligomeric compound using standard oligomer synthesis protocols. Modified nucleosides include abasic nucleosides but in general a heterocyclic base moiety is included for hybridization to a complementary nucleic acid target.

In certain embodiments, modified nucleosides include a furanose ring system or a modified furanose ring system. Modified furanose ring systems include 4'-S analogs, one or more substitutions at any position such as for example the 2', 3', 4' and 5' positions and addition of bridges for form additional rings such as a 2'-O—CH(CH$_3$)-4' bridge. Such modified nucleosides include without limitation, substituted nucleosides (such as 2', 5', and/or 4' substituted nucleosides) 4'-S-modified nucleosides, (such as 4'-S-ribonucleosides, 4'-S-2'-deoxyribonucleosides and 4'-S-2'-substituted ribonucleosides), bicyclic modified nucleosides (such as 2'-O—CH(CH$_3$)-4', 2'-O—CH$_2$-4' or 2'-O—(CH$_2$)$_2$-4' bridged furanose analogs) and base modified nucleosides. The sugar can be modified with more than one of these modifications listed such as for example a bicyclic modified nucleoside further including a 5'-substitution or a 5' or 4' substituted nucleoside further including a 2' substituent. The term modified nucleoside also includes combinations of these modifications such as base and sugar modified nucleosides. These modifications are meant to be illustrative and not exhaustive as other modifications are known in the art and are also envisioned as possible modifications for the modified nucleosides described herein.

In certain embodiments, modified nucleosides comprise a sugar surrogate wherein the furanose ring has been replaced with a mono or polycyclic ring system or a non-cyclic sugar surrogate such as that used in peptide nucleic acids. Illustrative examples of sugar moieties for such modified nucleosides includes without limitation morpholino, hexitol, cyclohexenyl, 2.2.2 and 3.2.1 cyclohexose and open non-cyclic groups.

In certain embodiments, modified nucleosides comprise a non-naturally occurring sugar moiety and a modified heterocyclic base moiety. Such modified nucleosides include without limitation modified nucleosides wherein the heterocyclic base moiety is replaced with a phenoxazine moiety (for example the 9-(2-aminoethoxy)-1,3-diazaphenoxazine-2-one group, also referred to as a G-clamp which forms four hydrogen bonds when hybridized with a guanosine base) and further replacement of the sugar moiety with a sugar surrogate group such as for example a morpholino, a cyclohexenyl or a bicyclo[3.1.0]hexyl.

As used herein the term "bicyclic nucleoside" refers to a nucleoside comprising at least a bicyclic sugar moiety. Examples of bicyclic nucleosides include without limitation nucleosides having a furanosyl sugar that comprises a bridge between two of the non-geminal carbons atoms. In certain embodiments, bicyclic nucleosides have a bridge between the 4' and 2' carbon atoms. Examples of such 4' to 2' bridged bicyclic nucleosides, include but are not limited to one of formulae: 4'-(CH$_2$)—O-2' (LNA); 4'-(CH$_2$)—S-2'; 4'-(CH$_2$)$_2$—O-2' (ENA); 4'-CH(CH$_3$)—O-2' and 4'-C—H(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO2008/150729, published Dec. 11, 2008); 4'-CH$_2$—O—N(CH$_3$)-2' (see U.S. Pat. No. 7,196,345, issued on Apr. 13, 2010); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya, et al., J. Org. Chem., 2009, 74, 118-134); and 4'-CH$_2$—CH$_2$-2' and 4'-CH$_2$—C(=CH$_2$)-2' (and analogs thereof see published International Application WO 2008/154401, published on Dec. 8, 2008). Further bicyclic nucleosides have been reported in published literature (see for example: Srivastava et al., J. Am. Chem. Soc., 2007, 129(26) 8362-8379; Frieden et al., Nucleic Acids Research, 2003, 21, 6365-6372; Elayadi et al., Curr. Opinion Invens. Drugs, 2001, 2, 558-561; Braasch et al., Chem. Biol., 2001, 8, 1-7; Orum et al., Curr. Opinion Mol. Ther., 2001, 3, 239-243; Wahlestedt et al., Proc. Natl. Acad. Sci. U.S.A, 2000, 97, 5633-5638; Singh et al., Chem. Commun., 1998, 4, 455-456; Koshkin et al., Tetrahedron, 1998, 54, 3607-3630; Kumar et al., Bioorg. Med. Chem. Lett., 1998, 8, 2219-2222; Singh et al., J. Org. Chem., 1998, 63, 10035-10039; U.S. Pat. Nos. 7,741,457; 7,696,345; 7,547,684; 7,399,845; 7,053,207; 7,034,133; 6,794,499; 6,770,748; 6,670,461; 6,525,191; 6,268,490; U.S. Patent Publication Nos.: US2008-0039618; U.S. patent application Ser. Nos. 61/099,844; 61/097,787; 61/086,231; 61/056,564; 61/026,998; 61/026,995; 60/989,574; International applications WO2009/006478; WO2008/154401; WO2008/150729; WO 2007/134181; WO 2005/021570; WO 2004/106356; WO 94/14226). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic nucleosides comprise a bridge between the 4' and the 2' carbon atoms of the pentofuranosyl sugar moiety including without limitation, bridges comprising 1 or from 1 to 4 linked groups (generally forming a 4 to 6 membered ring with the parent sugar moiety) independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, S(=O)$_x$—, and —N(R$_a$)—; wherein: x is 0, 1, or 2; n is 1, 2, 3, or 4; each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In certain embodiments, the bridge of a bicyclic sugar moiety is, —[C(R$_a$)(R$_b$)]$_n$—[C(R$_a$)(R$_b$)]$_n$—O—, —C(R$_a$R$_b$)—N(R)—O— or —C(R$_a$R$_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or C$_1$-C$_{12}$ alkyl.

In certain embodiments, bicyclic nucleosides are further defined by isomeric configuration. For example, a nucleoside comprising a 4'-(CH$_2$)—O-2' bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., Nucleic Acids Research, 2003, 21, 6365-6372).

In certain embodiments, bicyclic nucleosides include those having a 4' to 2' bridge wherein such bridges include without limitation, α-L-4'-(CH$_2$)—O-2', β-D-4'-CH$_2$—O-2', 4'-(CH$_2$)$_2$—O-2', 4'-CH$_2$—O—N(R)-2', 4'-CH$_2$—N(R)—O-2', 4'-CH(CH$_3$)—O-2', 4'-CH$_2$—S-2', 4'-CH$_2$—N(R)-2', 4'-CH$_2$—CH(CH$_3$)-2', and 4'-(CH$_2$)$_3$-2', wherein R is H, a protecting group or C$_1$-C$_{12}$ alkyl.

In certain embodiments, bicyclic nucleosides have the formula:

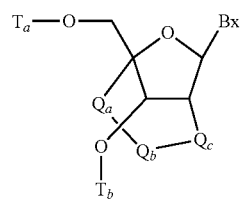

wherein:

Bx is a heterocyclic base moiety;

-$Q_a$-$Q_b$-$Q_c$- is —$CH_2$—N($R_c$)—$CH_2$—, —C(=O)—N($R_c$)—$CH_2$—, —$CH_2$—O—N($R_c$)—, —$CH_2$—N($R_c$)—O— or —N($R_c$)—O—$CH_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides have the formula:

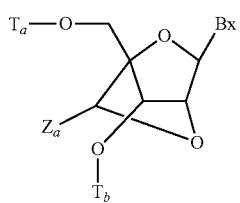

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thiol.

In one embodiment, each of the substituted groups, is, independently, mono or poly substituted with substituent groups independently selected from halogen, oxo, hydroxyl, $OJ_c$, $NJ_cJ_d$, $SJ_c$, $N_3$, OC(=X)$J_c$, and $NJ_eC$(=X)$NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides have the formula:

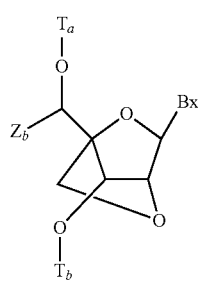

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides have the formula:

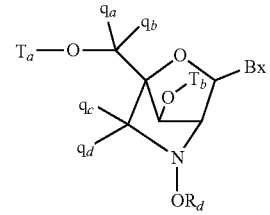

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides have the formula:

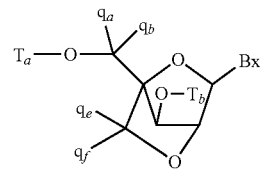

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of adenine, cytosine, guanine, 5-methyl-cytosine, thymine and uracil bicyclic nucleosides having a 4'-$CH_2$—O-2' bridge, along with their oligomerization, and nucleic acid recognition properties have been described (Koshkin et al., *Tetrahedron*, 1998, 54, 3607-3630). The synthesis of bicyclic nucleosides has also been described in WO 98/39352 and WO 99/14226.

Analogs of various bicyclic nucleosides that have 4' to 2' bridging groups such as 4'-$CH_2$—O-2' and 4'-$CH_2$—S-2', have also been prepared (Kumar et al., *Bioorg. Med. Chem. Lett.*, 1998, 8, 2219-2222). Preparation of oligodeoxyribonucleotide duplexes comprising bicyclic nucleosides for use as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides have the formula:

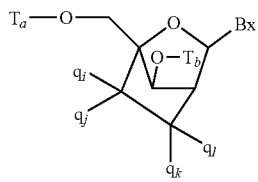

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-(CH$_2$)$_3$-2' bridge and the alkenyl analog bridge 4'-CH=CH—CH$_2$-2' have been described (Frier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.* 2007, 129(26), 8362-8379).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, (F) methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, (J) propylene carbocyclic (4'-(CH$_2$)$_3$-2') BNA, and (K) vinyl BNA as depicted below.

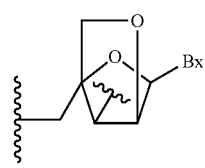 (A)

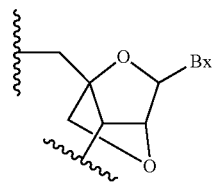 (B)

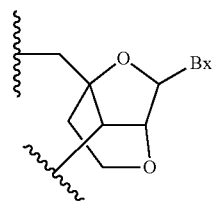 (C)

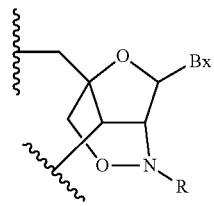 (D)

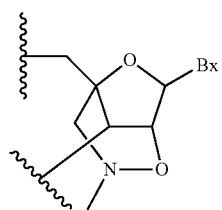 (E)

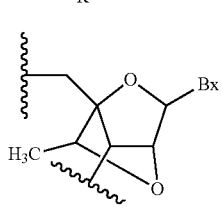 (F)

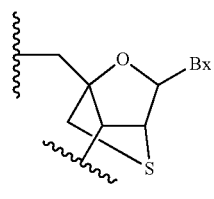 (G)

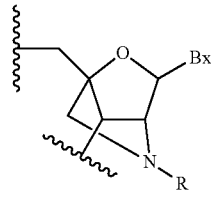 (H)

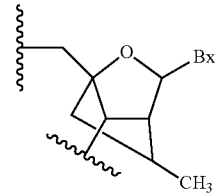 (I)

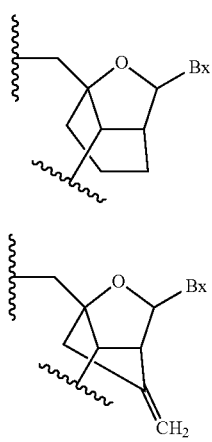

wherein Bx is the base moiety and R is, independently, H, a protecting group, $C_1$-$C_6$ alkyl or $C_1$-$C_6$ alkoxy.

In certain embodiments, modified nucleosides include nucleosides having sugar surrogate groups that include without limitation, replacement of the ribosyl ring with a sugar surrogate such as a tetrahydropyranyl ring system (also referred to as hexitol) as illustrated below:

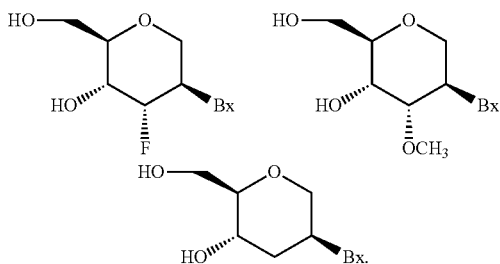

In certain embodiments, sugar surrogates are selected having the formula:

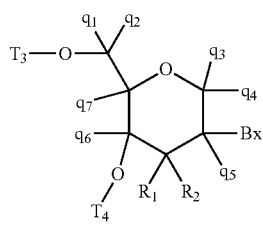

wherein:
Bx is a heterocyclic base moiety;
one of $T_3$ and $T_4$ is an internucleoside linking group attaching the tetrahydropyran nucleoside analog to the remainder of one of the 5' or 3' end of the oligomeric compound and the other of $T_3$ and $T_4$ is hydroxyl, a protected hydroxyl, a 5' or 3' terminal group or an internucleoside linking group attaching the tetrahydropyran nucleoside analog to the remainder of the other of the 5' or 3' end of the oligomeric compound;
$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides are provided wherein one of $R_1$ and $R_2$ is F. In certain embodiments, $R_1$ is fluoro and $R_2$ is H; $R_1$ is methoxy and $R_2$ is H, and $R_1$ is methoxyethoxy and $R_2$ is H.

Such sugar surrogates can be referred to as a "modified tetrahydropyran nucleoside" or "modified THP nucleoside". Modified THP nucleosides include, but are not limited to, what is referred to in the art as hexitol nucleic acid (HNA), altritol nucleic acid (ANA), and mannitol nucleic acid (MNA) (see Leumann, C. J., *Bioorg. & Med. Chem.*, 2002, 10, 841-854).

In certain embodiments, oligomeric compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130(6), 1979-1984; Horvith et al., *Tetrahedron Letters*, 2007, 48, 3621-3623; Nauwelaerts et al., *J. Am. Chem. Soc.*, 2007, 129(30), 9340-9348; Gu et al., *Nucleosides, Nucleotides & Nucleic Acids*, 2005, 24(5-7), 993-998; Nauwelaerts et al., *Nucleic Acids Research*, 2005, 33(8), 2452-2463; Robeyns et al., Acta Crystallographica, Section F: Structural Biology and Crystallization Communications, 2005, F61(6), 585-586; Gu et al., Tetrahedron, 2004, 60(9), 2111-2123; Gu et al., Oligonucleotides, 2003, 13(6), 479-489; Wang et al., *J. Org. Chem.*, 2003, 68, 4499-4505; Verbeure et al., Nucleic Acids Research, 2001, 29(24), 4941-4947; Wang et al., *J. Org. Chem.*, 2001, 66, 8478-82; Wang et al., *Nucleosides, Nucleotides & Nucleic Acids*, 2001, 20(4-7), 785-788; Wang et al., *J. Am. Chem.*, 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

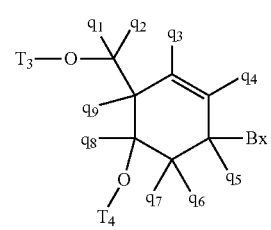

wherein independently for each of said at least one cyclohexenyl nucleoside analog of Formula X:
Bx is a heterocyclic base moiety;
one of $T_3$ and $T_4$ is an internucleoside linking group attaching the cyclohexenyl nucleoside to the remainder of one of the 5' or 3' end of the oligomeric compound and the other of $T_3$ and $T_4$ is hydroxyl, a protected hydroxyl, a 5' or 3' terminal group or an internucleoside linking group attaching the cyclohexenyl nucleoside to the remainder of the other of the 5' or 3' end of the oligomeric compound; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

Many other monocyclic, bicyclic and tricyclic ring systems are known in the art and are suitable as sugar surrogates that can be used to modify nucleosides for incorporation into oligomeric compounds as provided herein (see for example review article: Leumann, Christian *J. Bioorg. & Med. Chem.*, 2002, 10, 841-854). Such ring systems can undergo various additional substitutions to further enhance their activity.

Some representative U.S. patents that teach the preparation of such modified sugars include without limitation, U.S.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005 certain of which are commonly owned with the instant application, and each of which is herein incorporated by reference in its entirety.

The bicyclic carbocyclic nucleosides provided herein can be prepared by any of the applicable techniques of organic synthesis, as, for example, illustrated in the examples below. Many such techniques are well known in the art. However, many of the known techniques are elaborated in *Compendium of Organic Synthetic Methods*, John Wiley & Sons, New York: Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade Jr., 1980; Vol. 5, Leroy G. Wade Jr., 1984; and Vol. 6, Michael B. Smith; as well as March, J., *Advanced Organic Chemistry*, 3rd Edition, John Wiley & Sons, New York, 1985; *Comprehensive Organic Synthesis. Selectivity, Strategy & Efficiency in Modern Organic Chemistry*, in 9 Volumes, Barry M. Trost, Editor-in-Chief, Pergamon Press, New York, 1993; *Advanced Organic Chemistry, Part B: Reactions and Synthesis,* 4th Edition; Carey and Sundberg, Kluwer Academic/Plenum Publishers, New York, 2001; *Advanced Organic Chemistry, Reactions, Mechanisms, and Structure*, 2nd Edition, March, McGraw Hill, 1977; Greene, T. W., and Wutz, P. G. M., *Protecting Groups in Organic Synthesis*, 4th Edition, John Wiley & Sons, New York, 1991; and Larock, R. C., *Comprehensive Organic Transformations*, 2nd Edition, John Wiley & Sons, New York, 1999.

As used herein the term "reactive phosphorus" is meant to include groups that are covalently linked to a monomer subunit that can be further attached to an oligomeric compound that are useful for forming internucleoside linkages including for example phosphodiester and phosphorothioate internucleoside linkages. Such reactive phosphorus groups are known in the art and contain phosphorus atoms in $P^{III}$ or $P^V$ valence state including, but not limited to, phosphoramidite, H-phosphonate, phosphate triesters and phosphorus containing chiral auxiliaries. In certain embodiments, reactive phosphorus groups are selected from diisopropylcyanoethoxy phosphoramidite (—O*—P[N[(CH($CH_3$)$_2$]$_2$]O($CH_2$)$_2$CN) and H-phosphonate (—O*—P(=O)(H)OH), wherein the O* is normally attached to the 3'-position of the Markush group of Formula I. A preferred synthetic solid phase synthesis utilizes phosphoramidites ($P^{III}$ chemistry) as reactive phosphites. The intermediate phosphite compounds are subsequently oxidized to the phosphate or thiophosphate ($P^V$ chemistry) using known methods to yield, phosphodiester or phosphorothioate internucleoside linkages. Chiral auxiliaries are known in the art (see for example: Wang et al., *Tetrahedron Letters*, 1997, 38(5), 705-708; Jin et al., *J. Org. Chem*, 1997, 63, 3647-3654; Wang et al., *Tetrahedron Letters*, 1997, 38(22), 3797-3800; and U.S. Pat. No. 6,867,294, issued Mar. 15, 2005). Additional reactive phosphates and phosphites are disclosed in *Tetrahedron* Report Number 309 (Beaucage and Iyer, *Tetrahedron*, 1992, 48, 2223-2311).

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

The term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include without limitation, siloxane, sulfide, sulfoxide, sulfone, acetyl, formacetyl, thioformacetyl, methylene formacetyl, thioformacetyl, alkeneyl, sulfamate, methyleneimino, methylenehydrazino, sulfonate, sulfonamide, amide and others having mixed N, O, S and $CH_2$ component parts.

As used herein, the term "oligomeric compound" refers to a contiguous sequence of linked monomer subunits. Each linked monomer subunit normally includes a heterocyclic base moiety but monomer subunits also includes those without a heterocyclic base moiety such as abasic monomer subunits. At least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having one or a plurality of nucleosides having sugar surrogate groups.

In certain embodiments, oligomeric compounds comprise a plurality of monomer subunits independently selected from naturally occurring nucleosides, non-naturally occurring nucleosides, modified nucleosides and nucleosides having sugar surrogate groups. In certain embodiments, oligomeric compounds are single stranded. In certain embodiments, oligomeric compounds are double stranded comprising a double-stranded duplex. In certain embodiments, oligomeric compounds comprise one or more conjugate groups and/or terminal groups.

When preparing oligomeric compounds having specific motifs as disclosed herein it can be advantageous to mix non-naturally occurring monomer subunits such as the bicyclic carbocyclic nucleosides as provided herein with other non-naturally occurring monomer subunits, naturally occurring monomer subunits (nucleosides) or mixtures thereof. In certain embodiments, oligomeric compounds are provided herein comprising a contiguous sequence of linked monomer subunits wherein at least one monomer subunit is a bicyclic carbocyclic nucleoside as provided herein. In certain embodiments, oligomeric compounds are provided comprising a plurality of bicyclic carbocyclic nucleosides as provided herein.

Oligomeric compounds are routinely prepared linearly but can also be joined or otherwise prepared to be circular and/or can be prepared to include branching. Oligomeric compounds can form double stranded constructs such as for example two strands hybridized to form a double stranded composition. Double stranded compositions can be linked or separate and can include various other groups such as conjugates and/or overhangs on the ends.

As used herein, "antisense compound" refers to an oligomeric compound, at least a portion of which is at least partially complementary to a target nucleic acid to which it hybridizes. In certain embodiments, an antisense compound modulates (increases or decreases) expression or amount of a target nucleic acid. In certain embodiments, an antisense compound alters splicing of a target pre-mRNA resulting in a different splice variant. In certain embodiments, an antisense compound modulates expression of one or more different target proteins. Antisense mechanisms contemplated herein include, but are not limited to an RNase H mechanism, RNAi mechanisms, splicing modulation, translational arrest, altering RNA processing, inhibiting microRNA function, or mimicking microRNA function.

As used herein, "antisense activity" refers to any detectable and/or measurable activity attributable to the hybridization of an antisense compound to its target nucleic acid. In certain embodiments, such activity may be an increase or decrease in an amount of a nucleic acid or protein. In certain embodiments, such activity may be a change in the ratio of splice variants of a nucleic acid or protein. Detection and/or measuring of antisense activity may be direct or indirect. For example, in certain embodiments, antisense activity is assessed by detecting and/or measuring the amount of target protein or the relative amounts of splice variants of a target protein. In certain embodiments, antisense activity is assessed by detecting and/or measuring the amount of target nucleic acids and/or cleaved target nucleic acids and/or alternatively spliced target nucleic acids. In certain embodiments, antisense activity is assessed by observing a phenotypic change in a cell or animal.

As used herein the term "internucleoside linkage" or "internucleoside linking group" is meant to include all manner of internucleoside linking groups known in the art including but not limited to, phosphorus containing internucleoside linking groups such as phosphodiester and phosphorothioate, and non-phosphorus containing internucleoside linking groups such as formacetyl and methyleneimino. Internucleoside linkages also includes neutral non-ionic internucleoside linkages such as amide-3 (3'-CH$_2$—C(=O)—N(H)-5'), amide-4 (3'-CH$_2$—N(H)—C(=O)-5') and methylphosphonate wherein a phosphorus atom is not always present.

In certain embodiments, oligomeric compounds as provided herein can be prepared having one or more internucleoside linkages containing modified e.g. non-naturally occurring internucleoside linkages. The two main classes of internucleoside linkages are defined by the presence or absence of a phosphorus atom. Modified internucleoside linkages having a phosphorus atom include without limitation, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus containing linkages include without limitation, U.S.: 3,687,808; 4,469,863; 4,476,301; 5,023,243; 5,177,196; 5,188,897; 5,194,599; 5,264,423; 5,276,019; 5,278,302; 5,286,717; 5,321,131; 5,399,676; 5,405,939; 5,453,496; 5,455,233; 5,466,677; 5,476,925; 5,519,126; 5,527,899; 5,536,821; 5,541,306; 5,550,111; 5,563,253; 5,565,555; 5,571,799; 5,587,361; 5,625,050; 5,672,697 and 5,721,218, certain of which are commonly owned with this application, and each of which is herein incorporated by reference.

In certain embodiments, oligomeric compounds as provided herein can be prepared having one or more non-phosphorus containing internucleoside linkages. Such oligomeric compounds include without limitation, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Representative U.S. patents that teach the preparation of the above oligonucleosides include without limitation, U.S.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; 5,677,439; 5,646,269 and 5,792,608, certain of which are commonly owned with this application, and each of which is herein incorporated by reference.

As used herein "neutral internucleoside linkage" is intended to include internucleoside linkages that are non-ionic. Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

In certain embodiments, oligomeric compounds as provided herein can be prepared having one or more optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725,677 and Re. 34,069 (β-cyanoethyl); Beaucage et al., *Tetrahedron*, 1993, 49(10), 1925-1963; Beaucage et al., Tetrahedron, 1993, 49(46), 10441-10488; Beaucage et al., Tetrahedron, 1992, 48(12), 2223-2311.

As used herein the terms "linking groups" and "bifunctional linking moieties" are meant to include groups known in the art that are useful for attachment of chemical functional groups, conjugate groups, reporter groups and other groups to selective sites in a parent compound such as for example an oligomeric compound. In general, a bifunctional linking moiety comprises a hydrocarbyl moiety having two functional groups. One of the functional groups is selected to bind to a parent molecule or compound of interest and the other is selected to bind to essentially any selected group such as a chemical functional group or a conjugate group. In some embodiments, the linker comprises a chain structure or a polymer of repeating units such as ethylene glycols or amino acid units. Examples of functional groups that are routinely used in bifunctional linking moieties include without limitation, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include without limitation, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, the oligomeric compounds as provided herein can be modified by covalent attachment of one or more conjugate groups. In general, conjugate groups modify one or more properties of the oligomeric compounds they are attached to. Such oligonucleotide properties include without limitation, pharmacodynamics, pharmacokinetics, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

In certain embodiments, the oligomeric compounds as provided herein can be modified by covalent attachment of one or more terminal groups to the 5' or 3'-terminal groups. A terminal group can also be attached at any other position at one of the terminal ends of the oligomeric compound. As used herein the terms "5'-terminal group", "3'-terminal group", "terminal group" and combinations thereof are meant to include useful groups known to the art skilled that can be placed on one or both of the terminal ends, including but not limited to the 5' and 3'-ends of an oligomeric compound respectively, for various purposes such as enabling the tracking of the oligomeric compound (a fluorescent label or other reporter group), improving the pharmacokinetics or pharmacodynamics of the oligomeric compound (such as for example: uptake and/or delivery) or enhancing one or more other desirable properties of the oligomeric compound (a group for improving nuclease stability or binding affinity). In certain embodiments, 5' and 3'-terminal groups include without limitation, modified or unmodified nucleosides; two or more linked nucleosides that are independently, modified or unmodified; conjugate groups; capping groups; phosphate moieties; and protecting groups.

As used herein the term "phosphate moiety" refers to a terminal phosphate group that includes phosphates as well as modified phosphates. The phosphate moiety can be located at either terminus but is preferred at the 5'-terminal nucleoside. In one aspect, the terminal phosphate is unmodified having the formula —O—P(=O)(OH)OH. In another aspect, the terminal phosphate is modified such that one or more of the O and OH groups are replaced with H, O, S, N(R) or alkyl where R is H, an amino protecting group or unsubstituted or substituted alkyl. In certain embodiments, the 5' and or 3' terminal group can comprise from 1 to 3 phosphate moieties that are each, independently, unmodified (di or tri-phosphates) or modified.

As used herein, the term "phosphorus moiety" refers to a group having the formula:

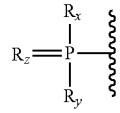

wherein:

$R_x$ and $R_y$ are each, independently, hydroxyl, protected hydroxyl group, thiol, protected thiol group, $C_1$-$C_6$ alkyl, substituted $C_1$-$C_6$ alkyl, $C_1$-$C_6$ alkoxy, substituted $C_1$-$C_6$ alkoxy, a protected amino or substituted amino; and $R_z$ is O or S.

As a monomer such as a phosphoramidite or H-phosphonate the protected phosphorus moiety is preferred to maintain stability during oligomer synthesis. After incorporation into an oligomeric compound the phosphorus moiety can include deprotected groups.

Phosphorus moieties included herein can be attached to a monomer, which can be used in the preparation of oligomeric compounds, wherein the monomer may be attached using O, S, $NR_d$ or $CR_eR_f$, wherein $R_d$ includes without limitation H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or substituted acyl, and $R_e$ and $R_f$ each, independently, include without limitation H, halogen, $C_1$-$C_6$ alkyl, substituted $C_1$-$C_6$ alkyl, $C_1$-$C_6$ alkoxy or substituted $C_1$-$C_6$ alkoxy. Such linked phosphorus moieties include without limitation, phosphates, modified phosphates, thiophosphates, modified thiophosphates, phosphonates, modified phosphonates, phosphoramidates and modified phosphoramidates.

RNA duplexes exist in what has been termed "A Form" geometry while DNA duplexes exist in "B Form" geometry. In general, RNA:RNA duplexes are more stable, or have higher melting temperatures ($T_m$) than DNA:DNA duplexes (Sanger et al., *Principles of Nucleic Acid Structure*, 1984, Springer-Verlag; New York, N.Y.; Lesnik et al., *Biochemistry*, 1995, 34, 10807-10815; Conte et al., *Nucleic Acids Res.*, 1997, 25, 2627-2634). The increased stability of RNA has been attributed to several structural features, most notably the improved base stacking interactions that result from an A-form geometry (Searle et al., *Nucleic Acids Res.*, 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., *Biochemistry*, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) *Principles of Nucleic Acid Structure*, Springer-Verlag, New York, N.Y.).

The relative ability of a chemically-modified oligomeric compound to bind to complementary nucleic acid strands, as compared to natural oligonucleotides, is measured by obtaining the melting temperature of a hybridization complex of said chemically-modified oligomeric compound with its complementary unmodified target nucleic acid. The melting temperature ($T_m$), a characteristic physical property of double helixes, denotes the temperature in degrees centigrade at which 50% helical versus coiled (unhybridized) forms are present. $T_m$ (also commonly referred to as binding affinity) is measured by using the UV spectrum to determine the formation and breakdown (melting) of hybridization. Base stacking, which occurs during hybridization, is accompanied by a reduction in UV absorption (hypochromicity). Consequently a reduction in UV absorption indicates a higher $T_m$.

It is known in the art that the relative duplex stability of an antisense compound:RNA target duplex can be modulated through incorporation of chemically-modified nucleosides into the antisense compound. Sugar-modified nucleosides have provided the most efficient means of modulating the $T_m$ of an antisense compound with its target RNA. Sugar-modified nucleosides that increase the population of or lock the sugar in the C3'-endo (Northern, RNA-like sugar pucker) configuration have predominantly provided a per modification $T_m$ increase for antisense compounds toward a complementary RNA target. Sugar-modified nucleosides that increase the population of or lock the sugar in the C2'-endo (Southern, DNA-like sugar pucker) configuration predominantly provide a per modification Tm decrease for antisense compounds toward a complementary RNA target. The sugar pucker of a given sugar-modified nucleoside is not the only factor that dictates the ability of the nucleoside to increase or decrease an antisense compound's $T_m$ toward complementary RNA. For example, the sugar-modified nucleoside tricycloDNA is predominantly in the C2'-endo conformation, however it imparts a 1.9 to 3° C. per modification increase in $T_m$ toward a complementary RNA. Another example of a sugar-modified high-affinity nucleoside that does not adopt the C3'-endo conformation is α-L-LNA (described in more detail herein).

As used herein, "$T_m$" means melting temperature which is the temperature at which the two strands of a duplex nucleic acid separate. $T_m$ is often used as a measure of duplex stability or the binding affinity of an antisense compound toward a complementary strand such as an RNA molecule.

As used herein, "complementarity" in reference to nucleobases refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases or more broadly, heterocyclic base moieties, comprising certain modifications may maintain the ability to pair with a counterpart nucleobase and thus, are still capable of complementarity.

As used herein, "non-complementary" in reference to nucleobases refers to a pair of nucleobases that do not form hydrogen bonds with one another or otherwise support hybridization.

As used herein, "complementary" in reference to linked nucleosides, oligonucleotides, oligomeric compounds, or nucleic acids, refers to the capacity of an oligomeric compound to hybridize to another oligomeric compound or nucleic acid through nucleobase or more broadly, heterocyclic base, complementarity. In certain embodiments, an antisense compound and its target are complementary to each other when a sufficient number of corresponding positions in each molecule are occupied by nucleobases that can bond with each other to allow stable association between the antisense compound and the target. One skilled in the art recognizes that the inclusion of mismatches is possible without eliminating the ability of the oligomeric compounds to remain in association. Therefore, described herein are antisense compounds that may comprise up to about 20% nucleotides that are mismatched (i.e., are not nucleobase complementary to the corresponding nucleotides of the target). Preferably the antisense compounds contain no more than about 15%, more preferably not more than about 10%, most preferably not more than 5% or no mismatches. The remaining nucleotides are nucleobase complementary or otherwise do not disrupt hybridization (e.g., universal bases). One of ordinary skill in the art would recognize the compounds provided herein are at least 80%, at least 85%, at least 90%, at least 95%, at least 96%, at least 97%, at least 98%, at least 99% or 100% complementary to a target nucleic acid.

It is understood in the art that the sequence of an oligomeric compound need not be 100% complementary to that of its target nucleic acid to be specifically hybridizable. Moreover, an oligomeric compound may hybridize over one or more segments such that intervening or adjacent segments are not involved in the hybridization event (e.g., a loop structure or hairpin structure). In certain embodiments, oligomeric compounds can comprise at least about 70%, at least about 80%, at least about 90%, at least about 95%, or at least about 99% sequence complementarity to a target region within the target nucleic acid sequence to which they are targeted. For example, an oligomeric compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within this scope. Percent complementarity of an oligomeric compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

As used herein, "hybridization" refers to the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is nucleobase complementary to the natural nucleobases thymidine and uracil which pair through the formation of hydrogen bonds. The natural base guanine is nucleobase complementary to the natural bases cytosine and 5-methyl cytosine. Hybridization can occur under varying circumstances.

As used herein, "target nucleic acid" refers to any nucleic acid molecule the expression, amount, or activity of which is capable of being modulated by an antisense compound. In certain embodiments, the target nucleic acid is DNA or RNA. In certain embodiments, the target RNA is mRNA, pre-mRNA, non-coding RNA, pri-microRNA, pre-microRNA, mature microRNA, promoter-directed RNA, or natural antisense transcripts. For example, the target nucleic acid can be a cellular gene (or mRNA transcribed from the gene) whose expression is associated with a particular disorder or disease state, or a nucleic acid molecule from an infectious agent. In certain embodiments, target nucleic acid is a viral or bacterial nucleic acid.

Further included herein are oligomeric compounds such as antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops. Once introduced to a system, the oligomeric compounds provided herein may elicit the action of one or more enzymes or structural proteins to effect modification of the target nucleic acid. Alternatively, the oligomeric compound may inhibit the activity the target nucleic acid through an occupancy-based method, thus interfering with the activity of the target nucleic acid.

One non-limiting example of such an enzyme is RNAse H, a cellular endonuclease which cleaves the RNA strand of an RNA:DNA duplex. It is known in the art that single-stranded oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of oligomeric compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

As used herein, "modulation" refers to a perturbation of amount or quality of a function or activity when compared to the function or activity prior to modulation. For example, modulation includes the change, either an increase (stimulation or induction) or a decrease (inhibition or reduction) in gene expression. As a further example, modulation of expression can include perturbing splice site selection of pre-mRNA processing, resulting in a change in the amount of a particular splice-variant present compared to conditions that were not perturbed. As a further example, modulation includes perturbing translation of a protein.

As used herein, the term "pharmaceutically acceptable salts" refers to salts that retain the desired activity of the compound and do not impart undesired toxicological effects thereto. The term "pharmaceutically acceptable salt" includes a salt prepared from pharmaceutically acceptable non-toxic acids or bases, including inorganic or organic acids and bases.

Pharmaceutically acceptable salts of the oligomeric compounds described herein may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Sodium salts of antisense oligonucleotides are useful and are well accepted for therapeutic administration to humans. Accordingly, in one embodiment the oligomeric compounds described herein are in the form of a sodium salt.

In certain embodiments, oligomeric compounds provided herein comprise from about 8 to about 80 monomer subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 monomer subunits in length, or any range therewithin.

In certain embodiments, oligomeric compounds provided herein comprise from about 8 to 40 monomer subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 monomer subunits in length, or any range therewithin.

In certain embodiments, oligomeric compounds provided herein comprise from about 8 to 20 monomer subunits in length. One having ordinary skill in the art will appreciate that this embodies oligomeric compounds of 8, 9, 10, 11, 12, 13, 14, 15, 16, 17, 18, 19 or 20 monomer subunits in length, or any range therewithin.

In certain embodiments, oligomeric compounds provided herein comprise from about 8 to 16 monomer subunits in length. One having ordinary skill in the art will appreciate that this embodies oligomeric compounds of 8, 9, 10, 11, 12, 13, 14, 15 or 16 monomer subunits in length, or any range therewithin.

In certain embodiments, oligomeric compounds provided herein comprise from about 10 to 14 monomer subunits in length. One having ordinary skill in the art will appreciate that this embodies oligomeric compounds of 10, 11, 12, 13 or 14 monomer subunits in length, or any range therewithin.

In certain embodiments, oligomeric compounds provided herein comprise from about 10 to 18 monomer subunits in length. One having ordinary skill in the art will appreciate that this embodies oligomeric compounds of 10, 11, 12, 13, 14, 15, 16, 17 or 18 monomer subunits in length, or any range therewithin.

In certain embodiments, oligomeric compounds provided herein comprise from about 10 to 21 monomer subunits in length. One having ordinary skill in the art will appreciate that this embodies oligomeric compounds of 10, 11, 12, 13, 14, 15, 16, 17, 18, 19, 20 or 21 monomer subunits in length, or any range therewithin.

In certain embodiments, oligomeric compounds provided herein comprise from about 12 to 14 monomer subunits in length. One having ordinary skill in the art will appreciate that this embodies oligomeric compounds of 12, 13 or 14 monomer subunits in length, or any range therewithin.

In certain embodiments, oligomeric compounds provided herein comprise from about 12 to 18 monomer subunits in length. One having ordinary skill in the art will appreciate that this embodies oligomeric compounds of 12, 13, 14, 15, 16, 17 or 18 monomer subunits in length, or any range therewithin.

In certain embodiments, oligomeric compounds provided herein comprise from about 12 to 21 monomer subunits in length. One having ordinary skill in the art will appreciate that this embodies oligomeric compounds of 12, 13, 14, 15, 16, 17, 18, 19, 20 or 21 monomer subunits in length, or any range therewithin.

In certain embodiments, oligomeric compounds provided herein comprise from about 14 to 18 monomer subunits in length. One having ordinary skill in the art will appreciate that this embodies oligomeric compounds of 14, 15, 16, 17 or 18 monomer subunits in length, or any range therewithin.

In certain embodiments, oligomeric compounds of any of a variety of ranges of lengths of linked monomer subunits are provided. In certain embodiments, oligomeric compounds are provided consisting of X—Y linked monomer subunits, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, this provides oligomeric compounds comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-27, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked monomer subunits.

In certain embodiments, the ranges for the oligomeric compounds listed herein are meant to limit the number of monomer subunits in the oligomeric compounds, however such oligomeric compounds may further include 5' and/or 3'-terminal groups including but not limited to protecting groups such as hydroxyl protecting groups, optionally linked conjugate groups and/or other substituent groups.

In certain embodiments, the preparation of oligomeric compounds as disclosed herein is performed according to literature procedures for DNA: Protocols for Oligonucleotides and Analogs, Agrawal, Ed., Humana Press, 1993, and/or RNA: Scaringe, *Methods,* 2001, 23, 206-217; Gait et al., *Applications of Chemically synthesized RNA in RNA: Protein Interactions*, Smith, Ed., 1998, 1-36; Gallo et al., *Tetrahedron,* 2001, 57, 5707-5713. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069.

Oligomeric compounds are routinely prepared using solid support methods as opposed to solution phase methods. Commercially available equipment commonly used for the preparation of oligomeric compounds that utilize the solid support method is sold by several vendors including, for example, Applied Biosystems (Foster City, Calif.). Any other means for such synthesis known in the art may additionally or alternatively be employed. Suitable solid phase techniques, including automated synthesis techniques, are described in *Oligonucleotides and Analogues, a Practical Approach*, F. Eckstein, Ed., Oxford University Press, New York, 1991.

The synthesis of RNA and related analogs relative to the synthesis of DNA and related analogs has been increasing as efforts in RNA interference and micro RNA increase. The primary RNA synthesis strategies that are presently being used commercially include 5'-O-DMT-2'-O-t-butyldimethylsilyl (TBDMS), 5'-O-DMT-2'-O-[1 (2-fluorophenyl)-4-methoxypiperidin-4-yl](FPMP), 2'-O-[(triisopropylsilyl)oxy]methyl (2'-O—$CH_2$—O—$Si(iPr)_3$ (TOM) and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. The primary groups being used for commercial RNA synthesis are: TBDMS: 5'-O-DMT-2'-O-t-butyldimethylsilyl; TOM: 2'-O-[(triisopropylsilyl)oxy]methyl; DOD/ACE: (5'-O-bis(trimethylsiloxy)cyclododecyloxysilyl ether-2'-O-bis(2-acetoxyethoxy)methyl; and FPMP: 5'-O-DMT-2'-O-[1 (2-fluorophenyl)-4-ethoxypiperidin-4-yl]. In certain embodiments, each of the aforementioned RNA synthesis strategies can be used herein. In certain embodiments, the aforementioned RNA synthesis strategies can be performed together in a hybrid fashion e.g. using a 5'-protecting group from one strategy with a 2'-O-protecting from another strategy.

In some embodiments, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed herein in further investigative studies of the function of the peptide, or for use as a research, diagnostic, or therapeutic agent. In the case of oligomeric compounds targeted to microRNA, candidate modulators may be evaluated by the extent to which they increase the expression of a microRNA target RNA or protein (as interference with the activity of a microRNA will result in the increased expression of one or more targets of the microRNA).

As used herein, "expression" refers to the process by which a gene ultimately results in a protein. Expression includes, but is not limited to, transcription, splicing, post-transcriptional modification, and translation.

Suitable target segments may also be combined with their respective complementary oligomeric compounds provided herein to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., *Nature*, 1998, 391, 806-811; Timmons and Fire, *Nature*, 1998, 395, 854; Timmons et al., *Gene*, 2001, 263, 103-112; Tabara et al., *Science*, 1998, 282, 430-431; Montgomery et al., *Proc. Natl. Acad. Sci. USA*, 1998, 95, 15502-15507; Tuschl et al., *Genes Dev.*, 1999, 13, 3191-3197; Elbashir et al., *Nature*, 2001, 411, 494-498; Elbashir et al., *Genes Dev.*, 2001, 15, 188-200). For example, such double-stranded moieties have been shown to inhibit the target by the classical hybridization of antisense strand of the duplex to the target, thereby triggering enzymatic degradation of the target (Tijsterman et al., *Science*, 2002, 295, 694-697).

The oligomeric compounds provided herein can also be applied in the areas of drug discovery and target validation. In certain embodiments, provided herein is the use of the oligomeric compounds and targets identified herein in drug discovery efforts to elucidate relationships that exist between proteins and a disease state, phenotype, or condition. These methods include detecting or modulating a target peptide comprising contacting a sample, tissue, cell, or organism with one or more oligomeric compounds provided herein, measuring the nucleic acid or protein level of the target and/or a related phenotypic or chemical endpoint at some time after treatment, and optionally comparing the measured value to a non-treated sample or sample treated with a further oligomeric compound as provided herein. These methods can also be performed in parallel or in combination with other experiments to determine the function of unknown genes for the process of target validation or to determine the validity of a particular gene product as a target for treatment or prevention of a particular disease, condition, or phenotype. In certain embodiments, oligomeric compounds are provided for use in therapy. In certain embodiments, the therapy is reducing target messenger RNA.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

In certain embodiments, chemically-modified oligomeric compounds are provided herein that may have a higher affinity for target RNAs than does non-modified DNA. In certain such embodiments, higher affinity in turn provides increased potency allowing for the administration of lower doses of such compounds, reduced potential for toxicity, improvement in therapeutic index and decreased overall cost of therapy.

Effect of nucleoside modifications on RNAi activity is evaluated according to existing literature (Elbashir et al., *Nature*, 2001, 411, 494-498; Nishikura et al., *Cell*, 2001, 107, 415-416; and Bass et al., *Cell*, 2000, 101, 235-238.)

In certain embodiments, oligomeric compounds provided herein can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway. In certain embodiments, oligomeric compounds provided herein can be utilized either alone or in combination with other oligomeric compounds or other therapeutics as tools in differential and/or combinatorial analyses to elucidate expression patterns of a portion or the entire complement of genes expressed within cells and tissues. Oligomeric compounds can also be effectively used as primers and probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of oligomeric compounds as provided herein, particularly the primers and probes, with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

As one nonlimiting example, expression patterns within cells or tissues treated with one or more of the oligomeric compounds provided herein are compared to control cells or tissues not treated with oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. USA*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J.*

Biotechnol., 2000, 80, 143-57), subtractive RNA fingerprinting (SuRF) (Fuchs, et al., *Anal. Biochem.,* 2000, 286, 91-98; Larson, et al., *Cytometry,* 2000, 41, 203-208), subtractive cloning, differential display (DD) (Jurecic and Belmont, *Curr. Opin. Microbiol.,* 2000, 3, 316-21), comparative genomic hybridization (Carulli, et al., *J. Cell Biochem. Suppl.,* 1998, 31, 286-96), FISH (fluorescent in situ hybridization) techniques (Going and Gusterson, *Eur. J. Cancer,* 1999, 35, 1895-904) and mass spectrometry methods (To, *Comb. Chem. High Throughput Screen,* 2000, 3, 235-41).

Those skilled in the art, having possession of the present disclosure will be able to prepare oligomeric compounds, comprising a contiguous sequence of linked monomer subunits, of essentially any viable length to practice the methods disclosed herein. Such oligomeric compounds will include at least one and preferably a plurality of the bicyclic carbocyclic nucleosides provided herein and may also include other monomer subunits including but not limited to nucleosides, modified nucleosides and nucleosides comprising sugar surrogate groups.

All documents, or portions of documents, cited in this application, including, but not limited to, patents, patent applications, articles, books, and treatises, are hereby expressly incorporated by reference in their entirety for any purpose.

While in certain embodiments, oligomeric compounds provided herein can be utilized as described, the following examples serve only to illustrate and are not intended to be limiting.

EXAMPLES (GENERAL)

NMR spectra were recorded on Bruker spectrometers at 400 or 500 MHz for $^1$H, 100 or 125 MHz for $^{13}$C, and 375 MHz for $^{19}$F. High resolution mass spectra were obtained from the UCLA Molecular Instrumentation Center. Optical rotation measurements were carried out using a Rudolph Research Autopol IV automatic polarimeter. Reagents were purchased through Fischer Scientific or Sigma-Aldrich. ACS grade solvents were purchased from Fischer Scientific. Toluene, benzene, THF, and diethyl ether solvents were dried prior to use by distilling over sodium metal and benzoquinone. Dichloromethane was distilled over calcium hydride. Methanol was distilled over magnesium turnings. Ethanol (200 proof) was purchased from Fischer Scientific and was used without further drying. Silica gel P60 was purchased from Silicycle. All oxygen or moisture sensitive reactions were performed under an inert Argon atmosphere unless otherwise noted. X-ray crystallography was performed at the J. D. McCullough Crystallography Laboratory.

Example 1

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

Example 2

Synthesis of Oligomeric Compounds

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as alkylated derivatives and those having phosphorothioate linkages.

Oligomeric compounds: Unsubstituted and substituted phosphodiester (P=O) oligomeric compounds, including without limitation, oligonucleotides can be synthesized on an automated DNA synthesizer (Applied Biosystems model 394) using standard phosphoramidite chemistry with oxidation by iodine.

In certain embodiments, phosphorothioate internucleoside linkages (P=S) are synthesized similar to phosphodiester internucleoside linkages with the following exceptions: thiation is effected by utilizing a 10% w/v solution of 3,H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligomeric compounds are recovered by precipitating with greater than 3 volumes of ethanol from a 1 M NH$_4$OAc solution. Phosphinate internucleoside linkages can be prepared as described in U.S. Pat. No. 5,508,270.

Alkyl phosphonate internucleoside linkages can be prepared as described in U.S. Pat. No. 4,469,863.

3'-Deoxy-3'-methylene phosphonate internucleoside linkages can be prepared as described in U.S. Pat. No. 5,610,289 or 5,625,050.

Phosphoramidite internucleoside linkages can be prepared as described in U.S. Pat. No. 5,256,775 or U.S. Pat. No. 5,366,878.

Alkylphosphonothioate internucleoside linkages can be prepared as described in published PCT applications PCT/US94/00902 and PCT/US93/06976 (published as WO 94/17093 and WO 94/02499, respectively).

3'-Deoxy-3'-amino phosphoramidate internucleoside linkages can be prepared as described in U.S. Pat. No. 5,476,925.

Phosphotriester internucleoside linkages can be prepared as described in U.S. Pat. No. 5,023,243.

Borano phosphate internucleoside linkages can be prepared as described in U.S. Pat. Nos. 5,130,302 and 5,177,198.

Oligomeric compounds having one or more non-phosphorus containing internucleoside linkages including without limitation methylenemethylimino linked oligonucleosides, also identified as MMI linked oligonucleosides, methylenedimethylhydrazo linked oligonucleosides, also identified as MDH linked oligonucleosides, methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal internucleoside linkages can be prepared as described in U.S. Pat. Nos. 5,264,562 and 5,264,564.

Ethylene oxide internucleoside linkages can be prepared as described in U.S. Pat. No. 5,223,618.

Example 3

Isolation and Purification of Oligomeric Compounds

After cleavage from the controlled pore glass solid support or other support medium and deblocking in concentrated ammonium hydroxide at 55° C. for 12-16 hours, the oligomeric compounds, including without limitation oligonucleotides and oligonucleosides, are recovered by precipitation out of 1 M NH$_4$OAc with >3 volumes of ethanol. Synthesized oligomeric compounds are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32+/−48). For some studies oligomeric compounds are purified by HPLC, as described by Chiang et al., *J. Biol. Chem.* 1991, 266, 18162-18171. Results obtained with HPLC-purified material are generally similar to those obtained with non-HPLC purified material.

Example 4

Synthesis of Oligomeric Compounds Using the 96 Well Plate Format

Oligomeric compounds, including without limitation oligonucleotides, can be synthesized via solid phase P(III) phosphoramidite chemistry on an automated synthesizer capable of assembling 96 sequences simultaneously in a 96-well format. Phosphodiester internucleoside linkages are afforded by oxidation with aqueous iodine. Phosphorothioate internucleoside linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites can be purchased from commercial vendors (e.g. PE-Applied Biosystems, Foster City, Calif., or Pharmacia, Piscataway, N.J.). Non-standard nucleosides are synthesized as per standard or patented methods and can be functionalized as base protected beta-cyanoethyldiisopropyl phosphoramidites.

Oligomeric compounds can be cleaved from support and deprotected with concentrated NH$_4$OH at elevated temperature (55-60° C.) for 12-16 hours and the released product then dried in vacuo. The dried product is then re-suspended in sterile water to afford a master plate from which all analytical and test plate samples are then diluted utilizing robotic pipettors.

Example 5

Analysis of Oligomeric Compounds Using the 96-Well Plate Format

The concentration of oligomeric compounds in each well can be assessed by dilution of samples and UV absorption spectroscopy. The full-length integrity of the individual products can be evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

Example 6

In Vitro Treatment of Cells with Oligomeric Compounds

The effect of oligomeric compounds on target nucleic acid expression is tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

b.END cells: The mouse brain endothelial cell line b.END was obtained from Dr. Werner Risau at the Max Plank Institute (Bad Nauheim, Germany). b.END cells are routinely cultured in DMEM, high glucose (Invitrogen Life Technologies, Carlsbad, Calif.) supplemented with 10% fetal bovine serum (Invitrogen Life Technologies, Carlsbad, Calif.). Cells are routinely passaged by trypsinization and dilution when they reached approximately 90% confluence. Cells are seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

Lipofectin™

When cells reached 65-75% confluency, they are treated with one or more oligomeric compounds. The oligomeric compound is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of the oligomeric compound(s) and a LIPOFECTIN™ concentration of 2.5 or 3 µg/mL per 100 nM oligomeric compound(s). This transfection mixture is incubated at room temperature for approximately 0.5 hours. For cells grown in 96-well plates, wells are washed once with 100 µL OPTI-MEM™-1 and then treated with 130 µL of the transfection mixture. Cells grown in 24-well plates or other standard tissue culture plates are treated similarly, using appropriate volumes of medium and oligomeric compound(s). Cells are treated and data are obtained in duplicate or triplicate. After approximately 4-7 hours of treatment at 37° C., the medium containing the transfection mixture is replaced with fresh culture medium. Cells are harvested 16-24 hours after treatment with oligomeric compound(s).

Other suitable transfection reagents known in the art include, but are not limited to, CYTOFECTIN™, LIPOFECTAMINE™, OLIGOFECTAMINE™, and FUGENE™. Other suitable transfection methods known in the art include, but are not limited to, electroporation.

Example 7

Real-Time Quantitative PCR Analysis of Target mRNA Levels

Quantitation of target mRNA levels is accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5'-end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction.

In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents are obtained from Invitrogen Life Technologies (Carlsbad, Calif.). RT, real-time PCR is carried out by adding 20 μL PCR cocktail (2.5×PCR buffer minus $MgCl_2$, 6.6 mM $MgCl_2$, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 μL total RNA solution (20-200 ng). The RT reaction is carried out by incubation for 30 minutes at 48° C. Following a 10 minute incubation at 95° C. to activate the PLATINUM® Taq, 40 cycles of a two-step PCR protocol are carried out: 95° C. for 15 seconds (denaturation) followed by 60° C. for 1.5 minutes (annealing/-extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 μL of RIBOGREEN™ working reagent (RIBOGREEN™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

Example 8

Analysis of Oligonucleotide Inhibition of Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+ mRNA. One method of RNA analysis of the present disclosure is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F.

M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 9

Design of Phenotypic Assays and In Vivo Studies for the Use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the a target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

Example 10

RNA Isolation

Poly(A)+ mRNA Isolation

Poly(A)+ mRNA is isolated according to Miura et al., (Clin. Chem., 1996, 42, 1758-1764). Other methods for poly(A)+ mRNA isolation are routine in the art. Briefly, for cells grown on 96-well plates, growth medium is removed from the cells and each well is washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 µL of lysate is transferred to Oligo d(T) coated 96-well plates (AGCT Inc., Irvine Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 µL cold PBS. 150 µL Buffer RLT is added to each well and the plate vigorously agitated for 20 seconds. 150 µL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 µL of Buffer RW1 is added to each well of the RNEASY 96™ plate and incubated for 15 minutes and the vacuum is again applied for 1 minute. An additional 500 µL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 11

Target-Specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 01).

```
                              (SEQ ID NO: 02)
Forward primer: AATGGCTAAGTGAAGATGACAATCAT (SEQ ID NO: 03)
Reverse primer: TGCACATATCATTACACCAGTTCGT
```

And the PCR probe:

```
                              (SEQ ID NO: 04)
FAM-TTGCAGCAATTCACTGTAAAGCTGGAAAGG-TAMRA,
``` where FAM is the fluorescent dye and TAMRA is the quencher dye.

Example 12

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 µl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 13

2-[((1,1-Dimethylethyl)dimethylsilyloxy)methyl]-cyclopent-2-en-1-one (Compound 3)

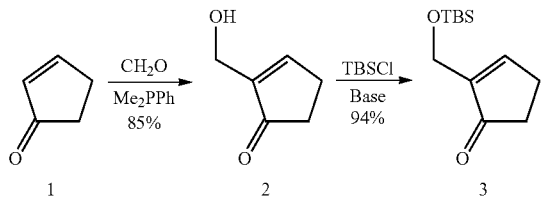

Compound 1 (commercially available) was dissolved in CH$_2$O and dimethyl(phenyl)-phosphane was added to provide Compound 2 (85%). To a solution of 2 (8.72 g, 77.8 mmol) in dichloromethane (220 mL) was added tert-butyldimethylsilyl chloride (TBSCl, 14.07 g, 93.3 mmol) and imidazole (11.65 g, 171.1 mmol). The solution was stirred at 22° C. for 12 h. The reaction mixture was partitioned with brine and extracted with dichloromethane (4×). The combined extracts were dried with magnesium sulfate, filtered, and concentrated in vacuo. The crude residue was purified by flash column chromatography on silica gel (10% ethyl acetate in hexanes, R$_f$=0.35). The silyl ether, Compound 3, was obtained as a colorless oil (16.88 g, 74.6 mmol) in 96% yield.

$^1$H NMR (400 MHz, CDCl$_3$): δ 7.54-7.51 (m, 1H), 4.38-4.33 (m, 2H), 2.63-2.57 (m, 2H), 2.46-2.40 (m, 2H), 0.91 (s, 9H), 0.07 (s, 6H); $^{13}$C NMR (100 MHz, CDCl$_3$): δ 208.5, 157.9, 146.4, 58.3, 35.4, 26.7, 25.9, 18.3, −5.44; HRMS-ESI (m/z) [M+Na]$^+$ calcd for C$_{12}$H$_{22}$O$_2$Si=249.1287, found=249.1314.

Example 14

(S)-2-[((1,1-Dimethylethyl)dimethylsilyloxy)methyl]-cyclopent-2-en-1-ol, Compound 4

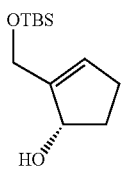

To a solution of (R)—CBS (1M in toluene, 8.24 mL, 8.24 mmol) in dichloromethane (80 mL) was added borane (1M in THF, 24.7 mL, 24.7 mmol) at 0° C. After 5 min, Compound 3 (9.33 g, 41.2 mmol) in dichloromethane (20 mL) was added with rapid stirring over 4 min via a syringe pump. The reaction was stirred for a further 4 min before adding methanol (40 mL). The solution was concentrated in vacuo and the crude residue purified by flash column chromatography on silica gel (gradient: 5% to 15% ethyl acetate in hexanes). The alcohol, Compound 4 was obtained as a colorless oil (8.29 g, 36.29 mmol, 88%).

$^1$H NMR (400 MHz, CDCl$_3$): δ 5.72 (m, 1H), 4.83-4.77 (m, 1H), 4.39-4.29 (m, 2H), 2.68-2.37 (m, 2H), 2.31-2.14 (m, 2H), 1.82-1.69 (m, 1H), 0.90 (s, 9H), 0.079 (s, 3H), 0.075 (s, 3H); $^{13}$C NMR (100 MHz, CDCl$_3$): δ 144.3, 129.3, 77.8, 61.5, 33.5, 30.0, 25.9, 18.3, −5.44, −5.46; HRMS-ESI (m/z) [M+Na]$^+$ calcd for C$_{12}$H$_{24}$O$_2$Si=251.1443, found=251.1485; [α]$_D^{22}$=−44.1° (c=0.79, CHCl$_3$).

Enantiopurity: The optical rotation was established to be levorotatory after synthesizing the allylic alcohol, Compound 4 using an alternative procedure. The enantioenriched ester 4a was made using conditions outlined in the literature (Candish, L.; Lupton, D. W. Org. Lett. 2010, 12, 4836.).

The ester was reduced using DIBAL and the primary alcohol subsequently silylated using TBSCl to give the allylic alcohol, Compound 4 with excellent enantiopurity. The corresponding Mosher's esters were prepared and the enantiopurities assessed by means of $^{19}$F NMR. The CBS reduction was found to give the desired enantiomer in 93.4% ee (29.4:1 er).

Example 15

(1R,2S,5S)-1-[((1,1-Dimethylethyl)dimethylsilyloxy)methyl]bicyclo[3.1.0]hexan-2-ol, Compound 5

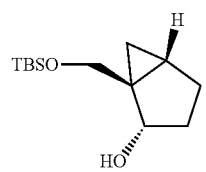

Solution A: To a solution of Compound 4 (11.37 g, 49.8 mmol) in dichloromethane (125 mL) at 0° C. was added diethylzinc (1M in hexanes, 54.7 mL, 54.7 mmol) over 2 min. Solution B: To dichloromethane (125 mL) cooled to 0° C., was added diethylzinc (1M in hexanes, 49.8 mL, 49.8 mmol) followed by diiodomethane (8.42 mL, 104.5 mmol). After 10 min, solution A was transferred via cannula to solution B. The reaction mixture was allowed to warm to 22° C. over 16 h, whereupon a solution of saturated aqueous sodium bicarbonate was added followed by a small quantity of water. A precipitate develops and the biphasic mixture is filtered. The precipitate was washed with dichloromethane. The biphasic mixture was separated and the aqueous layer further extracted with dichloromethane (5×). The combined filtrate and dichloromethane extracts were dried over sodium sulfate, filtered, and concentrated in vacuo. The crude residue was separated by flash column chromatography on silica gel (10% ethyl acetate in hexanes). Compound 5 was isolated as a colorless oil (11.67 g, 48.14 mmol, 97%).

$^1$H NMR (400 MHz, CDCl$_3$): δ 4.49 (t, J=8.1 Hz, 1H), 3.92 (d, J=10.3 Hz, 1H), 3.52 (d, J=10.4 Hz, 1H), 2.49 (brs, 1H), 1.95-1.85 (m, 1H), 1.77-1.61 (m, 2H), 1.26-1.10 (m, 2H), 0.88 (s, 9H), 0.84 (t, J=4.52 Hz, 1H), 0.37 (dd, J=8.0, 5.1 Hz, 1H), 0.04 (s, 6H); $^{13}$C NMR (100 MHz, CDCl$_3$): δ 76.6, 67.9, 34.2, 29.2, 25.9, 24.7, 21.1, 18.2, 9.9, −5.35, −5.43; HRMS-ESI (m/z) [M+Na]$^+$ calcd for C$_{13}$H$_{26}$O$_2$Si=265.1600, found=265.1636.

Example 16

(1R,5S)-1-[((1,1-Dimethylethyl)dimethylsilyloxy)methyl]bicycle[3.1.0]hexan-2-one, Compound

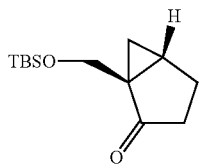

6

To a solution of Compound 5 (11.66 g, 48.10 mmol) and pyridine (15.50 mL, 192.39 mmol) in dichloromethane (240 mL) was added Dess-Martin periodinane (24.48 g, 57.71 mmol). The reaction mixture was stirred for 1.5 h before quenching with a 1:1 saturated solution of aqueous sodium bicarbonate and aqueous sodium thiosulfate. The biphasic mixture was stirred rapidly for several hours. The organic layer was removed and the aqueous layer was further extracted with dichloromethane (4×). The combined organic layers were dried over magnesium sulfate, filtered, and concentrated. The crude residue was separated by flash column chromatography on silica gel (10% ethyl acetate in hexanes, R$_f$=0.30). Compound 6 was isolated as a colorless oil (10.72 g, 44.59 mmol) in 92% yield.

$^1$H NMR (400 MHz, CDCl$_3$): δ 4.04 (d, J=10.9 Hz, 1H), 3.77 (d, J=10.9 Hz, 1H), 2.24-2.02 (m, 4H), 2.00-1.91 (m, 1H), 1.36-1.29 (m, 1H), 0.94 (t, J=4.3 Hz, 1H), 0.86 (s, 9H), 0.040 (s, 3H), 0.036 (s, 3H); $^{13}$C NMR (100 MHz, CDCl$_3$): δ=214.64, 59.2, 39.0, 33.0, 25.8, 25.7, 21.6, 18.3, 16.4, −5.42, −5.46; HRMS-ESI (m/z) [M+Na]$^+$ calcd for C$_{13}$H$_{26}$O$_2$Si=263.1443, found=263.1465.

Example 17

(1R,3R,5R)-1-[((1,1-Dimethylethyl)dimethylsilyloxy)methyl]-3-fluorobicyclo[3.1.0]hexan-2one, Compound 7a and (1R,3S,5R)-1-[((1,1-Dimethylethyl)dimethylsilyloxy)methyl]-3-fluorobicyclo[3.1.0]hexan-2-one, Compound 7b

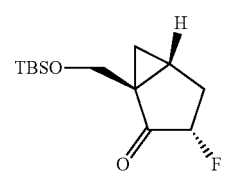

7a

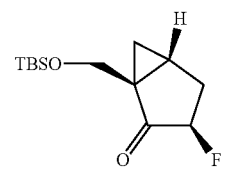

7b

To a solution of lithium bis(trimethylsilyl)amide (1M in THF, 18.86 mL, 18.86 mmol) in THF (171.5 mL) cooled to −78° C. was added a solution of the Compound 6 (4.12 g, 17.13 mmol) in THF (4 mL) dropwise. The solution was stirred for 30 min before rapidly adding a solution of N-fluorobenzenesulfonimide (NFSI, 6.48 g, 20.56 mmol) in THF (30 mL). The solution was further stirred for 1 h before warming to 22° C. The reaction was quenched with a saturated aqueous ammonium chloride solution. Hexanes (60 mL) were added and the organic layer separated from the aqueous layer. The aqueous layer was further extracted with dichloromethane (5×). The combined organic layers were dried with magnesium sulfate, filtered, and concentrated in vacuo. To the residue was added hexanes and the mixture was sonicated. The solid that arose was filtered and washed with hexanes. The combined washes were concentrated. The crude residue was purified by flash column chromatography on silica gel (40% hexanes in dichloromethane). The fluorinated compounds 7a and 7b were isolated together as a colorless oil (3.23 g, 12.50 mmol) in a combined yield of 73%.

7a: $^1$H NMR (400 MHz, CDCl$_3$): δ 4.54 (dd, J=51.2, 8.1 Hz, 1H), 4.08 (d, J=11.1 Hz, 1H), 3.66 (d, J=11.1, 1H), 2.39 (ddddd, J=31.6, 15.3, 7.9, 5.1, 2.3 Hz, 1H), 2.12-1.96 (m, 2H), 1.44-1.37 (m, 1H), 1.30 (ddd, J=4.7, 4.7, 1.7 Hz, 1H), 0.83 (s, 9H), 0.011 (s, 3H), 0.003 (s, 3H); $^{13}$C NMR (100 MHz, CDCl$_3$): δ=206.7 (d, J=12.6 Hz), 90.4 (d, J=183.2 Hz), 59.4, 38.7, 30.1 (d, J=20.5 Hz), 25.8, 23.2, 18.2, 18.0 (d, J=1.7 Hz), −5.50, −5.53; $^{19}$F NMR (376 MHz, CDCl$_3$): δ 159.5 (proton decoupled); HRMS-ESI (m/z) [2M+H]$^+$ calcd for C$_{13}$H$_{23}$FO$_2$Si=517.2981, found=517.3038 (acquired as a mixture of both 9a and 9b).

7b: $^1$H NMR (500 MHz, CDCl$_3$): δ 4.93 (ddd, J=51.1, 9.0, 7.9 Hz, 1H), 4.00 (d, J=10.9 Hz, 1H), 3.93 (d, J=10.9, 1H), 2.63-2.55 (m, 1H), 2.27-2.08 (m, 2H), 1.48-1.40 (m, 1H), 1.06 (t, J=4.8 Hz, 1H), 0.86 (s, 9H), 0.041 (s, 6H); $^{13}$C NMR (125 MHz, CDCl$_3$): δ=207.0 (d, J=15.5 Hz), 89.9 (d, J=191.1 Hz), 58.4 (d, J=1.2 Hz), 36.1, 29.2 (d, J=20.0 Hz), 25.8, 24.2 (d, J=8.3 Hz), 18.2, 18.0, −5.26, −5.49; $^{19}$F NMR (376 MHz, CDCl$_3$): δ 128.7 (proton decoupled); HRMS-ESI (m/z) [2M+H]+ calcd for C₁₃H₂₃FO₂Si=517.2981, found=517.3038 (acquired as a mixture of both 7a and 7b).

Example 18

(1R,5R)-1-[((1,1-Dimethylethyl)dimethylsilyloxy)methyl]-3-fluorobicyclo[3.1.0]hex-3-en-2one, Compound 8

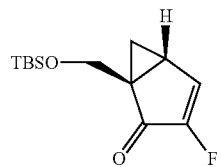

8

To a solution of 7ab (480 mg, 1.86 mmol) in THF (14.88 mL) cooled to −78° C. was added lithium bis(trimethylsilyl)amide (1M in THF, 2.04 mL, 2.04 mmol). After stirring for 10 min, a solution of phenylselenyl chloride (427 mg, 2.23 mmol) in THF (3.72 mL) was added dropwise. After the addition was complete, the reaction was allowed to warm to 22° C. A solution of 1:1 saturated aqueous sodium bicarbonate and brine were added and the mixture subsequently partitioned with dichloromethane. The aqueous layer was further extracted with dichloromethane (5×). The combined extracts were dried over magnesium sulfate, filtered, and concentrated in vacuo. The residue was dissolved in dichloromethane (7.44 mL) and pyridine (0.45 mL) was added. The solution was cooled to 0° C. and aqueous hydrogen peroxide (30%, 2.37 mL) was added. The resulting biphasic mixture was rapidly stirred for 2 h and the organic layer was separated from the aqueous layer. The aqueous layer was further extracted with dichloromethane (4×). The combined extracts were dried over sodium sulfate, filtered, and then concentrated in vacuo. The crude residue was purified by flash column chromatography on silica gel (40% hexanes in dichloromethane). Compound 8 was isolated as a colorless oil (350 mg, 1.37 mmol, 73%).

¹H NMR (400 MHz, CDCl₃): δ 6.94 (bm, 1H), 4.22 (d, J=10.8 Hz, 1H), 3.85 (d, J=10.8 Hz, 1H), 2.39-2.30 (m, 1H), 1.62 (dt, J=6.4, 4.0 Hz, 1H), 1.55-1.52 (m, 1H), 0.86 (s, 9H), 0.055 (s, 3H), 0.049 (s, 3H); ¹³C NMR (125 MHz, CDCl₃): δ=196.2 (d, J=20.0 Hz), 155.8 (d, J=285.0 Hz), 134.8 (d, J=8.8 Hz), 59.0 (d, J=1.2 Hz), 39.5 (d, J=5.0 Hz), 33.2 (d, J=5.0 Hz), 25.8, 18.4 (d, J=7.5 Hz), −5.46, −5.49; ¹⁹F NMR (376 MHz, CDCl₃): δ −140.87 (t, J=4.7, 1F); HRMS-ESI (m/z) [M+Na]+ calcd for C₁₃H₂₁FO₂Si=279.1193, found=279.1099.

Example 19

(1R,3S,4R,5S)-1-[((1,1-Dimethylethyl)dimethylsilyloxy)methyl]-4-(dibenzylamino)-3-fluorobicyclo[3.1.0]hexan-2-one, Compound 9a and (1R,3R,4R,5S)-1-[((1,1-Dimethylethyl)dimethylsilyloxy)methyl]-4-(dibenzylamino)-3-fluorobicyclo[3.1.0]hexan-2-one, Compound 9b

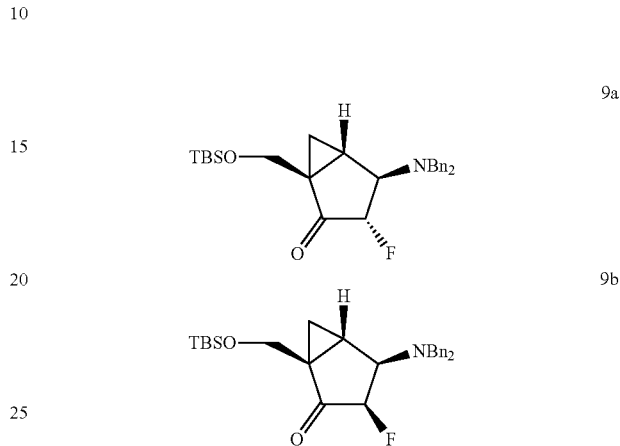

To a solution of Compound 8 10 (3.66 g, 14.26 mmol) and 4-dimethylaminopyridine (1.74 g, 21.40 mmol) in dimethyl sulfoxide (11 mL) was added dibenzylamine (3.03 mL, 17.10 mmol) and the mixture was stirred at 22° C. for 3 d. Lithium chloride (1.81 g, 42.78 mmol) was added in 3 portions at 6 h intervals. A white solid precipitated slowly from the solution with each incremental addition. Water (100 mL) was added and the heterogeneous mixture was filtered and washed with a small quantity of water. The solid was dissolved in dichloromethane and then dried over sodium sulfate. The solution was concentrated in vacuo and the residue purified by flash column chromatography on silica gel (5% ethyl acetate in hexanes). The adducts 9a (3.82 g, 8.42 mmol) and 9b (1.00 g, 2.20 mmol) were isolated as white solids in 59% and 15% yield respectively.

9a: ¹H NMR (400 MHz, CDCl₃): δ 7.40-7.21 (m, 10H), 4.66 (d, J=49.7 Hz, 1H), 4.34 (d, J=9.6 Hz, 1H), 3.94 (d, J=14.4 Hz, 2H), 3.50-3.31 (m, 4H), 2.17 (m, 1H), 1.35 (app. q, J=6.1, 7.7 Hz, 1H), 1.10 (ddd, J=5.1, 5.1, 2.25, 1H), 0.76 (s, 9H), −0.02 (s, 3H), −0.04 (s, 3H); ¹³C NMR (125 MHz, CDCl₃): δ 205.4, 138.7, 128.7, 128.4, 127.3, 91.9 (d, J=189.2 Hz), 60.7 (d, J=19.9 Hz), 60.38, 54.3, 39.9, 25.9, 25.7, 18.2, 15.5, −5.61, −5.64; ¹⁹F NMR (376 MHz, CDCl₃): δ −178.4 (dddd, J=48.8, 22.1, 2.8, 2.8 Hz, 1F); HRMS-ESI (m/z) [M+H]+ calcd for C₂₇H₃₆FNO₂Si=454.2578, found=454.2550.

9b: ¹H NMR (400 MHz, CDCl₃): δ 7.37 (d, J=6.2 Hz, 4H), 7.30 (t, J=7.3 Hz, 4H), 7.22 (app. t, J=7.3 Hz, 1H), 5.03 (ddd, J=48.4, 6.9, 2.2 Hz, 1H), 4.18 (d, J=10.7 Hz, 1H), 3.91 (d, J=13.5 Hz, 2H), 3.8-3.65 (m, 4H), 2.29 (m, 1H), 1.36 (m, 1H), 0.94 (app. dd, J=6.1, 5.0 Hz, 1H, 0.79 (s, 9H), −0.02 (s, 3H), −0.03 (s, 3H); ¹³C NMR (125 MHz, C₆D₆): δ 204.7 (d, J=15.0 Hz), 140.0, 128.8, 128.2, 127.0, 92.8 (d, J=203.0 Hz), 60.1, 54.1 (d, J=3.1 Hz), 53.9 (d, J=14.1 Hz), 35.5, 28.5 (d, J=3.9 Hz), 25.6, 18.1, 6.1, −5.81, −5.93; ¹⁹F NMR (376 MHz, CDCl₃): δ≥−219.7 (dd, J=48.5, 2.9 Hz, 1F); HRMS-ESI (m/z) [M+H]+ calcd for C₂₇H₃₆FNO₂Si=454.2578, found=454.2554.

Example 20

(1R,2R,3S,4R,5S)-1-[((1,1-Dimethylethyl)dimethylsilyloxy)methyl]-4-(dibenzylamino)-3-fluorobicyclo[3.1.0]hexan-2-ol, Compound 10a and (1R,2S,3S,4R,5S)-1-[((1,1-Dimethylethyl)dimethylsilyloxy)methyl]-4-(dibenzylamino)-3-fluorobicyclo[3.1.0]hexan-2-ol, Compound 10b

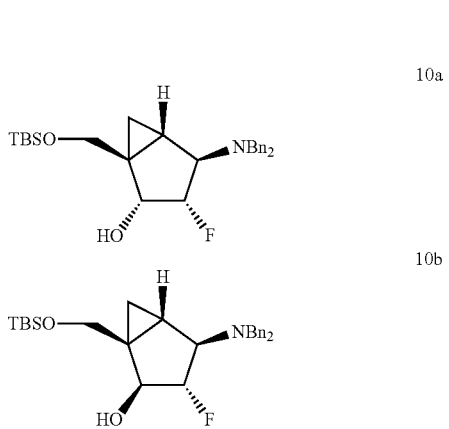

To a solution of 9a (139.8 mg, 0.308 mmol) in 1:1 methanol/dichloromethane (1.66 mL) was added sodium borohydride (11.7 mg, 0.308 mmol) at 0° C. After 30 min, the reaction mixture was concentrated. The residue was dissolved in dichloromethane and partitioned with water. The organic layer was separated and the water layer further extracted with dichloromethane (5×). The combined organic layers were dried with sodium sulfate, filtered, and concentrated in vacuo. The crude residue was separated by flash column chromatography on silica gel (gradient: 5% to 15% ethyl acetate in hexanes). The alcohols Compound 10a (116.0 mg, 0.255 mmol, 83%) and Compound 10b (16.2 mg, 0.036 mmol, 12%) were isolated as white solids.

10a: $^1$H NMR (400 MHz, $C_6D_6$): δ 7.36 (d, J=7.3 Hz, 4H), 7.19 (t, J=7.9 Hz, 4H), 7.08 (t, J=7.4 Hz, 2H), 4.88-4.71 (dd, J=51.4, 6.32 Hz, 1H), 4.71-4.59 (m, 1H), 4.13 (d, J=10.7 Hz, 1H), 3.97 (d, J=13.6 Hz, 2H), 3.54 (d, J=22.7 Hz, 1H), 3.11 (d, J=13.6 Hz, 2H), 3.95 (d, J=10.8 Hz, 1H), 1.78 (dd, J=10.6, 4.2 Hz, 1H), 1.3-1.19 (m, 1H), 0.80 (s, 9H), 0.62-0.56 (m, 1H), 0.23-0.15 (m, 1H), −0.02 (s, 3H), −0.11 (s, 3H); $^{13}$C-NMR (100 MHz, $C_6D_6$): δ=139.9, 129.1, 128.6, 127.4, 93.1 (d, J=230.0 Hz), 73.1 (d, J=20.7 Hz), 66.0 (d, J=25.6 Hz), 64.7, 54.7, 36.5, 26.0, 23.7, 18.4, 10.4 (d, J=6.2 Hz), −5.4, −5.5; $^{19}$F NMR (376 MHz, $C_6D_6$): δ 140.1 (proton decoupled); HRMS-ESI (m/z) [M+H]$^+$ calcd for $C_{27}H_{38}FNO_2Si$=456.2734, found=456.2742.

10b: $^1$H NMR (400 MHz, $C_6D_6$): δ 7.51 (d, J=7.2 Hz, 4H), 7.27 (t, J=7.3 Hz, 4H), 7.16 (t, J=7.4 Hz, 2H), 5.38-5.20 (d, J=48.7 Hz, 1H), 4.51 (dd, J=17.7, 3.6 Hz, 1H), 4.20 (dd, J=3.6, 2.6 Hz, 1H), 4.09 (d, J=13.9 Hz, 2H), 3.95 (d, J=11.1 Hz, 1H), 3.63 (t, J=11.2 Hz, 2H), 3.60 (s, 1H), 3.15 (d, J=11.1 Hz, 1H), 1.48-1.41 (m, 1H), 0.82 (s, 9H), 0.43-0.37 (m, 1H), 0.37-0.29 (m, 1H), −0.06 (s, 3H), −0.12 (s, 3H); $^{19}$F NMR (376 MHz, $C_6D_6$): δ=162.9 (proton decoupled); HRMS-ESI (m/z) [M+H]$^+$ calcd for $C_{27}H_{38}FNO_2Si$=456.2734, found=456.2717.

Example 21

(1S,2R,3S,4R,5R)—N,N-Dibenzyl-4-[(1,1-dimethylethyl)dimethylsilyloxy)]-5-[((1,1-dimethyl-ethyl)dimethylsilyloxy)methyl]-3-fluorobicyclo[3.1.0]hexan-2-amine, Compound 11

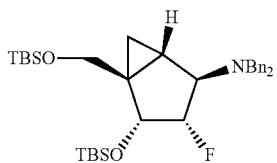

To a solution of the alcohol 10a (116.0 mg, 0.255 mmol) and imidazole (38.1 mg, 0.560 mmol) in dichloromethane (2.55 mL) was added tert-butyldimethylsilyl chloride (46.0 mg, 0.305 mmol) at 22° C. The reaction was stirred for 16 h before adding brine. The organic layer was removed and the aqueous layer further extracted with dichloromethane (3×). The combined organic layers were dried with sodium sulfate, filtered, and concentrated in vacuo. The crude residue was purified by flash column chromatography on silica gel (5% ethyl acetate in hexanes). Compound 11 was isolated as a white solid (132.8 mg, 0.233 mmol, 91%).

$^1$H NMR (400 MHz, CDCl$_3$): δ 7.40 (d, J=7.3 Hz, 4H), 7.33 (t, J=7.2 Hz, 4H), 7.25 (t, J=7.2 Hz, 2H), 4.87-4.71 (dd, J=43.4, 6.2 Hz, 1H), 4.71-4.66 (m, 1H), 4.19 (d, J=10.7 Hz, 1H), 4.02 (d, J=13.7 Hz, 2H), 3.42 (s, 1H), 3.39 (d, J=13.7 Hz, 2H), 3.36 (s, 1H), 3.10 (d, J=10.8 Hz, 1H), 1.31-1.23 (m, 1H), 0.97 (s, 9H), 0.92-0.86 (m, 1H), 0.78 (s, 9H), 0.55-0.48 (m, 1H), 0.17 (s, 3H), 0.16 (s, 3H), 0.01 (s, 3H), −0.06 (s, 3H); $^{13}$C NMR (100 MHz, CDCl$_3$): δ 139.7, 128.8, 128.2, 126.9, 92.5 (d, J=192.6 Hz), 72.7 (d, J=16.2), 66.3 (d, J=21.2 Hz), 64.5, 54.6, 36.2, 25.8 (d, J=10.8 Hz), 22.2 (d, J=2.3 Hz), 18.3 (d, J=24.2 Hz), 11.1 (d, J=4.8 Hz), −4.62, −4.83, −5.58, −5.61; $^{19}$F NMR (376 MHz, CDCl$_3$): δ 142.9 (proton decoupled); HRMS-ESI (m/z) [M+H]$^+$ calcd for $C_{33}H_{52}FNO_2Si_2$=470.3599, found=470.3563.

Example 22

(1S,2R,3S,4R,5R)-4-[(1,1-Dimethylethyl)dimethylsilyloxy)]-5-[((1,1-dimethylethyl)dimethyl-silyloxy)methyl]-3-fluorobicyclo[3.1.0]hexan-2-amine, Compound 12

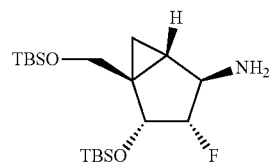

To a solution of Compound 11 (3.37 g, 5.91 mmol) in a small quantity of ethyl acetate was added palladium on carbon (337 mg, 10 wt %). Methanol (60 mL) was added, followed by ammonium formate (1.86 g, 29.6 mmol). The heterogeneous mixture was heated to reflux for 3 h. The solution was allowed to cool to 22° C. and then filtered through a pad of Celite. The Celite was further rinsed with a small quantity of methanol. The methanol was removed under reduced pressure and the crude residue was purified using flash column chromatography with a small quantity of silica gel (3% saturated ammonia/methanol in dichloromethane). Compound 12 was isolated as a colorless oil (2.26 g, 5.79 mmol, 98%).

$^1$H NMR (400 MHz, CDCl$_3$): δ 4.68 (dd, J=18.4, 5.4 Hz, 1H), 4.36-4.15 (dd, J=52.2, 5.4 Hz, 1H), 4.09 (d, J=10.6 Hz, 1H), 3.33 (d, J=15.3 Hz, 1H), 3.05 (d, J=10.6 Hz, 1H), 1.34 (bs, 2H), 1.16-1.11 (m, 1H), 1.10-1.03 (m, 1H), 0.91 (s, 9H), 0.89 (s, 9H), 0.56-0.48 (m, 1H), 0.10 (s, 3H), 0.09 (s, 3H), 0.04 (s, 3H), 0.03 (s, 3H); $^{13}$C NMR (100 MHz, CDCl$_3$): δ 98.3 (d, J=241.7 Hz), 71.6 (d, J=20.0 Hz), 63.9, 56.8 (d, J=47.2 Hz), 34.5, 26.4, 25.9, 25.8, 18.3, 18.2, 11.5 (d, J=10.0 Hz), −4.75, −4.86, −5.36, −5.40; $^{19}$F NMR (376 MHz, CDCl$_3$): δ 144.0 (proton decoupled); HRMSESI (m/z) [M+H]$^+$ calcd for C$_{19}$H$_{40}$FNO$_2$Si$_2$=390.2660, found=390.2637.

Example 23

1-((1S,2R,3S,4R,5R)-3-Fluoro-4-hydroxy-5-(hydroxymethyl)bicycle[3.1.0]hexan-2-yl)-5-methylpyrimidine-2,4(1H,3H)-dione, Compound 13

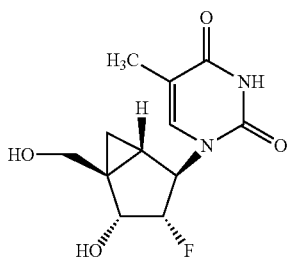

13

To the sodium salt of 3-methoxy-2-methylpropenoic acid (2.33 g, 16.92 mmol) in 1:1 dichloromethane/pentane was added dropwise oxalyl chloride (7.26 mL, 84.6 mmol) at 0° C. The reaction mixture was allowed to warm to 22° C. and further stirred for 4 h. The heterogeneous mixture was quickly filtered through a course porosity sintered glass funnel and the funnel was washed once with pentane. The filtrate was concentrated slowly under reduced pressure and the flask was briefly exposed to a separate vacuum (20 mmHg). The acid chloride was dissolved in toluene (50 mL) and silver cyanate (3.04 g, 20.30 mmol) was added. The heterogeneous mixture was refluxed under an argon atmosphere for 1.5 h before allowing to cool to 22° C. The precipitate was allowed to settle and the supernatant was transferred via cannula to a flask fitted with a rubber septum. The precipitate was further washed with a small quantity of dry dichloromethane and also transferred to the same flask. The solution was cooled to −78° C. and Compound 12 (2.20 g, 5.64 mmol) in dichloromethane (10 mL) was added dropwise over 3 min. The solution was allowed to warm to 22° C. and stirred for 16 h. Ethanol (5 mL) was added and the reaction mixture was concentrated in vacuo. The intermediate has an R$_f$ value of 0.30 by thin layer chromatography (2% ethyl acetate in dichloromethane). To the crude residue was added ethanol (37 mL) and 2M HCl (12 mL). The reaction mixture was refluxed for 20 h. The reaction was cooled to 22° C. and the solution was concentrated. The residual water was azeotroped four times with ethanol (100 mL). The crude residue was dissolved in ethanol and concentrated in vacuo onto a small quantity of silica gel before purifying by flash column chromatography (gradient: 5% to 10% methanol in dichloromethane). Compound 13 (1.37 g, 5.06 mmol, 90%) was isolated as a white solid.

$^1$H NMR (500 MHz, (CD$_3$)$_2$SO): δ 11.29 (s, 1H), 7.86 (s, 1H), 5.14 (t, J=4.9 Hz, 1H), 4.97 (d, J=7.5 Hz, 1H), 4.75 (d, J=17.8 Hz, 1H), 4.58-4.40 (m, 2H), 4.05 (dd, J=11.4, 5.1 Hz, 1H), 3.06 (dd, J=11.5, 4.7 Hz, 1H), 1.71 (s, 3H), 1.38-1.27 (m, 1H), 1.03-0.91 (m, 1H), 0.73-0.60 (m, 1H); $^{13}$C NMR (125 MHz, (CD$_3$)$_2$SO): δ 164.2, 151.2, 137.7, 109.4, 95.9 (d, J=190.0 Hz), 70.3 (d, J=38.2 Hz), 61.9, 60.0 (d, J=26.2 Hz), 36.6, 21.4, 12.7, 11.4 (d, J=6.2 Hz); $^{19}$F-NMR (376 MHz, (CD$_3$)$_2$SO): δ=−186.5 (app. dtd, J=45.0, 18.8, 3.8 Hz, 1F); HRMS-ESI (m/z) [M+H]$^+$ calcd for C$_{12}$H$_{15}$FN$_2$O$_4$=271.1094, found=271.1115.

Example 24

(1R,2S,3R,4R,5S)-1-[((1,1-Dimethylethyl)dimethylsilyloxy)methyl]-4-(dibenzylamino)-3-fluorobicyclo[3.1.0]hexan-2-ol, Compound 14

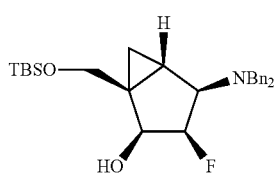

14

To a solution of Compound 9b (72.2 mg, 0.159 mmol) in 1:1 methanol/dichloromethane (1.59 mL) was added sodium borohydride (12.1 mg, 0.320 mmol) at 22° C. The reaction mixture was stirred for 2 h before removing the solvent under reduced pressure. The residue was partitioned between aqueous saturated sodium bicarbonate and dichloromethane. The organic layer was removed and the aqueous layer was extracted with dichloromethane (4×). The combined organic layers were dried with sodium sulfate, filtered, and concentrated in vacuo. The crude residue was purified by flash column chromatography on silica gel (10% ethyl acetate in hexanes, R$_f$=0.30). Compound 14 (68.0 mg, 0.149 mmol, 94%) was isolated as a white solid.

$^1$H NMR (400 MHz, CDCl$_3$): δ 7.39 (d, J=7.2 Hz, 4H), 7.31 (t, J=7.7 Hz, 4H), 7.22 (t, J=7.2 Hz, 2H), 4.86-4.67 (dt, J=49.2 Hz, 5.8, 1H), 4.27-4.18 (m, 1H), 4.00 (d, J=14.1 Hz, 2H), 3.86 (d, J=14.2 Hz, 2H), 3.51 (dd, J=5.1, 2.0 Hz, 1H), 3.43 (t, J=5.7 Hz, 1H), 1.54 (dt, J=9.0, 3.7 Hz, 1H), 0.84 (s, 9H), 0.69 (dd, J=8.6, 5.9 Hz, 1H), 0.06 (dd, J=5.7, 4.1 Hz, 1H), 0.03 (s, 3H), 0.003 (s, 3H); $^{13}$C NMR (100 MHz, CDCl$_3$): δ 140.7, 128.7, 128.2, 126.7, 97.5 (d, J=197.3 Hz), 72.3 (d, J=15.9 Hz), 64.4, 60.6 (d, J=14.9 Hz), 55.7 (d, J=3.2 Hz), 32.9 (d, J=2.3 Hz), 25.8, 24.3 (d, J=2.7 Hz), 18.2, 13.5, −5.48, −5.52; $^{19}$F NMR (376 MHz, CDCl$_3$): δ 113.8 (d, J=49, 1F); HRMS-ESI (m/z) [M+H]$^+$ calcd for C$_{27}$H$_{38}$FNO$_2$Si=456.2734, found=456.2712.

Example 25

(1R,2R,3R,4R,5S)-1-[((1,1-Dimethylethyl)dimethylsilyloxy)methyl]-4-(dibenzylamino)-3-fluorobicyclo[3.1.0]hexan-2-yl-4-nitrobenzoate, Compound 15

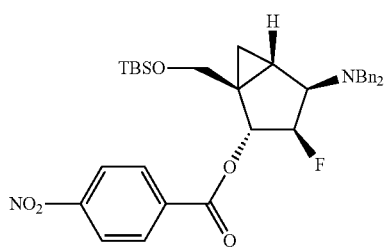

To a solution of Compound 14 (53.0 mg, 0.116 mmol), triphenylphosphine (81.0 mg, 0.465 mmol), and 4-nitrobenzoic acid (77.8 mg, 0.465 mmol) in THF (0.89 mL) at 0° C., was slowly added diethyl azodicarboxylate (40% wt./toluene, 81.0 mg, 0.465 mmol). The reaction mixture was allowed to warm to 22° C. with stirring for 2 days. The solution was diluted with diethyl ether and saturated aqueous sodium bicarbonate was added. The organic layer was separated and the aqueous layer further extracted with diethyl ether (4×). The combined organic extracts were washed with brine, dried with magnesium sulfate, filtered, and concentrated in vacuo. The crude residue was purified by flash column chromatography on silica gel (5% ethyl acetate in hexanes, $R_f$=0.25). Compound 15 (56.7 mg, 0.094 mmol, 81%) was isolated as a colorless oil.

$^1$H NMR (400 MHz, CDCl$_3$): δ 8.31 (d, J=9.0 Hz, 2H), 8.24 (d, J=9.0 Hz, 2H), 7.42 (d, J=7.1 Hz, 4H), 7.32 (t, J=7.6 Hz, 4H), 7.24 (t, J=7.3 Hz, 2H), 6.30 (dd, J=21.7, 5.4 Hz, 1H), 5.08-4.86 (dt, J=50.4, 6.4 Hz, 1H), 4.15 (d, J=13.7 Hz, 2H), 4.00 (d, J=10.8 Hz, 1H), 3.88 (d, J=13.6 Hz, 2H), 3.57 (d, J=6.8 Hz, 1H), 3.36 (d, J=10.4 Hz, 1H), 1.64 (dt, J=8.7, 4.0 Hz, 1H), 0.76 (s, 9H), 0.75-0.68 (m, 1H), 0.59 (t, J=4.6 Hz, 1H), −0.04 (s, 3H), −0.09 (s, 3H); $^{13}$C NMR (100 MHz, CDCl$_3$): δ 164.3, 150.6, 140.3, 135.6, 130.9, 129.1, 128.8, 128.2, 126.8, 123.5, 101.3 (d, J=196.1 Hz), 81.2 (d, J=25.6 Hz), 64.2, 57.4 (d, J=15.6 Hz), 54.5 (d, J=3.6 Hz), 31.9 (d, J=8.6 Hz), 25.7, 25.4 (d, J=2.8 Hz), 18.2, 11.4, −5.70, −5.71; $^{19}$F NMR (376 MHz, CDCl$_3$): δ 125.62 (dd, J=50.6, 23.4 Hz, 1F); HRMS-ESI (m/z) [M+H]$^+$ calcd for C$_{34}$H$_{41}$FN$_2$O$_5$Si=605.2847, found=605.2821.

Example 26

(1R,2R,3R,4R,5S)-1-[((1,1-Dimethylethyl)dimethylsilyloxy)methyl]-4-(dibenzylamino)-3-fluorobicyclo[3.1.0]hexan-2-ol, Compound 16

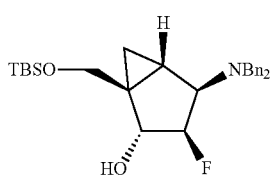

To a solution of Compound 15 (54.4 mg, 0.090 mmol) in dry methanol (3.0 mL) was added potassium carbonate (130.0 mg, 0.941 mmol). The heterogeneous solution was stirred at 22° C. for 2 days. The solvent was removed and the crude residue was partitioned between water and dichloromethane. The organic layer was removed and the aqueous layer was further extracted with dichloromethane (5×). The combined organic layers were dried with magnesium sulfate, filtered, and then concentrated in vacuo. The crude residue was purified by flash chromatography on silica gel (40% ethyl acetate in hexanes). Compound 16 (38.0 mg, 0.083 mmol, 93%) was isolated as a colorless solid.

$^1$H NMR (400 MHz, CDCl$_3$): δ 7.41 (d, J=7.3 Hz, 4H), 7.32 (t, J=7.23 Hz, 4H), 7.23 (t, J=7.23 Hz, 2H), 4.89 (bdd, J=24, 5.63 Hz, 1H), 4.77-4.55 (ddd, J=50.7, 6.5, 6.5 Hz, 1H), 4.01 (d, J=13.83 Hz, 2H), 3.88-3.77 (m, 3H), 3.59 (d, J=10.63 Hz, 1H), 3.49 (d, J=6.83 Hz, 1H), 2.50 (bs, 1H), 1.64 (ddd, J=8.4, 4.1, 4.1 Hz, 1H), 0.84 (s, 9H), 0.56-0.41 (m, 2H), 0.04 (s, 3H), −0.002 (s, 3H); $^{13}$C NMR (100 MHz, CDCl$_3$): δ 140.6, 128.7, 128.2, 126.8, 103.7 (d, J=192.3 Hz), 78.7 (d, J=23.4 Hz), 66.2, 57.7 (d, J=15.8 Hz), 54.6 (d, J=3.6 Hz), 32.8 (d, J=10.3 Hz), 25.8, 23.8 (d, J=3.1 Hz), 18.2, 11.5, −5.52, −5.55; $^{19}$F NMR (376 MHz, CDCl$_3$): δ 124.62 (ddd, J=53.8, 25.4, 2.6 Hz, 1F); HRMS-ESI (m/z) [M+H]$^+$ calcd for C$_{27}$H$_{38}$FNO$_2$Si=456.2734, found=605.2703.

Example 27

(1R,2R,3R,4R,5S)-1-[((1,1-Dimethylethyl)dimethylsilyloxy)methyl]-4-(bis(phenylmethyl)-amino)-3-fluorobicyclo[3.1.0]hexan-2-yl-(R)-3,3,3-trifluoro-2-methoxy-2-phenylpropanoate, Compound 17

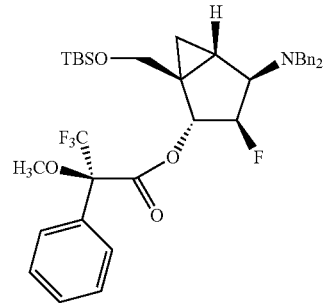

To a solution of (R)-(+)-α-methoxy-α-trifluoromethylacetic acid (26.2 mg, 0.112 mmol) and dimethylformamide (1 μL) in dichloromethane (0.75 mL) was added dropwise oxalyl chloride (32 μL, 0.373 mmol). The solution was stirred at 22° C. for 30 min and then concentrated in vacuo. The acid chloride was left under high vacuum (1.0 mm Hg) for a short period of time. The acid chloride was dissolved in dichloromethane (0.15 mL) and subsequently added dropwise to a solution of Compound 16 (34.0 mg, 0.075 mmol) in pyridine (0.15 mL). Upon solidification of the reaction mixture, dichloromethane (0.45 mL) was added and the resulting solution was stirred for 1 h at 22° C. The solution was purified directly by flash column chromatography on silica gel (gradient: 30% to 100% dichloromethane in hexanes). Compound 17 (45.1 mg, 0.067 mmol, 90%) was isolated as a colorless oil.

$^1$H NMR (400 MHz, CDCl$_3$): δ 7.65-7.55 (m, 2H), 7.47-7.39 (m, 7H), 7.33 (t, J=7.2 Hz, 4H), 7.28-7.21 (m,

2H), 6.34 (dd, J=21.5, 5.8 Hz, 1H), 4.99-4.77 (ddd, J=50.5, 6.4, 6.4 Hz, 1H), 4.19 (d, J=13.7 Hz, 2H), 4.05 (d, J=10.8 Hz, 1H), 3.88 (d, J=13.6 Hz, 2H), 3.60 (s, 3H), 3.53 (d, J=6.8 Hz, 1H), 3.16 (d, J=10.9 Hz, 1H), 1.62 (ddd, J=8.8, 4.1, 4.1 Hz, 1H), 0.80 (s, 9H), 0.59 (dd, J=6.9, 6.9 Hz, 1H), 0.42 (dd, J=6.2, 4.6 Hz, 1H), 0.03 (s, 3H), −0.05 (s, 3H); $^{13}$C NMR (100 MHz, CDCl$_3$): δ 166.2, 140.3, 132.3, 129.7, 128.8, 128.5, 128.2, 127.4, 126.8, 123.5 (d, J=290 Hz), 101.0 (d, J=195.3 Hz), 81.3 (d, J=25.2 Hz), 63.7, 57.1 (d, J=15.5 Hz), 55.3, 54.4 (d, J=3.3 Hz), 31.6 (d, J=8.7 Hz), 25.7, 25.6 (d, J=2.8 Hz), 18.2, 10.9, −5.67, −5.79; $^{19}$F NMR (376 MHz, CDCl$_3$): δ 124.8 (bdd, J=50.4, 21.3 Hz, 1F), −72.1 (s, 3F); HRMS-ESI (m/z) [M+H]$^+$ calcd for C$_{37}$H$_{45}$F$_4$NO$_4$Si=672.3132, found=672.3115.

Example 28

(1R,2R,3R,4R,5S)-4-Amino-1-[((1,1-dimethylethyl) dimethylsilyloxy)methyl]-3-fluorobicyclo[3.1.0] hexan-2-yl-(R)-3,3,3-trifluoro-2-methoxy-2-phenyl-propanoate, Compound 18

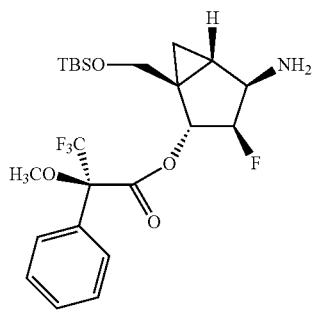

Compound 17 (210.0 mg, 0.313 mmol) in methanol (3.0 mL) was added to palladium on carbon (10% wt., 21.0 mg) prewetted with a small quantity of THF. Ammonium formate (100.0 mg, 1.586 mmol) was added and the resulting solution was refluxed for 6 h. The heterogeneous solution was filtered through a pad of Celite. The filtrate was concentrated in vacuo and the crude residue purified by flash column chromatography on silica gel (2% ammonia/methanol (saturated) in dichloromethane). Compound 18 (141.7 mg, 0.288 mmol, 93%) was isolated as a colorless oil.

$^1$H NMR (400 MHz, CDCl$_3$): δ 7.56-7.48 (m, 2H), 7.43-7.35 (m, 3H), 6.02 (dd, J=19.2, 6.3 Hz, 1H), 4.65-4.42 (ddd, J=52.5, 5.8, 5.8, 1H), 3.97 (d, J=10.7 Hz, 1H), 3.55 (s, 3H), 3.44 (d, J=5.4 Hz, 1H), 3.07 (dd, J=10.7, 1.6 Hz, 1H), 3.46 (ddd, J=8.6, 4.6, 4.6, 1H), 1.46-1.21 (brs, 2H), 0.91 (s, 9H), 0.77-0.62 (m, 2H), 0.08 (s, 3H), 0.04 (s, 3H); $^{13}$C NMR (100 MHz, CDCl$_3$): δ 166.2, 132.2, 129.7, 128.4, 127.4, 123.4 (d, J=288 Hz), 96.7 (d, J=189.0 Hz), 84.8 (d, J=27.3 Hz), 79.2 (d, J=24.7 Hz), 63.2, 55.3, 51.4 (d, J=18.1 Hz), 30.9 (d, J=7.7 Hz), 26.7 (d, J=2.3 Hz), 25.9, 18.2, 11.1, −5.53, −5.55; $^{19}$F NMR (376 MHz, CDCl$_3$): δ 119.8 (ddd, J=52.5, 19.1, 4.1 Hz, 1F), −72.2 (s, 3F); HRMS-ESI (m/z) [M+H]$^+$ calcd for C$_{23}$H$_{33}$F$_4$NO$_4$Si=492.2193, found=492.2190.

Example 29

1-((1S,2R,3R,4R,5R)-3-Fluoro-4-hydroxy-5-(hydroxymethyl)bicycle[3.1.0]hexan-2-yl)-5-methylpyrimidine-2,4(1H,3H)-dione, Compound 19

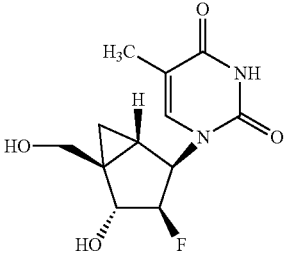

To the sodium salt of 3-methoxy-2-methylpropenoic acid (114.4 mg, 0.828 mmol) in 1:1 dichloromethane/pentane (1.10 mL) was added oxalyl chloride (0.36 mL, 4.14 mmol) dropwise at 0° C. The solution was stirred for 1 h before rapidly filtering through a course sintered glass funnel. The filtrate was slowly concentrated in vacuo and the residue left briefly on a vacuum pump (20 mmHg). The acid chloride was dissolved in toluene (2.76 mL) and silver cyanate (149.0 mg, 0.994 mmol) was added. The heterogeneous mixture was refluxed under an argon atmosphere for 1.5 h before allowing to cool to 22° C. The precipitate was allowed to settle and the supernatant was transferred via syringe to a flask fitted with a rubber septum. The precipitate was further washed with a small quantity of dry dichloromethane and also transferred to the same flask. The solution was cooled to −78° C. and Compound 18 (135.7 mg, 0.276 mmol) in dichloromethane (1 mL) was added dropwise over 3 min. The solution was allowed to warm to 22° C. and stirred for 16 h. Ethanol (1 mL) was added and the reaction mixture was concentrated in vacuo.

To the crude residue was added ethanol (1.8 mL) and 2M HCl (0.6 mL) and the reaction was refluxed for 20 h. The reaction was cooled to 22° C. and the solution was concentrated. The residual water was azeotroped four times with ethanol (100 mL). The crude residue was dissolved in dry methanol (4 mL) and an abundance of potassium carbonate was added. The heterogeneous solution was heated to 55° C. for 8 h. The solution was slowly acidified to pH 1 with concentrated hydrochloric acid and then concentrated in vacuo. Residual water was removed from the crude residue by azeotroping once with a small quantity of ethanol. The solid was dissolved in hot ethanol and concentrated onto a small quantity of silica gel, which was subsequently applied to a silica gel column and separated using 10% methanol in ethyl acetate. Compound 19 (37.0 mg, 0.137 mmol, 50%) was isolated as a white solid.

$^1$H NMR (500 MHz, C$_6$D$_6$/MeOD 3.5:1): δ 8.11 (s, 1H), 5.08 (d, J=6.7 Hz, 1H), 4.72 (dd, J=23.4, 6.4, 1H), 4.56 (ddd, J=50.5, 6.5, 6.5 Hz, 1H), 4.28 (d, J=11.7 Hz, 1H), 2.99 (dd, J=11.7, 1.9 Hz, 1H), 1.84 (d, J=1.1 Hz, 3H), 1.13 (ddd, J=8.8, 3.8, 3.8 Hz, 1H), 0.64 (dd, J=6.4, 4.0, 1H), 0.45 (dd, J=7.7, 7.7 Hz, 1H); $^{13}$C NMR (100 MHz, MeOD): δ 166.3, 153.4, 139.9, 111.3, 99.0 (d, J=192.9 Hz), 75.4 (d, J=23.6 Hz), 63.6, 55.3 (d, J=16.2 Hz), 34.5 (d, J=9.9 Hz), 22.6, 12.3, 11.6; $^{19}$F NMR (376 MHz, MeOD): δ 122.7 (app. dd, J=51.7, 25.4 Hz, 1F); HRMS-ESI (m/z) [M+H]$^+$ calcd for C$_{12}$H$_{15}$FN$_2$O$_4$=271.1094, found=271.1085.

Example 30

2'F-NMC DMTr Nucleoside, 20

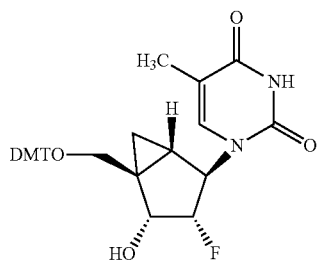

Dimethoxytrityl chloride (0.65 mmol, 217 mg) was added to a solution of Compound 13 (0.54 mmol, 146 mg) in pyridine (2.5 mL). The reaction was stirred at 22° C. for 4 h after which it was diluted with ethyl acetate and the organic layer was washed with brine, dried (Na$_2$SO$_4$) and concentrated in vacuo. Purification of the residue by column chromatography (silica gel, eluting with a gradient of 25 to 80% ethyl acetate in hexanes) provided the DMT protected nucleoside, Compound 20 (235 mg, 75%) as a white solid.

$^1$H NMR (500 MHz, C$_6$D$_6$): δ 8.13 (bs, 1H), 7.52 (dd, J=8.4, 1.3 Hz, 2H), 7.20-7.10 (m, 2H), 7.08 (ddt, J=9.9, 9.0, 2.2 Hz, 4H), 7.06-6.99 (m, 2H), 6.76-6.71 (m, 4H), 4.75 (d, J=26.5 Hz, 1H), 4.76-4.66 (m, 1H), 4.15 (ddd, J=50.5, 6.0, 1.2 Hz, 1H), 3.88 (d, J=9.9 Hz, 1H), 3.254 (s, 3H), 3.253 (s, 3H), 2.55 (d, J=10.1 Hz, 1H), 1.55 (d, J=1.2 Hz, 3H), 1.49 (dd, J=10.8, 3.3 Hz, 1H), 0.70-0.63 (m, 1H), 0.61-0.54 (m, 1H), 0.03 (m, 1H); $^{13}$C-NMR (125 MHz, C$_6$D$_6$): δ=162.7, 159.0, 158.9, 149.9, 145.2, 135.8, 135.6, 135.4, 130.2, 130.1, 128.2, 128.1, 127.2, 127.0, 113.4, 113.3, 110.7, 95.3 (d, J=189.4 Hz), 86.6, 71.8 (d, J=17.4 Hz), 67.5, 63.8, 60.3 (d, J=26.8 Hz), 54.4, 34.7, 25.4, 22.2, 12.3, 9.68 (d, J=7.4 Hz); $^{19}$F NMR (376 MHz, C$_6$D$_6$): δ-187.7 (bdt, J=51.8, 17.7 Hz, 1F); HRMS-ESI (m/z) [M-C$_{21}$H$_{19}$O$_2$+H]$^+$ calcd for C$_{33}$H$_{33}$FN$_2$O$_6$=271.1094, found=271.1079.

Example 31

2'F-NMC Amidite, Compound 21

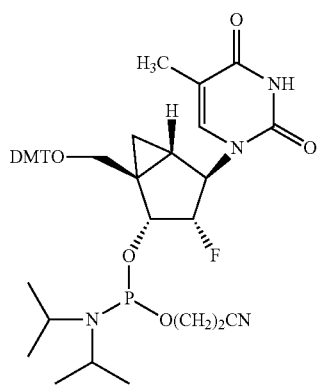

To a solution of Compound 20 (0.41 mmol, 230 mg) and tetrazole (0.32 mmol, 0.02 g) in DMF (2 mL) at 0° C. was added 1-methylimidazole (1 drop) and 2-cyanoethyl tetraisopropyl phosphorodiamidite (0.61 mmol, 0.18 mL). The reaction was warmed to 22° C. and stirred for five h. The reaction was diluted with ethyl acetate and the organic layer was washed with brine, dried (Na$_2$SO$_4$) and concentrated under reduced pressure. Purification of the residue by column chromatography (silica gel, eluting with 33 to 60% ethyl acetate in hexanes) provided the DMT phosphoramidite, Compound 21 (0.29 g, 90%).

$^1$H NMR (300 MHz, CDCl$_3$): δ 7.71 (s, 1H), 7.63 (s, 1H), 7.40 (t, J=6.2 Hz, 6H), 7.34-7.19 (m, 29H), 6.90-6.74 (m, 13H), 5.17-4.98 (m, 3H), 4.86-4.50 (m, 2H), 4.12 (q, J=7.2 Hz, 2H), 3.89 (dd, J=5.5, 10.1 Hz, 4H), 3.82-3.75 (m, 20H), 3.68-3.40 (m, 9H), 2.79 (d, J=10.0 Hz, 3H), 2.61 (t, J=6.2 Hz, 3H), 2.40 (t, J=6.5 Hz, 4H), 1.37-1.10 (m, 58H), 1.05 (d, J=6.8 Hz, 8H); $^{31}$P NMR (121 MHz, CDCl$_3$): δ 151.71 (d, J=10.9 Hz, 1P), 150.39 (d, J=9.7 Hz, 1P); HRMS-ESI (m/z) [M-H]$^-$ calcd for C$_{42}$H$_{49}$FN$_4$O$_7$P=771.3328, found=771.3351.

Example 32

Ara-F-NMC DMTr Nucleoside, Compound 22

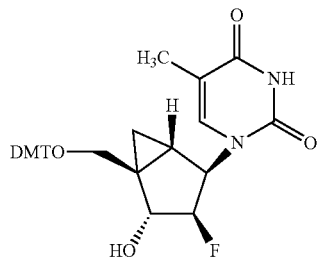

Dimethoxytrityl chloride (0.13 mmol, 42 mg) was added to a solution of Compound 19 (0.11 mmol, 30 mg) in pyridine (1.1 mL). The reaction was stirred at 22° C. for 4 h after which it was diluted with ethyl acetate and the organic layer was washed with brine, dried (Na$_2$SO$_4$) and concentrated in vacuo. Purification of the residue by column chromatography (silica gel, eluting with a gradient of 25 to 80% ethyl acetate in hexanes) provided Compound 22 (45 mg, 71%) as a white solid.

$^1$H NMR (500 MHz, C$_6$D$_6$): δ 8.49 (bs, 1H), 7.47 (dd, J=8.3, 1.2 Hz, 2H), 7.32 (m, 5H), 7.20-7.09 (m, 2H), 7.03-6.98 (m, 1H), 6.70 (d, J=8 Hz, 4H), 5.04 (d, J=7.0 Hz, 1H), 4.71 (dd, J=23.7, 5.9 Hz, 1H), 4.20 (ddd, J=50.5, 6.3, 6.3 Hz, 1H), 3.68 (d, J=10.1 Hz, 1H), 3.250 (s, 3H), 3.248 (s, 3H), 2.65 (d, J=9.4 Hz, 1H), 1.62 (d, J=1.1 Hz, 3H), 1.46 (bs, 1H), 0.70 (ddd, J=8.9, 3.6, 3.6 Hz, 1H), 0.06 (dd, J=6.2, 3.9 Hz, 1H), −0.06 (app. dd, J=7.7, 7.2 Hz, 1H); $^{13}$C NMR (125 MHz, C$_6$D$_6$): δ 162.8, 159.01, 159.00, 151.0, 144.9, 136.1, 135.7, 135.6, 130.12, 130.11, 128.2, app. 128.3 (hidden under solvent), 127.2, 127.0, 113.4, 110.8, 98.1, 97.3 (d, J=194.7 Hz), 86.7, 75.9 (d, J=24.3 Hz), 64.2, 54.5, 31.5 (d, J=9.8 Hz), 22.3, 12.3, 10.0; $^{19}$F NMR (376 MHz, C$_6$D$_6$): δ-205.3 (app. ddd, J=51.0, 23.4, 2.6 Hz, 1F); HRMS-ESI (m/z) [M−C$_{21}$H$_{19}$O$_2$+H]$^+$ calcd for C$_{33}$H$_{33}$FN$_2$O$_6$=271.1094, found=271.1063.

Example 33

AraF-NMC Amidite, Compound 23

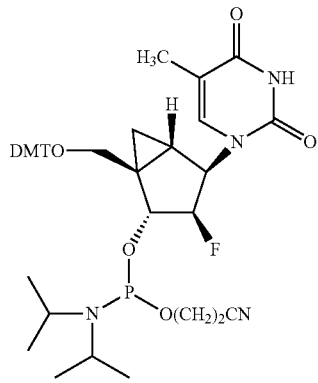

To a solution of Compound 22 (0.07 mmol, 41 mg) and DIPEA (0.15 mmol, 0.02 mL) in dichloromethane (0.7 mL) at 0° C. was added chloro 2-cyanoethyldiisopropyl phosphoramidite (0.14 mmol, 0.03 mL). The reaction was warmed to 22° C. and stirred for 20 min. The reaction was quenched with additional DIPEA (0.1 mL) and methanol (0.1 mL) and the solvents were evaporated in vacuo. Purification of the residue by column chromatography (silica gel, eluting with 33 to 60% ethyl acetate in hexanes) provided the DMT phosphoramidite, Compound 23 (31 mg, 56%).

$^1$H NMR (300 MHz, CDCl$_3$): δ 7.82 (s, 1H), 7.70 (s, 1H), 7.46-7.17 (m, 28H), 6.91-6.74 (m, 11H), 5.40-5.24 (m, 4H), 5.06 (d, J=5.1 Hz, 2H), 4.90-4.59 (m, 2H), 3.94-3.74 (m, 18H), 3.57 (dt, J=6.4, 11.5 Hz, 5H), 3.42 (q, J=6.7 Hz, 3H), 2.80 (d, J=9.7 Hz, 3H), 2.59 (t, J=6.3 Hz, 2H), 2.37 (t, J=6.3 Hz, 3H), 1.46-1.09 (m, 42H), 1.06-0.93 (m, 7H); $^{19}$F NMR (282 MHz, CDCl$_3$): δ−203.19 (d, J=8.5 Hz, 1F), 203.68 (d, J=5.6 Hz, 1F); $^{31}$P NMR (121 MHz, CDCl$_3$): δ 151.95 (d, J=4.8 Hz, 1P), 151.16 (m, 1P); HRMS-ESI (m/z) [M−H]$^−$ calcd for C$_{42}$H$_{49}$FN$_4$O$_7$P=771.3328, found=771.3341.

Example 34

(1R,5R)-1-[(((1,1-Dimethylethyl)dimethylsilyloxy)methyl)]bicyclo[3.1.0]hex-3-en-2-one, Compound 24

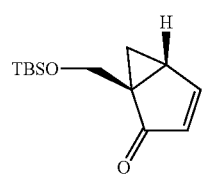

To a solution of Compound 6 (0.647 g, 2.69 mmol) in dichloromethane (13.5 mL) was added tert-butyldimethylsilyl triflate (TBSOTf, 0.742 mL, 3.23 mmol). Triethylamine (1.12 mL, mmol) was added dropwise and the reaction was subsequently stirred at 22° C. for 1 h. The reaction mixture was partitioned over a saturated aqueous solution of sodium bicarbonate. The organic layer was removed and the aqueous layer was further extracted with dichloromethane (4×). The combined extracts were dried over anhydrous sodium sulfate, filtered, and concentrated in vacuo. The crude residue was submitted to a short column of silica pretreated with 3% triethylamine in hexanes. The residue was eluted with 1% triethylamine in hexanes. The fractions were concentrated in vacuo to give a colorless liquid that was dissolved in dimethyl sulfoxide (26.9 mL). To the solution was added palladium(II) acetate (60.4 mg, 0.269 mmol) and the flask head-space was purged with molecular oxygen before fixing the top with a balloon filled with oxygen. The flask was heated in an oil bath to 55° C. for 2 d. After cooling to 22° C., the reaction mixture was extracted directly with hexanes (5×). The combined hexanes fractions were dried with anhydrous sodium sulfate, filtered, and concentrated in vacuo. The crude residue was purified by flash column chromatography on silica gel (gradient: 3% to 8% ethyl acetate in hexanes, R$_f$=0.3). Compound 24 (0.495 g, 2.08 mmol, 77%/2 steps) was isolated as a colorless oil.

$^1$H NMR (400 MHz, C$_6$D$_6$): δ 6.90 (dd, J=5.7, 2.8 Hz, 1H), 5.42 (d, J=5.7 Hz, 1H), 4.22 (d, J=10.5 Hz, 1H), 3.68 (d, J=10.5 Hz, 1H), 2.02 (ddd, J=6.8, 2.9, 2.9, 1H), 1.11 (app. dd, J=6.9, 3.3 Hz, 1H), 0.93-0.82 (m, 10H), 0.022 (s, 6H); $^{13}$C NMR (100 MHz, C$_6$D$_6$): δ 204.5, 162.0, 128.8, 60.0, 37.6, 36.1, 26.3, 26.1, 18.5, −5.27, −5.34; HRMSESI (m/z) [M+Na]$^+$ calcd for C$_{13}$H$_{22}$O$_2$Si=261.1287, found=261.1300.

Example 35

N-(9-((1S,2S,5R)-5-[(((1,1-Dimethylethyl)dimethylsilyloxy)methyl]-4-oxobicyclo[3.1.0]hexan2-yl)-9H-purin-6-yl)benzamide, Compound 25

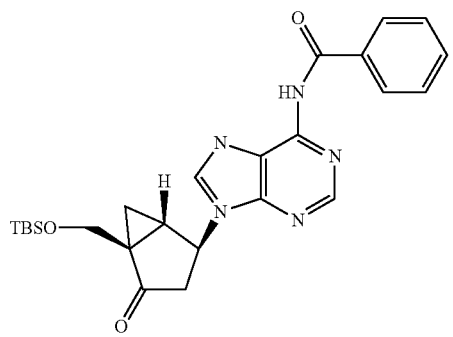

Compound 24 (100 mg, 0.42 mmol), N-methylimidazole (3.35 μL, 0.042 mmol), and N-(9H-purin-6-yl)benzamide (120 mg, 0.50 mmol) were dissolved in dimethyl sulfoxide (0.42 mL) in a sealed pressure vessel. The reaction mixture was heated to 90° C. in a μwave reactor (120 W, 50 psi) for 12 h. The reaction mixture was allowed to cool to 22° C. before adding 5 mL of water. The heterogeneous mixture was briefly sonicated and then allowed to stand for 5 min before filtering. The precipitate was washed with a small quantity of water and then dissolved in dichloromethane. The solution was dried over anhydrous sodium sulfate, filtered, and concentrated in vacuo. The crude residue was purified by flash column chromatography on silica gel (gradient: 1% to 6% methanol in dichloromethane). The desired compound co-elutes with another isomer. A small quantity of diethyl ether was added after these fractions were concentrated and the desired adduct Compound 25 (47 mg, 98.5 μmol, 23%) crystallized out of solution slowly as colorless crystals.

$^1$H NMR (400 MHz, CDCl$_3$): δ 9.23 (s, 1H), 8.78 (s, 1H), 8.41 (s, 1H), 8.01 (d, J=7.5 Hz, 2H), 7.59 (t, J=7.5 Hz, 1H), 7.50 (t, J=6.9 Hz, 2H), 5.40 (d, J=7.1 Hz, 1H), 4.52 (d, J=11.1 Hz, 1H), 3.61 (d, J=11.0 Hz, 1H), 2.87 (ddd, J=18.9, 7.2, 1.8 Hz, 1H), 2.42 (dd, J=8.1, 4.3 Hz, 1H), 2.31 (bs, 1H), 2.29 (d, J=18.9 Hz, 1H), 1.53 (ddd, J=8.6, 6.2, 1.4 Hz, 1H), 1.21 (m, 2H), 0.88 (s, 9H), 0.10 (s, 3H), 0.07 (s, 3H); $^{13}$C NMR (100 MHz, CDCl$_3$): δ 208.2, 164.7, 152.7, 151.3, 149.7, 140.8, 133.8, 132.7, 128.8, 127.9, 122.9, 59.8, 50.5, 41.7, 39.7, 29.7, 25.9, 18.4, 16.1, −5.40, −5.53; HRMS-ESI (m/z) [M+H]$^+$ calcd for C$_{25}$H$_{31}$NO$_3$Si=478.2274, found=478.2251.

Example 36

Preparation of Compound 26

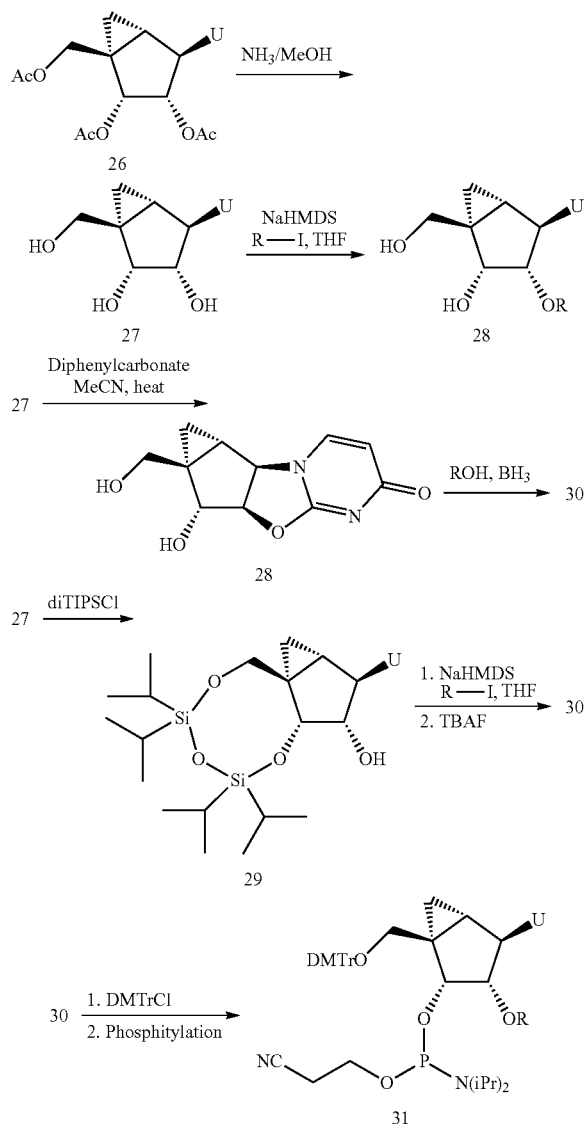

R = alkyl or substituted alky (such as for example methyl or methoxyethyl)

Compound 26 is prepared as per published procedures (Terrazas et al., *Organic Letters*, 2011, 13, 2888-2891). The DMT phosphoramidite, Compound 31, is prepared from Compound 30 as per the procedures illustrated in examples 30 and 31.

Example 37

Single Nucleotide Polymorphisms (SNPs) in the Huntingtin (HTT) Gene Sequence

SNP positions (identified by Hayden et al, WO/2009/135322) associated with the HTT gene were mapped to the HTT genomic sequence, designated herein as SEQ ID NO: 05 (NT_006081.18 truncated from nucleotides 1566000 to 1768000). The chart below provides SNP positions associated with the HTT gene and a reference SNP ID number from the Entrez SNP database at the National Center for Biotechnology Information (NCBI, http://www.ncbi.nlm.nih.gov/sites/-entrez?db=snp), incorporated herein by reference. The chart below furnishes further details on each SNP. The 'Reference SNP ID number' or 'RS number' is the number designated to each SNP from the Entrez SNP database at NCBI, incorporated herein by reference. 'SNP position' refers to the nucleotide position of the SNP on SEQ ID NO: 05. 'Polymorphism' indicates the nucleotide variants at that SNP position. 'Major allele' indicates the nucleotide associated with the major allele, or the nucleotide present in a statistically significant proportion of individuals in the human population. 'Minor allele' indicates the nucleotide associated with the minor allele, or the nucleotide present in a relatively small proportion of individuals in the human population.

| Single Nuclear Polymorphisms (SNPs) and their positions on SEQ ID NO: 05 | | | | |
|---|---|---|---|---|
| RS No. | SNP position | Polymorphism | Major allele | Minor allele |
| rs2857936 | 1963 | C/T | C | T |
| rs12506200 | 3707 | A/G | G | A |
| rs762855 | 14449 | A/G | G | A |
| rs3856973 | 19826 | G/A | G | A |
| rs2285086 | 28912 | G/A | A | G |
| rs7659144 | 37974 | C/G | C | G |
| rs16843804 | 44043 | C/T | C | T |
| rs2024115 | 44221 | G/A | A | G |
| rs10015979 | 49095 | A/G | A | G |
| rs7691627 | 51063 | A/G | G | A |
| rs2798235 | 54485 | G/A | G | A |
| rs4690072 | 62160 | G/T | T | G |
| rs6446723 | 66466 | C/T | T | C |
| rs363081 | 73280 | G/A | G | A |

-continued

Single Nuclear Polymorphisms (SNPs) and their positions on SEQ ID NO: 05

| RS No. | SNP position | Polymorphism | Major allele | Minor allele |
|---|---|---|---|---|
| rs363080 | 73564 | T/C | C | T |
| rs363075 | 77327 | G/A | G | A |
| rs363064 | 81063 | T/C | C | T |
| rs3025849 | 83420 | A/G | A | G |
| rs6855981 | 87929 | A/G | G | A |
| rs363102 | 88669 | G/A | A | G |
| rs11731237 | 91466 | C/T | C | T |
| rs4690073 | 99803 | A/G | G | A |
| rs363144 | 100948 | T/G | T | G |
| rs3025838 | 101099 | C/T | C | T |
| rs34315806 | 101687 | A/G | G | A |
| rs363099 | 101709 | T/C | C | T |
| rs363096 | 119674 | T/C | T | C |
| rs2298967 | 125400 | C/T | T | C |
| rs2298969 | 125897 | A/G | G | A |
| rs6844859 | 130139 | C/T | T | C |
| rs363092 | 135682 | C/A | C | A |
| rs7685686 | 146795 | A/G | A | G |
| rs363088 | 149983 | A/T | A | T |
| rs362331 | 155488 | C/T | T | C |
| rs916171 | 156468 | G/C | C | G |
| rs362322 | 161018 | A/G | A | G |
| rs362275 | 164255 | T/C | C | T |
| rs362273 | 167080 | A/G | A | G |
| rs2276881 | 171314 | G/A | G | A |
| rs3121419 | 171910 | T/C | C | T |
| rs362272 | 174633 | G/A | G | A |
| rs362271 | 175171 | G/A | G | A |
| rs3775061 | 178407 | C/T | C | T |
| rs362310 | 179429 | A/G | G | A |
| rs362307 | 181498 | T/C | C | T |
| rs362306 | 181753 | G/A | G | A |
| rs362303 | 181960 | T/C | C | T |
| rs362296 | 186660 | C/A | C | A |
| rs1006798 | 198026 | A/G | A | G. |

Example 38

Oligonucleotide Synthesis

The syntheses of oligonucleotides (ONs) were performed on a 1.0 µmol scale using an ABI 394 DNA synthesizer using VIMAD UnyLinker support (100 µmol/g). Standard conditions were used for incorporation of DNA amidites, i.e. 3% dichloroacetic acid in DCM for deblocking; 1 M 4,5-dicyanoimidazole 0.1 M N-methylimidazole in acetonitrile as activator, acetic anhydride in THF as Cap A; 10% methylimidazole in THF/pyridine as Cap B and 10% tert-butyl hydroperoxide as oxidizing agent. DNA amidites were dissolved to 0.1 M in acetonitrile and coupled for 2 times 3 min. Modified amidite (7 mg, 11 gmol) was dissolved in DCM (0.4 mL) and activator (0.6 mL) was added and coupled manually for 30 min, the remaining part of the cycle is identical to DNA amidites. After synthesis was completed, the support-bound oligonucleotides were treated with a solution of $Et_3N/CH_3CN$ (1:1, v/v) for 25 min. and then deprotected and detached from solid support with 33% aqueous $NH_3$ for 48 h at room temperature. The crude material was purified by ion-exchange HPLC with a linear gradients (019%) of buffer B (0.05 M $NaHCO_3$, $H_2O$: $CH_3CN$ 7:3, 1.5 M NaBr) in buffer A (0.1 M $NaHCO_3$, $H_2O$:$CH_3CN$ 7:3) as eluent. Oligonucleotides were desalted using a reverse-phase cartridge and lyophilized.

| SEQ ID NO. | Sequence 5'-3' | Mass (calc.) | Mass (exp.) | UV purity |
|---|---|---|---|---|
| 06 | GGAT$_z$GTTCTCGA | 3704.5 | 3703.8 | 98.8% |
| 06 | GGATGT$_z$TCTCGA | 3704.5 | 3703.8 | 98.8% |
| 06 | GGATGTT$_z$CTCGA | 3704.5 | 3703.8 | 98.4% |
| 06 | GGATGTTCT$_z$CGA | 3704.5 | 3703.8 | 99.2% |
| 06 | GGAT$_x$GTTCTCGA | 3704.0 | 3703.8 | 97.2% |
| 06 | GGATGT$_x$TCTCGA | 3704.0 | 3703.8 | 97.5% |
| 06 | GGATGTT$_x$CTCGA | 3704.0 | 3703.8 | 97.8% |
| 06 | GGATGTTCT$_x$CGA | 3704.0 | 3703.8 | 97.7% |

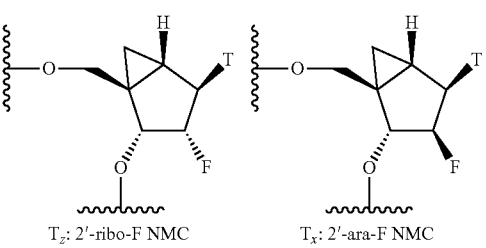

$T_z$: 2'-ribo-F NMC    $T_x$: 2'-ara-F NMC

Wherein $T_z$ is 2'-ribo-F NMC thymidine and $T_x$ is 2'ara-F NMC thymidine the structures of which are illustrated above. 2'ribo-F-NMC thymidine DMT amidite was prepared as illustrated in Example 31 and 2'ara-F-NMC thymidine DMT amidite was prepared as illustrated in Example 33. All nucleosides are 2'-deoxyribonucleosides except for those followed by a subscript z or x which are illustrated above. All internucleoside linkages are phosphodiester.

Example 39

Thermal Stability Assay

A series of modified oligomeric compounds were evaluated in a thermal stability ($T_m$) assay. A Cary 100 Bio spectrophotometer with the Cary Win UV Thermal program was used to measure absorbance vs. temperature. For the $T_m$ experiments, oligomeric compounds were prepared at a concentration of 8 μM in a buffer of 100 mM Na+, 10 mM phosphate, 0.1 mM EDTA, pH 7. The concentration of the oligonucleotides was determined at 85° C. The concentration of each oligomeric compound was 4 μM after mixing of equal volumes of test oligomeric compound and complimentary RNA strand. Oligomeric compounds were hybridized with the complimentary RNA strand by heating the duplex to 90° C. for 5 minutes followed by cooling to room temperature. Using the spectrophotometer, $T_m$ measurements were taken by heating the duplex solution at a rate of 0.5 C/min in cuvette starting @ 15° C. and heating to 85° C. $T_m$ values were determined using Vant Hoff calculations ($A_{260}$ vs temperature curve) using non self-complementary sequences where the minimum absorbance which relates to the duplex and the maximum absorbance which relates to the non-duplex single strand are manually integrated into the program. The modified oligomeric compounds are hybridized separately to complementary RNA and DNA strands for the assay.

Example 40

Thermal Stability Assay

A series of modified oligomeric compounds were evaluated in a thermal stability ($T_m$) assay. A Cary 100 Bio spectrophotometer with the Cary Win UV Thermal program was used to measure absorbance vs. temperature. For the $T_m$ experiments, oligomeric compounds were prepared at a concentration of 8 μM in a buffer of 100 mM Na+, 10 mM phosphate, 0.1 mM EDTA, pH 7. The concentration of the oligonucleotides was determined at 85° C. The concentration of each oligomeric compound was 4 μM after mixing of equal volumes of test oligomeric compound and complimentary RNA strand (or the RNA strand having a single base mismatch). Oligomeric compounds were hybridized with the complimentary RNA strand by heating the duplex to 90° C. for 5 minutes followed by cooling to room temperature. Using the spectrophotometer, $T_m$ measurements were taken by heating the duplex solution at a rate of 0.5 C/min in cuvette starting @15° C. and heating to 85° C. $T_m$ values were determined using Vant Hoff calculations ($A_{260}$ vs temperature curve) using non self-complementary sequences where the minimum absorbance which relates to the duplex and the maximum absorbance which relates to the non-duplex single strand are manually integrated into the program. The oligomeric compounds are hybridized to a complementary region of 30mer RNA SEQ ID NO.: 08 ($Tm^1$), and also to a single base mismatch 30mer RNA SEQ ID NO.: 09 ($Tm^2$). The results are presented below.

| SEQ ID NO. | Composition (5' to 3') |
|---|---|
| 07 | CCTACAAGAGCT RNA complement |
| 07 | CCTACAAGAGCT DNA complement |

| NMC nucleoside: | | 2'-F<br>$Tm^1/\Delta Tm$ | 2'-ara-F<br>$Tm^2/\Delta Tm$ | 2'-F<br>$Tm^1/\Delta Tm$ | 2'-ara-F<br>$Tm^2/\Delta$ |
|---|---|---|---|---|---|
| SEQ ID NO. | Composition<br>(5' to 3') | vs. RNA<br>N = $T_z$ | vs. RNA<br>N = $T_x$ | vs. DNA<br>N = $T_z$ | vs. DNA<br>N = $T_x$ |
| 06 | GGATGTTCTCGA | 49.7/Ref. | 47.5/Ref. | 49.7/Ref. | 47.5/Ref. |
| 06 | GGANGTTCTCGA | 51.9/2.2 | 44.9/-2.6 | 47.0/-2.7 | 40.2/-7.3 |
| 06 | GGATGNTCTCGA | 52.4/2.7 | 45.3/-2.2 | 48.8/-0.9 | 42.9/-4.6 |
| 06 | GGATGTNCTCGA | 51.7/2.0 | 43.2/-4.3 | 46.7/-3.0 | 39.4/-8.1 |
| 06 | GGATGTTCNCGA | 52.3/2.6 | 45.3/-2.1 | 47.8/-1.9 | 41.3/-6.2 |

Each internucleoside linkage is a phosphodiester and each nucleoside is a β-D-2'-deoxyribonucleoside except for the RNA complement where each nucleoside is a β-D-ribonucleoside. Each N is as defined in the respective column $T_z$ or $T_x$ as illustrated in Example 38 above.

The NMC modified nucleosides were inserted at four different locations and were flanked on either side by different nucleosides to provide Tms for position and base variations. Incorporation of a single 2'-F NMC modified nucleoside ($T_z$) provided increased thermal stability for the resulting duplex against RNA complement.

| SEQ ID NO./<br>ISIS NO. | Composition (5' to 3') |
|---|---|
| 08/539568 (mu) | AGACUUUUUCUGGUGAUGACAAUUUAUUAA<br>full complement |
| 09/539569 (wt) | AGACUUUUUCUGGUGAUGGCAAUUUAUUAA<br>single base mismatch |

Each internucleoside linkage is a phosphodiester and each nucleoside is a β-D-ribonucleoside. The mismatched nucleoside is underlined.

| SEQ ID NO./ ISIS NO. | Composition (5' to 3') | $Tm^1/\Delta Tm$ | $Tm^2/\Delta Tm$ |
|---|---|---|---|
| 10/460209 | $T_e A_k A_k ATTGT^{Me}CAT^{Me}CA_k{}^{Me}C_k{}^{Me}C_e$ | 54.4/Ref. | 52.2/Ref. |
| 10/620509 | $T_e A_k A_k AT_z TGT^{Me}CAT^{Me}CA_k{}^{Me}C_k{}^{Me}C_e$ | 55.6/1.2 | 53.2/1.1 |
| 10/620510 | $T_e A_k A_k ATT_z GT^{Me}CAT^{Me}CA_k{}^{Me}C_k{}^{Me}C_e$ | 56.3/1.9 | 54.1/1.9 |
| 10/620511 | $T_e A_k A_k ATTGT_z{}^{Me}CAT^{Me}CA_k{}^{Me}C_k{}^{Me}C_e$ | 57.9/3.5 | 52.9/0.7 |
| 10/620512 | $T_e A_k A_k ATTGT^{Me}CAT_z{}^{Me}CA_k{}^{Me}C_k{}^{Me}C_e$ | 56.1/1.7 | 53.2/1.0 |

Each internucleoside linkage is a phosphorothioate and each nucleoside not followed by a subscript e, k or z is a β-D-2'-deoxyribonucleoside. Each $^{Me}C$ is a 5-methyl cytosine modified nucleoside. Each nucleoside followed by a subscript "e" is a 2'-O-methoxyethyl (MOE) modified nucleoside. Each nucleoside followed by a subscript "k" is a bicyclic nucleoside having a 4'-CH((S)—CH$_3$)—O-2' bridge also referred to as a (S)-cEt modified nucleoside. Each nucleoside followed by a subscript "z" is a bicyclic carbocyclic nucleoside having the structure shown below. $Tm^1$ lists the Tm's against the full complement RNA and $Tm^2$ lists the Tm's against the single base mismatch RNA.

Nucleosides followed by subscripts "e", "k" or "z" are further illustrated below.

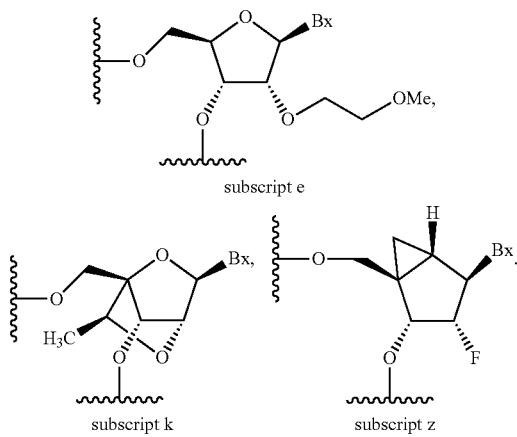

Example 41

Oligomeric Compounds Targeting Huntingtin (HTT) Single Nucleotide Polymorphism (SNP)—In Vitro Study A series of oligomeric compounds were designed based on a parent gapmer, ISIS 460209, a gapped oligomeric compound having a 3/9/3 motif wherein the gap region contains nine β-D-2'-deoxyribonucleosides. The oligomeric compounds were designed by introducing a single bicyclic carbocyclic nucleoside, as provided herein, into the gap region. The resulting oligomeric compounds were tested for their ability to selectively inhibit mutant (mut) HTT mRNA expression levels targeting rs7685686 while leaving the expression of the wild-type (wt) intact. The potency and selectivity of the oligomeric compounds was evaluated and compared to ISIS 460209.

The position on the oligomeric compounds opposite to the SNP position, as counted from the 5'-terminus is position 8.

Cell Culture and Transfection

Cultured heterozygous fibroblast GM04022 cells at a density of 25,000 cells per well were transfected using electroporation with a single 2 μM dose of the selected oligomeric compound. After treatment for approximately 24 hours, cells were washed with DPBS buffer and lysed. RNA was extracted using Qiagen RNeasy and mRNA levels were measured by quantitative real-time PCR using ABI assay C_2229297_10 which measures at dbSNP rs362303. Real-time PCR method in short; A mixture was made using 2020 uL 2×PCR buffer, 101 uL primers (300 uM from ABI), 1000 uL water and 40.4 uL RT MIX. 15 uL of this mixture and 5 uL of purified RNA was added to each well. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN with the results presented below.

Analysis of $IC_{50}$'s and Selectivity

The half maximal inhibitory concentration ($IC_{50}$) of each oligomeric compound was calculated by plotting the concentrations of oligomeric compounds used versus the percent inhibition of HTT mRNA expression achieved at each concentration, and noting the concentration of oligomeric compound at which 50% inhibition of HTT mRNA expression was achieved compared to the control. The $IC_{50}$ at which each oligomeric compound inhibits the mutant HTT mRNA expression is denoted as "mut $IC_{50}$". The $IC_{50}$ at which each oligomeric compound inhibits the wild-type HTT mRNA expression is denoted as "wt $IC_{50}$". Selectivity as expressed in fold was calculated by dividing the $IC_{50}$ for inhibition of the wild-type HTT versus the $IC_{50}$ for inhibiting expression of the mutant HTT mRNA.

| SEQ ID NO./ ISIS NO. | Composition (5' to 3') |
|---|---|
| 10/460209 | $T_e A_k A_k ATTGT^{Me}CAT^{Me}CA_k{}^{Me}C_k{}^{Me}C_e$ |
| 10/620509 | $T_e A_k A_k AT_z TGT^{Me}CAT^{Me}CA_k{}^{Me}C_k{}^{Me}C_e$ |
| 10/620510 | $T_e A_k A_k ATT_z GT^{Me}CAT^{Me}CA_k{}^{Me}C_k{}^{Me}C_e$ |
| 10/620511 | $T_e A_k A_k ATTGT_z{}^{Me}CAT^{Me}CA_k{}^{Me}C_k{}^{Me}C_e$ |
| 10/620512 | $T_e A_k A_k ATTGT^{Me}CAT_z{}^{Me}CA_k{}^{Me}C_k{}^{Me}C_e$ |

Each internucleoside linkage is a phosphorothioate and each nucleoside not followed by a subscript e, k or z is a β-D-2'-deoxyribonucleoside. Each $^{Me}C$ is a 5-methyl cytosine modified nucleoside. Each nucleoside followed by a subscript "e" is a 2'-O-methoxyethyl (MOE) modified nucleoside. Each nucleoside followed by a subscript "k" is a bicyclic nucleoside having a 4'-CH((S)—CH$_3$)—O-2' bridge also referred to as a (S)-cEt modified nucleoside. Each nucleoside followed by a subscript "z" is a bicyclic carbocyclic nucleoside having the structure shown below.

Nucleosides followed by subscripts "e", "k" or "x" are illustrated above in Example 40.

| SEQ ID NO./ ISIS NO. | IC$_{50}$ mutant (µM) | IC$_{50}$ wildtype (µM) | Fold Selectivity | Gap Chemistry |
|---|---|---|---|---|
| 10/460209 | 0.19 | 1.4 | 7.4 | unmodified gapmer (3/9/3) |
| 10/620509 | 0.37 | 12.6 | 34 | T$_z$ at position 5 |
| 10/620510 | 0.60 | >15 | >25 | T$_z$ at position 6 |
| 10/620511 | 0.06 | 0.93 | 16 | T$_z$ at position 8 |
| 10/620512 | 0.33 | 9.6 | 29 | T$_z$ at position 11. |

Example 42

NMC Oligonucleotide Synthesis

Oligonucleotides (638985, 638986, 638987 and 638988) were synthesized on a 2 gmol scale on an ABI 394 DNA/RNA synthesizer using MOE $^m$C primer support. Fully protected nucleoside phosphoramidites were incorporated using standard solid-phase oligonucleotide synthesis, i.e. 3% dichloroacetic acid in DCM for deblocking, 1 M 4,5-dicyanoimidazole 0.1 M N-methylimidazole in acetonitrile as activator for amidite couplings, acetic acid in THF and 10% 1-methylimidazole in THF/pyridine for capping and 0.2 M phenylacetyl disulfide in pyridine:acetonitrile 1:1 (v:v) for thiolation. DNA building blocks were dissolved in acetonitrile (0.1 M) and incorporated using 2 times 4 min coupling time while NMC and 2'-ribo-F NMC were dissolved in acetonitrile:toluene 1:1 (v:v) and coupled for 2 times 6 min. After conclusion of the synthesis, the 5' DMT group was removed and cyanoethyl protecting groups cleaved using triethylamine:acetonitrile 1:1 (v:v). The remaining protecting groups were removed in conc. aq. ammonia at room temperature for 24 h. ONs were purified by ion-exchange-HPLC using a linear gradient of buffer A and B. Buffer A: 50 mM NaHCO$_3$ in acetonitrile:water 3:7 (v:v), buffer B: 1.5 M NaBr, 50 mM NaHCO$_3$ in acetonitrile:water 3:7 (v:v). Purified ONs were desalted using C18 reverse-phase cartridges and lyophilized. Identity and purity of ONs were established using LCMS. The oligomeric compounds are hybridized to a complementary region of 30mer RNA SEQ ID NO.: 08. The results are presented below.

| SEQ ID NO./ ISIS NO. | Composition (5' to 3') |
|---|---|
| 08/539568 (mu) | AGACUUUUUCUGGUGAUGACAAUUUAUUAA full complement |

Each internucleoside linkage is a phosphodiester and each nucleoside is a β-D-ribonucleoside.

| SEQ ID NO./ ISIS NO. | Composition (5' to 3') | Tm/ΔTm |
|---|---|---|
| 10/460209 | T$_e$A$_k$A$_k$ATTGT$^{Me}$CAT$^{Me}$CA$_k^{Me}$C$_k^{Me}$C$_e$ | 54.4/Ref. |
| 10/638985 | T$_e$A$_k$A$_k$AT$_y$TGT$^{Me}$CAT$^{Me}$CA$_k^{Me}$C$_k^{Me}$C$_e$ | 54.8/0.4 |
| 10/638986 | T$_e$A$_k$A$_k$ATT$_y$GT$^{Me}$CAT$^{Me}$CA$_k^{Me}$C$_k^{Me}$C$_e$ | 56.0/1.6 |
| 10/638987 | T$_e$A$_k$A$_k$ATTGT$_y^{Me}$CAT$^{Me}$CA$_k^{Me}$C$_k^{Me}$C$_e$ | 56.9/2.5 |
| 10/638988 | T$_e$A$_k$A$_k$ATTGT$^{Me}$CAT$_y^{Me}$CAk$^{Me}$C$_k^{Me}$C$_e$ | 56.1/1.7 |

Each internucleoside linkage is a phosphorothioate and each nucleoside not followed by a subscript e, k or y is a β-D-2'-deoxyribonucleoside. Each $^{Me}$C is a 5-methyl cytosine modified nucleoside. Each nucleoside followed by a subscript "e" is a 2'-O-methoxyethyl (MOE) modified nucleoside. Each nucleoside followed by a subscript "k" is a bicyclic nucleoside having a 4'-CH((S)—CH$_3$)—O-2' bridge also referred to as a (S)-cEt modified nucleoside. Each nucleoside followed by a subscript "y" is a bicyclic carbocyclic nucleoside having the structure shown below (NMC). Tm$^1$ lists the Tm's against the full complement RNA and Tm$^2$ lists the Tm's against the single base mismatch RNA.

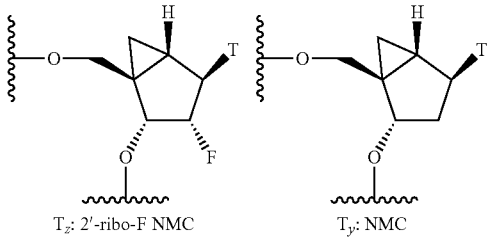

T$_z$: 2'-ribo-F NMC    T$_y$: NMC

Wherein T$_z$ is 2'-ribo-F NMC thymidine and T$_y$ is NMC thymidine the structures of which are illustrated above.

Example 43

Oligomeric Compounds Targeting Huntingtin (HTT) Single Nucleotide Polymorphism (SNP)—In Vitro Study A series of oligomeric compounds were designed based on a parent gapmer, ISIS 460209, a gapped oligomeric compound having a 3/9/3 motif wherein the gap region contains nine β-D-2'-deoxyribonucleosides. The oligomeric compounds were designed by introducing a single bicyclic carbocyclic nucleoside, as provided herein, into the gap region. The resulting oligomeric compounds were tested for their ability to selectively inhibit mutant (mut) HTT mRNA expression levels targeting rs7685686 while leaving the expression of the wild-type (wt) intact. The potency and selectivity of the oligomeric compounds was evaluated and compared to ISIS 460209.

The position on the oligomeric compounds opposite to the SNP position, as counted from the 5'-terminus is position 8.

Cell Culture and Transfection

Cultured heterozygous fibroblast GM04022 cells at a density of 25,000 cells per well were transfected using electroporation with a single 2 µM dose of the selected oligomeric compound. After treatment for approximately 24 hours, cells were washed with DPBS buffer and lysed. RNA was extracted using Qiagen RNeasy and mRNA levels were measured by quantitative real-time PCR using ABI assay C_2229297_10 which measures at dbSNP rs362303. Real-time PCR method in short; A mixture was made using 2020 uL 2×PCR buffer, 101 uL primers (300 uM from ABI), 1000 uL water and 40.4 uL RT MIX. 15 uL of this mixture and 5 uL of purified RNA was added to each well. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN with the results presented below.

Analysis of $IC_{50}$'s and Selectivity

The half maximal inhibitory concentration ($IC_{50}$) of each oligomeric compound was calculated by plotting the concentrations of oligomeric compounds used versus the percent inhibition of HTT mRNA expression achieved at each concentration, and noting the concentration of oligomeric compound at which 50% inhibition of HTT mRNA expression was achieved compared to the control. The $IC_{50}$ at which each oligomeric compound inhibits the mutant HTT mRNA expression is denoted as "mut $IC_{50}$". The $IC_{50}$ at which each oligomeric compound inhibits the wild-type HTT mRNA expression is denoted as "wt $IC_{50}$". Selectivity as expressed in fold was calculated by dividing the $IC_{50}$ for inhibition of the wild-type HTT versus the $IC_{50}$ for inhibiting expression of the mutant HTT mRNA.

| SEQ ID NO./ ISIS NO. | Composition (5' to 3') |
|---|---|
| 10/460209 | $T_eA_kA_kATTGT^{Me}CAT^{Me}CA_k^{Me}C_k^{Me}C_e$ |
| 10/638985 | $T_eA_kA_kAT_yTGT^{Me}CAT^{Me}CA_k^{Me}C_k^{Me}C_e$ |
| 10/638986 | $T_eA_kA_kATT_yGT^{Me}CAT^{Me}CA_k^{Me}C_k^{Me}C_e$ |
| 10/638987 | $T_eA_kA_kATTGT_{y'}^{Me}CAT^{Me}CA_k^{Me}C_k^{Me}C_e$ |
| 10/638988 | $T_eA_kA_kATTGT^{Me}CAT_{y'}^{Me}CA_k^{Me}C_k^{Me}C_e$ |

See Example 42 for definitions and illustrations of nucleoside chemistries.

| SEQ ID NO./ ISIS NO. | $IC_{50}$ mutant (μM) | $IC_{50}$ wildtype (μM) | Fold Selectivity | Gap Chemistry |
|---|---|---|---|---|
| 10/460209 | 0.19 | 1.4 | 7.4 | unmodified gapmer (3/9/3) |
| 10/638985 | 0.61 | >10 | >16 | $T_y$ at position 5 |
| 10/638986 | 3.9 | >10 | >3 | $T_y$ at position 6 |
| 10/638987 | 0.49 | 6.4 | 21 | $T_y$ at position 8 |
| 10/638988 | 0.38 | 8.4 | 1 | $T_y$ at position 11. |

What is claimed is:

1. A bicyclic carbocyclic nucleoside having Formula I:

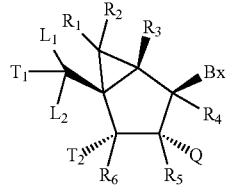

I wherein:

Bx is an optionally protected heterocyclic base moiety;

$T_1$ is a protected hydroxyl;

$T_2$ is a reactive phosphorus group capable of forming an internucleoside linkage selected from diisopropylcyanoethoxy phosphoramidite and H-phosphonate;

Q is halogen or O—$[C(A_1)(A_2)]n$-$[(C=O)_m$—$X]_j$—Z wherein Q is other than a protected hydroxyl group;

$A_1$ and $A_2$ are each, independently, H, halogen, $C_1$-$C_6$ alkyl or substituted $C_1$-$C_6$ alkyl;

X is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1 provided that when j is 1 then Z is other than halogen or $N(E_2)(E_3)$;

$L_1$ and $L_2$ are each H or one of $L_1$ and $L_2$ is H and the other of $L_1$ and $L_2$ is $C_1$-$C_6$ alkyl or substituted $C_1$-$C_6$ alkyl;

$R_1$, $R_2$, $R_3$, $R_4$, $R_5$ and $R_6$ are each H or one of $R_1$, $R_2$, $R_3$, $R_4$, $R_5$ and $R_6$ is F, $CH_3$ or $OCH_3$ and the remaining of $R_1$, $R_2$, $R_3$, $R_4$, $R_5$ and $R_6$ are each H;

each substituted group comprises one or more optionally protected substituent groups independently selected from halogen, $OJ_1$, $N(J_1)(J_2)$, =$NJ_1$, $SJ_1$, $N_3$, OC(=G)$J_1$, OC(=G)N($J_1$)($J_2$) and C(=G)N($J_1$)($J_2$);

G is O, S or $NJ_3$; and each $J_1$, $J_2$ and $J_3$ is, independently, H or $C_1$-$C_6$ alkyl.

2. The bicyclic carbocyclic nucleoside of claim 1 wherein one of $L_1$ and $L_2$ is H and the other of $L_1$ and $L_2$ is $CH_3$.

3. The bicyclic carbocyclic nucleoside of claim 1 wherein $L_1$ and $L_2$ are each H.

4. The bicyclic carbocyclic nucleoside of claim 1 wherein $L_1$, $L_2$, $R_1$, $R_2$, $R_3$, $R_4$, $R_5$ and $R_6$ are each H.

5. The bicyclic carbocyclic nucleoside claim 1 wherein Q is F.

6. The bicyclic nucleoside of claim 1 wherein Q is O($CH_2$)$_2$—$OCH_3$.

7. The bicyclic carbocyclic nucleoside of claim 1 wherein Bx is uracil, thymine, cytosine, 4-N-benzoylcytosine, 5-methylcytosine, 4-N-benzoyl-5-methylcytosine, adenine, 6-N-benzoyladenine, guanine or 2-N-isobutyrylguanine.

8. The bicyclic carbocyclic nucleoside of claim 1 wherein $T_1$ is O-4,4'-dimethoxytrityl and $T_2$ is diisopropylcyanoethoxy phosphoramidite.

9. An oligomeric compound comprising at least one bicyclic carbocyclic nucleoside having Formula II:

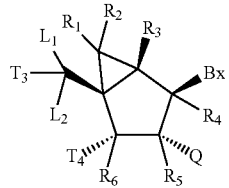

wherein independently for each bicyclic carbocyclic nucleoside of Formula II

Bx is an optionally protected heterocyclic base moiety;
one of $T_3$ and $T_4$ is an internucleoside linking group attaching the bicyclic nucleoside to the remainder of one of the 5' or 3' end of the oligomeric compound and the other of $T_3$ and $T_4$ is hydroxyl, a protected hydroxyl, a 5' or 3' terminal group or an internucleoside linking group attaching the bicyclic nucleoside to the remainder of the other of the 5' or 3' end of the oligomeric compound;
Q is halogen or $O-[C(A_1)(A_2)]_n-[(C=O)_m-X]_j-Z$ wherein Q is other than a protected hydroxyl group;
$A_1$ and $A_2$ are each, independently, H, halogen, $C_1$-$C_6$ alkyl or substituted $C_1$-$C_6$ alkyl;
X is O, S or $N(E_1)$;
Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;
$E_1$, $E_2$ and $E_3$ are each, independently, H, $C_1$-$C_6$ alkyl or substituted $C_1$-$C_6$ alkyl;
n is from 1 to about 6;
m is 0 or 1;
j is 0 or 1 provided that when j is 1 then Z is other than halogen or $N(E_2)(E_3)$;
$L_1$ and $L_2$ are each H or one of $L_1$ and $L_2$ is H and the other of $L_1$ and $L_2$ is $C_1$-$C_6$ alkyl, or substituted $C_1$-$C_6$ alkyl;
$R_1$, $R_2$, $R_3$, $R_4$, $R_5$ and $R_6$ are each H or one of $R_1$, $R_2$, $R_3$, $R_4$, $R_5$ and $R_6$ is F, $CH_3$ or $OCH_3$ and the remaining of $R_1$, $R_2$, $R_3$, $R_4$, $R_5$ and $R_6$ are each H;
each substituted group comprises one or more optionally protected substituent groups independently selected from halogen, $OJ_1$, $N(J_1)(J_2)$, $=NJ_1$, $SJ_1$, $N_3$, $OC(=G)$ $J_1$, $OC(=G)N(J_1)(J_2)$ and $C(=G)N(J_1)(J_2)$;
G is O, S or $NJ_3$;
each $J_1$, $J_2$ and $J_3$ is, independently, H or $C_1$-$C_6$ alkyl; and
wherein said oligomeric compound comprises from 8 to 40 monomeric subunits linked by internucleoside linking groups and wherein at least some of the heterocyclic base moieties are capable of hybridizing to a nucleic acid molecule.

10. The oligomeric compound of claim 9 wherein one of $L_1$ and $L_2$ is H and the other of $L_1$ and $L_2$ is $CH_3$ for each bicyclic carbocyclic nucleoside having Formula II.

11. The oligomeric compound of claim 9 wherein $L_1$ and $L_2$ are each H for each bicyclic carbocyclic nucleoside having Formula II.

12. The oligomeric compound of claim 9 wherein $L_1$, $L_2$, $R_1$, $R_2$, $R_3$, $R_4$, $R_5$ and $R_6$ are each H for each bicyclic carbocyclic nucleoside having Formula II.

13. The oligomeric compound of claim 9 wherein Q is F for each bicyclic carbocyclic nucleoside having Formula II.

14. The oligomeric compound of claim 9 wherein Q is $O(CH_2)_2-OCH_3$ for each bicyclic carbocyclic nucleoside having Formula II.

15. The oligomeric compound of claim 9 wherein each Bx is, independently, uracil, thymine, cytosine, 5-methylcytosine, adenine or guanine.

16. The oligomeric compound of claim 9 wherein one $T_3$ and or one $T_4$ is a terminal group.

17. The oligomeric compound of claim 9 wherein one $T_3$ or one $T_4$ is a conjugate group that may include a bifunctional linking moiety.

18. The oligomeric compound of claim 9 comprising a first region consisting of from 2 to 5 modified nucleosides, a second region consisting of from 2 to 5 modified nucleosides and a gap region consisting of from 6 to 14 monomer subunits located between the first and second region wherein at least one of the monomer subunits in the gap region or at least one of the modified nucleosides in the first region is a bicyclic carbocyclic nucleoside having Formula II.

19. The oligomeric compound of claim 18 wherein the gap region comprises from about 8 to about 10 monomer subunits.

20. The oligomeric compound of claim 18 wherein each monomer subunit in the gap region other than bicyclic carbocyclic nucleosides of Formula II is a β-D-2'-deoxyribonucleoside.

21. The oligomeric compound of claim 18 wherein each modified nucleoside in the first and second region is, independently, a bicyclic nucleoside comprising a bicyclic furanosyl sugar moiety or a modified nucleoside comprising a furanosyl sugar moiety having at least one substituent group.

22. The oligomeric compound of claim 18 wherein each modified nucleoside in the first and second region is, independently, a bicyclic nucleoside comprising a 4'-CH((S)—$CH_3$)—O-2' bridge or a 2'-O-methoxyethyl substituted nucleoside.

23. The oligomeric compound of claim 18 wherein each monomer subunit in the gap region is a β-D-2'-deoxyribonucleoside.

24. The oligomeric compound of claim 9 wherein each internucleoside linking group is, independently, a phosphodiester internucleoside linking group or a phosphorothioate internucleoside linking group.

25. A method of inhibiting gene expression comprising contacting a cell with an oligomeric compound of claim 9 wherein said oligomeric compound is complementary to a target RNA.

26. The method of claim 25 wherein said target RNA is selected from mRNA, pre-mRNA and micro RNA.

27. The method of claim 25 further comprising detecting the levels of target RNA.

28. An in vitro method of inhibiting gene expression comprising contacting one or more cells or a tissue with an oligomeric compound of claim 9.

* * * * *

SEQUENCE LISTING

<160> NUMBER OF SEQ ID NOS: 10

<210> SEQ ID NO 1
<211> LENGTH: 3160
<212> TYPE: DNA
<213> ORGANISM: Homo sapiens

<400> SEQUENCE: 1

```
cctccctcg cccggcgcgg tcccgtccgc ctctcgctcg cctcccgcct ccctcggtc      60 ttccgaggcg cccgggctcc cggcgcggcg gcggaggggg cgggcaggcc ggcgggcggt    120
gatgtggcag gactctttat gcgctgcggc aggatacgcg ctcggcgctg ggacgcgact    180
gcgctcagtt ctctcctctc ggaagctgca gccatgatgg aagtttgaga gttgagccgc    240
tgtgaggcga ggccggggctc aggcgaggga gatgagagac ggcggcggcc gcggcccgga    300
gcccctctca gcgcctgtga gcagccgcgg gggcagcgcc ctcggggagc cggccggcct    360
gcggcggcgg cagcggcggc gtttctcgcc tcctcttcgt cttttctaac cgtgcagcct    420
cttcctcggc ttctcctgaa agggaaggtg gaagccgtgg gctcgggcgg gagccggctg    480
aggcgcggcg gcggcggcgg cggcacctcc cgctcctgga gcggggggga gaagcggcgg    540
cggcggcggc cgcggcggct gcagctccag ggaggggtc tgagtcgcct gtcaccattt     600
ccagggctgg gaacgccgga gagttggtct ctcccttct actgcctcca acacggcggc     660
ggcggcggcg gcacatccag ggaccgggc cggttttaaa cctcccgtcc gccgccgccg    720
caccccccgt ggccccgggct ccggaggccg ccggcggagg cagccgttcg gaggattatt    780
cgtcttctcc ccattccgct gccgccgctg ccaggcctct ggctgctgag gagaagcagg    840
cccagtcgct gcaaccatcc agcagccgcc gcagcagcca ttacccggct gcggtccaga    900
gccaagcggc ggcagagcga ggggcatcag ctaccgccaa gtccagagcc atttccatcc    960
tgcagaagaa gccccgccac cagcagcttc tgccatctct ctcctccttt ttcttcagcc   1020
acaggctccc agacatgaca gccatcatca aagagatcgt tagcagaaac aaaaggagat   1080
```

```
atcaagagga tggattcgac ttagacttga cctatattta tccaaacatt attgctatgg    1140
gatttcctgc agaaagactt gaaggcgtat acaggaacaa tattgatgat gtagtaaggt    1200
ttttggattc aaagcataaa aaccattaca agatatacaa tctttgtgct gaaagacatt    1260
atgacaccgc caaatttaat tgcagagttg cacaatatcc ttttgaagac cataacccac    1320
cacagctaga acttatcaaa ccctttgtg aagatcttga ccaatggcta agtgaagatg    1380
acaatcatgt tgcagcaatt cactgtaaag ctggaaaggg acgaactggt gtaatgatat    1440
gtgcatattt attacatcgg ggcaaatttt taaaggcaca agaggcccta gatttctatg    1500
gggaagtaag gaccagagac aaaaagggag taactattcc cagtcagagg cgctatgtgt    1560
attattatag ctacctgtta aagaatcatc tggattatag accagtggca ctgttgtttc    1620
acaagatgat gtttgaaact attccaatgt tcagtggcgg aacttgcaat cctcagtttg    1680
tggtctgcca gctaaaggtg aagatatatt cctccaattc aggacccaca cgacgggaag    1740
acaagttcat gtactttgag ttccctcagc cgttacctgt gtgtggtgat atcaaagtag    1800
agttcttcca caaacagaac aagatgctaa aaaaggacaa aatgtttcac ttttgggtaa    1860
atacattctt cataccagga ccagaggaaa cctcagaaaa agtagaaaat ggaagtctat    1920
gtgatcaaga aatcgatagc atttgcagta tagagcgtgc agataatgac aaggaatatc    1980
tagtacttac tttaacaaaa aatgatcttg acaaagcaaa taaagacaaa gccaaccgat    2040
actttctcc aaattttaag gtgaagctgt acttcacaaa aacagtagag gagccgtcaa    2100
atccagaggc tagcagttca acttctgtaa caccagatgt tagtgacaat gaacctgatc    2160
attatagata ttctgacacc actgactctg atccagagaa tgaaccttt gatgaagatc    2220
agcatacaca aattacaaaa gtctgaattt tttttatca agagggataa aacaccatga    2280
aaataaactt gaataaactg aaaatggacc ttttttttt taatggcaat aggacattgt    2340
gtcagattac cagttatagg aacaattctc ttttcctgac caatcttgtt ttaccctata    2400
catccacagg gttttgacac ttgttgtcca gttgaaaaaa ggttgtgtag ctgtgtcatg    2460
tatataccct tttgtgtcaa aaggacattt aaaattcaat taggattaat aaagatggca    2520
ctttcccgtt ttattccagt tttataaaaa gtggagacag actgatgtgt atacgtagga    2580
attttttcct tttgtgttct gtcaccaact gaagtggcta aagagctttg tgatatactg    2640
gttcacatcc taccccttg cacttgtggc aacagataag tttgcagttg gctaagagag    2700
gtttccgaaa ggttttgcta ccattctaat gcatgtattc gggttagggc aatggagggg    2760
aatgctcaga aaggaaataa ttttatgctg gactctggac catataccat ctccagctat    2820
ttacacacac ctttctttag catgctacag ttattaatct ggacattcga ggaattggcc    2880
gctgtcactg cttgttgttt gcgcattttt ttttaaagca tattggtgct agaaaaggca    2940
gctaaaggaa gtgaatctgt attggggtac aggaatgaac cttctgcaac atcttaagat    3000
ccacaaatga agggatataa aaataatgtc ataggtaaga aacacagcaa caatgactta    3060
accatataaa tgtggaggct atcaacaaag aatgggcttg aaacattata aaaattgaca    3120
atgatttatt aaatatgttt tctcaattgt aaaaaaaaaa                          3160
```

<210> SEQ ID NO 2
<211> LENGTH: 26
<212> TYPE: DNA
<213> ORGANISM: Artificial sequence
<220> FEATURE:
<223> OTHER INFORMATION: Primer

<400> SEQUENCE: 2
aatggctaag tgaagatgac aatcat                                          26

<210> SEQ ID NO 3
<211> LENGTH: 25
<212> TYPE: DNA
<213> ORGANISM: Artificial sequence
<220> FEATURE:
<223> OTHER INFORMATION: Primer

<400> SEQUENCE: 3
tgcacatatc attacaccag ttcgt                                           25

<210> SEQ ID NO 4
<211> LENGTH: 30
<212> TYPE: DNA
<213> ORGANISM: Artificial sequence
<220> FEATURE:
<223> OTHER INFORMATION: Probe

<400> SEQUENCE: 4
ttgcagcaat tcactgtaaa gctggaaagg                                      30

<210> SEQ ID NO 5
<211> LENGTH: 202001
<212> TYPE: DNA
<213> ORGANISM: Homo sapiens

<400> SEQUENCE: 5
gcccagcagg tgtcagcctc attttacccc gccccctattc aagatgaagt tgttctggtt      60
ccaacgcctc tgacatatta gctgcatcat tttacatttc tttttttttt ttccttttaa     120
atggggtctt gctctgtcac ccaggctgga gtgctgtggt atgatctcgg ctcactgcaa     180
tctccacctc cgaggttcca gcgattctct tgcctcagcc tcccgagtag ctgggactac     240
aggcacccac catcatactg gctaattttt tgtgttttta gtagagatgg ggtttcccca     300
tgttgcccag gctgatctca aactcctggg cttaagcaat acagccgcgt tggcctccca     360
aagtgttggg attacaagca tgagctaccc cacccagctc attttacatt tccacttgtt     420
aaactgaaaa ctggcccgag aaagcttctg tactgccatc cttgcgtcct tgcagatgaa     480
tcgtaaccta gcatagtagg taggcagact gaaaacctaa cttagcagta ggcttctgta     540
acaacagctg tgtctcagcc agttcctgca gccagacttc aaccactcac aggccgcaaa     600
ctgttcaaac tgtgttcgga gaaggcgaat tcatctggct gttaacgtgc ctcacttctg     660
cttttctgtg gccactttccc ttttctgtcc ataaatttgc tttgaccaca cagcatccct     720
agagtctccc tgaatctgct gtgattctgg gacctgcacc atttgtgaat tgttttttt      780
ttccttgatc agctaaactc tgttcaattc aatttgttgg aagttttaa cataccaatg      840
gtgcaccaag gttccaattt ctccacttcc tcataaataa gtcattttaa atggcttttc     900
agtattccaa tatttggaag tattaatgtt tctaccaatt ttctattttt ggacattgag     960
gttgtttcat tttttttttc tttttttgag acagagtctc gctccgtcac ccaggctgga    1020
gtgcagtggc ctgatcccgg cccactgcaa cctccacctc cctcctcagc ctcctgagta    1080
gctgggatta caggtgcatg caccaccaca cccagctaat ttttgtattt ttagtagaga    1140
tggggtttca ccatgttggt caggctggtc tcaaactcct gacctcaggt ggtccacctg    1200
ccttggcctc ccaaaatgct gggattacag gcctgagcca ctgcgcctgg cctcatcttc    1260
ttgatattaa tgttgcttta acatctttgt ccctgtgttt ttgttttttt tttttgagac    1320

```
ggagtctcat tcattctgtc acccaggctg gagttcagtg gcgtgatctc agctcactgc    1380
aacctctgtc tcctgggttc cagtgattct cctgcgtcgg tctcctgagt agctgtgttc    1440
ctgggtcttt cgatggttat ttaatacttc cctacagtaa tgccctgtgc gtacatgcta    1500
agtgtgatga aatggttggc acagttaaat cttttgaaag acattgccaa gtcactcttc    1560
agaaaagtga taggaggtca tagcaatttt aagaagtcct catttctaca tttccttact    1620
aatctcggtt ggtgtctctt caatctttcc tcacacttttt cttgggtttt tcctgaatca    1680
tgagtctact acatttacac attttaaagc atctttagaa acaggatctc attttgttgc    1740
ccaggctaga gtttggtggc atgattatag ctcctcatac tcctgggctc aagtgatcct    1800
tccacctctg aaaccccaaa atttgagaaa ggtctcattt aatttagaaa gtttattttg    1860
ccaaggttga gggtgcacac ctgtgatgat atacgagtta aaagaaatt atttaggcag    1920 atactgaggg taagaaagtc ctcggtaagg ttttcttttc aatgaaaagc agcccccaag    1980
cattttcttt tctaacaaag agcagcctgt aaaatcgagc tgcagacata cacaagcaag    2040
ctggaagctt gcacaggtga atgctggcag ctgtgccaat aagaaaaggc tacctggggc    2100
caggcagatc caacatggcg gctccatctt ccctttcctt gtcaaccatg tgcacagtaa    2160
ggagcaggca acatagtgtc ccccgagtag agaccaattt gcataataaa aggtgagggt    2220
agggtgggca gcttctttgc atgctatgta aacattatgc ctggtccaac caatctttgg    2280
gccctgtgta aattagacac cacctcctca agcctgtcta taaaccctg tccattctgc    2340 cgcaggctgg aagacccact ggggcacccc tctctctcta taggagacag ctattcattt    2400
ttctctttct ttcacctatt aaagctccac tcttaacccc actccgtgtg tatctatgtt    2460
cttgatttcc ttggcatgag gcaatgaacc ttgggtatta ccccagaacc ttgggtatta    2520
tgccacttca gtgacacagc ctcaggaaat cctgatgaca tgttcccaag atggtcgggg    2580
cacagcttgg ttttatacat tttagggaga catgagacgt caattcatat atgtaagaag    2640
tacattggtt ccgtccagaa aggcggggac aacttgaggc agggagagag cttctaggtc    2700
acaggtagac aaatggttgc attcttttga atctccgata agcctttcca aaggaggcaa    2760
tcagaatatg cgtctattga ctgggcgcag tggctcatgc ctgtaatgcc agcactttgg    2820
gaggcggagg tgggtggatc acctgaggtc aggagtttga gagcagcccg gccaacatgg    2880
tgaaaccctg tctctactaa aaatacaaaa aattagctgg gcgtggtggc gggcgcctgt    2940
aatcccagct actcgggagg ctgaggcagg agaatagctt gaacccagaa ggaagaggtt    3000
gcagtgagct gagatggtgc cattgcactc cagcctgggc aacaagagtg aaactccatc    3060
tcagaaaaaa aaaaaaaagg cctgggcaaa gtggctcacg cctgtaatcc cagcactttg    3120
ggaagccgag gcgggcaggt cacaaagtca ggagattgag accatcctgg ctaacatgat    3180 gaaacccat ctctactaaa aaatacaaaa aactagctgg gtgtggtggc gagcacctgt    3240
agtcccagct actcggcagg ctgaggcagg agaatggcgt gaaccgggga ggcggagctt    3300
gcagtgagcc gagatcacac cactgcactc cagcccggac gacagggcaa gactctatct    3360
caaattaaaa aaaaaaaaa aaaaaaaaa aagagagag agaatatgca tctatctcag    3420
tgagcagaag gatgactttg aatggaatgg gagcagttcc tagcttgaac ttccccttta    3480
gcttcagtga tttgggggct caaggtatgt tcctttcaca tacctcagcc tcccaagtag    3540 ctggaccac aagtgcatgc caccacacgt ggctaatgtt ttattttttt tgtaggaata    3600
gggtctcact atgtgtccag gctggtctaa aaccccctgag ctcaaatggt cctcccgcct    3660
cagcctcccg aaatgctggg attacaggca tgagccagca tgcccggcct agtctacatt    3720
```

```
tttataaatt gctaattcaa agttccctct ccaaaacctc atggttttcc ctgttctcat   3780
cccctgcacc ctcccttccc ctggagtact cacctggcct tggaggtctg gtgtgagccc   3840
ggacttcgat tctaggcaca gcatgtgatg agcgccccca ggtcaaacac ctcccctctg   3900
cggcctgtgc ttcaccgcct tgacagtgag aaaggtctcc cttcggctca ttctcgaagt   3960
ctcaaacttc acttctcctg tgcgctgatt ctgaattcag ccccgtcca aggtcctggc    4020 cccttctct tctgcttggc gtgttgttca tcaccactgt gcactgctga gggtaagtgc    4080
ggttctctgg acctctgctt tatcattaga acagactctt gcggtttccc acgacattcc   4140
tttcacttct cacttggaag atgagccgtg aggaaatcct gtgttgtgtg gtatgtgggc   4200
tgtgcttctg cttgacttga gggccaagca gcattgcaag ccatggtttt aaataagaaa   4260
gaacatttct aaccttcatc ttctagtaag aaacaagtg ggctttagag ttcttgctca    4320
ggaaagacct atgtcccagt ccaaccggac cttttactaa agagatcttc ctgatcctcc   4380
tccccaggcc aggggagggg tcctccctgg ggttggagcc tttagtaggg ggtcggagac   4440
acgacgtagc cttcatgaca ttcatagtct agttacacga tccctgtaag ggtcagttga   4500
agtaagtgct acaaaggaag ggaggtgctc agtggagagg gctctctttt atgtattata   4560
tttctttcat ggggagggat atggatcagg gatcagcaga ggtgtttcag tcccgaggga   4620
aagaaagtca gcgtggcttg ggagttggga gcagcaagac agtggctcaa gatatcttaa   4680
gactagtgga gtacaccttg catgttaaaa gccttgctca gggctgcctg gttcttgtag   4740
gacgacagag atggcctagc tctgcatact gcaccccag gggctcagaa cagtgcaaat    4800
gtcagtctat ctgtcagtgg cagagccagc cttggagcag gggtgcaagg aggtctctgc   4860
actggccagg catgcagaac attctgttca gtagcactgg acagaaggcc ccatctagat   4920
gagacagagc tggtggggca ggacaaagac tcctggcagc tcaaacggcc tggcagatgc   4980
ttggagagag ggggcttctt gagacagcac catttctggg aagagagtca cctgggaggg   5040
atgaggccac gctccggctt ggaggtgaag agaggggctg ctgcaagaaa gaattagaga   5100
catgccagcc tttgctgtgt tgcccaggct ggtcatgaac tcttggcctc aagcaatctt   5160
cccacctcag cctccccaag cgctgggatt atagacatga gccccatgc tggccaataa    5220 aagatgattt tatggagggg atggtggtga aggttgtggg tggtatgaaa tagtaagaaa   5280
tatatattgg tctgcaccca gttcctgcca cagagctcct aaaatcctga aacttcctg    5340 ggtgagcatc ttttgttcta atgaggtgac tcttggtggc tcctggatag gagtgaatca   5400
ccagaaagat caagccagag ttagaagcag aaagtgctgg ctataacaca ggaaagctgt   5460
aacacaaata taaagttttt ttttttttt tttgagatgg agcctcactc tgttgcccag    5520
gctggagtgc aatggtgcaa tctcagctca ctacaagctc tgcctccag gttcaagtga    5580 ttctcctgcc tcagcctcct gagcagttgg gactacaggt gtgtgccacc acatctggct   5640 aattttgta ttttagcag agacggggtt tcaccatatt aaccaggctg gcctcaaact    5700
ccttaccttg tgatccgcct gcctcagcct cccaaagtgc tgggattaca ggcatgagcc   5760
accgtgcctg gccaaaagac attgttctta aagaatcaa ctaactaacc aaataaataa    5820
aaatctaacc taattaagaa actaaaaata cacaaaaatt aatttcaagg ggagaaaat    5880 catgtaaaga gagaaagata atgaatactt tgcagaaatt tatgaacata acataaaac    5940 ttggatgaaa tgcatttcta ggaaaacata atttatcaaa actaaccaca agtaaaatag   6000
aagcctaaat aggatatttt caagagaaga agtaaagttg tcaaagtgct acccttcaaa   6060
```

```
aaaacaccag gctcaaacaa tctgacatgg gaatgttagc acaccttaga gagcaaataa    6120
aactttgaat gggcttgaaa tattccagac tctagaaaaa caaaacttcc caattctttt    6180
tataaagcaa gtataaattg ataccaaaat cttataaaga ccttatacaa aacttcatac    6240
caatctcttt tatgaataca aaacccttaa taaagtatta ccagacagaa cccaacaata    6300
cataaaaatg tcacatcata acatagtggg gtttatttca ataatgcatg gatggttcaa    6360
tacaaggaaa ttcagtaaca caatataata gatcatgtga atatacccaa agaaaaaata    6420
gattattttc atagatgctg taaaggcatt tgaccaaatt caacacctac tttttaggtg    6480
gtcaataaaa taaattagtt actccttctt tagcatgata aaatatattt atcagcccag    6540
aaggcatcat tttacccgat aagggcacac gctggaggga ataatgttaa aattaggaat    6600
aagaggatag ctagtttctt tcttctttt ttttttgag acggagtctt gctctgttgc    6660
caggctggag tgcagtggtg caatgttggc tcactgcacg ccccccgcct cccaggttca    6720
agcgattctc ctgcctcagc ctcccgagta gctgggacta caggcgcgca ccaccatgcc    6780
cggctaattt tttttttgtat tttagtagag atggggtttc accatgttgg tcaggctggt    6840
cttgaactcc caacctcacg tactgggatt accggtgtga gccaccacgc cagcccaact    6900
actttcaaca ttatccttaa tactgatgct tattgactta ctatgggtt acctctagat    6960
aaatccataa taagttgaaa atataagtaa aaaatgccct taatacacct aacctaccaa    7020
acatcatagc tgagcccagc ctgccttagc tatgctcaga cactgacgtc agcctacaat    7080
tggcaaaatc acacagcagc acagtctact gcagagcatc tgctgtttgc ccttgtgact    7140
gcgtggctgc ctgggagctt cccagcttca caagacagta ttacgtagca catcactagc    7200
ctggggaaag atcaaagttg aaaatttgaa gtgtggtttc cattgaatgt gtactgcttt    7260
tgcaccatca tcaagtcaaa aattttagt tgaaccagcc taagtttggg accatcttta    7320
ttttcaggag gaacttccat gtacattgat gacggacgat agaatccgtt tctatcatcc    7380
taatgaacat aatgaataaa tccagacaaa cataaacatt aacagagtaa gcagctttcg    7440
gggctggaag ccagaagagg gtgggagcgc agagagagag gccaaacacc agggctgctt    7500
ctgctttgcg ggtatttgct gatctggaca aggtatctgg aaggctgagc taagcctcct    7560
ttttttttga ggtggcgtct cactctgttg ccaggctgga gtgcaatggt gcgatctcag    7620
ctcactgcaa cctccacctc cctggttcaa gcgattctcc tgcctcagcc tcccgagtag    7680
ctgggattac aggctcccgc cactacaccc agctgatttt tgtaattta gtagagacgg    7740
ggtttcacca tgttggccag gatggtctcg atctcttgac gtcatgatct gtccactcg    7800
gcctcccaaa gtgctgggat tataggcgtg accaccgtg cccgtctga gctaagcctc    7860
ttgagcatag gggactaaaa atgaaatcta gcgcatgcca agtttagggt cccaggcaat    7920
tccttccac tttggggtcc actttgggt ccaccccacc caagaagaag gatgacttgg    7980
aagtaaacca gctctgaaat atggatggtc tctgggacc ataccaatcc cttcatatca    8040
accacatcca gttcctcaaa actggaactt ggattaagat ggcctaggac ttctagtgtc    8100
ccaggagcct ggcattgcaa acaaaaatcc tctccggaag aagataatac cttaagcttc    8160
aaatgactct ctaataaatt tcaaatacaa tgtccagcac acaaacacaa attaccagga    8220
acgtgatatg aggcctgatg gatgggaatt agcagaaact tcaggcatga gaaacatacc    8280
ctcagaggcc tagaatctat ctagtgtcta gataatggag atatgaaata cagacactta    8340
aacaactatg tttcccatgt tcaaagagga aatttgcaaa acttgaaagt gttggcagga    8400
aatcagaaac tataaaatgt gacaacagca tactttagag tcagtataaa ttacggtccc    8460
```

```
gaaaactgca gaattccaga acttaatggt aaagcaaggg tttaacagca gaatagaaat   8520
agccagagag aactaggaag taagtcagat gacactaccc agaataaggc actgagaggc   8580
caaggaatgg aaaatgcaga agaaaggata tggtgagagg atctaatata catttatttg   8640
gagtaccagg gagagagaga aggagaagaa cagaagccgt gtttcaagga cggtgactga   8700
gaggcttcga aactgatgaa agccatcagt tcacaaattc aaagcccagt gaattccaag   8760
gagaaaaaaa gaaatcccata ctgtgaaagc aagtccagac aatgacaaac accatcaaca   8820
atacacagga caggcataag atgcatttaa tgggacact cagaggcaga gggttatcag   8880
aaggaggcac ttctctccca agttctcatc atcccagggc cagggacagc tggtcacacc   8940
ttagggagtt cactaggaga gggatctggc ttcttgtcat tctgggtatt tgtagggaaa   9000
ttggaaggga accgagagca cctagccaat cgcatagcaa tgggagattt caggctgtgg   9060
ggaatgtctt tgctggtgaa aagaacatcc tgaccttaga aatctttcac cgaggggat   9120
ctgcgttcca gaacttctgg agctggtata ggtaaggctt tgagctttcc tactgagcca   9180
gcctgttgct aggttaccaa aggggacctc gagggccatc tggccaacaa gcagacttgt   9240
ctctccttac accccagac gtatcactgc aaaactacag aaaaccaaag acagagaaaa   9300
tcttaaaagc agccagattt aaaaaatggc atattagttt caaagcagca gccatgaaat   9360
tgacagctga tgtctcaaca gcaagaatga aaagtggaag acaggccagg tgtggtggct   9420
caggcctgta atcccagcac tttgggaggc cgaggcgggt ggatcacgag gtcaggagac   9480
caagaccatc ctggctaaca tggtgaaacc ccgtctctac taaaaataca aaaaaattag   9540
tcgggcatgg tggtgggtgc ctgtagtccc agctactcgg gaggctgagg caggagaatg   9600
gcgtgaaccc gggaggcgga gcttgcagtg agccgagatt gtgccactgc actccagcct   9660
gggtgacaga gcaagactct gtctcaaaaa aaaaaaaaaa aaaaaaaaaa aaagggtgac   9720
gaagcttcaa tctcctgaaa ggaagcaact gccgcctttg attcgatacc caccaaaatc   9780
cgtgaagaag gaaggcaaaa taaaaacact tcctgattga actggaaaga tttccgcaat   9840
agaagaccca ctgtccaagg aattctaaag gatgctttcc aggcagaaga aaatgacccc   9900
agaggaagat cagagattca ggaaagaaat ggagagtgat aaaaatgaaa aattcggggg   9960
ccaatttaaa caaagctga ctgctctaca actgttgtgt ctctatcttt tgtaacatat  10020
atgtgtgtgt agcttttttt tttttttttg tcaagatgga ttctcactct gtcgcccagg  10080
ctacagtgaa atggcacggt ctcggctcac tgcaacctct gccccttggg ctcaaatgat  10140
tctcttgcct cagcctcctg agtagctgag attacaggtg cctggcacaa tgcctggcta  10200
attttttgtat ttttactaga gatgggattt ctccatgttg gccaggctgg tcttgaacac  10260
ctgacctcag gtgatccacc tgcctgggcc tcccaaagtg ctaggattac aggcgcgagc  10320
cactgcatct ggcctatgtg tgtgtttata tggaattaaa acacatggca ataatacccct  10380
ccaaattggg agaaaccaaa aatagcattt aaatgttgta agctccctgc ataatcaaga  10440
agagaataga tttacgttag attttgatac ctggaggatg aatgttgtaa tttctagggt  10500
gaccatgaaa agaggagaca acggtgtatg tttttttttt tttgagatgg agtctcactt  10560
tgtcacccag gctggagtgt tgtggtgtga tcttggctca ctgcaacctc ctcctcttgg  10620
gttcaggcca tcctcccacc taggcctcca gagtaggtgg gatcacaggc acctgccacc  10680
acacctggct aatttttttt tttttttaaa tatttagtag agatgggggtt tcaccatgtt  10740
ggccaggctg gtcttgaact cctgacctca ggcgatctgc ctacctctgc ctctcaaagt  10800
```

```
gctgggatta caggtgtgag ccatcgcgcc cggccaacag tgatcacttt caaactaaca    10860
gaggttcaaa aataaaatca gacttaacca aaaaccaggt aacagagctg gtaggatata    10920
cagaaagact gacctcacgt atatcaacga ttacagttaa tattaatgaa ggaaatgctc    10980
tagtttaaaa acgagggttg tcaaagaccc cacataagaa gctccttacc agcggtgcac    11040
ctagaaccta aggaaacagg acagatgaag gaggacgcgc ccccgccgct gtcctgcgcc    11100
tcagccatcc tatgagacgg gaaaggtttc tgtctgcagc tgggcccgtg ctcttaccca    11160
gctcctggct ttcttctctg gaaggttcct gcctgttttg ccctcacacc tgctcctctc    11220
tcagccctct caggggtggg gctggaggcc accaaagagc ctcctctgct ctccagttgc    11280
tcgactgctc ctcatttccc cctggggtct gcgtcagggt ttccttcttt tccagcccca    11340
ccccgcgtgc atcccacctg gtctcgggtc ggggctgctc ccgcttactg ccccctgccc    11400
aggctggtgt gcacccctc tggctgcttt caaggcctct tctctcttct cggcaggaca    11460
ggcacaggca ggtggccagg tgtcatgctt agctccccgc ccagtgagat tctttcattt    11520
aacaatcttc ccctgaatag ttcatgttca ttgctgaaaa tttgaaaaat atggaaaagc    11580
acaaagatta agatataaac cgccctcaat tcccctgccc agagagagtc actgctatga    11640
cttggtgact aggaacctta tttctctctc gctctttttt ttttttttga dacagagtct    11700
tgctctgtca cccaggctgg agtgcagtgg ctcgatctca gctcactgca acctccgcct    11760
cctgggttca gcgattctc ctgcctcagc ctcttgagta gctgggatta caggcacctg    11820
ccaccatgcc cggctaattt ttgtattttt agttgagaga gggtttcatc ttgttggtca    11880
ggcggacttg aactcctgac ctcaggtgat cagcccacct cggcctccca aagtgctggg    11940
attacaggtg tgagccactg cgccttcatc tctcttctgt gtatgtgtac gctgttttt    12000
ctttagaatg ggggacgtta tcaggctcta catggtgtgt agtcggctag catgttgtaa    12060
gcctttccct gtgtcacaag tgctcatctg gaacaggatt ctaatgactg cctgtggcta    12120
tgtttgggatt cctttaactc agctccttct gcccagcatc tatcttttt ccatcttttg    12180
tcctaagtgt tgctataata aatcattgat cacacatgcc tgactgtttg cataggataa    12240
attacgggaa atgttttttgc tgttcaggga ctgtgcccat ttttaggcct cagagacacc    12300
atgccagact gcccagtatt gatctttact ctttttagat gatgccaaac ttttctgtga    12360
actttaaaaa cctgtgtctt gacagtccat ttctgtaagt cttcacatt agatttcctg    12420
tcaggatgat agtcaattct aggcagatga tgttttctca gccatggctg aagcagttgt    12480
gatttgttgt ggccatgtaa agtcccgatg atccattgcc tccctggatg ggttggaata    12540
atttggtttg ggagcatata acagaatgac ctggagtcac agcagctcag acggaagtgt    12600
atttctccct tacagatgaa agaattccag gccaggctgg aatgacaact gcacacagtc    12660
atctgggccc cctccttcca gctcccatca ccccaggatg tggctttat gcagatgatc    12720
caaaatggct gctcaagtcc cagccaacac atcccattcc agggagcagg aaaaggtgt    12780
gtctttccct tcattttatg tgattccttt ctagaagtac tactcattac ttctgcttgc    12840
atctccctgg ctagcactta cttagttata tggccatagc tagctgaagg aaggacaggg    12900
actgtcatac actagctaag aggcaaactg cttagataaa aaggtctcta agaaggtca    12960
gagcggctgc tagggtgcaa ctctattact tattgttatg ggacgaactg tgtccctcat    13020
tcaggttgat gtcctaagcc ccagaacctc agaatgggat tgtatttgga gacaggttct    13080
ttaaggaggt aaggaggcta aaatgagatc attagggtgg gccataatcc gactgatgtc    13140
ttacaagaag agattaggac acggacatgc tcagagggac ggccacgtga ggacaccaag    13200
```

```
aaaggcagct gtctgcaagt caaggacagg gctcagggga aaccaacctt gccaacacct   13260
tcatctcgga cttctagcct ctaggaccat gagaagatac atttctgttg tttaagctgc   13320
ccggtctgtg gtactttgtt atggcagccc aagtaaacaa atacagtcat ctgctgctgg   13380
aacaaatcac cccagcactg tggcttggca gcacacatgt ctagtcatag agttatatgt   13440
agttacgtgt agagccatat gtatcgtcac acgttctgtg ggtcaggaat ttggacccag   13500
cttaaccagc tccacttctc gccagggttc agtcaaatac cagctgcctc ccacctgaga   13560
gctcagccgg ggaagggtcc ctttccaatc tcacgtggtg ttggcaggat ccagttcctc   13620
atggcctgct ggactgagaa cctcagttct cactgcctgt tggccagagg ccgcctttat   13680
gtcctcgcca tgtgggcctc tccaacatgg cagctgactt catcagagca tccatgccaa   13740
gaaggcaaca gagagggcca gggagactga agtcataccc ttttgcgacc tagtcatggg   13800
gtgacattcc atcacctttg cccattggtt agaagcaggc caccaggtac agcccaagct   13860
cacggggagg ggtcatacaa gggtgtcaat accaggaggt gaggggtgct ggggccatct   13920
tatgagtctg cccactgagg taactaacaa ccttgaggcc tgacacagtg gacaaaggcc   13980
cttattaaca gcagagaact gggaacttta tttatttatt tattttgag acagagtctc   14040
actcttgtca cccaggctgg agtgcaatgg catgatcttg gctcactgca acctccacct   14100
cccaggttca gcaattctg cctcagcctc cggaatagct gggactacag gcatgcacca   14160
ctacacccgg ctaattttg tattttagt agagacaggg tttcgccatg ttggccaggc   14220
tggtctcgaa ctcctgacct ctggtgatct gcctgcctg gcctcccaaa gtgctgggat   14280
tacaggcgtg agccaccgca cctcgctgga acttaatttt tttagagaca gtgtcgctct   14340
atcacccaag ctggagtgca gtggtgcaat cctagctcac ttgcagcctc aaattcctgg   14400
gttcaggtga tcctcccaca tcagcctccc aagaactggg aactaacagc tgtttctctg   14460
ctgtccttct caagaaaagg gaggctactg ctaccccact ggggacaatg ctgggtttcc   14520
cttaggaca ggctctgaga caaggcggag gtgctgtttg tggccacaga gcaggggact   14580
ctgggttgca ggtgtggcct ggctaaagta ggctttactg ggctcctctc tgcctgcatc   14640
accccccggc tgggcggttg tctctgaggc caaccttact ccctgctggg caggctggac   14700
agctgccctc tccgtttgcc cctctaccac ccaaaaggca ggaggctctg gagaccagga   14760
ccctgcccgc cacggcctgt gtcccaggcg tgagggggtg ccccacagac ctctgctgag   14820
ctgctgctga atgacgcccc ttggggtcc tgccggaagg tcagagcagg ggtgcactcc   14880
cataaagaaa cgcccccagg tcgggactca ttcctgtggg cggcatcttg tggccatagc   14940
tgcttctcgc tgcactaatc acagtgcctc tgtgggcagc aggcgctgac cacccaggcc   15000
tgccccagac cctctcctcc cttccggggc gctgcgctgg gaccgatggg gggcgccagg   15060
cctgtggaca ccgccctgca ggggcctctc cagctcactg ggggtggggt gggggtcaca   15120
cttgggtcc tcaggtcgtg ccgaccacgc gcattctctg cgctctgcgc aggagctcgc   15180
ccacccctctc cccgtgcaga gagccccgca gctggctccc cgcagggctg tccgggtgag   15240
tatggctctg gccacgggcc agtgtggcgg gagggcaaac cccaaggcca cctcggctca   15300
gagtccacgg ccggctgtcg ccccgctcca ggcgtcggcg gggggatcctt tccgcatggg   15360
cctgcgcccg cgctcggcgc ccctccacg gccccgcccc gtccatggcc ccgtccttca   15420
tgggcgagcc cctccatggc cctgcccctc cgcgccccac ccctcccctcg ccccacctct   15480
caccttcctg ccccgccccc agcctccca cccctcaccg gccagtcccc tcccctatcc   15540
```

```
cgctccgccc ctcagccgcc ccgcccctca gccggcctgc ctaatgtccc cgtccccagc    15600
atcgccccgc cccgcccccg tctcgcccccg cccctcaggc ggcctccctg ctgtgccccg    15660
ccccggcctc gccacgcccc tacctcacca cgccccccgc atcgccacgc ccccgcatc     15720 gccacgcctc ccttaccatg cagtcccgcc ccgtcccttc ctcgtcccgc ctcgccgcga    15780
cacttcacac acagcttcgc ctcaccccat tacagtctca ccacgccccg tccctctcc     15840 gttgagcccc gcgccttcgc ccgggtgggg cgctgcgctg tcagcggcct tgctgtgtga    15900
ggcagaacct gcgggggcag gggcgggctg gttccctggc cagccattgg cagagtccgc    15960
aggctagggc tgtcaatcat gctggccggc gtggccccgc ctccgccggc gcggccccgc    16020
ctccgccggc gcagcgtctg ggacgcaagg cgccgtgggg gctgccggga cgggtccaag    16080
atggacggcc gctcaggttc tgcttttacc tgcggcccag agcccattc attgccccgg     16140 tgctgagcgg cgccgcgagt cggcccgagg cctccgggga ctgccgtgcc gggcgggaga    16200
ccgccatggc gaccctggaa aagctgatga aggccttcga gtccctcaag tccttccagc    16260
agcagcagca gcagcagcag cagcagcagc agcagcagca gcagcagcag cagcaacagc    16320
cgccaccgcc gccgccgccg ccgccgcctc ctcagcttcc tcagccgccg ccgcaggcac    16380
agccgctgct gcctcagccg cagccgcccc cgccgccgcc ccgccgcca cccggcccgg     16440 ctgtggctga ggagccgctg caccgaccgt gagtttgggc ccgctgcagc tccctgtccc    16500
ggcgggtccc aggctacggc ggggatggcg gtaaccctgc agcctgcggg ccggcgacac    16560 gaaccccccgg ccccgcagag acagagtgac ccagcaaccc agagcccatg agggacaccc    16620
gccccctcct ggggcgaggc cttccccac ttcagccccg ctccctcact tgggtcttcc     16680
cttgtcctct cgcgagggga ggcagagcct tgttggggcc tgtcctgaat tcaccgaggg    16740
gagtcacggc ctcagccctc tcgcccttcg caggatgcga agagttgggg cgagaacttg    16800 tttctttta tttgcgagaa accagggcgg gggttctttt aactgcgttg tgaagagaac     16860
ttggaggagc cgagatttgc tcagtgccac ttccctcttc tagtctgaga gggaagaggg    16920 ctggggcgc gggacacttc gagaggaggc ggggtttgga gctggagaga tgtggggca     16980 gtggatgaca taatgctttt aggacgcctc ggcgggagtg gcggggcagg ggggggcgg    17040 ggagtgaggg cgcgtccaat gggagatttc ttttcctagt ggcacttaaa acagcctgag    17100
atttgaggct cttcctacat tgtcaggaca tttcatttag ttcatgatca cggtggtagt    17160
aacacgattt taagcaccac ctaagagatc tgctcatcta agcctaagtt ggtctgcagg    17220
cgtttgaatg agttgtggtt gccaagtaaa gtggtgaact tacgtggtga ttaatgaaat    17280
tatcttaaat attaggaaga gttgattgaa gttttttgcc tatgtgtgtt gggaataaaa    17340
ccaacacgtt gctgatgggg aggttaattg ccgaggatg aatgaggtgt acattttacc    17400
agtattccag tcaggcttgc cagaatacgg ggggtccgca gactccgtgg gcatctcaga    17460
tgtgccagtg aaagggtttc tgtttgcttc attgctgaca gcttgttact ttttggaagc    17520 tagggggtttc tgttgcttgt tcttggggag aattttttgaa acaggaaaag agagaccatt    17580
aaaacatcta gcggaacccc aggactttcc ctggaagtct gtgtgtcgag tgtacagtag    17640
gagttaggaa gtactctggt gcagttcagg cctttctctt acctctcagt attctatttc    17700
cgatctggat gtgtcccaga tggcatttgg taagaatatc tctgttaaga ctgattaatt    17760
tttagtaata tttcttgttc tttgtttctg ttatgatcct tgtctcgtct tcaaagttta    17820
attagaaaat gattcggaga gcagtgttag cttatttgtt ggaataaaat ttaggaataa    17880
attattctaa aggatggaaa aacttttttgg atatttggag aaattttaaa acaatttggc    17940
```

```
ttatctcttc agtaagtaat ttctcatcca gaaatttact gtagtgcttt tctaggaggt    18000
aggtgtcata aaagttcaca cattgcatgt atcttgtgta aacactaaac agggctcctg    18060
atgggaagga agacctttct gctgggctgc ttcagacact tgatcattct aaaaatatgc    18120
cttctctttc ttatgctgat ttgacagaac ctgcatttgc ttatcttcaa aatatgggta    18180
tcaagaaatt tcctttgctg ccttgacaaa ggagatagat tttgtttcat tactttaagg    18240
taatatatga ttaccttatt taaaaaattt aatcaggact ggcaaggtgg cttacacctt    18300
taatccgagc actttgggag gcctaggtgg acgaatcacc tgaggtcagg agtttgagac    18360
cagcctggct aacatggtga aaccctgtct ctactaaaaa tacaaaaatt agctggtcat    18420
ggtggcacgt gcctgtaatc caagctacct gggaggctga ggcaggaaaa tcgcttgaac    18480
ccggaggca gagtctgcag tgagttgaga tcacgccact gcactccagc ctgggtgaca    18540
gagcgagact ctatctcaaa aaaaatttttt tttaatgtat tattttttgca taagtaatac    18600
attgacatga tacaaattct gtaattacaa aagggcaata attaaaatat cttccttcca    18660
cccctttcct ctgagtacct aactttgtcc ccaagaacaa gcactatttc agttcctcat    18720
gtatcctgcc agatataacc tgttcatatt gtaagataga tttaaaatgc tctaaaaaca    18780
aaagtagttt agaataatat atatctatat attttttgag atgtagtctc acattgtcac    18840
ccaggctgga gtgcagtgat acaatctcgg ctcactgcag tctctgcctc ccaggttcaa    18900
atgcttctcc tgcctcagcc ttctgagtag ctgggattac aggcgcccac caccatgtcc    18960
agctaatttt tgtattttta gtagagatgg ggtttcacca tgttggccag gctggtcttg    19020
aactcctgac cttgtgatct gtccacctcg gcctcccaaa gtgctgggat tacaggtgtg    19080
agccaccatg cctggctaga ataataactt ttaaaggttc ttagcatgct ctgaaatcaa    19140
ctgcattagg ttttatttata gttttatagt tatttaaat aaaatgcata tttgtcatat    19200
ttctctgtat tttgctgttg agaaaggagg tattcactaa ttttgagtaa caaacactgc    19260
tcacaaagtt tggattttgg cagttctgtt cacgtgcttc agccaaaaaa tcctcttctc    19320
aaagtaagat tgatgaaagc aatttagaaa gtatctgttc tgttttatg gctcttgctc    19380
tttggtgtgg aactgtggtg tcacgccatg catgggcctc agtttatgag tgtttgtgct    19440
ctgctcagca tacaggatgc aggagttcct tatgggctg gctgcaggct cagcaaatct    19500
agcatgcttg ggagggtcct cacagtaatt aggaggcaat taatacttgc ttctggcagt    19560
ttcttattct ccttcagatt cctatctggt gtttccctga ctttattcat tcatcagtaa    19620
atatttacta aacatgtact atgtgcctgg cactgttata ggtgcagggc tcagcagtga    19680
gcagacaaag ctctgccctc gtgaagcttt cattctaatg aaggacatag acagtaagca    19740
agatagataa gtaaaatata cagtacgtta atacgtggag gaacttcaaa gcagggaagg    19800
ggatagggaa atgtcagggt taatcgagtg ttaacttatt tttatttta aaaaaattgt    19860
taagggcttt ccagcaaaac ccagaaagcc tgctagacaa attccaaaag agctgtagca    19920
ctaagtgttg acatttttat tttatttgt tttgttttgt ttttttgag acagttcttg    19980
ctctatcagc caggctggag tgcactagtg tgatcttggc tcactgcaac ctctgcctct    20040
tgggttcaag tgattctcat gcctcagcct cctgtttagc tgggattata gacatgcact    20100
gccatgcctg ggtaattttt ttttttttccc ccgagacgga gtcttgctct gtcgcccagg    20160
ctggagtgca gtgcgcgat ctcagctcac tgcaagctcc gcttcccgag ttcacgccat    20220
tctcctgcct cagtctccca gtagctggg actacaggcg cctgccacca cgtccagcta    20280
```

```
attttttttgt  atttttaata  gagacggggt  ttcaccgtgt  tagccaggat  gatcttgatc  20340
tcctgacctc  gtcatccgcc  gaccttgtga  tccgcccacc  tcggcctccc  aaagtgctgg  20400
gattacaggc  atgagccact  gtgcccggcc  acgcctgggt  aattttttgta  ttttttagtag  20460 agatggggtt  ttgccatgat  gagcaggctg  gtctcgaact  cccggcctca  tgtgatctgc  20520
ctgccttggc  ctcccaaagt  gctaggatta  caggcatgag  ccaccatacc  tggccagtgt  20580
tgatatttta  aatacggtgt  tcagggaagg  tccactgaga  agacagcttt  ttttttttt   20640 tttttggggg  ttgggggggca aggtcttgct  ctttaaccca  ggctggaatg  cagtatcact  20700
atcgtagctc  acttcagcct  tgaactcctg  ggctcaagtg  atcctcccac  ctcaacctca  20760
caatgtgttg  ggactatagg  tgtgagccat  cacacctggc  cagatgatgg  cttttgagta  20820
aagacctcaa  gcgagttaag  agtctagtgt  aagggtgtat  gaagtagtgg  tattccagat  20880 gggggaaca   ggtccaaaat  cttcctgttt  caggaatagc  aaggatgtca  ttttagttgg  20940
gtgaattgag  tgaggggggac  atttgtagta  agaagtaagg  tccaagaggt  caagggagtg  21000
ccatatcaga  ccaatactac  ttgccttgta  gatggaataa  agatattggc  atttatgtga  21060
gtgagatggg  atgtcactgg  aggattagag  cagaggagta  gcatgatctg  aatttcaatc  21120
ttaagtgaac  tctggctgac  aacagagtga  agggaacac   cggcaaaagc  agaaaccagt  21180
taggaagcca  ctgcagtgct  cagataagca  tggtgggttc  tgtcagggta  ccggctgtcg  21240
gctgtgggca  gtgtgaggaa  tgactgactg  gattttgaat  gcgaaccaa   ctgcacttgt  21300 tgaactctgc  taagtataac  aatttagcag  tagcttgcgt  tatcaggttt  gtattcagct  21360
gcaagtaaca  gaaaatcctg  ctgcaatagc  ttaaactggt  aacaagcaag  agcttatcag  21420
aagacaaaaa  taagtctggg  gaaattcaac  aataagttaa  ggaacccagg  ctctttcttt  21480
tttttttttt  tgaaacggag  tttcgctctt  gtcacccggg  ctggagtgca  atgatgtgat  21540
ctcagctcac  taaaacctct  acctcctggg  ttcaagtgat  tcttctgcct  cagcctccca  21600
agtaactggg  attacaggcg  tataccacca  tgcccagcta  attttgtgt  ttttagtaga  21660 gatggggttt  caccatgttg  gccaggctgg  tctcgaactt  ctgacctcag  gtgatccact  21720
cgcctcagcc  tgccaaagtg  ctgggattac  aggtttgggc  cactgcaccc  ggtcagaacc  21780
caggctcttt  cttatactta  cctgcaaac   ccttgttctc  attttttccc  tttgtatttt  21840
tattgttgaa  ttgtaatagt  tcttatata   ttctggatac  tggattctta  tcagatagat  21900
gatttgtaaa  aactctccct  tcctttggat  tgtcttttta  cttcttgat   agtgtctttt  21960 gaagtgtaaa  agttttttaat tttgatgaag  tcgagtttat  ctattttgtc  tttggttgct  22020
gtgcttcaag  tgtcatatct  aagaaatcat  tgtctaatcc  aaagtcaaaa  aggtttactc  22080
ctatgttttc  ttctaagaat  tttagagttt  tacatttaag  tctgatccat  tttgagttaa  22140
tttttatata  tggttcaggt  agaagtccaa  ctttattctt  ttccatgtgg  ttattcagtt  22200
gtcccagcac  tgtttgttga  agagactatt  cttttccccat ggaattatct  tagtacccctt 22260 gttgaaaatt  aatcgtcctt  aattgtataa  atttatttct  agactgtcag  ttctacctgt  22320
tggtctttat  gtcgatcctg  tgccagtacc  atacagtctt  gattactgaa  gtttgtgtca  22380
cagtttaaat  tcatgaaatg  tgagttctcc  aactttgttc  cttttcaaga  ttgatttggc  22440
catgctgggt  cccttgcatt  tccgtacgaa  ttgtaggatc  agcttgtcag  tttcaacaaa  22500
gaagccaagt  aggattctga  gagggattgt  gttgaatctg  tagatcaact  tggggagtat  22560
tcgcatctta  acaatattgt  cttccaccta  tgaacatggg  caaactttgt  gtaaatggtc  22620
agattgtaag  tatttcgggc  tgtgtgggca  cagtgtctct  gtcacagcta  cgcggctctg  22680
```

```
ccattgtagc atgaaagtag ccataagcaa tatgtatgag tgtctgtgtt ccaatagaat    22740
tttattaatg acaaggaagt ttgaatttca tataatttc acctgtcatg agatagtatt     22800
tgattatttt ggtcaaccat ttaaaaatgt aaaacattt cttagcttgt gaactagcca     22860
aaaatatgca ggttatagtt ttcccactcc taggttaaaa tatgatagga ccacatttgg    22920
aaagcatttc tttttttttt tttttttttt tttttgagac ggagtttcac tcttgttgcc    22980
caggctggag tgcagtggcg cgatctcggc tcactgcaac ctctgcctcc caggttcaag    23040
acattctcct gcacggcctc cctagtagct gggattacag gcatgcgcca ccacacccag    23100 ctaatttgt attttagta gagacggggt ttctccatgt tggtcaggct ggtcttgaac     23160
tcctgacctc aggtgatcca cccgcctcag cctcccaaag tgctgggatt acagggtgtg    23220
agccaccaca ccctgctgga aagcatttct ttttggctg tttttgtttt ttttttaaac    23280
tagttttgaa aattataaaa gttacacata tacattataa aaatatcttc aagcagcaca   23340
gatgaaaaac aaagcccttc ttgcaagtct gtcatctttg tctaacttcc taagaacaaa    23400
agtgtttctt gtgtcttctt cccagatttt aatatgcata tacaagcatt taaatgtgtc   23460
attttttgtt tgcttgactg agatcacatt acatatgtat ttttttactt aacaatgtgt   23520
catagatatt gttccatagc agtacctgta attcttatta attgctatgt aatatttag     23580 aatttctttt taaagagga cttttggaga tgtaaaggca aaggtctcac attttgtgg     23640 ctgtagaatg tgctggtgac atattctctc taccttgaga agtccccatc cccatcacct    23700
ccatttcctg taaataagtc aaccacttga taaactacct ttgaatggat ccacactcaa    23760
aacatttagt cttattcaga caacaaggag gaaaaataaa ataccttata aagcactgtt    23820
taatattgta ttaaattgga tcaatttggg ggctagaatg tatgttagag acatgatatg    23880
tccataggtc cttgctatca cagtgaggtc tcagggacag tcgtttggta tcatttggga    23940
tctcataagc agactctctc tgcttgacct gacaaatcag agtctgtgtt ttaacaggtt    24000
cagtgagtga cttacatgca cattggagtt tgggaagctc cactgtaggt gcttagacct    24060 taccttgtt gttgctaata acaatgcaag catttgggag gaagacctgt gttgctcata    24120
tgtgtccagg tgtagctgag gtggccttgc ttatctgctg tagggccgtt gagcatttct    24180
gtagctgtga tgagtgagct gaggtgagcc tgcggagagc tcccagccat tggtagtggg    24240
actcgcttag atgaactgga aggacccttt catctgagca gccactatgg agaaaaacaa    24300
ccgaatgagg ggagagacaa tgtgcaattt tatttagggc acaaaggaga gctgtggtta    24360
gaaggtgaca tttgagtgga aaggggcaa gccatgtgta tagcgggaga agagaggtcc     24420
aggcagagtt aacagaaggc agaaatgctt tccatgtttg agaaccagta aggaggccag    24480
tggctgaagt aaggtgaagg gcagaaataa ggatgaggct gcgagagatg agaggttaga    24540
gacgagcgtc ttgtgcacca agataagctt gtgtggtcaa aacaagtagt ttaatttatg    24600 ttttaaaag atcatttgg ctgggcacaa tggttcatgc ctgtaatacc agtagtttga     24660
gacggtgtgg tgggaggatt gcctgaggcc agacgaccag catagccaac atagcagcac    24720
ctataaggtc tctacaaaaa actttaaaaa attagctggg catagtggtg tgtgcctgta    24780
gtcccagcta ctcaggaggc tgaggaggct ggaggattgc ttgagtccag gagtttgagg    24840
ctgcagtgag ctatgattat gccactacac tacaacctgg gcaagagagt gagaccctgt    24900
ctctaaatat acacacacac acacacacac acacacacac acacacacac acacacacac    24960
acacacatat atatgtatat atatgcattt agatgaaaag atcactttga caataccaca    25020
```

-continued

```
tgctggtgag gatttagaaa aactaggtca cttattgctg gtgggaatat aatatagtac    25080
ggccactctg gaaaacagtt tggcagtttg tcataaaact gaacataccg ttagtataca    25140
gcccagcagc aactacaatc ctgggcatta atcctagaga aatgaaacct taatgttcac    25200
ataaaaacct atactcaagt atgcatagca gctttaccca taatatctaa gaactggaat    25260
cagctcagat gtccttcaac aggtgaatgg ttaaactact cagtaataaa aaggaatgag    25320
ctactgatag catgcaacag tttaggtgaa gttatgctaa tgaaaaaagc caatcccaaa    25380
aggttataca tactgtatga ttctatgttt ttttgcaatg gcacagtttt agggatggag    25440
aatagattag tggttgcctg gggttagaga tggggtagta gagtaggtta gtggtggcag    25500
aggagagaaa agagagggag gtgaatgtgg ttataaaagg acaacacagg ggaatacttg    25560
taatggaaat gctttgtctt tttttttttt tttttttttt tggcgacaga gtcttgctct    25620
gttgcccagg ctggagtgca gtggcatgat cttttctcac tgcaacctct gcctcctggg    25680
ttcaagtgat acttgtgtct cagtctccca tgttcagagt gaaacaaacc agaggtaatg    25740
ttcatccaaa taatccaaca cacatgacat aaaacatca agatcaggtc ggacgtggtg    25800
gctcatgcct gtaatcccag cacttttggg aggccaaggt gggcagatca cttgaggtca    25860
ggagttcgag accagccggg ccaacatgat gaaaccccat cttgactaaa aatacaaaaa    25920
ttagccgggc atggtggtgt gcacctgtag tcccagctac ttgggaggct gaggcaagag    25980
aactgcttga acccgagggg cagaggttgc agtgagctga gagtgcgcca ttgcacttca    26040
gcctgtgtga cagagtaaga ctccatctcc aaaaaaaaaa aaccaagatc aattaaaata    26100
cagcattact gggccgggtg tggtggctca cacctgtaat cccagcactt tgggaggccg    26160
agatgggcag atcacgaggt caggagatcc agaccatccc ggctaacacg gtgaaacccc    26220
gtctctacta aaaatacaa aaaattagcc gggtatagtg gtgggtgcct gtagtcccag    26280
ctacttggga ggctgaagca ggagaatggt gtgaacccgg gaggcagagc tggcagtgag    26340
ctgagatcgc gccactgcac tccagcctgg gcgacagagc aagactccgt ctcggggaa    26400 aaaaaaaaat aaataaatag aatgctgtag tgtccttgag tttacatgcc cctccttacg    26460
cttgtgtgcc cgtgcagatt gcttgattac acaattagag gaggctggcg gaggattgtt    26520
ttaatttttt tttttttgag acagtctggc tctgttcccc aggctagagt gcaatggcgc    26580
aatcttggtg cactgcaacc tctgcctcct gggttcaagc agttcttctg ccgcagcctc    26640
ccgagtagct gggattatag gcgcccgcca ccacgcccaa ctatttttg tattttagt    26700 agagcagcgt ttcaccatgc tggccaggct ggtctcgaac tcctgacctc agatgatctg    26760
ctgccccagc ctcccaaagt gctgggatta caggcgtgag ccacacctgg ccgtttgttt    26820
taattttgaa ggtgaagtga aagtgactac atttaccaaa agtgattgaa agccaggac    26880 tgttcttacc ctgttttcc agttcttgct cagagcaagg tggtttcttt ttcacttaat    26940
caccatactt acttttcatg tagaacaagt cagtttgagt tatcagttca tcatcttaac    27000
taaattccat gggggaagga attagtttta gtttcttaaa cttccaggtt tgcttattgg    27060
acaaaatgag atagcaaggc agtgttttta agttagattt tttatttctt tggtaataca    27120 atttctcag aaactagta gtcttttagt ttagttgttt ttagttggtc ctatgttttg    27180
gatcacccct ctctacttta ttttgatagt gccaactgtg aagacatctg aagccatagg    27240
tttggatggg aaggaggcat ctttagcctg atcatcttcg ccaggctgtt tatctccttt    27300 tgcttggct agaagtctta ataggaggct tattcccagc tatttgggga catagaagca    27360
gttagccatt gcttatattt tactgaggtc tgtgtggtat gttgattgta gtcagttaac    27420
```

```
gattttgaga actgaaggca gcctggtata tatagagtag gtattagact gtgtttcttc   27480
taattgaatt tcccatctct tgtaatctat gccatcatct tctgtactgc tgagaaagaa   27540
agaaagtttc taatcaaact ataccactgg ttgtaagatg cagtttggct ttagtgatgt   27600
taacacatga ttcaaacgtg aaattgattg agtattggtg aaatacagag gagatttaaa   27660
gccagaagac ctgggtttaa atgctggctg tatgacttca tatctgtgtg atcttgggca   27720
tgtcatggtt ggcacttcaa tttcttctct ctataatggg ggaagtgagg ccagtcatgg   27780
tggctcatac ctataatccc agtgctttgg gaggccaaga tgggaagatc gcttgaggcc   27840
aggagtttga gcaattgggc aacatcgtga ggccccgtct ctacaaaata ttttgaaaaa   27900
attagccagg cccagtggtg cgtgcctgtg gtccgcgcca ctcaggaggc tgagacggga   27960
ggatcctttc agcctaggag tttaaggcta aagtgagcca tgattgtgct atcgtactcc   28020
agcctgggca gcagagcaag atcctgactc taaaaaaaag taaaataaag taaaatgggg   28080
gaaatgaact gctttagtaa catcatctgt tttttctgtg agcagcgtag cttgacagcc   28140
attggtgaac tcgtgccctg tgcttccctg tccagatccc cattctgccc gcaacatgga   28200
gtataacggt ttattcatag tagtcgagaa acactcactg aatgaatgaa tgaggtgtag   28260
aactaagtgg agtgggtaat tcaacacata ttaatttcct tctttttttt attttttagaa   28320
agaaagaact ttcagctacc aagaaagacc gtgtgaatca ttgtctgaca atatgtgaaa   28380
acatagtggc acagtctgtc aggtaattgc actttgaact gtctagagaa aataagaact   28440
ttgtatattt tcagtcttaa tgggctagaa tattctttgt gtcccagcta ttttaaatgg   28500
attcagaaat ccatttaaga tgaagaagga ccctttttccc atatttctgg ctatatacaa   28560
ggatatccag acactgaaat gaataatgtt ccctttttgt aatctttat gcaaaaatta   28620
aaaccattat ggtaattgaa caacatgttt atgtttagtt aacacccctta gcaactatag   28680
ttatttttaaa accatctatg gtttgatatt tttgcatttg ttgcaatagt aggaacagca   28740
caagacagtt cagtttgtct ctcttatttg cttttctctg gcagtttgct gtcctattgt   28800
acctctgctc ctagcagtgg ctggagccca ctcctctgtg cttcgggatt agtggggatc   28860
gtggggcatt gactgtaggt cagctttcct tgcttgatct ttctcactgg gatgaactag   28920
cagcaccttc ttttgtagct gctttgcttt tgactatctt tctgaccgtt gttcctagta   28980
gctgtagatg gtaaatatat ttaggcctgt ttccaatggc tcagtaggag acatattcac   29040
ctatgatatc tgaattctgt tacccacatg ggcatgcgtg aaatagttgc cttgccttac   29100
tttcccttgg aataaataat tcatgttatt ctcctggtag aagctagaaa aagcctttat   29160
agtcagtcag aaaaaaattt ttagacaaat aatcttgatt ttagtactga caaaaacgtg   29220
tggtgattct ttttttaatt tttttttgag acggagtttc actcttgttg cccaggctgg   29280
agtgcaatgg cgtgatctcg gctcactgca acctctgcct cctgggttca agtgattctc   29340
ctgcctcagc ctcccaagta gctggagtta caggcatgtg ctactgtgcc cagctaattt   29400
tgtattttta gtagagatgt tggtcaggct gatctcgaac tcccaacctt aggtgatctg   29460
cccgcctcag cctcccaaag tgctgggatt acaggcgtga gccagggcgc ccggtgattc   29520
atttgttttt tcaaaaaatt tcctcttggc cattgctttt cacttttgtt ttttttttt   29580
ttttgagacg gagtcacgat ctgtcaccca ggctggagtg cagtggcatg atcttggctt   29640
actgcaagct ctgcctccca ggttcacgcc attctcctgc ttcagcctgg cgagtagctg   29700
ggactacagg tgctcgccac cacacccggc taatttttg tatttttagt agagatgggg   29760
```

```
tttcaccgtg gtcttgatct cctgacctca tgacccgctc aactcagcct cccaaagtgc   29820
tgggattaca ggcgtgagcc accgcgcccg gccctctctt gtctttttat tgtggtaaaa   29880
tgcacataaa attgactgtc ttaaccattt ttaggggtac agttcagtat atatattcgt   29940
aatgttgtac agccatcact gccatctact tcataagttt ttcttctgtc aaaactgaac   30000
atctgtcttc attaaactcc ctatcatcca ttctttcctg tagtcccttt ctactttctg   30060
tctgtatgag tgtaactgct ctggagacct catgtaagtg gattcctaca ggatttgtgt   30120 ttttttttg gtgatctgct tattttaat gcctctgtgc atttgtatta tatactttca   30180
aagtgatttc acaaaccgt ttcattttag gttaactcat ttctgttgtt tgtgaaatac    30240
tgtgtatgat tctgttctgt ttctgtctaa tttgtggaaa tgttgtggga agaaaatgaa   30300
ataacaaatg agcatatgtc ctgaaaataa aaatataaaa attctaagtt agcatgctat   30360
tgtagaatac aacgctatga taaaagtagg aaaaaaaaag gtttgaattc tatctctgct   30420
acctgtgtaa gctgggtgac tttagataag ctgtaacgtg tttgagcctt actggctcat   30480
ttttgaaatg taatccctag ttacacagtt cttgtgggat cagatggtac atgtgaaaca   30540
ctgtgaaaaa gcaactgcat agatatgttc attagccacc tgagcgggaa gcgtatccca   30600
ttgcgatgcc catcatccaa agctatatgt tatctttact tttttttttt tgagacagag   30660
tcttgctctg ttgcccaggc tagagtgcag tggtgcaatc tcagctcact gcaagctcca   30720
cctcccgggt tcacgctatt ctcctgcccc agcctcccaa gtagctggga ctacaggcac   30780
ccgccaccat gcctggctaa attttgtat tttagtaga gatggggttt caccgtgtta   30840
gccaggatgg tcttgatctc ctgacctcgt gatccgcccg cctcggcctc ccaaagtgct   30900
gggattacag gcgtgagcca ctgcccctgg ccatctttac ttttttttgtg aaatgacttt   30960 aaatacttgg caaacatttg gtcattgttc atctgatctc caccatccag gtctcagaga   31020
acataatttc tctctgaaag cttattgacc caggaaataa gatctctttc aatctgagtg   31080
cgtcaggctt tattcttgtc atttgtctt ttgataattt tcaaatggaa ttcatggaat   31140
gttggcttat attcatatat tagtaaagta tgttgagaca tcttaagatt gatttgtggt   31200
tctatatgcc atattaaatc aaaataatag ctgttaatgg ttttcacatt agtctgtctc   31260 ttgttttttat ggagtaatgc tgagagttca ttatgcttgt tctacagaag agcatgttaa   31320
aaggagtttt tggagtcaga gaggttattc ttggtttcat aggatacact ctatactttt   31380
tagggatttc agagtatata gctgaaggtg atattttatg taaatatgtt ttatggaaac   31440
ttattgctca tcgctgtttc ctgttaactc tcctaaaata taattaaact tttggaactt   31500
ttttatagct tttgtgctag actaattttt gtctctaatg aggttatata aatggcagct   31560
tctgacgttt tcaatgtagg aagtcattta aaacttcatg tatattgtga aaatgtagtc   31620
tgctttaagc tctctaaagt ggtctaagtt actggttcct aagtatggat gagcatcaaa   31680
atcatctgga aaatttgtta aaaatacagt aatgaaggca cctcactgtc cttttttccca   31740 aacatacttc tgcattctgt ttgagtaggt agggactaca cattttttcac aagtatcctc   31800 ttgggaatac ccaggaatgc ttacttgagc aacctcttac taatatgtac cttgataagg   31860
tggctaggta aacataaata tacaaaaatc catgatctc ccatatatta gcataaatca   31920
gctagaaaat ataacgttta aagatctagt tcacagtagc accaatatat cgaactctaa   31980
ggaatcgata aatatgcaaa aactttataa aaacttctgt taatgttct gaaagatata   32040 ggtgaccact ttctagatag gaagatttta tattactaag ttgaattttc tctaaattaa   32100
cacagaaatt taaaataatc ttgatcaaaa ttctagtaga ggtattttg aacttgttca   32160
```

```
ctgcaagaat aaatacataa ttgcaaagaa tatctcaaaa tcatcaccag gcctggtgtg    32220
gtggcccatg cctgtaatcc cagcactttg ggaggctgag gcaggcagat cacctgaggt    32280
caagagtttg agaccagctg gaccagtgcg gtgaaacact gcctctacta aaaatacaaa    32340
aattagctgg gtgtggtggt gcatgcctgt agtcccagct acttgggagg ctgaggcagg    32400
agaattgctt gaacccagga ggtacaggtt gcggtgagcc tagatcgcac cactgcattc    32460
cagcctgggc gacaagagca aaattctgtc tcaagaaaaa agagaaaaaa gaaaagaaa    32520 tcaacactaa tatggtgaga cttaatgtat gtgacattaa aatagtgatt ggatgttaaa    32580
acaggtatag aacagaaaga agagtgtatg tgtgtatctg tatgaattta tgatgggtgt    32640
aacatatatg tattagggaa atgagggaaa tgatacattt ctctgacttt gggagaacat    32700
tatatctcta cctcatattg caaacaaaca taaagttcag attaattacc taaatgtgaa    32760
aaaatgaaat aatttctttta aaaaatgtaa tcttagtttg aggaaggtta acattataaa    32820
ggaaaaaact gttttgagtg aatatagtt caatatgtca aaatccacct tcaacaaaat    32880
tgaaagtaaa ttgaacttgg ggaaagtatt gacagcatat agatcaaagg ttactagcct    32940
gtgtaaagag cagttataaa tatcgttaag aaaaacactg tcgacctgtc ggcaccttgt    33000
tctccgactc ccagcctcca gaactgtgac gagtaagtgc ttattgttta aaccacccag    33060
tctgtatgtg gtattttgtt atagaaactc aagctgatta ggacactagt aatcagtaga    33120
ctgaaactga acaaaaata agaaccttt ttacctgtca aattggcaaa cattaagaat    33180
attcagattt ttgtcagagg tgatacaacc ttctaagaag gcaatttggg aaaatataaa    33240
gctttagatt attatatgtc tgacctagca gttttacctc tagggtgctt acccctagga    33300
aagtgtgtaa tgatattggt gcagtgccct tcatcccatt agaaaattaa aaataaccttt   33360 aatggcctac cactaaaagg ggattgaaaa tttaagatat atttattttat gtgtttattg    33420 agatggagtc ttgcactgtc cgcctgggcc agagtgcaat ggtgcgatct cggctcactg    33480
caacctctgc ttcccgggtt catgtgattc tcctgcctca gcctcctgag tagctgggat    33540
tacaggctca caccaccgca cccggctaat ttttgtatt tttagtagag atggggtttc    33600
actgtgttgg ccagactggt ctcgaactcc tgacctcatg atccgcgccc ctcggcctcc    33660
cagtgttggg attacaggtg tgagccactg cgcctggcca gatacattta tacaagagaa    33720
tgttagttaa cattcataga tatttatatt ttgtttactt tttattaaaa aattttttt    33780 tagagacagg atcttactct gtcacccagg caggatgcag ttgcacaatc atagcccact    33840
gcagcctgaa ctcctgggct taagtgatcc ttctgcctca gccttttgag tacctggggg    33900
actttaggca gtgctactat acctggctaa ttttaaaatg ttttatagat gagatcttgc    33960
tgtattgccc aggctggtct agaattcctg ggcccaagtg atcctccac cttggcctcc    34020 caaagcgctg agattacagg catgagccac cacttctgac caatagatat ttatatttgt    34080
gactggaaaa tatattaaca atgtgttaaa aaattcagtt aaaaaataat gaaagatttt    34140
tgcttctggc taagatagaa taacaaggac agcatttatc ttcttgcctt gaaatagttg    34200
aaaacggaag aaatatatgt aacagtggtt ttcaagttat tgggcatcag gcaaagaaga    34260
atagttatcc caggaaaatg aatgtggaga gccctacaat ttccttacat tactgcctgg    34320
tcatggcaag aggaaaaact gagaggagac tgaggctgag ccagtggttt gctgggttga    34380
ggaggcagag ctgggagtgc agagatgcaa ggtggtgaga gcccatatgg aagaatacca    34440
gggaagagag ctgcagaggg agctccggag acctgcaccc tgccctctca gtaccctgtc    34500
```

```
atgtgtgtag ctgagtactg acgagcactt gcttgtgcgg aaatgaccca gggctggagg   34560
tagagccacc tgaaaggatt agaaggaaca gttgctgaaa gtcacacagg gccaggaaga   34620
atttctaatc acaccagttg gagtggaaaa cctcagctct catagagcag gtagggtact   34680
cagaagggtt tgcccaccta gccccagact aagtttcgtt actctgaccc tacctaatat   34740
taaaaagaga ttaattaaat tgttcgcaac aaaaataata tatttcagtg tttgtaacac   34800
gtagaagtga attgtatgac aatagcataa aggctggaag agcagaaatt gacatgtatt   34860
tgcgctgggc agaataatgc tcccctcttt ccccaaaaga tatcaagtcc taatccctgg   34920
agcctgtaaa tattacttta tatggaaaat tgttttatga tgtgattaaa ttcaggatct   34980
tgagatgagg gggctatctt ggatgatctg gtaggcact aaatgcaatc acatatatat   35040
aaaaaggagg cagagggaga ttttacacac agagagaagg ccctgtgaag atggaacaga   35100
aagatttgaa ggtgctggcc ttgaaaattg gagtgatgaa gctataagcc aaggaatgca   35160
gcagccacca aagctggaag aggcacggag cagttctcat ttagagccta ctccagaggg   35220
aatgtggtgc tgccaattcc tttttttttt ttttttttaa gatatcattt accccttta   35280 gttggttttt tttttttttt tttttttta gtatttattg atcattcttg ggtgtttctt   35340 ggagagggggg atttggcagg gtcataggac aatagtggag ggaaggtcag cagataaaca   35400
tgtaaacaaa ggtctctggt tttcctaggc agagggccct gccacgttct gcagtgtttg   35460
tgtccctggg tacttgagat tagggagtgg tgatgactct taacgagtat gctgccttca   35520
agcatctgtt taacaaagca catcttgcac cgcccttaat ccatttaacc cttagtggac   35580
acagcacatg tttcagagag cacggggttg ggggtaaggt tatagattaa cagcatccca   35640
aggcagaaga attttttctta gtacagaaca aaatggagtg tcctatgtct acttctttct   35700
acgcagacac agtaacaatc tgatctctct ttcttttccc acatttcctc cttttctatt   35760
cgacaaaact gccaccgtca tcatggactg ttctcaatga gctattgggt acacctccca   35820 gatgggggtgg cggccgggca gaggggctcc tcacttccca gatggggcgg ccgggcagag   35880
gcgcccccca acctcccaga cggggcggcg gctgggcggg ggctgccccc cacctcccgg   35940
acggggcggg tggccgggcg ggggctgccc accacctccc ggacggggcg gctggccggg   36000
cgggggctgc cccccacctc ccggacgggg cgggtggccg ggcgggggct gcccccacc   36060 tcccggacgg ggcggctggc cgggcggggg ctgcccccca cctcccggac ggagcggctg   36120
ccgggcggag gggctcctca cttcccggac ggggcggctg ctgggcggag gggctcctca   36180
cttctcagac ggggcggctg gtcagagacg ctcctcacct cccagacggg gtggcagtgg   36240
ggcagagaca ttcttaagtt cccagacgga gtcacggccg gcagaggtg ctcttcacat   36300 ctcagacggg gcggcgggc agaggtgctc cccacttccc agacgatggg cggccgggca   36360
gagatgctcc tcacttccta gatgggatga cagccgggaa gaggcgctcc tcacttccca   36420
gactgggcag ccaggcagag gggctcctca catcccagac gatgggcggc caggcagaaa   36480
cgctcctcac ttcctagacg gggtggcggc tgggcagagg ccgcaatctt ggcactttgg   36540
gaggccaagg caggcggctg ggaggtgaag gttgtagtga cccgagatca cgccactgca   36600
ctccagcctg gcaacactg agcactgagt gagcgagact ccgtctgcaa tcccggcacc   36660
tcgggaggcc gaggctggca gatcacttgc agtcaggagc tggagaccag cccggccaac   36720
acggcgaaac cccgtctcca ccaaaaaaca cgaaaaccag tcagacatgg cggtgcgtgc   36780
ctgcaatccc aggcacttgg caggctgagg caggagaatc aggtagggag gttgcagtga   36840
gtagagatgg tggcagtaca gtccagcctt ggctcggcat cagagggaga ctgtgcgagg   36900
```

```
gcgagggcga gggcgaggga attccttaat ttcagtttag tgatactaat tttggactct   36960
ggcctctaaa actgtgaaag aaaaaatttt ttgtttgttt gtttcttttta agccacatag   37020 tttgtggtaa tttgttacag cagctgcagg aaactaattt atgctgcatg tgaaatggtg   37080
taataaggta gattgtgatg aagatacata gtataaacaa ttaagcaaca actaaaagca   37140
caacaaggaa ttatagctaa tgaaccaaaa aaggagatta gaataataaa aatggtgaat   37200
cccaaagaag ccagaaatag gggaagaggc aaataaagga agaaagagc ttgatggtag    37260 atttcaaccct aactatgtca aaaggacat tacatgtaaa aggcagcgat ttttcagatt   37320
gaatggaaaa gtaagactcg gtatatgctg ctgcctgcaa gaaacacatt ctaaatataa   37380
aggcaaaaat aacctacagg taacagaacg gaaagaagtt cactgtgctt acaagaatta   37440
gatgcaagct agactggttc tgttaatatc agacaaagtg gatttcaaag caaaggctct   37500
tgcccaggat gagatggtca tttcataatg atgaagggga ttcgttcatc agcctggcat   37560
agcaagctga aatgtttatg caccggacta cagagctaaa atacatgaag caaagcctga   37620
cagaactaca agtagaaaca gacaaatcca cagtgataga gatttcagta gccgctctca   37680
atgatttgta gaacacgtag ccataatatc tggatctaga acacttgacc aacactgtcc   37740
cctgtgcaac ctcattggca tttacaggac actccaccca gcaccagcag aagagacact   37800
ctctcaagtg ctcacagaat gtttgccaag atagagcaga tgctgggcca taaaacaagt   37860
ctctaaatta aaagcattca aattattcag agtatgtttt ctgacctcag tatcattaag   37920
ttggaatata ttataggaag ataacctgga aaagcctcag atatgtggaa aaacccattt   37980
ccacatggcc catgggtcag aagtgaagtc aaaagggaaa tttgaaagtc ttttggattg   38040
actgatataa aaacaataga tttctaaact tgtggggtgc tgttacagca tagtaaatgg   38100
aaatttctag cattaaatgc ctgttttagg aaagaaagat ttcaaatcaa tgacctcagc   38160 ttctacccttt ggaaacttga aaatgacaag caaatggaat ccagagttac cagaagggcc   38220
aggtacggtg gcttatgcct gcagttctgc cactttggga ggccgaggca ggtggattgt   38280
ttgagactgg cagttgaaga ccagcctggg cagcctaggg agaccccata tctacaaaaa   38340
acaaaaaaat tagccaggtg tggtggcatg tgcctgtagt cccagctaac caggagtcta   38400
aggtgggagg attgcttgag tctgggaggt tgaggctgca gtgaactgtg attgtgccac   38460
tgtgttccat cctgggcaac agaatgagac cctgtctcaa aaacaaaaac agttactaga   38520
agaatggaca tcataaagat aggagcagaa gtcagtaaaa tagaaaacaa aaatacatag   38580
gaaatcaata aaaccaaaag ctggttcatc aagaacatca ataaattggt aaagctgata   38640
ggaaaaacag tgaagtcaca aattagcaat atcaggaatg agggagatga cagtagtata   38700
gattatatag atattaaaag gactgtatga ggcaggtgtg gtggttcacg cctgtaatcc   38760
cagcaccttg ggaggccgag gtggacagat cacctgaggt caggagtttg gaccagcct   38820 ggccaacatg gtgaaactct gtctctacta aaaatacaaa aattagttgg tcgtggtgct   38880
gtgtgcctgt aatcccagct acttgggagg ctgaggcagg agaattgctt gaacctggga   38940
ggcggaggtt gcagtgagct gagattgtgc cgttgcactc cagcctgggt gacagagcaa   39000
gactccatct caaacaaat aaataaataa aaggactat atggtaatat tatgaacaac   39060
tttatgccaa taaatttgac aacttataga tgaaatggat gagttccttg aaagacacag   39120
aaactattaa agctctctca agaagatata gataagctga ttagccctat atctatttta   39180
ttgaatttaa atgtaaaaat caatatttag ttactggaaa acttttaagt gtggttggaa   39240
```

-continued

```
atggtatacg aacttttca actgaatttt atgaagtcta atcacaggta aaggttttct    39300
gatgaaaatt tagtgtctga attgagatat actgtaaaaa atgttatata tcttaattat    39360
ttcttcacat taattacatg ttgaaataat actttgggtg tattgggtta aattaaatat    39420
tatgaaaatc ttgcctgttt tcttttact tttgatgcgt cagctaggaa atataaaagt    39480
gtagctcaca ttctgtttct gttgacagta ctgctttgga gcacagtgtt tgaatgatct    39540
atcatttcaa agacctttcc tcagttcgtt attcatggct gtctgtattc cacatagata    39600
aggtctgaaa tactgctaag tggcatgttt tgttttatgc ttttataagt ttgttgatca    39660
ttactgatgt ggacttttgg tgcctcttag gctcattgct atcttccaac cattgtttgc    39720
aattttacc tagagataaa gagaaagaga catttggttt cagagtagtt agattgggat    39780
catgaaagag caacctcatt tgatgcttc aaaaatagca catccccgt attactggga    39840
tttgctattc ttgggattac ttcaagaaca tccttgtgtt actggtttgg atgcttctga    39900
atgctgtgaa gtcagtttca tgtacatggc tcatcagttt agctctctct ggctttgtt    39960
tagacagttg gagcatgatg gcctaaacag cttctttcaa ttaaacattt taaaatagtt    40020
tacaaatagt aaacaaactc cagttttttgt gactctttgt ctcgcacaac aaaaacacaa    40080
tctgaccatg atcatctggc atcttagggt gaaatatggt tatactttgg cccataccga    40140
aagcaagatt aaaaaggggc aggagagata gactgctgaa ctgattttca aggttccaag    40200
aatattgtag gttaagagta aaagtaaact tttggtagaa agcagtgggt tgtctaggat    40260
tgaagtatct gaagtttta aacgaaaatt taaaaagaaa aatgagaatt gccttacaag    40320
tacaatctct tctttttaa aaaataaact ttattttgaa atagttttag atttatagaa    40380
aaaaattaga tagggtagga agttttcata taccctacat ccagttaccc cagttattat    40440
catcctaatt tagtgtgaga cattttcatg tttaatgaat caatattgat atgctattaa    40500
cttaagtcca gactttattc agatttcctt aatttctatg taatgtcctt tttctgttcc    40560
agaattccat gcaggacacc ggatacctca ttacatttca ttgtcatgtc accttaggct    40620
cctcttgaca gtttctcttc tttttttgct tagaaattct ccagaatttc agaaacttct    40680
gggcatcgct atggaacttt ttctgctgtg cagtgatgac gcagagtcag atgtcaggat    40740
ggtggctgac gaatgcctca acaaagttat caaagtaaga accgtgtgga tgatgttctc    40800
ctcagagcta tcattgttgt aggctgagag aagaagcgat cattgagtgt tcttctgttt    40860
tgagtccctg aggatgtctg cactttttc ctttctgatg tatggtttgg aggtgctctg    40920
ttgtatggtt tggaggtgct ctgttgtatg gtttggaggt gctctattgt atggtttgga    40980
ggtgctctgt tgtatggttt ggaggtgctc ttgtatggtt tggaggtgct cttgtatggt    41040
ttggaggtgc tctgttgtat ggtttggagg tggtcttgta tggtttgcag gtgctctatt    41100
gcatggtttg caggtgctct attgtatggt ttggaagtgc tcttgtatgg tttggaggtg    41160
ctcttgtatg gtttggagat gctctattgt atggtttgca ggtgctctat tgtatggttt    41220
ggaagtgctc ttgtatggtt tggaggtgct cttgtatggt tggaggtgc tctgttgtat    41280
ggtttggagg tgctctgttg tatggtttgg aggtgctctt gtatggtttg gaggtgctct    41340
attgtatggt ttggagatgc tctggtatct gcctgcattg cttgccacac ctgcccggtc    41400
agaaggcgct atgttgacaa ttgtgcctgc acggtgccta ggtcaatgaa gggaaccgat    41460
ggtagccact ggatgctcct gggaaaatgt cactacaggc accagagaag ccagagctat    41520
gcccaaattt ctatgagtct cagttttctt aaccataaaa tgggatcaat gttttgtggg    41580
catgtgtatg agtgtgtgtc tgtgtatgtg tgaggattaa attgtgtatg tgtgaggact    41640
```

```
aattgccact actggatcct caaagtggta agaagtgttc ttattaataa tgacatcctt   41700
acactcttac ccagcaagat tgatgggtgt ggcactgctt ctcttttcc atcacatggt    41760
ttccatggta tccttttgcc cagggaatct ttgctttgtg gctagcactt tgttgtttgg   41820
ctaatcacgc tttctgtggt caggacgctg gcttctctgg agccatggga ttctagctcc   41880
ctgtcttgtc cctagagtgg tcactgtctt ctctctccgc ttgcaattcc tgctttgctc   41940
gcatctcact tatgcagtga cgtatatcag tttcaccttg ttctccgtgc ctgctgatca   42000
ttggcaccac ttgcatggtg ccatttaggg cctgcttcca gttaagcttg cttctccaca   42060
ggcctaaata tccttgcttg cttctttat tctcactggc aggaccaggg cggtctgtct    42120
ttgcatgaga cagggtctcg ctcagtcacc caggctggag tgcagtggct gatcacggct   42180
cattgcagcc ttgagctacc gggctcaagc tatcctcctg gcttggcccc ttgagtagct   42240
gggactacag gcgtgcacca ccatgcccag ctaatttta aaattatttg tagagatggg    42300
atctcgccag gttgcccagg ctggtcttga acgcctgggc tcaagtgatc ctccctcctt   42360
ggtttcccaa agtgctggga tcacaggtgt gagccactgt gcctggccct tgatgtttca   42420
gttcttgata tttgatcctc agagtcagaa aatctaaaaa gagggctatc ccaggttgcc   42480
ttggttcatg gcaaatggga cgttaagagg gcagagagaa tatgaacaga aactgttcta   42540
atattggtca tttaatgtgt aagtattgtt ctttttaaa cctccttcat ttttttcca    42600
ggaattgctg gacacagtgg cttggtgtgt gtctgaggac tgtaggccat ggccctaggt   42660
tgtggtttta ggtctcaggt gctcttcctg gctgtctcct tgcttctttc ccatgtcctc   42720
ttctttgttt ccagccattt ctcccttatg cttaagtttg gtgcagcagg gtttggctgc   42780
tctcagattc ctgcttcctc agatgctgta gttgtcaggc ccagcgggct ggcagcggga   42840
tcaggatctg gctaggtttg ctctcactgt ggcagagtag ggggaggcgt gggagagcac   42900
gtgtgacccc aggccagctg tagggagcat aggcatggtc acgtagcctt caggtcctag   42960
actttgtctt ctcatgagta tggctgtgtg tgtatggtga aaactaggtt ctacttagcc   43020
caagaaaatg ggcacatttt gcatgtggtt tctgtagaga aatgcactgg gtatctgaca   43080
tagcctggca gcatgcctcc ctcaggtagg ttagtctcag gcggtgaagc acgtgtgtcc   43140
agcaagaact tcatatgtgg cataaagtct ccgttctgtg aggtgctggc aaatcaccac   43200
caccgtcaag aggctgaagt gattttttgtc tagggaggca ggaaaggctt cctggagtca   43260
gcagccagta ggtgaaagag tagattggag accttcttaa tcatcaccgc ctcttgtctc   43320
aaggggtgcc aggaagctgt ggaggctgaa cccatcttat gctgccagag agtgggacac   43380
catgagggtc aggtcaaggg gttgtacctt gtttggtaga gaattagggg ctcttgaaga   43440
ctttggatgt ggtcagggga gtgtatcatt taggaagagt gacccggtga ggacgtgggg   43500
tagaggagga caggtgggag ggagtccagg tgggagtgag tagacccagc aggagtgcag   43560
ggcctcgagc caggatggtg gcagggctgt gaggagaggc agccacctgt gtgtctgcgg   43620
aagcagggc aagagggaag aggccagcag cgtgctgcca tcacccagcg actggcgtag    43680
attgtgagag accattccct gctcttagga ggggctgagt tttagttttc tcttgttata   43740
caataagctt ggtatttgtt tacaaaacat ttgtaaagct aaatcaaggt ttgataaggc   43800
ttctagttt atttaagaag taatgttgaa ataaatgttt gtccaattcg ctttgctcat    43860
ttaaggactt tcagtacaaa ctgcaacaac aggattagga tttaaacgtt tctgagatgt   43920
ttttactcct cagaatttcc cagaatgtga tctggttttg attttcaagc ttgctgaccc   43980
```

-continued

```
aataggttaa cccacaagtt ttacgaagac catctcagtc cacttacatc aactgcccat    44040
gccacggtta aagagatcat cgactgatgt ttggcacagc ttcctccctc ttgggtgggc    44100
aagcatttgg aagagaaggc tcctatgggt gagagtgggg caccaaagtc ttccctgtcc    44160
catcccctag cttgagaagc ccttctctaa tgtggacttt gtgccgttag catcgttact    44220
agcttgaagt tgaccatctg gacgtacttt ctggtttagc ctcacaagtg agcaaggagg    44280
gttgagagat gtgctgtgag gaatgtgggg ccccagctgg cagcaggctc tgggtcaggg    44340
gggcagggac cacgggcata cctgacagtg aggaggggcc acacctgcag aaaaggatgc    44400
aggactccgc cttgggaagt gttctaggcc agagcgaggg tctgtggttt ataagtacac    44460
ccacagtgct cgggaccctg cagatgtcca gggtgccgtc tgagcccgta tcatccaaca    44520
gaatgttctg ctagtgaaga ttaaagattt actccagggg ctttaggatt tattatatat    44580
atataaatcc tatatatata atttttttt tttttttttt tgagatggag tttcgctctt    44640
gttgcccagg ctggagtgca atggcgtgat cttggctcac tgcaacctcc gcctcccggg    44700
ttcaaactat tctcctgcct cagcctctcg agtagctggg attacaggcg cccaccacca    44760
cacccggcta attttgtat tttttagtag agacggagtt tctccatgtt ggtcaggctg    44820
gtcttgaact cctgacctca ggtgatctgc ccgccttggc ctcccaaagt gctgggatta    44880
caggcatgag ccaccccacc tggccaggat ttattgtatt tgaaccatct accattttaa    44940
ttttgatgtt atgtagtatt tgatgataat gaaagttaaa ttgttttttct ttccattttt    45000 ctgtttaagt gaatgacctg tatctagttt attcagtaac ttcctgcata tatttgtttc    45060
tttcattctt aatgaatata ttcttaattt agttgctatt atgttttgct ttgccccaaa    45120
attgaaatct tagtttcctt ttagctcgtt ttagaactag tgatgggatg tgtcttccat    45180
aaatctcttg tgatttgttg taggcttga tggattctaa tcttccaagg ttacagctcg    45240
agctctataa ggaaattaaa aaggtgggcc ttgcttttct tttttaaaaa tgtttaaat    45300 tttaaatttt tataggtaca cgtatttgt aggtacatgt aaatgtatat atttatgggg    45360
tacatgagat atttttgatac aggtatacaa tacataataa tcacaccatg gaaagttgga    45420
tatccatgcc ctcaagcatt tatcctttgt gttacaaaca atccagttac atgctttact    45480 tattttatt tatttttgag acagagtctt gctttcaccc atgctagagt acagtggcat    45540
gaccttggct cactgcaacc tccgcctccc gggttcaacc gaactttggg ctggtctcaa    45600
actcctgacc tcaggtgatc cgcccgcctc ggcctcccaa agtgttggga ttacaggcgt    45660
gagccactgt gccgggcctg attgtacatt ttaaaataac taaaacagtc agggcacagt    45720
ggctcatgcc tgtaatccca gcatttgggg aggctgaggc aggtgatcac ctgagatcag    45780
gagttcgaga ccagcctggc caacatgag aaacccgtc tctactaaaa atacaaaaat    45840
tagccaagtg tggtggcggg cgcctgtaat cctggctact cgggaggctg aggtagggga    45900
atcgcttgaa cctgggggtg gaggttgcag tgagccgaga tcacgccact gcattccagc    45960
ctgagcgaca gagtgagact ttgtctcaaa aaataaaaat gaaataaaat tgggccgggt    46020
gtggtggctc acaccttagt cccagcactt tgggaacctg aggcaggtgg atgcttgaga    46080
ccaggagttt gagaccagca tgggcaacat ggcaaaacgc tgtctgtaca gaaattagct    46140
gggtgtggtg gtgcacaact atagtctcag ctacttggga gattgaggtg ggaggattaa    46200
ttgagcctgg aaggttgaat ctataggtag ctgagattgt gccactgccc ttcagcctgg    46260
gcgaccaagt gagaccctgt ctcaaaagaa aacaaaaaaa acaaaaaaca aaccactatt    46320
atcgactata tattattgtc tatgatccct ctgctgtgct gtcgaatacc aggtcttggg    46380
```

```
cccttatttc catcactgag caaacttcac tctgttaagc agcaggtgtg ggatttcatc    46440
gttattcagt aattcacaat gttagaagga aatgctgttt ggtagacgat tgctttactt    46500
ttcttcaaaa ggttactctt tattagatga gatgagaatt aaaaatggta acttacttta    46560
tatctttata attgaagccc actagacctt aaagtagtta ccagatgttt tatgcattta    46620
aatggccttt tctctaaaat tagaaagtaa caaggaaaga aatgcttcg tttctatgca    46680 accctcttgg tgactagtat gtgactctta atgcaaccct cattgcaccc cctcagaatg    46740 gtgccctcg gagtttgcgt gctgccctgt ggaggtttgc tgagctggct cacctggttc    46800
ggcctcagaa atgcaggtaa gttgtacact ctggatgttg gttttgtcg ggggccagct    46860 gctactgatc ctttatgtct cagctcagat gtcatttcaa aagtctgctc tgccctctcc    46920
aaattgcagt cgaccttgcc ctgtttatgt ttccctcata gcactaatcc atgtcagaaa    46980
ttgtcacgta cagtctatct gtgtgcttgt ttattttcta tcccacccctt ccgcaagaga    47040 cttatgggat gtgtgcccca ggacagcagg ggtcttactg tcttatgctc tgttgcagcc    47100
cagcagcgat aacagtgtct gcacatagta cttgcttaaa agatacttgc caaattgttg    47160
aaggttgagg taccaatttc attattgctg actataggag ttatagcaaa atatccattt    47220
gtctgttaca tgagttaaaa atatggttgt tgcactgtga atagtttggt ttagtcaaaa    47280
cagttgtatc ttaacggatt gagaaacaaa agcaggacca cttttcatca gctccctcct    47340
tctccttaac cagcaataca tgctgatgct gatatcccat agaccctcag ctccatcctg    47400
agtcactggg aatgtggtct aaaccctcac tattaatatg aactgagttt caataagaat    47460
cttatatggg tcgggcatag tggctcatac ctttgatccc agcacttcag gaggccaagg    47520
caggtggatt gcttgaccca gactaggcaa catggtgaaa cgccgcctct acaaaaaata    47580
caaaacttag ccaggcatgg tggtgcgtgc ctgtggtcac agccactcga gaggctgagg    47640
tgggaggatc acttgagcct gggaggtgga ggtcgtgttg agccaagatc gcaccactgc    47700
actccagcct gggcaacaga gtgagacctg tctcaaaaaa accaaaatcc agaaaagaac    47760
ttatatggct gcagaggtat aatcactaag gaaatttcct tttgtataat cttttttctt    47820
ttactatcat ttaaaaaaat gtgttatatt tctgaagcaa cacatccagg ttctgcacat    47880
agcagccaaa gtgaccttaa agaatataac tgggtcttgt cattcccctta tttaaactct    47940 tgtacccatt tcccagtgcc gtttagatag agattccaga ctcgtcaatg gctctgtcac    48000
ctcagacacc ctgcattgac tcattagtct gattagagtc aggtttttct tcctcctgat    48060 ggttttttt tcccccttag ttctcagcgg aacagtcact tccttaggga ggtttcccca    48120
gccaccctct gaggccgtgc ttgttgccag actctgccac tagagggcag ggctgcacca    48180
ctcctggcac ctcgcacccg gcctgccctg tcactctgtg tgttgggtga attcctgtga    48240
tctgtgactc actgctctgt gtcctacaca ttcggctttt cttctctccc cacaaccccca    48300 ttttataatt ctccttttc aggaaagctt tattcccatt taaaaatttt tgttttaaa    48360 atggtatttt cttacactta ttttctaatt aaaaatgagt gttttaagaa gtattatgat    48420
ttactgcaaa taatttttaa acccagcctt ttagatcctc tgtgatcata agagaaatga    48480
aggatgtctc ccaacacttg agcttcatcc acatttcatc ctcctgttct ttcagctgag    48540
ttttccccat cccattaggg actgttggaa tataaaactg ctttccct aacagggaat    48600 gaattgcttc tgtttctcct gaaggagagc tggaagaatg acttgcgttc ttttgcatac    48660
acaggcctta cctggtgaac cttctgccgt gcctgactcg aacaagcaag agacccgaag    48720
```

```
aatcagtcca ggagaccttg gctgcagctg ttcccaaaat tatggcttct tttggcaatt    48780
ttgcaaatga caatgaaatt aaggtatgat tgttgcctca ggtcacaaac atgcgagtga    48840
tgctgtgagt gagtctgtgg agggtgaggg cttctgaaca gggagtcctg tgggagtgct    48900
tcttggggta tgttgtatgt cgtaatttag actaccatca tttgtgttat ttttgaggca    48960
cctaaggact tctttccact tctcatttct tactgtgggg tgaagagttg aattgggaga    49020
tggtttctag atgcaaattg aaaaggcatt tttccagagc agatttgttt tcggcgtact    49080
agagtgactc tttaacctag ctgcgggaag atgactgtgc caagactgca ggtaggagaa    49140
agctcactga cgaggccttg tgggtctgaa cgtcctgcag ctatcagagc ctgttggctt    49200
cctgttgtgc attccaacaa atcatcttca aacccacttt agtgttttgt ttataatgtc    49260
cagaaatagt gaccctgtca catgctctac agattacagg attcttagcc tcttcctttt    49320
tggtaggtca gtcctgggtt tgagcccaag tgaccctcct ggaggtgat  gatacacact    49380 gggtagagtg gaatcagatg gacttggatt agaattctgt cctctttact agttattttc    49440
ctctaggcaa actgcccaac agctctaagc tatttccttc gtattctgaa aaataagcct    49500
taatgggacc catataggc  aactctgaga gtaaaataaa ggaatatgtg ttagagtgta    49560
gcatagtcac ccacgggaag ggcttagatg ttagctgcta ctgctcttat tagctgaatg    49620
atttggaata aactgttagc ctctctcatg ttttttctct tgagcttcga agttttcttg    49680
ttaatactaa ggagatattc aaactagtca tggggttttg gaatgacgaa gggagatgat    49740
gaatctaaag aatttagtgt aatatttctt catgctcagt aaatggtagt ttctgctgct    49800
gttattttta ttaccatctc tttggaatgg gagtaggtgc tcctttgtgg tcagaggctg    49860
tgagagctcc acagcgccag tttgcccatc tgtacactgg ggtctgttga aggcagtccc    49920
ctctgtgata tctctggctg tcagagctca gatgatagat ggtattttg  tactcttagt    49980 tctcatcatt ttcatgattt cgatcaccat ttgagtatga tgatgctaac actttgttga    50040
acgtagaatc cgttaattac ttccttcctg aacctttggc attaaaaaaa atctattctg    50100
ctacctctct gctcatttat ggttattcaa atttattatc aagagcctgg tacagtggct    50160
tgtgcctata attgtagcta cttgggaggc tgaggtagga ggattgcttg aggccaggag    50220
tttgagacca gcctgggcaa gatagtgaga ccctatctct aaaaaaactg aaaaaaaatt    50280
agctggacat gatggcatgt gcctgtggtc ctagctactc aggaggctga cacaggaggc    50340
tcggttgagc ccaggagttg gagttcgagg ctacactgag ctgtgattgt gccaccacac    50400
tccagcatgg gtggtaaaac aagatgccat ttcttaaaaa aaaaaaatat atatatatat    50460
attatcaatg aaattcagta gtaccaacag gattataaac aaagatagta gttcccttcc    50520 tacttttct  cttaatcctt gtgtctcaca ggcaaacata actcttagta tttcttccaa    50580
tatttacttt catgtttctt tctttctttc tttttttttc tttgagatgg agttttgctc    50640
ttgttgccaa ggctggagtg caatgacgca atcttggctc accacaacct ctgtctcccg    50700
ggttcaagcg attctcctgc ctcagcctcc tagtagctgg gattacaggc atgcatcacc    50760
acgctcggct aatttttgtac ttttagtaga gatggggttt ctccggggttg gtcaggctgg    50820 tctcgaactc ctgacctcag gtgatcctcc cacctcagcc tcccaaagtg ctgggattac    50880
aggcgtgagc cactgcgccc agcaacttcc acatttctaa ataacatgct tctactgcta    50940
tttttttttt caattttaga cattttttta ctttcactat agttctatca gaattcagtg    51000
tgtacgttat tatgcctaag taaatagtca tggttgctta cgtattatat ttctttgatt    51060
gtgtttctta tttgatgaga aagctgtgtt ttttgctctg ggttgaaact ggagagagga    51120
```

```
cctgggagg aggaggagga cagatgaagt tggtgactgt accttcatgg ccatagctgg   51180
gttctcagca cccgggatc tgctgatcac ctactcatag gccaggcccc tatcgaagtt   51240
ctaggtgacc cagtgctggg gacgggggg ccacctgcaa ggtctaatca tggaggtggg   51300
ggctacagtg ttggcttgtg ctgggccag catccttagg aaggcatctt ggaggtggag   51360
gagacagccg cccacttctt gattgggggcc ttcagcagca ccagcttctt gggcaggctg   51420
gtgctggctt tcatcaccat gtcgtgttca atcttcttcc agatcctgac ttctaggttc   51480
agctttcctc agaccctggt tcctttcaga ggccattgct gctgccttgc tctttgctgg   51540
cttgtgcctt gattatatgt ctttgtacaa ctttttgttt tcctggagtt aatcttcaca   51600
tctgttttct tggagttaat cgttacctct atatcgcttg cttattattc tttggccttt   51660
ttgtcttctc acaccttcca acttctttgt aatatgtgtt tagtacaatt tttcatgaca   51720
ggtagtttac tgaatcagtt ttccccagt gtggtcatcc aacttgagtt atccagctct   51780
ctgccccagt ctgggcaggt tgatcttcag gtctgtagta cacttgtatc ctaggacttc   51840
tctttgccat tagcctggaa tttcctttgc agttctcccg ttggatgccc agttcctaga   51900
tgccatatgt ttttctatcg tctagtagct tcctgagaga agatgaatgg gagggaaatt   51960
gtatgaggtt ttgcattcat aaaaatgcca ttttttttcc tgtacacttg gctgggtatg   52020
gtgttctggg gtagaaatca ttttccctca gaaatgcaaa gtcttgccc tgttgtctta   52080 aaatctccaa cgtgacccga ttccttaacc tatgaatgta cttttctttg gaagctttcc   52140 attttttgggg aggtgaagtg ctaggtactt agtaggcctt ttaatttgga aacttacatc   52200
ccttcagttc tgggaaaatt ttcttaacat ttctctgaga agttcttgcc ttttattttc   52260
tgtgttctct cctgaaattg gttagttgga tgttggtcct cctagattga ctcacatctt   52320 accttttttct tttctttttc tggtactttt tagatatcca tctcaaactc ttctattcat   52380
tgttatgttt ttaacttctt tcttttcttt gtctcttgat ggggtcttgc cctgttgccc   52440
aggttgtggt gcagtggtgc gatcatagct cactgcagcc tcaaattcct gggctcaagc   52500
agctgttctg cctcaccctc ccaagtagtt gggactacag gtatgcacca ccacgtccag   52560 ctatttttctt tacttttttt tttttttttt tgagatggag tcctactctg tcgcccaggc   52620
tagagtgcgg tggtgggatt ttggctcact taagcctctg cctcccaggt tcaagcagtt   52680
ctcctgcctc agcctctcaa gtagctggga ttacaggtgt gcaccaccat gcccggctaa   52740 ttttttgtatt tttagtagag ccagagtttc accatgttgg ccaggctggt ctcgaacgcc   52800
tgacctcagg tgatccgcct gccttggcct ccgaaagtgc cgggattaca ggcgtgagcc   52860
catcattaga tctttaaata ccagtatcta taagtctttt cctcttgagt cagctagtat   52920
ccctggaagg aaattactca ttttcctgct tggaggctat aagcttggct atgtttatcc   52980
tgcaaccggg gactggaagg gagggactg acagtgttgc tggtcagggt gccctcttac   53040 ttttttgtttt ctgtgtgcat ctcacgtctg tcctcagcct atgtaaacac ctcttggagat   53100 tatccctctc aatctttgcc ggaggtgggg gaggggctgc ttcctgggct gccttggatt   53160
ggagggaaga cctcaggtga gtgggtggga atttgcccaa ggagccatga accagccac   53220 tatttcaccc tctccatccc tccactttca gatgtatgtg cgcctccaa agcccgagct   53280 cttcttggcg tctgtggctt caataagctt gcttttttgct ggtatccctc ctaccctccc   53340
ctgtccccag caaagcttgc atttgaactt cttcctacgg gctaacaaat cagtcagtta   53400
tgtagctctt gttactttttt agcttccgaa gttttgttga cacccgtagt ctgctaatgt   53460
```

```
ccctgttctg ttctttctgt tcgtgtaaat atatgcttta tacaacttct ttacatgatt   53520
tttgtggggt ttctgggtag cagagcttca caagttcaat ccagcgtgtt ggattagaaa   53580
tctcccaccc tctggtttat tcttattctc aaaattacct gccaaacact gatactccct   53640 tgttttcct tttcctgaca ggaaatgtac ataccataca ggacagaaat cattagtgta   53700
tcccttggtg aataaccaca aagtgaactt aacccttgta accgccaccc aggtcaagac   53760
agaatattac caagcactca gaagcctctc ccctattccc ccgtcactgc tcctgccttc   53820
ctccccaagg tcatgactgc tggcttctaa ttccagagtc tgttttaaa ttctgtgtac   53880 atagaccatg gattaagtgt tcttttttgtc tggtttattt tggtcgacat taagttcatg   53940
agagtcttct atattatcgt gtgtattagt attcctgtag ttttaggagc ttcatagcat   54000
tccattgtag ggatatacca cagtttattc attgtattat cactgggttg tttctagttc   54060
ttggctattg cgagcagtgc tactgtgacc actcttaggt gtgtcttttg gagtacatgt   54120
gcaggtttcc atcttgcaca gctagaggtg gagttgttgg gtgatagggt gtgtgcatct   54180
cagctgcagt agaaactgcc aaatagcttt ccttgagtgc ttgtaccagc tcacccttttt   54240 gccactgtgt atgggattc caggagctct ggtcctcgct agcacttgga attgctgatg   54300
cttttactct tagccttcct gatgggtgtt ttctggaatc acattatgat tttaatttcc   54360
attccttaaa gtaccttggg ctctgaagtt taatgattca tgcatctctt cccttttgaa   54420
gtactcttac aggtatgttg tgcatgtgtt gaaaagtggc actatctatt ctaaaataca   54480
gtatgcctcc tctgtgtttg aacagttgta gcgtggcctt ggggcctcct gttagctggc   54540
ttggagaagg gattcttggg attgtagaga ttagacctga ggaggcccct tggagctctc   54600
tgactaaatt ttattcttta ttattccaaa ctatttaagc tcaccgtgtg ctgactcatc   54660
ataataatga gtagctctca ttgtgcttgt ctatttggac tcatacaatg atttttttt   54720 tttctttgag acagagtctt gctctgttgc ctaggctgga gtgcagtggc acaatctcgg   54780
ctcactgcag cctccacctc ccaggttcaa gtgattcttg tgcctcagct tctcaagtag   54840
ctgagactgc aggtgcgtac caccatgcct ggctaatgtt tgtatttta gtagagacgg   54900 ggtttcacca tgttggccag gttggtctca aactcctgac ctcaagtgat ctgccttctt   54960
cagcctccca aagtgctggg attacaggtg tgagccactg agcttggcca aagtagtttt   55020
ttaagatgtt agtatctttt cttgcagcta aaaaagtttg tcagagatga ttctactttg   55080
ttctccaggt gtttctcag ggagaaattg gaggcagtaa gccactgggg gagtcctgtg   55140 gctgggggt ggggtagtcc tgtggctcct tgtcagggag tcctgtggct ggcaaggaga   55200
gaagtcctgt ggctgggttg ggagggagtc ctgtggctgg ggtctcatcc tgtgcctaac   55260
agtgtccaga ggtgccgaga ccagctcagt cggggagacc ctaacccagc agcgctagag   55320
gaattaaaga cacacacaca gaaatataga ggtgtgaagt gggaaatcag gggtctcaca   55380
gcctttagag ctgagagccc tgaacagaga tttacccaca tatttattaa tagcaaacca   55440
gtcattagca ttgtttctat agatgttaaa ttaactaaaa gtatccctta tgggaaacga   55500
ggggatgggc cgaattaaaa gaagaggttg ggctagttaa ccgcagcagg agcatgtcct   55560
taaggcacag atcgctcatg ctattgtttg tggcttaaga atgcctttaa gcggttttcc   55620
accctgggtg ggccaggtgt tccttgccct cattcctgtc aacccacaac cttccagtgt   55680
gggcattagg gccattatga acatgttaca gtgcttcaga gatttgtttt atggccagtt   55740
ttggggccag tttatggcca gattttgggg ggcctgctcc caatacagag gtctcgtgta   55800
aattccctgg gaggcgataa gcctctgaga aacagactat gctaaccacg ccatgaaaga   55860
```

```
gaaacttatt tataaatcag atgccagtta ctagtttact gcttatttgc ccaggcgtag   55920
ctctgacaga gtccccgact catagtgctt gctcagtgca tgctgaacaa tgattggaat   55980
caagtcatgg ctcagagcat agtttttgaat aatgggaaat ggatgttctt aagtaacata   56040
gtcaccaaga taatgcgact agctgggtca ccccttttca atttttaggat attttttatca   56100
agatttaaat ggccatcatt agagttatag cactttctcc tttggattgt cctagaggcc   56160
catgagaaag tattccctaa tttcttagga gaacagtttg tgggtagtat gcggtcatgt   56220
ccagttaaat tgcagatatt tccgatcgaa gatgttccag tcctgagaac ttcgtgacat   56280
tagcaggact tctacaagcc atctcttagg gtggggcatt tactgcagtt ggctagtact   56340
cttttctcct taactttgtc atttgttgat tttttttttaa ctgtcccaa atactgtggg   56400
cagagtgtat ctagaattga ggcctccacc attgcggaga ggacatggat gctgagcagt   56460
cccctgagtg aaggttataa agaagcaaat agactacaca tgtctgtaaa ctgctcttga   56520
gtgtcccaaa tttggggtac ttcagttcag ctgtaggaaa agcctcaaac tgtttatact   56580
ttgcaagaat tggaaacttc taattcacgt taagtttat gtaatacatg ataagcttca   56640
taggagcttc atcttttatc tacttggact tttgcttccg taggttttgt taaaggcctt   56700
catagcgaac ctgaagtcaa gctcccccac cattcggcgg acagcggctg gatcagcagt   56760
gagcatctgc cagcactcaa gaaggacaca atatttctat agttggctac taaatgtgct   56820
cttaggtaag gtggaggcat atgagtggaa gagtctccag catgtactca agatagacct   56880
ttgaaataaa taaaaccaga tgatccctca gcttctagac caggctattt ggcactggtt   56940
gattgaatgt gaactgcact ggggctgctg tgagcccgca tgggtctctg tgaccctgca   57000
gatgcagccg tgcccaggga ctgggcagtg ggtgtgggct ggtgtgagcc ctgtctgcca   57060
cccagggcct ggccctctgt ctgtgtcggc catgactatg gtgagtcttg taggcttgag   57120
actgtgcctc gggttcctgc gggttctctg taggtcagtt gacagtttct cctgttgttt   57180
gggtaactgt ggaaacgaac actggcaagt gctgaagcga gcatgtggac gtgcgatatg   57240
aaataacgac ctggctttca aaggcagtga ggctctctgg aaaggacctt gctgagctag   57300
ggatgtgggt gtgtagccat tcccagtggg cctcatggcg tactcgttca tgatcatgtt   57360
tgtgccatct tgatctctca ggatctcttc ttttttaaca gattaagccg ggaatctcca   57420
aacagtgagt cagatgttaa gatgtcttgc ttccaccccc acaggcttac tcgttcctgt   57480
cgaggatgaa cactccactc tgctgattct tggcgtgctg ctcaccctga ggtatttggt   57540
gcccttgctg cagcagcagg tcaaggacac aagcctgaaa ggcagcttcg gagtgacaag   57600
gaaagaaatg gaagtctctc cttctgcaga gcagcttgtc caggtaggag cacagggttt   57660
actctaggcc ctgcatgtga atgactgaca ttcaaagaac cgattaattt ggaagagaag   57720
cggcagaacc gagagttaga ggtgtggact ctggagctgc gctgctcgtt ccaacccta   57780
ggtgctgacc tctagctgtc ttccctctgt atgtccctgt caccgtgagt caaatgcggg   57840
tgatgcctcc tcaggtgccg tgttacctaa gcctctcaga gaccactgct accctgtttc   57900
taaaaccaga ggtcacgata tgtgttcatc cacccagtaa atactgattg agcacccact   57960
gtgtgctagg ctctgggata ggggctgggt atacaatggt gagtatttca gctgcagctt   58020
ctgccccgtg gaggctgtgg cctagcacac tggtctaggc acggtggtat atgctcactc   58080
aaggagatag ggacgtggtc gtttggggtg tcggaacaaa atgtcggaac ttctctttcc   58140
aatgcagaga aaccttgcag taattctaat gtactgtgat tggcagttga cttcagttct   58200
```

```
ttgtagcacg cttactcagg ttatttcact aactatgtaa ccatgcagcc tcattttaag    58260
caattggatt ttttgaactt tacttaaaat gttatgtcag ggttttatt gtgcttaatg     58320 tgtgccattt agctaagttt tgtaggatac gaaattgtaa gtggcttaaa atgattctta    58380
atagaatcat gaattgaaga taatgctaat aatttaagca ctgagttagg tagtgtttgt    58440
aaaatgctta gaatgcttcc tggcacatgt taaggccatg taagtgctgc gtgttgataa    58500
acagctgagc aaaagtggac tcttaagaaa gtattgggc tgagagttct gttccaacca    58560
gctgcccttt ggttatttt cagaataaaa gcagagtctc atgggatatg acatttatat     58620
ttccttcaca aaaacactg ctgagtgttt tgttgagtaa aaagggtgta gccatggtaa      58680
taatacattt aaaatatagt ttatttcatc tttaccttgc cttgtttttt ttttaagcta    58740 gcttttatt gagaattcca cacatacaaa agtatcaact catgaccagt tatatttcat     58800
ttataatcct acttctccct tttttttatta tttgaaagca aaccccaatt atcctcttat   58860
ttcatctata agtatttcag tatctctata gatgaggact cttctttatt tttaaaactt    58920
tatttttaaa atgatggtca gatgcagtgt tcatgcctgt aatcccagaa ctttgggagg    58980
ccaagctggg cggatcactt gaacctggga gtttgagacc agcccgggaa acatggcgaa   59040
accccatgtc ttaaagaaaa aaatcagcca agtgtggtga tgcatgcctg tagtcccagc   59100
tacttgggag gctgagatgg gagggtcaca tgagcctgga agatcaaggc tgcagtgatc   59160
catgattgta ccactgcact ccatcctggg tgatggagca agattctgtc tcaaaaaaac   59220
aaaactgcaa acaacgtca caaaacagtg ccattgttag acctgaaaat attaaacatt     59280
tcctacatca aatacccacc aactcattat caatttttct ctctactctt ttggaatcag   59340
catctaaata aaattggtcg ataaggattg taaatctctt tgatgaactg gttcccctcc   59400
atcccagttt ttttcccta gagttcattt attgagaaac cagattgttt gtcttctaag    59460
ttttcctgtg gtctgatata ctgcttccat ctccactgtg taaattaaca cctttttctc   59520
ttctctgtat ttcctgtaaa tcaataattg gaggaaaagc cttgtcagat ttagtgtata   59580
ttttatatct gagtccagta tttcttatat aatatttaa gataagtgta ctcttttaaa    59640
aagtattgaa actatatgct caatttttt taactgatgc ttttaagaag gctgcttgat    59700
cataaaagtt tagagatcat tggtctgatg ggaaaagcaa ataattacta aaccgtttag   59760
caaggttgag gtgcacatgg tgggggcctgg agaagttcag tcatgagccg tcacttatgg  59820
gcacgtggaa tctgaccccgg cacagagttg ggagaagaca ggagctttat agacagaaaa  59880
tgtggtcttt gctaagtccc aggagtgaaa gggtgagaca gtgctcacag cacacgagtg   59940
tgggtgcgta gacagagcaa gggtgggtcc tgaaaaggcc tgcaggcttt ctcatagatt    60000
agcaagagtg ctggttacgg aggtttctaa catttgtgaa cagatcgaaa ctgtgttaaa    60060
ttgggattgc agtaatcctg gaaggacagg gatagagggt gaagggaa aaagggtatg      60120 gatgtgagac ttaattgctg atttttcttaa gacctttctc caaagtaaat aaatgatgtg  60180
gcacattttt gaactggcaa attctaaact ctagatatga ttatctctat aacatatctt   60240
actccatctt cttttgacta aaaactgttc ttaattaaat taccatgaga cgttcaattc   60300
agcaaatgta gtttggctaa ccatattaa ttagaattta atataatcct aggcctggcc    60360
aaactattaa gcaagtgtgg gcaaaatatt gataatttta gatatgcagg aacttagttt   60420
gctttccatg tgtgcttttc gaaaaggaa taaattgaaa aatagaggaa gccctgaaat    60480
ccaagaagca aactctctca cctaggcatg cagtaaaagc aattctagga tgattgctgt   60540
ttggcgcgta gttcgtatta gaaaccattc ttcttgaata aatagtatgt ttaagaagct   60600
```

```
gggcagaggg aaggcatatg catatattat caacaaggag ggagaaaaag gcaattagta   60660
accatccata ggagggtcag caagatttat aaaggaaatt tgtgatccaa gtatgaagca   60720
aaataaggtg cagaataaat tttaagcaag taatagatta gagtaagaga acccatttga   60780
ccattaacct tgggacattc tctttcaaat gacatggagt agtactgaaa tctttctttc   60840
tttctgagtc taggttattg tgactggact cagaaagaaa tatttcatta ttgcagtgaa   60900
taacatttgt gaacattatt gttcataaat tatgcagtga ataacattta tgaacacgtg   60960
atgtgtaaga tacatactgt ttatttttag ttaagttttt tggctcaact tctaggcaga   61020
gaacattaaa tgtaaatagt gttacctagg agcatgtaaa tggaaatctc catagtatga   61080
aagcagtgct gttgctaaca gaatttagga gggggcagat gaggtgaagg aaatgtgggt   61140
gctgatttcc ttattacatt gagaggagcc aggagattct tgttcaaaa tggatggctt    61200 aagaagtcaa agtataagct gattacgtag agcaggtacc caaaaatgtt ttgtgtaagg   61260
ggccagatag taaatatttt cagtcttgca ggccatccca agtctgtggc agctactcaa   61320 cactacctt gtagcatgaa agcagccaca ggcagcccat aaatgtggct ctgttccggt     61380
gaaactttag gtacaaaagc aggtgcaggc cagacctgac ctgtgcactg tggtttgctg   61440
acctgggatt cagggtata gaagttacca tcagaagagc taaaagtgag acttttact     61500 ttatactctt ctacactgtc tgattttgaa aaaagaaac atgtatttta taatattaaa    61560
gatagggttg gcaaatagca aataaaaata cagaatacca gtgaaatttg aacttcagat   61620
acattatgag taattttatg gtgtaagtat attccaaatc atgtgggaca tacttacact   61680
acaaaattat ttgttgtttg tttacagttt aaatttgagt gccttgtatt ttatctggca   61740
actgtaatta aagggaaaaa gaataaaattc attatgttca taatgtgta tatagcaggg   61800 gtccccaacc cccaggctgc agagtggtac tggtccatgg gtccccaacc cccaggctgc   61860
agagcggtat tggtccatgg cctgttagga accaggctgc ccagcaggaa gtgagcagca   61920
ggtgagctgg cattcccacc tgagcaccgc ctcctgtcag atcagtggca gcattagatt   61980
cccataggag tgcaaaccct attgtgaact gcacatgtga ggggtctagg ttgtgcgctc   62040
cttatgagaa tctaatgcct gatgatctga ggtggaacag tctcgtcttg aaaccatccc   62100
ctggccctgt ggaaaaattg tctcccatga aaccagtctc tggtgccaga aaggttgggt   62160
agcactgtga tatagtatta aaagtgctaa taaatatggc atactgcctt taaaatgtct   62220
ggtagctctt tctcagtggc actcataata gtgttttttg attttaaat gtgtgtcaag    62280 ctgactctcc cctccgtgta tgctgggctt tattttccct ttcctagtca ccagttttgg   62340
gaaatagaga tcttcattct catgctgctc ctctagtgca agtgctccat ttattttaa    62400 ggaattaata taacaaaaaa tcatgggaat ttagaaaaca acatggaagc taatgatcac   62460
attggtggaa gtgataggga aatatttagg gggagaagtt aaggtataaa ctttgtcaat   62520
gaagtcctat taaaaacaac aaaaaagtga agcttaggat gcattttata aactctgacc   62580
agaacacctg tgtttctctg tttctaggtt tatgaactga cgttacatca tacacagcac   62640
caagaccaca atgttgtgac cggagccctg gagctgttgc agcagctctt cagaacgcct   62700
ccacccgagc ttctgcaaac cctgaccgca gtcgggggca ttgggcagct caccgctgct   62760
aaggaggagt ctggtggccg aagccgtagt gggagtattg tggaacttat aggcaagtta   62820
ttagcaaggt ctactcttac aattaacttt gcagtaatac tagttacact ctattgatta   62880
tgggcctgcc ctgtgctaag cagtctgcat tccatcttcc ttgccaaaac ttataataca   62940
```

-continued

```
aatttcatct ttatttata aatagggga ttgggctggg tgtggtggct cacgcctgta    63000
atttcagcac tttggaagga tcgcttcagc ccaggagttt gagacaacct ggccaagtga    63060
gaccctgtct ctacaaaaaa aaaaaaaaa aaaaaattag ctgggcatgg tggcacatgc    63120
ctgtagtccc agctgctttg gaggctgagg tggtaggatt gcttaagccc aagaggttga    63180
ggctgcagtg aatcttgatg gcagctgcac tgagcctggt gacagagcaa gatgctgtct    63240
caaaataaat ttaaaaataa aataagagaa ttaaagttta gcaggttggg tggcaaaatg    63300
aggccacaca tttaaagccc ctcctcctga ttcttttctc tgccttggct gcctcctgtg    63360
gcattttagg tgctgagaaa tgaaaacagt agggaaaata gttccaggat cctcatgtta    63420
atttgccaga aatggcatct tcaagtcgtc agagggatct gagagttcct tcctggcctg    63480
acttgagaaa atccgtctgt ccccagctct gcgtctgcct ccactgccca gtcacctcct    63540
ctccatgctc ttgggctggg ccctacccc accatgcagt gctgcctgg agcagtgagc    63600
ttggtgggtc ctgtctggca tgagagctgc ctttgggagc tggatcccag cctctaccac    63660
tgggtctggt gcctagcagg ctatggataa acttctgctg actccggcct ctcctaagcc    63720
actgcaacgt ggtcggtgta gtgcacagtg tgtgtgcagc gtggccttac tcacagcctc    63780
cacattagag agaatctgac tgaagtctta ctgctgcctc gtgtgaacat aaatgtttgc    63840
cagaaccatg agcaggaaat gttaatctgc cttgtttcct gtcctttaca cggaagaatt    63900
tttttctgta tggaatgcgt gccttacaaa taatgagtgg aaatacccat cgctaatgaa    63960
aagttatact tgactgttag tcagctaaat aatctgagat ttctaatact tttaatttgg    64020
cttttacaat gcaatttatc ttagcttttt tgatttctta ggtcatatct ttagaactat    64080
atatttgaat gttaatgtaa ttttcatatt gaattaaaa tgttgaactg cgatgttaag    64140
tgtttcctgt ggaaaaacgt tcacattttc tctagtttta aagttgaatc aagctgtttg    64200
aagattttca catttcttct agattttatc agcttgttac tttatctgtc actttctgtg    64260
atttgcagct ggaggggtt cctcatgcag ccctgtcctt tcaagaaaac aaaaaggtga    64320
ttatttcaga aatcagagtc ttgtgttgaa tcttactgat tttcttgtat ttctgtaatg    64380
taatgtatct tgtatttctt gtaatactgt attggactct gtgtatatct cttctcagat    64440
gagtgattat atgtgtgaat gttgctggaa tctgataacc aggcctgaat agttttgtag    64500
ggtggctttt aaaaattact ttcatatcag aattgctttg tcataaattt tgaacgcatc    64560
ataaatttct aatgttcggg gtcagcagac tttttttgta aagggacaga gtgtaaacat    64620
cttagcttta tgggccatat ggtctctttt gcaacattca gctctgccct gtgacaggaa    64680
tgcagttgta aagacatgag ctactggcca gctatgttcc agtagaactt tacttacaga    64740
aacagacagg ctgtagtttg ccaataccctg ccttagggaa tgtgttgtta tattttgtga    64800
gttaccttct cagtaaattt tatttagtat tagtcaggaa tattattaag tagcttcttt    64860
tccagcctgg tcaacatagt gagacccggt ctctaccaaa acaaacaaa acaaaaaaac    64920
agccacgcat gtggcatgtg cctgtagcct cagctgctgc tcagggggct gaggcaagag    64980
gattgtttga gcccaggagt ttgaggtcac agtgagctgt agtcatgcca ctgcactcca    65040
gcctaggcaa cagaatgaga ccttgtgtct taaaaaaaa aagtttcctt tgttgggtta    65100
ttttaatttg gacctggtta tcattttca gccatattta actttgtaca tatcagaatg    65160
ttctgataaa acttaacttt tattaaagtg tttgtgatat aatctgctag ttttggtaca    65220
cattatcttt tgcaatgcca gttatttct tttccagtgt gggttgcat aggaaaagaa    65280
ttgctgtcac tttctatttt gaaatcttaa aagactgatc cttttttgtg tcatgatttg    65340
```

```
agtatttaat tgagagccta atgcctaata ttatttgcag tattaaatgg gatcttaaca    65400
ggaatagcat tctagccttc attgaattaa gtaaacattt cttaagagaa cttggaatct    65460
ataatatttg cgtcatcata gtatgagata cttaatcaag tttgagattt tagtgaaaca    65520
ttgtttagaa gccaaaagga ttctaggaaa aattaatgtc tatattcttg aattaggaga    65580
gattttggga cgtgtgacta agttacgctg acacttgttt gtttcttagt cgcttttcc    65640 agtggcggtg agaacgaaga tgactgattc acattgctca gatgagttta tcctcttctg    65700
gctgggacat gggatatatc ctgtctcttt taagcctttt tggtattttt cccccattga    65760
gagctgtgtc ttcaaactct tctgttatag ctggaaaatc cttttaagt gaaatctgcc    65820 caaattataa gacagatgaa ggtagagttg tgttggatat aggattaggg tgaaagtagt    65880
gggggtgtcc tggagcctct cttctggtgg cagcctagct cttgtgcctt tgaggaaatt    65940
accctgggga cggctctgtg gaacatattt gcaaaccact gatttggaag atagagatgg    66000
cttttgttaa gatctgaatt caccttttg gcattttatt tgatttctca aggtaaagaa    66060
cttattttgt aataaagttt cctattattt agtagatagg ccaagttgct gtgttaattc    66120
catgtagatt ttgggtttcc tttgctcatt ttttcactct taatctcaca tcattgtaag    66180
tttatggaag ttatcatact tctgactttt tctttgaaga gcagaaatta gaaattccca    66240
ataattattt tgatagtgtc atttaatgac actcacatgt gatgtagcca caaagattta    66300
atgagttcag ttttaaatca tattaagact gttggtttca tttgttctca ttaatgtaat    66360
tctgaagatg aacaataaaa tgtatttta gaactttcaa atgaaatatt atttcatcct    66420
tccagatcat ataatgctta agttctgatt gttaatcata aagtctagaa aattaaaaga    66480
taataaaatg aaagtgactt ttaggtatta gagtttatt ataaattctg gtgtgtcatt    66540
ggagctatga catgaatatt tcaaaggcca atagcattgg atctttacag ttataactta    66600
ccatttttaa gtttaagtag taatatagat tatttaataa tcaaaatcaa taaatattaa    66660
ttattaaaat gttttgtggt atagtttgag aatcattgct tttaacttt tccatatagg    66720 tttattgact ttaatagcat tctaaacata acatctctac attctttgtg tttaatactg    66780
tggaggtata aaaatactta tatatgatga taaactatat tagagtaaat taaatattct    66840
tatgagtttc attttagagt gcatttactt aattttgaag tccttatttt tagcaaacta    66900
aaaggaatgt tggtacatta tttactaggc aaagtgctct taggagaaga agaagccttg    66960
gaggatgact ctgaatcgag atcggatgtc agcagctctg ccttaacagg tagttctcac    67020
tagttagccg ctggtgtgga ccttcactgt ctgccttcca cccttgccc ttcctgctcg    67080 tcccctgca cctggtggac agcacgactg ggggcagcag tggagccagg ttgcttaaat    67140
ggggcatatt cgggcttctt ttataatact tactctgaag cttgtgtgtc tgtggtgttt    67200
gcatcatata tttgttgttt tccatggttt aggctgtttt aaaattaggt ttatggcttg    67260
agcatagggc tttgtgagta ggggatggca ggtcgaaaca tctcatgagt tggatggggt    67320
atgctggggg ttgggaaatg ggatgaaaaa ttatgggatg aaaaattgcc tatggatagt    67380
ttaacttgaa agaatctgcc tttgtttaca gatagttatc ttttttcttt tttgagatag    67440
agtctcacac tgtcacccag tgcagatacc cagtgtcact ggagtgcagt ggtgtgctct    67500
tggtgcactg cagcctccgc cttctggggtt ccagcgattc tcctgcctca gcctcccaag    67560
tagctgggac tacaggtgcc cgccaccacg cttggctaat ttttgtattt ttttgtggag    67620
acgggttttt gccatgttgg tcaggctggt cttgaactcc tgacctcaag tgatctgcct    67680
```

-continued

```
gcctcagcct cccacagtgc cgggattaca ggagtgagcc actgtcccg gccagttaca    67740 gatacttatc taatgaaatt ctctgtgtac tttataaaag atgaggatta actgaaggta    67800
ctaataactg gattatatga gggtggtttt ggttgtataa tcctatctaa aagaatattt    67860
tagctataac tgaaagtaag acttaaatat ttagagagga aaatctgaat aattctagta    67920
gtaattattt atttacaaaa taaaaataga ttttttttg attacacaaa ttaaacaaca    67980
ataaaacatc acagcaatcc ggatactata aagctcacat gcttaccgac ccaactgccc    68040
caggagtgac cactgccaac agcttcatgt cgaccttttt gccataattt ttatatagcc    68100
ttttttgttt ttaaatggta atttagaaag tcaactagga aaatgtgtta caggtttatc    68160
ttccaggaga ataggactgg agtcgagatc ttgaatgtgg cttggaagaa ggcaagccca    68220
ccccagagag atgagttgac agttgtttct gaccactgct tgcttagagg gcctgcgtgt    68280
ctgtgaccgc ctagctttgc gccctgact aggctgcccc ttaattacaa atgtctttat    68340
atattgctcc agctaaggct tggagtagtc ggttaagaac ttgaacttcg gttttttgcag    68400 tgaaacagca tttgagaata tcaccttctg ataagcctta ttttataagg tgggtactgt    68460
agtgggaggc agtgtgagag atgcttgaag gatgcactgc tgtcctgcat ttcagcatct    68520
tcaggatgct gtgcagctga acatttgat aacggtggaa ctgttcgtta ttttgcaagc    68580
ctgtgattcc ctattgaatg ttttctctcg ccatttgaca aatgagtgtt tctctgtctt    68640
cagcctcagt gaaggatgag atcagtggag agctggctgc ttcttcaggg gtttccactc    68700
cagggtcagc aggtcatgac atcatcacag aacagccacg gtcacagcac acactgcagg    68760
cggactcagt ggatctggcc agctgtgact tgacaagctc tgccactgat ggggatgagg    68820
aggatatctt gagccacagc tccagccagg tcagcgccgt cccatctgac cctgccatgg    68880
acctgaatga tgggacccag gcctcgtcgc ccatcagcga cagctcccag accaccaccg    68940
aagggcctga ttcagctgtt accccttcag acagttctga aattgtaagt gggcagaggg    69000
gcctgacatc ttttttttta tttttattt gagacagagt ctcactccat agtgcagtgg    69060
aggccgggca caggggctca tgcctgtaat cccagcactt gggagactg aggcaggcgg    69120 atcacttgag gtcaggagtt cgagaccagc ctggccaaca tggtgaaacc ctgtctctac    69180
taaaaataca aaaattagtt gggcgtggtg gcacatgtct gtagtcccag ctgttaggga    69240
ggctgaggca ggagaattgc ttgagcctgg gaggcagagg ttgcaatgag ccagatcgt    69300 gacactgcac tccagcccgg gcaacagagc aagactccat ttcaaaaaaa ataaaaaaat    69360
aaagtgcagt ggctcgttct cagcccactg caacttctgc ctcccaggct cgagcgattc    69420
tcccgcctca gcctcctgag taggtgggat tacaggtggg caccaccaca ctcagctaat    69480
gtttgtattt tcagtagaga cagggtttca ccatgttggc caggctggtc tcaaactcct    69540
gaccttagat gatccaccca ccttggcctc ctaaagtatt gggattatag ttgtgagcca    69600
ccatgcccgg ccctgccacc tgccatcttt tgagttcttc cctggagacc tagacctgaa    69660
ccctcctgct tgttctcttg ttatctaata cccctattga cagcgcagct tagatcatta    69720
atggagagct tgacctcatc tgataccttc actgaaggaa acaacttagt gtcttttgtg    69780
ttgaacactg aggtaaaaaa ttggaatagt tgattatatg aactctgcta aaattgagtg    69840
cattttacat ttttttaaggc cttgttgggc cctggttaaa taattatttt taaaaatcct    69900
taaggagcct attataaaca gatctgtggt cttaatgaaa tgtgattaat actgtgcatt    69960
attttaagaa cttttgactt ttcaaaaaac ttttacaaca tttcccattt gatagcggca    70020
taggtttaag cacttctcat ctctaagtta gtggacaaaa aaccctcatg gatagtctaa    70080
```

```
taatgtttgc tacaagtcca tgttgagttt tatactccat tttattttca gttttaaaaa    70140
ctgtggttaa atatgtgtaa cataaaattt atgttcttaa ccattttttg cgtatacagt    70200
tcgctggtat taaatacatt taaataatgt catggaatca ttgctaccac ccatctctgt    70260 aacctttga tcatgtaaca ctgaagctct gttcccattg aactctattc ctcctttccc    70320
gccaagtccc tggcaaccac gattcttctt tctgtcttct gaatttgact actttgggtt    70380
ctcatatact ttaggagtca cacagtattt gttttactta gcataatgtc cccaaagctc    70440
atgcatgttg tagcctatgt tagaacttcc taatgtttca ggccaaatac tattccattg    70500 tatgatagg ccacattttg cttttccatt cctctgtcca tggacacttg tattgcttca    70560
tgttttagcc attgtgaatc atgctgttat gaacgtgggt gtacagatag ctcctggaga    70620
ctctgctttc cattttttg gctaaatacc cagaaatgga gttgctttta cattccaatt    70680
ttaatttaaa acattcatat cattgagtgt tttacttaat agtatagtag ttaacaaact    70740
taataaaata gtattttggt aataatttgc tggtagtcca ttgttcagtt tttttaggta    70800
aattacacag gacatttcaa gtggacatga acatcttgt gatgtggaat catgccccaa     70860
gctgatggct aaacatatga aataccatac cctaaattta gtagatttag tctttgcaat    70920
ttaggagata acctgttata ttgttaggtt tttgtcgaaa agctttgtcc tcatatttcc    70980
aacttgctgt aaaatttgtt tgtgaagaca aatattttg tatgggtttt ttcttttca     71040 tattaaaaag aaatgtccac attggaattt ttttggagtt tttagagcta atagagcttt    71100
tcataatgta gtgggaatga gtgatcagta agctcttagc agtttccatg cgtgcatttc    71160
tgtgccttga aataaatgac agatgagtac atttgtgttc tgtgtgtaaa atgtgctctt    71220
tcctcattgc acttccatgt tggagggctt gtctcttggt gatcacactt caaaattctc    71280 acagccccc ttgaaccgtt taggtgttag acggtaccga caaccagtat ttgggcctgc     71340
agattggaca gccccaggat gaagatgagg aagccacagg tattcttcct gatgaagcct    71400
cggaggcctt caggaactct tccatgggta tgtggactac aggtgatgcg ctacaaagtg    71460
gtttgtattc agacctggac atcttaatta tatctttgct tccaagaaga agtcctttga    71520
tactgttttc tgagttctga atagctgatg aaaatgacca attgaggaat aatcatactt    71580
tttcttgatc taaatcttat acttttgagt tatcttagca taaatgtata attgtatttt    71640
aagtggaaat ttgtcactta atcttgattt ctctgttttt aaagcccttc aacaggcaca    71700
tttattgaaa aacatgagtc actgcaggca gccttctgac agcagtgttg ataaatttgt    71760
gttgagagat gaagctactg aaccgggtga tcaagaaaac aaggtgaggg acataggctt    71820
gagacgactt ggtgtttctg agcttgtgtg aggatttaaa atcgccctgg ctactgtcta    71880
ctttattgct ttcccatccc tgggccttta aatttcccct ttaaatacca gctcttccca    71940
ggcctgttgt tttctgcctt tccaggtact acccacagcc ttgagaattg cctgagttct    72000
gcctcctttg agagtgtgcc ccagacaaat ctattctgta ctgaatgttt ccttgtctga    72060
tttcttggat cattcatttg atggttgcgt atggcctgca acgtttcttg ttttggttct    72120
actgaactgt tctaaaagtc tctcttcata ttatctttt acatgtaaat gtaactgtct     72180
tcacttttaa ttcctcaagg acaaggaata gcgtttcaca gttcgtccca tcaatcagaa    72240
ttatagcctt tggcatctcc ctatctacca ggcccacttc ctcttagatt tgggcttccc    72300
caggctgttg ccttttcccca agtagcttct gcttgtcctg tagaagacct ttcatgcttt    72360
gcttctgcag cagccgttcc tgaatgccta gtgtcaactg ccttcttacc acgcccaccc    72420
```

```
tccctgcatg ctgcatttat ccmctgccac agccctgtga ccctgtgtcc tgctgcctct    72480
gacttgtctg tttctgcttg gccatggtct ctgtgaggtc aggtgtgcat atgggcacaa    72540
accagggcat ctctttatcc ccagcacctg gcttaagtgc tgctctggaa ctatctgttg    72600
aatgaactaa tgcatgaatg tattgttgag tatgagacaa acaagtgtca ttgtctcctt    72660
tctagccttg ccgcatcaaa ggtgacattg gacagtccac tgatgatgac tctgcacctc    72720
ttgtccattg tgtccgcctt ttatctgctt cgttttgct aacagggga aaaaatggtg     72780 agtacaaaag gggatgtgca cagttgaagg aaataactag gtttcagagg tcagcttggt    72840
ggcctgtttt tgccttgcgt gcagcagagg aagtagaatc tgaggatgag tttggttttc    72900
actagccgag gggagggagg aaatgatggg agcaggtagg ttattgggtc tggttttgtt    72960
catttgaaaa caatctgttg tttgaggctg aaggtggctt gggtgatttc ttggcagtgc    73020
tggttccgga cagggatgtg agggtcagcg tgaaggccct ggccctcagc tgtgtgggag    73080
cagctgtggc cctccacccg gaatctttct tcagcaaact ctataaagtt cctcttgaca    73140
ccacggaata ccctggtatg ttaaaagttc acatcttatt ttctcagatt taatcattat    73200
tgtaaaaact atttcagtat tgactatttt agttttagag cagtaagtgt tttgagttca    73260
tttgggatat ttgacctgcg ttgtagctct tcagaaaaca catgaatagt gaagttcttt    73320
gtttcatggg ttcccttag atgaaaccca tagaggagaa aagtagaaac ctcagcacgt     73380
aagagccaac atatatacac atcggattta aacctaaagc acaaattgtg cctggtcgca    73440
gtggcgctga gtcgcactca gccaggccag gcattcacac tcagggtgag tgggaaccag    73500
gactggctga ggcagcagtg gacccaagtc tccatcgcgc ccatgcttac tatggagcct    73560
tctcgttctc tctttttctt tgggtgagag ggtacacttg tgtttttgaa tttatatgag    73620
gtaagtgtgt aatagggttt tttctaatct tttttaagtg gaatctggaa ttttaatcag    73680
atttattatc tgacaaccta gaattataat ccagaaagtc tgtggtattg aggacatatt    73740
ggcaatatga tgaatctcta attcttaaat cctgaaactt tttttttttt aatcacttag    73800
ggttattata gtgaagtcat ttctgaattt ggatcttctc ttcacacctc tttttctctt    73860
tcctgagaat taagcttttg tttcgagtta gaaagttgat agtagggaat tgttccatgg    73920
ctgagcaatt tatctccaca gaggaacagt atgtctcaga catcttgaac tacatcgatc    73980
atggagaccc acaggttcga ggagccactg ccattctctg tgggaccctc atctgctcca    74040
tcctcagcag gtcccgcttc cacgtgggag attggatggg caccattaga accctcacag    74100
gtaacggcca gttttcagc tgtgtttttt ctagttatgc ttactaaggt ttaagtttag      74160
atgatgatgt tgttgcttg ttcttctggt taggaaatac atttttctttg gcggattgca     74220 ttcctttgct gcggaaaaca ctgaaggatg agtcttctgt tacttgcaag ttagcttgta    74280
cagctgtgag ggtgagcata atcttctgtg gaaccatttc ttcacttagt ggacatttta    74340
tcattgctac aattaaaatt ggagcttaat aggaaatatt tccatgcact ctaaagctgt    74400
aaccagtaat acccaccatg tatccatctc tcagctttag aaagaaaacg ttgccagtaa    74460
agttaatgct tcataaactt cagtttaagt tctaattctc agaatatttg tttgaaatag    74520
acctcttcct aaaggatata tttagaaata acctatcatt aagtgtaaag tctgttgaat    74580
atgctgggca cggtgactca cacctgtaat ctgaccactt tgggaggcca aggtggaagg    74640
attgcttgag cccaggagtt caagactatg ggcaacatag ttgaccctgt ccctacagaa    74700
aattaaaaaa aaaaaaaaaa aaagtagctg ggtatggtgg tgcatacctg tagtctcagc    74760
tactcgggaa gctgaggtgg aggggggatt gcttgagccc cagagatcaa ggctgcagta    74820
```

```
aggcgtggtt acaccactgc cctctagcct gggcaacaga gtgagactgt ctcaaaaata   74880
atagtaataa taatcagttg aattaaaaaa aaaaaaaaaa aaaccactgt gctaggccca   74940
tagtatggta agagttaaag tgagccttag ggattattta ctcaacctct gtttctgtat   75000
aaagtggaat aggctcaatt ctttaagtga tagcatgttg aacctttcca taccaactgg   75060
ctcataagtc acaactggcc agtcaacaag agtaaaaatt aactggtaaa aatcaaagca   75120
aaaaacctac aattgtcaaa tttgtgggat aactccccct tttaaaatgt catgcctgac   75180
agtaatttct ctctagtttc caggttttca gtcagttgtg tctttttga gcagaaggaa    75240 gcatgctaag agctcaatct tgtgctagc tgggggtctt tgtgtcagcc atgcatgtga    75300
tggtgcccct gggtgcttgg ggctgcaggg gaggggtaca gcagtagggg cctgttctgt   75360
tctctcgtgc tgtggagtac atagtgacat agtggggtgg tccttggtgt aggtcccttg   75420
ttcctacccc tgggtctgag atttatttag aagtggtgtt ggggctgtgc ggcaggcccc   75480
tctgtaactg atcaatgttt gtgaagttgc tgtttgagag ttgaaaccat gacataagca   75540
gaaatggaag gaagaaagaa ccagttatgt gaaagggaca catttacttt taagcttgta   75600
tttactgaga taaagtattc ttaatcaatg ttcttgagag gtgtgggaaa aatgcaacat   75660
cctggttgca gttaaaccca gaacattgtg tgttgaagag tgacggttct caaaccgtca   75720
agacgcgggt actgagtggg actaacctgc tgtcctcttg ccttggacct tgtgttccag   75780
aactgtgtca tgagtctctg cagcagcagc tacagtgagt taggactgca gctgatcatc   75840
gatgtgctga ctctgaggaa cagttcctat tggctggtga ggacagagct tctggaaacc   75900
cttgcagaga ttgacttcag gtaagtgagt cacatccatt agatttcatg aactaagctc   75960
aattgaaagt tctgggatca cttgatgcaa ggaatgatgt tatcaagtac cctgtccatc   76020
agaaatccga gtggtttagg tagatgacag tgattttctc ctcccagtgg ctttttgctg   76080
aactttgccc tatgcttgga attttatttt attttattat ttatttagag acaagatctt   76140
gctctgtcgc ccaggcttga atgcagtagc acaatcatag ctcactgaag ctttgaactc   76200
taggactcaa gtggtcctcc tgcctcagcc tcccgattag ctaggagaat aggtgtgtgc   76260
cgtcacactg gctaatattt tttgtagaaa tggggtcttg ctatgttgcc caggctggtc   76320
tcaaactcct gggcttgatt gatcctccat cttggcctcc caaagtgctg ggattacagg   76380
catgagccac tgtgcctggc ctagaatttt aaaatataag tagaagagta gatttttttt   76440
tttggtagtc ctcgtcattt aagtattctg gatagtggga ataaaagagc ttagaatttt   76500
tcatctttgt cttaaacttt taaaaaaatg tagcttatat taattctgct tgtttaaaaa   76560
gaatatactc ttcattatac tgaacctagg taagacagct ggtttatatt ttgttgcaat   76620
taaaaaacgt gagctgtggt tgcagtgagc caagattgtg gccattgcac ttcagcctgg   76680
caacagagtg agacttggcc tcaaaaaaaa aaaataaca tgagctgtgt tggcactttc    76740
attttctaag agtagttttg gctggagaag ttttctttca gtactttctt ttagaaggga   76800
aattttcctt tataatttag ggtttgtttt tttttttcc aagccacctt ttatagagcc    76860
cttgtgggtt atttcattta atccttagaa tgttttataaa tctgggcttg ttctcggctc   76920
cacccacaga tagggacgct gagcgtgcat gagtgggcag caagatagca ggttatggag   76980
ggcccagctc acccccttctg tggcttgagc caatttttata gggcacttac agagtcttt    77040 gaaatagtat ttattttgaa gaaaagaaa aacagtttac tgagtactgt cttattgagt     77100
ctggaattgt gagaggaatg ccacctctat ttatttaaag ccattggcct tttttgttgt    77160
```

```
tttgagtaag tgctgcccaa ggtccttcca gggcacctgg atgagcctgc tctggagcaa   77220
gctggcggta agtgtttact gagtaactaa atgatttcat tgttaaatgt gctcttttgt   77280
taggctggtg agcttttTgg aggcaaaagc agaaaactta cacagagggg ctcatcatta   77340
tacaggggta agcggtttat ttttgtgaga tgctgtttta ccttcaagaa ggtgaaagtg   77400
aggctttcct tgtggaattt ctctaaatgc attcgtcatg ttttagatgt ttatttcaca   77460
gtttatatca tgaaagttat aatcttgtca tatggattta agtctagtaa tgttgagttc   77520
tttctcacta gctttccaaa atatcttacc taaaatttag tcaaatacaa gattatgttt   77580
atttttatta tccttctctc taaagctttt aaaactgcaa gaacgagtgc tcaataatgt   77640
tgtcatccat ttgcttggag atgaagaccc cagggtgcga catgttgccg cagcatcact   77700
aattaggtat ttaccaatat tttatctctt ttccttttTt ggttgaagta ctaaaagata   77760
cgagaatgga aagagaggga agaattcaaa ggatgtagag cagtattcct gaatctgagc   77820
tcatttcagc cattctattc ttaaactata atgaaaaaaa aatccaaaaa agtctaaaat   77880
tataattaaa aaacaacaa aatactaact gtccattgta aaaagtaatg cacttTcatt   77940
gtaaaaattt tggactatag agaatagtac taagaagaaa aaaaaaatca ccttcaattc   78000
tgctgccacc tggaggtaat cactgttaat attttgctat atactctatg agtttcttgt   78060
tcaaaatcag gtcaaaatta catgcaattt tgtaatctga caatttccac ttaatatttt   78120
attagcattt tcctgttatg aaacagtaat tttagttatg ggtcgttgtt ttgctatgcg   78180
gttgggataa aattttatat acttttTttg gcaattactt attatacata aatgtttgtg   78240
tatagttttc tttttctgag aattcctgga agttgagtta ccaggcccgg ctttgaattt   78300
tttttTttat ttttTtTttg agacagagtc ctgctctatt gtccaggtgc tatctcggct   78360
cactgcaacc tctgtctccc tggttcaagc gattctcctg cctcagcctc ccgagtagct   78420
gggattacag gggcacacca ccacgcccaa ttaattTttg tattttTagt agagacaggg   78480
tttcacgata ttggccaggc tggtctcgaa cttctgaccc cgtgatccac ctgcattggc   78540
ctcccaaagt gctgggatta caggcgtgag ccatggcgcc tggccaggct ttaaatttaa   78600
aacaaatctt ctaatagctt tatggaggtt ataatttaca tttcttgaaa tgtactcact   78660
ttgagtgtat agtaaactcc aatttTatca catttctgtc accccaaatg tatccttgtg   78720
cccatttgct gtaacctccg gttcctgccc caactcctag gcagccactc atctattttc   78780
tgtcccttaa gatttgtgtt ttcgccaggc gctcatgcct gtaatcccag cactttggga   78840
ggccgaggtt ggtggatcac ttgaggtcag gagttcgaga ccagcctggc caacatggtg   78900
aaaccttgtc tctactaaaa atacaaaaat tagtcggatg tggtggcaca cgcctgtaat   78960
cccagctact cgggaggctg aggcaggaga atcacttgaa cctgggaggc ggaggttgca   79020
gtgagcagag atcgcgccac tgccttccaa cctgggcaac agagagagac tgtctcaaaa   79080
caaacaaaga tttgtatttt ctggacattt tatagtactg gggtcatagt atagatggac   79140
ttttgcattt ggcttctttt acttaattgt gagattggtt cttgttgtag catgtatcag   79200
tagtttgttc attttTattg gcgaaagtat tctattatat gaataatacc atatTttatc   79260
tatccatcag atggatatta tagagttcat gttttggcta atttatgaat tatggtactg   79320
tgaacatttg cctgcaagat tttgtgtaga catgtcttca tttctcttga gtagatcacc   79380
tagaagtgga ttTttaaata atttTggtac ttactgtgaa actgctcttc aaaaacatac   79440
cattgttcct tccttccttc cttccttcct tccttcttc tttccttcct cccttcctcc   79500
ctcccttccc tacttccctc tcccttTtccc tttcccttcc ccttttccct tccccttccc   79560
```

```
gcctgcctgc ctgcctgcct tccttccttc cttccttcgt ttctttctac atatacacat   79620 tttttttaaat ttcaatggtt tttggggtac aagtggtttt tggttacatg gctgaatttt   79680
ggttacatgg tgaagtctga gattttagta cacctgtcac ccgagtagtg taccttgtac   79740
ccaatatgta gttttttgtc cctcaccttc cagccttccg ccttgtgagt ctccaatgtc   79800
cattatacca cactgtatgc ccttgcgtac ccacagctca gctcccactt ctgagaacat   79860
atagcagaaa catgccaaag tatactccca ctaccagaat gtgattgtgc ctgattcttc   79920
tcaccagtac aaatatttca aaaaagtta aatatgtatc agttttttgg gcagaagttg    79980
atacttctct ttatttattt attttttttg agatagggtc tcattctatg atgcccaggc   80040
tggagtgtgg tggtgcgatc tcggctcact gcagtctctg cctcccaggt tcaagtgatt   80100
cccacgtcag cctcccagga agctggaatt acaggcgagg ccaccactg ccagctaatt    80160 tttgtatttt ttggtagaga tggggtttca ccatgttggc cagactggtc tcaagctcct   80220
gacctcaagt gatccacctg ccttggcctt ccaaagtgct gggattacag gcgtgagcta   80280
ccacacccgg ctgatatttc tttttaaaat aacttacctt cttttgaaag taatacatgt   80340
ttaatgaaca gaatttaagg aaaatataaa aaaacgaaat aatctttgta atcaaactac    80400
tgaaaagaaa accaaagtta cattttggtg catattcttt ttcattttca tcattgtaat   80460
ttgcatttct ttgattactt gtgagacact cctttcattt acttaatagg tttatatgac   80520
ttgcctattc agagattttg cagctttacc attttctgca aatgatagca acttcttttt    80580
gtttgtttgt ttgtggagac agagtctcgc tctgtcactc aggcaggaat gcagtggtgg   80640
aatcttggct cattgcaact attgcctcct gggttcaagc gattttcctg cctcagcctc   80700
ccaagtagct gggattacag gagtgtgcca ccatgcccgg ctaattttg tatctttagt    80760 agagatgggg ttttgccatg ttggccgggc tgatcttgaa ctcctggcct caagcggtcc   80820
ccctgtctcg gcctcccaaa gtgctgggat tacaggcgtg agccaccgta cccagccagt   80880
agttacttct tatattctag aaaaaattct actcatgatc aagtctccat gaggaaagag   80940
actttaattg aagatcatgg ggcttgcaga ccaatatgat aaaatagttc attgtttcta   81000
aaagtattac tgagtgttga tggcagatat gaaccctttt gtttttgtag gaaaatgtta   81060
cccgtattct ccatttgaat tcagtttaga tttgttagga atcgcagctt aagctttgcc   81120
atctgggagt gtttgggaca gttttgcaga caaaattgca aaagtgccta aggaatgcag   81180
ctggcattca gacctgctct gtgctcagta ctctgtggac agacactgtt cagcacttgt   81240
tgatcagaag gtttagaaag agaactttca aagttggttt ttaattaaag catttaatag   81300
tgtaaataga aagggattaa attttatgac agacaaaaga aagtacagca cccagctggg   81360 cgtggggggct cacgcctgta atcccagcact atgggggct gaggtgggtg gatcacgagg    81420
tcaggagttc aagagttcaa gaacagcctg gccaaggtga tgaaccctg tctctactaa     81480 aactacaaaa attagccggg cgcggtggca ggcgcctgta atcccagcta ctcaggaggc   81540
tgaggcagga gaatcacttg aacctggacg gcagaggttg cagtgagcca agattgcacc   81600
attgtactcc ggcctgggcc acagagtgac attctgtctc aaaaaaaaaa aaaaagaaa    81660 aaagaaagt acagcaccca gttatgtccg agtgggtgca tgagagtgac cctgagattg    81720
gagacaacgc tgtcacgtgc ttgaagaacg ccacctgaga aaggggggcga gaagtggtgt   81780 ccgctggtaa ccagaggtgt tggcttagcc atctgcaggg aggagggtgg tctatcacag   81840
gtgagtttca tctactttct taagcaaatt aaccttactt ttgtgttagg cttgtcccaa   81900
```

```
agctgtttta taaatgtgac caaggacaag ctgatccagt agtggccgtg gcaagagatc   81960
aaagcagtgt ttacctgaaa cttctcatgc atgagacgca gcctccatct catttctccg   82020
tcagcacaat aaccaggtat gctgacccag tggcatcttc acattgtcgg gaaaatgccc   82080
tttcctgatg cctttcttta ggctttaatt gaaaacattt tattttctag aaaaaagctt   82140
cagctcagga tgtttgagtg taggtcagtc ctttgatagg atattatcat tttgaggatt   82200
gaccacacca cctctgtatt taagctctgc acaatcact cagctgtgac actgtaaatc    82260
tcttaatagt ttattacatt ccatgtgctg acagttgtat ttttgtttgt gacacttacg   82320
tattatctgt taaacatttt tcactttagt tgtgttacct ttaaagagga ttgtattcta   82380
tcatgcctgt tgattttttg gtgagcgggc tattaaagtc agtgttattt agggttatcc   82440
actagttcag tgatttgcga gattatcatt cacatttatt gtggagcttt tgaatatcgt   82500
gtcaaatggc cacatatatc ccattcttat ctgcttctta ggtgagtggg acacagtgct   82560
ttaatgaagc tataatcttc agaattctag cttgcagaga agattgcaga agtgataaga   82620
cttgtgcttt ttaattttgt cttttaaatg ttattttaaa aattggcttt atatgatact   82680 cttttttct gctgagtaac agtgttttac aaaacttgga ctaaatgact tctaagctta    82740
aatgatcact tgatgctttt tttctgaatt aggaactcag cttatcaaat atcaaagtca   82800
taattcctga ataaataacg tcttttttca tgtaaagact gctttaaaaa acacatggaa   82860
ggctgggtgc ggtggctcac gcctgtaatc ctaacacttt gggaggccca ggtgggcagg   82920
tcgcttgagc tcaggggttc aagaccaccc agggcaacat ggcaaaaccc acctctactc   82980
aaatacaaaa aattagccag gcgtggtggc gggcccctgt aatcccagct actcgggagg   83040
ctgagggatg agaatcactt gagccccgga ggcagaggtt gcagtgagcc aagattgtgc   83100
cattgcactc ccagcttggg ctacagagtg agactctgtc tcaaaaaaag acacacacac   83160
aaacaaaaaa aacatggaga cattttttttg gccaccttaa tatttcccct cagataattt   83220
cctttgttta aactcagaac tggcattttc tctcttggag aagattcagg acaaatactc   83280
ctttaagata agtagaagca gtgaaagagg atttgattat caggaatttg ataagcttag   83340
aataaattgt tgcttcttaa tgtcatttca gaagatgaat atttattaat agatgccaac   83400
tgagatatca ttaaaattga ttactaacta ctacttggaa aagtctccca gttccaaact   83460
tcagcaggcc tcttgacaat tcagctgtgg tcaattgggt cttgcgtgat agatacaatg   83520
accaattgtg cagcagagtg tgctgcttag ctgcctattc tgttagcatt catgtgttaa   83580
cttaaaatca taatctcctt agttttgttg agtgtctccg tggacaagac actgtgaggg   83640
atacaaaatc agattggctt tattcaaacc actggggtat tataattcat ttataattta   83700
ttttattttt tgccttttttt ccatgtgttc taaaggaatt agagtttgta tataactata   83760
atgggggata gaaattgaca tgtgccatga agggaatgca aaaaagtgcc gtgggagatg   83820
agaagtggag aaaggaattt ctttttttctt ggaagcagga ataacttcat gaagcatgta   83880
tttcaactta aacagatagt aggcaacgct gtaagggag tatggctgca gcaaaagtgt    83940
tcggggcaga ctgggaggaa gggagggaat aaattcagcc attgttatgg aataatgatc   84000
aaaatttatt ttcagcccgt ttcacttaaa agttgagact gcttaacttt ttttaatctt   84060
taatcttaaa cttttaaatg ccatttgatc tttaaaaata tatgttttaa tagtgtattt   84120
taagtctcta tattttgtt attagaatat atagaggcta taacctacta ccaagcataa    84180
cagacgtcac tatggaaaat aacctttcaa gagttattgc agcagtttct catgaactaa   84240
tcacatcaac caccagagca ctcacagtaa gtctctttct tgatcggtct tactgacatt   84300
```

```
gtaatagttt ttggtagctt gtatggccag ttagttgtat ggtcatctta cggtgaggtg   84360
cttgtcttac agctcttact tatccatgag gcttgctaag aaattgtgct tctgtgaaaa   84420
gaatctcagc ttactccagg aatgtaaatg actatgtttt ttctgattat taaagtaata   84480
cacgcccaaa ataaaaaaat tcagccaatt taggaagaca caacaattaa aataagccag   84540
gcatggtggc tcatgcctgt aatcccagca ctttgggagg ccaaggttgg gggctcactt   84600
gaggtcagga gtcggatacc agcctggcca acgtggtgaa accccatctc tactaaaaat   84660
acaaaaatta gctgggcgtg gtggcgggcg cctgtaatcc cagctactca ggaggctgag   84720
gcaggagaat cgcttgaacc tgggaggtag aggttgcagt gagctgaggt caagccactg   84780
cactccagcc tgtgcaatag agcgagactc tgtctcaaaa aaaaaaaaa aaaagaaaa    84840 gaaaaaagta aactactgtc acctgcattg gtaatgtatc agaagtttaa aatgtctaga   84900
ttataattaa ctcagtgacc tggtaatata tactaaggga aaaatattta taatttacat   84960
ttttacattt ttattttttt aattttatta tttttttttt gagacagagt tttgctcttg   85020
ttgcccaggc tggagtgcaa tggcatgatc tcagctcacc acaacctcca cctcccgggt   85080
tcaagcaatt ctcctgcctc agcctcctga gtagctggga ttacaggcat gcaccaccat   85140
gcccggctaa ttttgtattt ttagtagaga cagggtttct ccatgttggt caggctggtc   85200
tcaaactccc aacctcaggt gatccgccct cctcgacccc ccaaagtgct gggattacag   85260
gtgtgagcca ccatgcctgg ccttacattt ttataataag aatttatgtt gctgacatta   85320
gaaaagaacc ataatatcca agaatccaag aataattaaa ttatgtacat atgctagtat   85380
atagtgtgat gctttggaga atttttaaca atatggagat gtataatctg gattgtaata   85440
ttgagtgaaa aaaggcagaa tacaaacctg gtgggggtat agtcggattt cagttaagaa   85500
aaataatatt tacatatata catttctcac actggcagat aatcaccaag ataaattttg   85560
ggattgtgga tgattttttt cttctttata tttttcagat attctcaaat tttctaaaat   85620
gagcaagtat aacttttgtt atcagaaaaa aataatatac aaaagtaatg ttaatttgct   85680
ggtgaccagg ttaaaccttt ttatttttat tttttgagat ggaatctcac tctgttgccc   85740
aggctagagc acagtggcat gatcttggct cactgcagcc tccgcttcct gggttcaaat   85800
gattctctgg ccccagcctc ctgagtggct ggaattacag gcgtgtggca ccacacctgg   85860 ctaattttg tattttttagt agaggtaggg tttcaccagg ttggtcaggc tggtctcgaa   85920
ctcctgacct cgtgatccac ccacctcggc ctcccaaagt gctgggatta caggcgtgag   85980
ctactgcgcc cagccagacc ttttattttt atttgacaaa agaaatactt ccatgttata   86040
gaagactaaa tattgtttgg gctgtctgca gtatggtctt cccttgattt gttcaaaata   86100
tcgtaaactt tgcttattta ttttattgt ggccgactgt gtcgggcact gttgtaggct   86160
tgggatggaa aaacaggatt cctgcccctta gggtttctgc aggctggtca gggagacgat   86220
gtggtaagct ggagctcagc tcctaaggat gtgcaggggc agttgagagg cggaagggtg   86280
ggagatcatt ccagggtgtg ggcagcacag gaacctctct tcattgggat ataattgcca   86340
ttctgataac acgtgtttga ggtgtctaaa gtaggaagtt gtaccatggt gggacagata   86400
tcctgtggtt atcatacaca gatctcagtt ttcttctcat tgtttgtact ttttataaag   86460
ggtaacagga gatataattc aataaacctt tgtggtgttt gggtgtgatt ttattgtttc   86520
tttcttctca gtttggatgc tgtgaagctt tgtgtcttct ttccactgcc ttcccagttt   86580
gcatttggag tttaggttgg cactgtgggt atgtattttc ctcagtatat attaatagtt   86640
```

```
gtctacaaca gtatgacata aacatagtta ttaggatgcc cttttctttt cttttttaagt    86700 cttttatcaa tttggctttt tggaaaaata tctgatggaa tacttgtttc tgctatatta    86760
gctgtgtgag actagtgaca ggagctgtgg gaaatgaatg ccaaatgttc ttaggcattg    86820
atgggaattt cagggtgtgg tcttcaagtt catttaaggg aattttcata tgctggcaaa    86880
aggcttttct cattagcttg actctttcca aaattatttg ctgtgaatta gaagtttagg    86940 aaccttttt cacttaattg tgacctagca tacgaaatgg tgatgattta ggaactactg    87000
ttcttgtatt aacagctttt atttaaaaat gattttcctc cagtagatgg ccctactagc    87060
atctgggaaa taatttcaag tcttctccag cattcaggaa taggcttca ttttgtgtat    87120 caattactga gaatgatttt ggtgactcac atcacatttg agaagtaaac ctgcagattt    87180
cttgtgtgtg tcagcaaatg accaactgat atttgcttga agtggattac attatctgct    87240
ctagaatgat tgctttccca ccttcctcac atacagactg agcagctacg gtttctaatc    87300
ataggtctgg cactagactt cacttctggg caactttggc attggagtaa aatgtattaa    87360 tttaagaaa gttaaaaatc cgttcaagta aacatacagt tctaatactt tttacaattt    87420
aaaatataga tttaaatgat aaaataaaaa agaaatatg ggtagacacc ataatcctcg    87480
tttctgcatc tgttcacaag gggttgatat ttatgagttc tattctccat atccattcta    87540
tgttctctta atgctcagtc agcacctcag gtggttggag ttcaatgctt ggtagtttga    87600
cttacactgt cttttctagg ggattgagcc ctgggtagtc ctgcttattt gaggttgcaa    87660
tttgtctttc aataactttt actacaagat atggcgtgtt aaaggatacc attggggaac    87720
caacataata atatcaggaa aactaaccac gtcagacctg ccccattgtg tatcaagtac    87780 actattttc catagtaata aagagttcac cccagccaat tctcttttat tttgtgcctg    87840
tttactcaat ggcattaaca tgcccaaatg tctgggtagc tgtctcatct ccagttcagc    87900
agaaccattg tcatatgccc tagtaaaagc attccttcat tggacactta ggccccaata    87960
ctttcattca gatctactac ctgatttcat ttctcaaatg atttttatgg agctctgatt    88020
tataggaaag atgttagttg attaaaaata aaacaatttc tgagctggta taaaatgtat    88080
tgtgacatgc cttcctcttg gaattgcaag agaaaggaag actgttgttt gcttaaaaat    88140
tgtctataat ttgactttgc aaatgtctgc ttccagagtg cctccactga gtgcctcaga    88200
tgagtctagg aagagctgta ccgttgggat ggccacaatg attctgaccc tgctctcgtc    88260
agcttggttc ccattggatc tctcagccca tcaagatgct ttgattttgg ccggaaactt    88320
gcttgcaggt actggtactg agttgaaaca gggactccag gacttggatt ttgatttcct    88380 taggggaat ggggtggtg agcatatgag gggaaaatac tataaggtca ttgccagtga    88440
tggcttgtcc ctttagtcaa atttcagatg ttacctatat gcataaacac atgcagttgg    88500
cagctgttct gtgctgagta ttttaaagta gcctcttccc aatatagccc ctcagttaac    88560
tacaagtaaa ctcattttga atttcatttt aatgggcacc atatgccagt actccctcgg    88620
gcactgggat gttaagaaag tataatgtat ggacttcatt ctcaagttag ttttagatta    88680
gagggggata cacgtaaaca aaagtgcagt ggtcacacag agtggcccta atcactctcc    88740
ttgggcagat ttatgggctg gtaggaaaga gcacaacacg gagagggtgt agcaccttgg    88800
cgatgataat ggaggatgtg gccagcaagg aagacggagt ccattgaaat tgattttggg    88860
agaagttgcc aatctccatg aaagaattgg ggcctgtgct atttgcttca ggggggctata    88920 ggagagtttc gtgaagggga ctaaaagatg agtattttaa taagatcatt catccaactt    88980
gaacatgggc tggaggagaa ggtagggaga ctcaggagat taatgttgat gctaaggcaa    89040
```

```
gataatggct ttgggactgt agggaagaca ctgattgtaa gagaatgaag gaggcagaat   89100
tgccaggcct ggttcaccaa ctgaacttcg gttgtgaaga caaagaaacc tgggatgact   89160
tcacatcctg ggcaggtgtg tggtggtgac agtcatggaa attgggaaca cagatttgtg   89220
cgggaaacat cagtttcagt ttgagtttgg cttatcagtt gaatatcagg cacagatgtc   89280
tggccaactc tcaacatagg gtcttaaatg acttcagttc cccaagcaat ttgtccttcc   89340
catgctattg gggtggagag gtaatgtctg tgcccatatc acagccagtg ctcccaaatc   89400
tctgagaagt tcatgggcct ctgaagaaga agccaaccca gcagccacca agcaagagga   89460
ggtctggcca gccctggggg accgggccct ggtgcccatg gtggagcagc tcttctctca   89520
cctgctgaag gtgattaaca tttgtgccca cgtcctggat gacgtggctc ctggacccgc   89580
aataaaggta atgtcccact tgggtgctgg attcatacag ccttaatgac tatgggtttc   89640
cagactacct tgtttagta atctgtccct tctttattct cttttttgctt taaatgaaca   89700 aaattgctca gattgtgaca ctaaatttaa catcaaaatg tgaccatgtg gatgggtgca   89760
gtggctcgtg cctgttattc cagcactttg ggagactgag gcaagtggat cacttgaggc   89820
caagagttcg agaccagcct gggcaacatc acgaaacccc ctctctacta aaaatacaaa   89880
aaattagatg ggttgggccg ggcgtggtgg ctcaagcctg taatcccagc actttgggag   89940
gccgaggtgg gcggatcacg aggtcaagag atcaagacca tcctggctaa cacagtgaaa   90000
ccccgtctct actaaaaata caaaaaaatt atctgagcat ggtggcgggc gcctgtagtc   90060
ccagctgctc gggaggctga ggcaggagaa tggcgtgaat ccgggaggcg gagcttgcag   90120
tgagccgaga tcgtgccact gcactccagc ctgggtgaca gagcgagact ccgtctcaaa   90180
aaaaaaatta gatgggcatg gtggtgcgtg cctgtaatcc cagctacttg ggaggctgag   90240
gcaagagagt tgcttgaacc tgggaggcgg agtttgcagt aagccttgat tgtgccgctg   90300
cactccagcc tgggtgacag agtcagactc tttccaaaag aagaaaaaaa tgtgaccatg   90360
tgttttatag ctctttttagt atcatcagtc actgttatcc ctaagaggga aatacctagc   90420
tttagtttta ggtttccagc attagccaag aaagctcaga attgatgttc ctggccaagt   90480
acctcattgc tgtctcctta aatcttggtt aatggctact gtcctggcta gcatagttat   90540
ggagcatttc catggttgta gaatgttctg ccaatctcag ggacagtttt gcttttctgt   90600
gaagcaataa aatcaacttc aaaacaaatg ttaactattt gtacaatgga tttaagatag   90660
accagttcac atacttttt ttttttttt ttttgagatg gagtttcatt cttgttgcct   90720
gggctggagt gcaatggtgt gatctcagct cactgcaact tctgcctcct gggttcaaac   90780
gattcttctg cctcagcctc tcgaggcaga ttacagctgg gattacaggc atgcaccacc   90840
acacccagct aattttttg tagttttagt agagacgggg tttcaccatg ttggtcaggt   90900
tggtctcaaa ctcctgacct gaagtgatct atccgcttcg gcctcccaaa gtgttgggat   90960
tacgggcatg agccaccacg cccagcctaa gatagaccag ttcacttact gtttatatct   91020
gattactctc tctttgcctt gtcttctacc tttaaaaatc tccctactaa cttcccattc   91080
tcctttagct gccatcagtc ttctcccttc tctgcaaaca tctctggaga gtcccagcct   91140
cagcccacag agcttcccac tgctctgagg tggaccttgt ttgcaaggct tctttggctc   91200
tcttggcctg gaccctgtct actacttcag ccatccttcc ttaaccctg ctggtggttt   91260 ctgttgccac actccatagc agcgtttccc gcccagatca tgtctttaca tctctgggca   91320
ctgctctggt cctgcctgcc tttccctctt tgtatcctgc aggctgctac ccccatcttg   91380
```

```
agtgtcctct tcagttggct ttcagagggc ctcctgggtg ttcccttacc cacttgccac    91440
tccccagtca ctgggttcag tccttcctgc ccaccagcac atgctttcta ggctctgtcc    91500
taggccgtct tctctctttg tagtctctgg gccagtgctg ttctagagag tggcagaatt    91560
ttctataacc atggcagtgc tccatagcta tgccaggcaa gacagtagcc actaaacaca    91620
tatagctgtt gagcccttga aatgcagcta gtgtgactga agaactgaac cccgattcgg    91680
tttaattttc attaaattta aatttaaata accttatgtg ggtagtggct ccagtattgg    91740
gcagggcagc ctgagagtcg gggctgttct cctgtcttca gtgtctagat gagggacctc    91800
agaggacctg tctctggagc tgcagttcaa tgtagccagc tgccccgtga cacttacata    91860
tagctgattt gtggatatgt cagacacggt gtgatgagct cagctttctg tcctcctccc    91920
cacatctgcc cctgccccat ttaccccact ttgtgtctta tcaagctaga aacaggtcac    91980
cacaagtctt catttccact caccaagtct tttgtttccc ctactaaata ttttgcgaga    92040
agaaagtgtg tacctttgta ttcacataca tgtacatgca catatacatg cacatatgca    92100
ggggtcccca acctctgtta aaaaccggac tgcaggccgt gcgtggtggc tcacgcctgt    92160
aattccagaa ctttgggagg ccgagaccag tgcatcacaa ggtcaggaga tcgagaccat    92220
tccggctcac acggtgaaac cccgtctcta ctaaaaatac aaaaaaaaat tagccgggtg    92280
tggtggcggg cgcccatagt cccagctacc tgggaggctg atgcaggaga acggcgtgaa    92340
cctgggaggc ggagcttgca gtgagccgag attgtgccat tgcactccag cctgggcgac    92400
agagcgagac tctgtctcaa aaacaaaaca aaacaaaaaa aaaaaaaacc aggctgcaca    92460
ggaagaagtg agcaagcatt accatctgag ctctatctcc tctcaggcca gtggtggcat    92520
tagattctca taggagcgtg tatgagttcg ttctcacact tctgtaaaga catacctgag    92580
acatataaag aaaagaggtt taattggctc acagttctgc aggctgtaca ggcttctgtt    92640
tctgggaagg cctcaggaaa cttgcagtca tggcagaagg tgaagggaa gtaggcacat    92700 cttcacatgg cccacaggaa aaagagagaa ggagagagag agagagacag agagagagag    92760
agaaaaagaa agattgagag ggagagagga gggagaaagg agagtgcctg tagggggagt    92820
tgctacacaa aggagcacca gggggatggt gctcaaccat tagaaactac ccccatgatc    92880
caatcacctc ccaccaggcc ccacctccga cactggagat tacaattcag catgagattt    92940
gggtggggac acagagccaa accatatcag agcatgaacc ctattgtgaa ctgcacatttt   93000 gagggatcta ggttgcatgc tccttatgag aatctaatgc ctgatgatga tttgaggtgg    93060
aacagtttca tcccgaaacc atccccgcc aaccctggtt tgtggaaaaa ttgtcttcca    93120
cagaaccggt ccctggtgcc aaaaagtttg gggacctctg cacatatgca tgcacctgta    93180
catggacaca taatacatgt acatatgcat actttatatt ctctgccact tctggtccag    93240
actgatatac tatctcattt ggattactgc actagccttt tgttttggaa acagcatttt    93300
ttaaaaaatt taatttaatt ttttttgagat agggtgtcat tctgttgccc agcttggagt    93360
gcagtgtcat gatcatagct cactgcggcc tcgatctccc aggctcaagt gatccttctg    93420
cctcagcctt ctcagtagtt gggactacag gcatacccac catgcccagc taatttttttg   93480 atttttttttt tttttgaga cagagtctca gcctgtcgcc caggctggag tgggttggcg    93540
cgatctcagc tcactgcaac ttctgcctcc caggttcaag tgattctcct gcctcagcct    93600
cccgagtagt tgggattaca ggcgcctgcc accacaccca gctaactttt tgtatttta    93660 gtagagacgg gtttcaccca tgttggccag gctggtctcg aacttgtgac ctcgtgatta    93720
gcccgcctcg gcctcccaaa gtgctgggat tacaggcgtg agctaccgct cccagccagg    93780
```

```
aaacagcatt cttgagataa ttcatataat tcacccattt aaagtatata attcattctc   93840
tttagtatgc ccacagagtt gtacagccat caccagaatc agttttagaa cccataaagg   93900
aactctgtac tctttaccca aaacctccat gcctccagct gcaggcagcc actaacctgc   93960
cttctgtctc tgtgactcta cgtcttctgg acattactgt ggatgggctc atacagtcag   94020
tgagcttgtg actggtgcct tctaccaagc agggttttca gtgtagcagc ctctctgttt   94080 ttctttttt tttaaattgt gacggaactt ctgcctcccg ggttcaagcg attctcctgc   94140
ctcagcctcc cgagtggctg ggactacagg cccatgtcac catgcctggc taatttttt   94200 tttttttt tttagtagag atgggtttca acatgttagc cagggtggtc tcgatctcct   94260
gacttcatga tccgcctgcc tcggcctccc aaagtgctgg gattacaggc gtgagccacc   94320
atgcccggct aacctttcat ttactgtctg catttcttcc ctgatgcctt ccagtccatg   94380
cacccgattg tagccattca tcctattatg gtttaaggtg actgtcttag tcagcatggg   94440
ttgccataac aaaataccat agcctgggtg gcttcaacaa cagaatttac ttctcacact   94500
tctggaggtt gggaagtcca agatccagga cttt cgcctt gccctcatgt ggtgaggggg   94560
tgaggaagct ctgtggggcc tcttatatat ggatgctaat ctcattcatg aggggtctgc   94620
cctcatgacc cagtcacctc ccaaaggccc cacctcctaa taccatcacc ctggtaatta   94680
agtttcagtg tataaatttg ggggactata gacattgaaa ccataacaag cacttttcta   94740
agatcaggga gtgagtaagt agcagagcta ggacctcaat tccacatgtc agtcatcttg   94800
ccttcactct gctccatgat ggctgcctcc tagagcattg ggagtctcga tgttctatat   94860
gctctcatgt gttgtgtatt ggagatagtt gaggctttat gaatacatct ggatttgttg   94920
acttctagct ttgctggtaa ccagctgtga ccttgaataa gttacttcat ctctgagcct   94980
gtttcctctt ttagaaacag gagtttaaaa tgctgctttg ggttgggcac ggtggctcat   95040
gcctgtaatt ccagcacttt gggaggctga gatgggagga tcactggagc ttggagttcg   95100
agaccagcct gggcatcata gtgtgagatc ctgtctcctc aagaaattaa aaaattagct   95160
gggtgatgtg gcgtgtgcct gtggtcccat ctactctgga ggctgaggtg ggaggattgc   95220
ttgagcccag gaggttgagg ctacaatgaa atatgattgc accccatcct gggtgacgag   95280
tgagaccctg tctcaaaaaa gaaaaaaaaa atgctgcttt gtaccccttt catgtcatgg   95340
cgtcatggcc aacatagaat gccctggttg tttgctgttg gagggcatgg gcctgggggc   95400
tccctgaggg ctccttccat cttcaactca ttctctgtgc acctgttagg aagttgtggg   95460
ccagtcccta ccatgtatca ttgtgtgggt aaaagtaaat aaaatgtgta cagtgtctga   95520
actgtacata tcagggtcca agaacaaaat gagtgacatg ggttagctct ttttaataaa   95580
tggtaaaacc aaatattcta attttcagtt ttgttatact tccatcacat gttttgttt   95640 ttttgttttt tgttttt gtt tttctatttt aggcagcctt gccttctcta acaaaccccc   95700
cttctctaag tccatccga cgaaagggga aggagaaaga accaggagaa caagcatctg   95760
taccgttgag tcccaagaaa ggcagtgagg ccagtgcagg taggaaacag cgtggggaag   95820
ggagggacat gagtgcagca tctgtcatgt agaaacatag gatttaagta acttggtgtt   95880
ttagagaaat aaatataata cacatcagta aagtgagaga aagtttctcc aggtgcggtt   95940
caagatatta gaaactaatg actgatgtac acagaccacc ttttggtctg aagcatttct   96000
aagtgccact ggctgacatg cagccctac agcctccagg cttccagccc tagcatggag   96060
catcactctc ctatgcttcc ctggttgcag gtgatggctg gagaggcctc ctgatttttca   96120
```

| | |
|---|---|
| gtaagggaag tggtgtagat gcttaggaat agatgtagtg agtgaaaaaa ctgattctga | 96180 |
| tatgtcaaaa attctgattg gaaatggaat atttacattt ggaagagcta aaggcgagag | 96240 |
| aaagtgggga taaagtcatc tgagttggag gagcttaaac cattcacaag tttggaggac | 96300 |
| cttttttac ccatgaaaag gtcagaacag aaggggctag gatttaggtg tgactgcagt | 96360 |
| ttattgaatt cccatccata ctgctctcgg tgggcagtgg caggggcagg agaggagcct | 96420 |
| ggcaaagcat gaagtgactg ctgctgcctc tgctatctgg gacgcctggc cacctgtctg | 96480 |
| tacagtctcc ctccagaccc attctcacgc tgtctcttgg cacccagggg ccagtgatgg | 96540 |
| ttctcccatt tgttttgtgt atatagcatt tatatcaagg ctatttattt atttatttat | 96600 |
| tttatttatt tatttttttg agacagagtc tcactctgtc acccaggctg gagtgcagtg | 96660 |
| gtgcaatctc ggctcagtgc aagctctgcc tcctgggttc aagcaattct cctgcctcag | 96720 |
| cctcctgagt agctgggact acaggtgtgc accaccacac ctggctaatt ttttgtattt | 96780 |
| tttattagtg gagacggggt ttcaccttgt tggccaggat ggtcttgatc tcctgacctc | 96840 |
| gtgatccgtc cacctcagcc tctcaaagtg ctgggattac aggcatgagt cactgtaccc | 96900 |
| ggcctattta tttatttta attgacaaaa ttgtatatat ctgtaatata caacatgatg | 96960 |
| tttgaaatat gtgtacattg gccaggcgtg gtggctcaca cctgtaatcc cagcactttg | 97020 |
| ggaggctgag gtgggcggat cacgaggtcg ggagttcaag accaaactgg ccagcatggt | 97080 |
| gaaatcctgt ctctactaaa aataccacaa aaaaaaaaaa aaaaaaaaaa agccgggcat | 97140 |
| ggtggctcgc gccagtcgtc ccagctactt gggaggctga ggcaggagaa ttgcttgaat | 97200 |
| ctggcaggtg gaggttgcag tgagctgagt tcatgccact gcactctagc ctgggcgata | 97260 |
| gagcgagact ccgtctcaaa aaaaaaaaaa aaagaagaaa tacatatgca ttgtggaatg | 97320 |
| gctaattaac ctgtgcatca cctcacgtat cattgttttg tggtgagaac acttaaaatc | 97380 |
| tactctttca gtgattttct tgcatatggt acattgctat taactgcagt caccatgcta | 97440 |
| tacagtagat ctcttgaact cattcctcct gtctataaat gaaattttgt atccttgacc | 97500 |
| aacacattca aggttttttt tgagatggag tcttcttcac ccaggctgga gtaccatggc | 97560 |
| acgatctcat ctcactgcaa cctccgcctc ccaggttcaa gcaattctcc tgcctcagcc | 97620 |
| tcctgagtag ctgggattac aggcacatgc tactgcacct ggctaatttt tgtattttta | 97680 |
| gtagaagtgg agtttcacca tgttggccag gctggtctcg aactcctgac ctcaagtgat | 97740 |
| ccgcctgcct tggcctgcca aagtgctggg attacaggtg tgagccactg cacccggcct | 97800 |
| caagcgtttt aaaagatgct cttttctaag gattgactgt agtacaggag gaagattgac | 97860 |
| ctgttgaaaa gcctcagcct ttacaagtgt aaaattatca gtatattact atcatctttc | 97920 |
| tgatgaatta aataaactaa ggactccaag tcaaagtct tcaaactgaa gtagaatagt | 97980 |
| tgtatatagt gcttggcact ttaatattta gtatcggttt aatgataatg tttgtgcctt | 98040 |
| tgccgtcttt aaaacatttt tacatcatcc ctgtttgatt acttggtgtg ctcatgaagt | 98100 |
| tgttggccac taaggaatct taggctcaga gaggttctgg aattggccag tggtccttga | 98160 |
| atcagctgct cctatgattc tctaactgat ttctcacaaa gcaaacaagc aatcataaca | 98220 |
| aaacaactgt gcacactgct cttcttattt tgttatttaa aaagtactta ggctctactt | 98280 |
| atgtttgtta gtcaatttct cattacttct agttaatcaa aaggtcagag gaaatacttg | 98340 |
| aatatttca tactagaata ctttaaaaaa tcatgatttc cagtaatctc tttaaaactt | 98400 |
| ggcaagttat tttgatctaa aagtttatct tttgtgtgca tatttttaaa gcttctagac | 98460 |
| aatctgatac ctcaggtcct gttacaacaa gtaaatcctc atcactgggg agtttctatc | 98520 |

```
atcttccttc atacctcaaa ctgcatgatg tcctgaaagc tacacacgct aactacaagg    98580
tatgggcctc tgcatctttt aaaaatatat atgcacacat acttacgtct aatggatagt    98640
tgatgttttt cttatgattt gtaggatgta taagcccttt gagatatgag ttacatttag    98700 tttttcaag  tttgtttgtc tttcagcttt gtttatgata gcttctatca tacaggtgtt    98760
ttggattttc atattgtttg tactcacagc taagattgat tacagtgaca gagctaggat    98820
gtgcagccag gttataggggg gaagtggccc tggtggagtc tggagggatc cgtgtacagg   98880
cttccttccc tcccgtgagg ctcacacaaa aatacagcaa catgctggtc ctgcaggtac    98940
cctctgccta acatgagcca caattccaga ctcacagaag aaaagcaggt gttcggcata    99000
aaccatgtgt ttcaaatagt ctgggcatgg tgagccactt gttatcagct agggaaagtt    99060
tatgtcagcg taagaaactg ttcaccagat accccccaaga gccagccttt ctgtctaggg   99120
atgttttagt ttttttagttc atttttttttt ttaactttaa aattttctgt tcatctgcaa  99180
tttgttagat atgaagtatg tgtctaattt aattttttgtt tttggttgtc cccaataatg   99240
tttacagaag aattttttctg cactaattgg cttgagttac ttacattctc atagttctct   99300
agtttcagta gtttcatttta ttattttgtt atatcaatct atctgtctgc tcatctatta   99360
gaagcatcct tgttttttt ttttcttttt tagacagagt cttgctctgt ccccaggttg     99420
gagtgcagtg tgcaaccat gcctccctgc agtctcaggg ctcaagtgat cctcccacct    99480
cagctcctga gtacctggga ctaccggcat gtgccaccac acccagctaa tttttacatt    99540
ttttgtagag acagggtctc cctaagttgc ctgggctggt ctcaagctcc tggcttaagt    99600
aatcctccct ccttggcctc ccaaagtgct gggattacag gtgtgagcaa ctgcacccgg    99660
ctacaagtat acttcttaat tattgtagct taatggtatt tatgagggga tcagttcccc    99720
tgttgttctt tagaattttc tggatattct tctttattga ttttgggatg tgaacaatag    99780
aatcaacttc tacttgtaga ttgatttagg gagaacttat acctcagatg ttaagtcacc    99840
ctgtccagaa tgtgggatgc tttcctattt gttcagaact ttttaaatta cctcagaagc    99900
acatgaaatt taaggatttt taaaaaaaac ttaaagatta tttcacatag ctcttgcaca    99960
tttcttgata aatgaatcct caggtattcc tctgtttttg ttactaatag ttacttctta    100020 tgggttttt  ttcccctgaa aatcatttat caaacgtatg tggcttattt tctgaaggat    100080
gtttgataat tttggaagat atgaaagtct tcatatttta caaggtttga ggtctcttta    100140
agctgcatgg ttctcatgtc agctcccaaa gcagaagacg gcatgttgaa aaatgccgta   100200
gagaagatac ttcttttcca cctgttttca actcatatca tcttgaattt cagggcacct  100260
ttccatgctc ctagtgcttg ctatctgttt attattttcc ttcctgaata ccctgaactc  100320
cagcatgttc tgctgtaatt ctggcctccc tggcatcttg gactcctgtt tcctttgctc  100380
tgtcatcccc gcggtcagct cctgctgcgc agcttctcag ctgaagtgcg tttggagtgc  100440
ctggcgtgtc ttgctggatc tttgagtatt gcctctggtt tccttggttc cttctgctga  100500
gttgctcagc gtctccactc cccatttctt gtgtggccct tcctgcactc ctctgattcc  100560
ttttgtcttc cctggtttct tgctttggtt tcgagtctcc acagaacttt tgcagctctt  100620
ctgaagacct ggaagctttt tcatcttaat tctcatctca tgacctcttt tcccttcttt  100680
gagagctaga acttcccatg gtgaacttct cttttccagaa ttccatgcct tctttttccct 100740 cccacttacc tgttgtccag gagaggtcag attgctgtgc atattggagg agaacccttt  100800
cttccctggg ctcttcatct cacatgacat caccacatca cctcgttcct tggaccctca  100860
```

```
gtggtgtcac tgctggattt ttctttcctt tggctggcct tagggcacac ccaggttgac   100920
tagcgtagtc atggtattta gatccactca cattttcagt ttctgtgtct gtctcttgcc   100980
tgcttctgac ttcgcccaga gaaagcttct cttcacaag ggttcttaga tttatgttca   101040
ctgagcacct tcttttctga ggcagtgttt taccaatatt tattttccta gtcagtctcg   101100
ccttaccttt cttgttatgc atgtctttgg tcctgaccca ttctctgagt ctgtaaaata   101160
gaattgctgt ataatttaat tacatgaaat cctttagaat cttaacacat cttacacctg   101220
atttaatatt ttattgtatc caaattgaac caaccctatg tgaatttgac agtgatttct   101280
cccagggatc ctagtgtata aggaatagga cttagtattt tctattttt gatataccac   101340 ataccagata ctgattatga tggacattta acccttttt ctcattatga agaaagtta   101400 ggaattattt cttccagtag cgccagtgta acctgaaagc ctttgaaaga gtagttttg   101460 tatagctatc tgaaaggaat ttctttccaa aatatttttc cagtgctgac aacaaacacg   101520
cagacacacc ctgcaaggtg agtgtacggc gccgcacagt ggaggcatct gctgcagccg   101580
tcgatgtttg tgtctttggt tgtacattat gagatcgtga cagggccagt aaccgtgtgt   101640
tctctccttc accttcccaa ggtcacgctg gatcttcaga acagcacgga aaagtttgga   101700
gggtttctcc gctcagcctt ggatgttctt tctcagatac tagagctggc cacactgcag   101760
gacattggga aggtttgtgt cttgttttt ctccttgggt tgtggctggc acacttgatg   101820
tgcgtcttct gggctgagtt catctaggat ggagcctggt tctccagggt gcctccggga   101880
gactcctccc tgccccacgt gcttgcgtca caggacccaa gtctgactct gccttagcca   101940
tgaagtttag ggggaagttt ctatttgtat tctatttttg tctgttatca tgtattagct   102000
tagacccagt ttagtttgga aaatcagtgg gtttcaaaat gtgtttgtag agtccttat   102060 ttcttaactt gacctttca gtggaaagg ggcaaaacag acgggtaagg gggcggggcg   102120
ggaggtgtga cttgctcttt tgtgcctgag gaagtaacag agctggggtt gacagtcata   102180
ttctctgaca cagatagtct ctgacttatc tcacagaaag tcagcggcag agcctgagtt   102240
aaaagtctcg tagattttct ttttcttttt tttggtggct aatttcagtt ttatttatat   102300 ttgttatt atttattata ctttaagttc tgggttacat gtgcagaatg tgcagttttg   102360
ttacataggt atacacgtgc catgatggtt tgctgcaccc atcaacccat cacctacatt   102420
aggtatttct cctaatgtta tccctccccc agtcccctca ctccccatgg gccccggtgt   102480
gtgatgttct cctccctgtg cccatgtgtt ctcattgttc aatttccact tgtgagtgag   102540
aacatgcggt gtttggtttt ctgatcttgt gatagtttgc tgagaatgat ggtttccagc   102600
atcatccatg tgcctgcaaa ggacatgaac tcatccttt ttatggctgt atagtattcc   102660
atggtgtata tgtgccacat tttcttaatc cagtctatca ttgatggaca ttcgggttgg   102720
ttccaagtct ttgctattgt gactagtgcc acaataaaca tacatgtgca tgtgtcttta   102780
tcgtagaatg atttataatc ctttgggtat atgcccagta atgggattgc tgggtcaaat   102840
ggtatttcta gttctagacc tttgaggaat cgccagactg tcttccacaa tagttgaact   102900
aatttacact cccaccaaca gtgtaaaagt gttcctattt tccacaacc tctccagcat   102960 ctgttgtttc gtgactttt aacgatcgcc atcctaactg gcgtgagatg gtatctcatt   103020 gtgatttga tctgcatttc tctaatgacc agtggtgatg agcatttttt cgtatgtctg   103080
ttggctgcat aaatgtcttc tttgcgaag tgtctgttca tatccttgt ccatttttg   103140 atggggttgg ttgcttttt ttcgtaaatt tgtttaagtt ctttgtagat tctggatgtt   103200
aatcttttgt cagatgggta gattgcaaaa attttatccc attctgtagg ttgcctgttc   103260
```

```
actctgatga tagtttcttt tgctatgcag aagctcttta gtttaattag atcccgtttg   103320
tcaattttgg cttttgttgc cattgctttt ggtgttttag acatgaagtc tttgcctatg   103380
cctatgtcct gaatgttatg gcccaggttt tcttctagga ttttatggt cctaggtctt    103440 atgtttaagt ctttgatcca tcttgagttg attttgtgt aaggtataag gaaggggtcc    103500
agtttcagtt ttctgcatgt ggctagccag ttttcccaac accatttatt aaatagggaa   103560
tcttttcccc attgcttatg tgtgtcaggt ttgtcaaaga tcagatgatt gtagatgtgt   103620
ggtggtattt ctgaggcctc tgttctgttc cattggtcta tatatctgtt ttggtaccag   103680
taccatgcag ttttggttac tgtagtgttg tagtatagtt tgaagtcagg tagtgtgatg   103740
cctccagctt tgttcttcta gcccaggatt gtcttggcta tgcaggctct tttttggttc   103800
catatgaagt ttaaaatagt tttttccaat tctgtgaaga aagtcagtga tagcttgatg   103860
gggggatagc attgaatcta taaattactt tgggcagcaa ggccattttc acgatattga   103920
ttcgtcctat ccatgaacat ggaatgtttt tctatttgtt tgtgtcctct cttatttcct   103980
tgagcagtgg tttgtagttc tccttgaaga ggtccttcac atcccttgta agttgtcttc   104040
ctaggtgttt cattcccta gtagcatttg tgaatgggag ttcactcatg atttggctct    104100
ctgtttgtct gttattggtg tataggaatg cttgtgattt ttgcacattg attttgtatc   104160
ctgagacttt gctgaagttg ctaatcagct taaggagatt ttgagctgaa ccaatagggt   104220
tttctaaata tacaatcatg tcatctgcaa acagggacag ttttacttcc tctcttccta   104280
tttgaatacc ctttattgct ttctcttgcc tgattgcgct ggccagaact tccaatacta   104340
tgttgaatag gagtggtgag agagggcatc cttgtcttgt gccggttttc gaagggaatg   104400
cttccagttt ttgcccattc agtatgatat tagctgtggg tttgtcataa atagctctta   104460
ctatgttgag atacgttcca tcgatacctc gtttattgag agttttttagc atgaaaggct   104520 gttgaatttt gtcaaaggcc ttttctgcat ctgttgagat aatcatatgg tttttgttgt   104580
tggttctgtt tatgtgatgg attacgttta ttgatttgcg tatgttgaac cagccttgca   104640
ttccagggat gaagctgact tgattgtggt ggataagctt tttgatgtgc tgctggattc   104700
agtttgccag tattttattg aggattttca catcgatgtt catcagggat attggcctaa    104760
aattctcttt ttttgttgtg tctctgccag gctttggtat caggatgatg ctggcctcat   104820
aaaatgagtt agggaggatt ctctcttttt ctattgattg gaatagtttc agaaggaatg   104880
gtaccatctc ctctttgtac ctctggtaga attcggctgt gaatccatcc tggactttt    104940 ttggttagta ggctattaac tattgcctca agtttagaac ctgttatcag tctattcaga   105000
gattcagctt ttttctggtt tagtcttggg agggtgtatg tgtccaggaa tttatccatt   105060
tcttctagat tttctagttt atttgggtag agatgtttat agtattctct gatggtagtt   105120
tgtatttctg tgggatcggt ggtgatatcc cctttatcgt ttttattgag tctatttgat   105180
tcttctctct tttcttcttt attagtcttg ctagcggtct acctattta ttgatctttt    105240 caaaaaacca gcacctggat tcattgattt tttttggagg gttttttttc gtgtctctat   105300
ctccttcagt tctgctctga tcttagttat tttttgtctt ctgctagctt ttgaatttgt   105360
ttgctcttgc ttttctagtt cttttaattg tgatgttagg gtgttaattt tagatctttt   105420
ctgctttctc ttgtgggcat ttagtgctat aaatttccct ctacacactg ctttaaatgt   105480
gtcccagaga ttctggtatg ttgtgtcttc gttctcattg gttccaaga aaatttttat    105540 ttctgccttc atttcgttat ttacccagta gtcattcaag agcaggttgt tcagtttcca   105600
```

-continued

```
tgtagttgtg tggttttgag tgagattctc aatcctgagt tctaatttga ttgcactgtg    105660
gtctgacaga cagtttgttg tgatttctgt tcttttacat ttgctgagga gtgttttact    105720
tccaactatg tggtcagttt tagaataagt gcaatgtggt gctgagaaga atgtatgttc    105780
tgttgatttg gggtgcagag ttctgtagat gtctattagg tccgcttggt ccagtgctga    105840
gttcaagtcc tggatatcct tgttaatttt ctggctcatt gatctgccta atattgacag    105900
tggggtgtta aagtctccca ctattaccgg gtgggagtct cttgtaggt ctctaagaac     105960 ttgcttcatg aatctgggtg ctcctgtatt ggggcgtgt atatttagga tagttagctc     106020
ttcttgttga attgatccct ttaccattat gtaatggcct tctttgtctc ctttgaactt    106080
tgttgattta aagtctgttt tatcagagac taggattgca atccctgctt tttttttgct    106140
ttccatttgc ttgttagatc ttcctccatc cctttatttt gagccaatga gtgtctttgc    106200
atgtgagatg ggtctcctga atacagcaca ccaatgggtc ttgactcttt atccaatttg    106260
ccagtctgtg tcttttaatt ggggcattta gcccatttac atttaaggtt aatattgcta    106320
tgtgtgaatt tgatcctgtc attatgatcc tagttggtta ttttgcccgt taactgatgc    106380
agtttcttca tagcgtcagt agtctttaca atttggcatg ttttgcagt ggctggtact     106440 ggttgttcct ttccatgttt agtgcttcct tcaggagctc ttgtaaggca ggcctggtgg    106500
tgacaaaatc tctgcatttg cttgtctgta aaggatttta tttctcgttc acttatgaag    106560
cttagtttgg ctggatatga aattctgggt tgaaaatact ttttttaaag aatgttgaat    106620
attggctccc actctttctt ggcttgtagg atttctgcag agagatctgc tgttagtctg    106680
atgggcttcc ctttgtgggt aaccccgacct ttctctctgg ctgcccttc cttcatttca    106740 atcttggtgg atctgatgat tatgtgtctt ggggttgctc ttctcgagga gtatctttgt    106800
ggtgttctct gtatttcctg aatttgaatg ttggtctgcc ttgctaggtt ggggaagttc    106860
tcctggataa tatcctgaag agtgttttct aacttggttc tattctcccc atcactttca    106920
ggtacaccaa tcaaacgtag atttggtctt ttcacatagt cccatatttc ttggaggctt    106980
ggttcatttc ttttcactct tttttctcta atcttgtctt ctcgctttat ttcattaatt     107040
tgatcttcaa tcactgatat cctttcttct gcttgattga atcggctgtc gaagcttgtg    107100
tatacttcac aaaattctcg ttctgtggtt tttagctcca tcaggtcatt taagctcttc    107160
tctacactgg ttattctagc cattagtcta acattttttt caaggttttt agcttccttg    107220
tgatgggtta gaacatgctc ctttagctcg gagaagtttg ttattaccga ccttctgaag    107280
cctacttctg tcaattcatc aaactcattc tccatccagt tttgttccct tgctggtgag    107340
gagttgtgat cctttggagg agaagaggtg ttctggtttt tggaattttc agcctttctg    107400
ctatggtttc tccccatcat tgtggtttta tctacctttg gtctttgatg ttggtgacct    107460
acggatgggg ttttggtgtg ggtgtccttt ttgttgatgt tgatgctatt cctttctgtt    107520
tgttagtttt ccttctaaca gacaggcccc tcagctgcag gtctgttgga gtttgctgga    107580
ggtccactcc aggccctgtt tgcctgggca tcaccagcag aggctgcaga acagcaaata    107640
ttgctgcctg atccttcctc tggaaacatc gtcccagagc acgaaggtgt ctgcctgtat    107700
gaggtgtttg ttggcccta ctgggagtg tctcccagtc aggctacatg ggggtcaggg      107760
acccacttga ggcagtctgt tcattatcgg agcttgaatg ccgtaccggg agaaccactg    107820
ctctcttcag agctgtcagg cacgtatgtt taaatctgga gaagctgtct gctgcctttt    107880
gttcagatgt gcccttcccc cagaggtgga atctagagag gcagtaggcc ttgctgagct    107940
gcagtgggct ctgcccagtt cgagcttccc tgctgctttg tttacactgt gagcatagaa    108000
```

```
ccacctactc tagcctcagc agtggtggac acccctcccc cagccaagct cctgcatccc 108060
aggtcgattt cagagtgctg cgctagcagt gagcaaggcc ccatgggcgt gggacccgct 108120
gagccaggca caggagagaa tctcctggtc tgctggttgt gaagactgtg ggaaaagtgc 108180
agtatttggg caggagtgta ctgctccttc aggtacagtc actcatggct tcctttggct 108240
tggaaaggga agtcccccga cccccttgtgc ttcccaggtg aggcaacacc ccgccctgct 108300
tcggcttgcc ctccgtgggc tgcacccact gtccagcaag tcccagtgag atgaactagg 108360
tacctcagtt ggaaatgcag aaatcacctg tcttctgtgt cgatctcact gggagctgta 108420
gactggagct gttcctattc ggccattttg aagcatccc ttgtttttg aggtggagtc 108480
ttgctctgtc gcccaggctg acgtgcatcg gcacaatctc ggcccactgc aacctttgcc 108540
tcctggtttc aagcgattct cctacctcag cctccggagt agctgggatt acaggcacct 108600
gccaccatgc ctggctaatt ttttgtattt ttagtggaga tggggtttca ccacattggc 108660
caggctagtc tcgaactcct gaccttgtga tccacccacc tcagcctcct agagtgctgg 108720
gatcacaggt gtcagccacc acgcccagcc atattttcag atctccctct ctttgcccta 108780
aaccactgtg cttaataagt agttttagt ggccagcagt ctccatgtat aacacatttt 108840
agcaaaatgg aaaatactat atgttttaaa tttgaacgtg agattatact gaaataaaaa 108900
tcatctaact gggattcttt aaatagtaag attttcttt ttgtatgtgg ttttttttt 108960
aaccttatta ttatgactgt catatataga aatggctgtt tttcagttac agtcagtgaa 109020
tgtatcaaat gctgccttat ccaaataata aagtaaatt attaataagt cacaatttaa 109080
tgaagattga tgttagttga tctttatatt cttgaaatca gccatatggt tgtgtgtgta 109140
tgtatatatt tttaaaggta cataaagata ataagctcat ctctgaaaat ttttacattt 109200
ggcataagaa taactggata attaagcatc ttattctctg gcctgtgtct ttacagttaa 109260
aggtagattt actcacctct ccttttttgt ttttctaagt tcatctttt tgctgtttca 109320
agacagaggc ccattttagc tttctcgcat atccttttgt ttgtactttg gaagcctcac 109380
ctgcttaatt gttgagtttt tatccgtggt ctttttagagg gggatatgta gggtagaagc 109440
tttcacaggt tcttgtttgc acttggcccc tgactgtttt gaggaatctc cctcactgac 109500
tcacagcatg gcaaggtttc agatctcttt ctgccacaca gcagttctga ggcagctgga 109560
aagatatcca gatgcttaga ttgtcaggcc aggcttgaga tatacaaact attgagcctt 109620
atctgtgacc ttgcttaggt gaaggcatca gagcccctgc accaacatgc ataggcctct 109680
gcatgtgtgc ggggctgggt gttgaggtct gagcacaagt gtagctggag aggtgagctt 109740
gatgtggcga cgggtatgag caggttttct tcagacttct gtgagtttac ctagttccag 109800
gatttaaagg cacagagact ttagaattaa aatagaatca ttttctttt ctaaatgca 109860
acactaggaa taaaaaataa taattccaca ttcttgacag gtaatgtttt tcttgtctt 109920
ctaatcctta tttattccat actcattttt atacataatt gaaatgtatt atgcattgga 109980
tttttctttt gcattatatt atagacgatt tttcatgtaa ctccttactg ttccatttta 110040
tatgttttgt ctggtttaag actttatctg caaaccggga aactgtctct acaaaaagaa 110100
aaacaaaaat agttggccgc agtggcatgc gtctgtggtc ccagctactc ggggctgagg 110160
tgggaggatt gcttgagcct tgggaggttg aggctgcaaa gagccatgat catgccattg 110220
cactccagca tgggtgacag actttatact gtctgttttg ggtgatttga taatgatatg 110280
ccctgatgta gtttttttat atcttgtgtt tcttgtgcct gggtttattg aggttgggtc 110340
```

```
tgtggcttca tagtattttt aaagtttgga aaatttttagg ccattctttc tttctttctt   110400
tctttttttt ttttttgaga cagtgtctcg ctctgtcgcc tgcgttggag tgcagtgaca   110460
ctatcttggc tcactgcaag ctctgcctcc tgggttcacg ccattctcct gcctcagcct   110520
cctgagtagc tgggactaca ggcgcctgcc accacgcctg gctaattttt tgtatttttta  110580
gtagagacga ggtttcactg tgttagccag gatggtctca atctcctgac ctcgtgatct   110640
gcccgcctgg gcctcccaaa gtgctgggat tacaggcgtg agccactgca cccagctagg   110700
ccattatttc ttcaaagatt ttttttctgc cctgcctccc tcctttttc cctctcttaa    110760
aggggctgtg atttcctgaa tgattgctta gtgttgtccc atagcttact gatgctcttt   110820
tcagtgtttg attgttttat gtgttttctg ttttgtatag tttctattat tgtgttttca   110880
agttctctga tcttttcttc tacagtgtct actctgttgt taatctgtta atctgttgtt   110940
aatcctgtcc agcgtatttt ttttttttgtt tttgaaacag tctcactctg ttgcccaggc  111000
tggagtttag tggtgcgata tcagctcact gcaacctcca cctcccaggc tcaagcaatt   111060
cttctgcctc agcctcccga gtagctggga ctataggcac gtgccaccac acctggctaa   111120
tttgtgtatt tttattagag atggggtttc accatgttgg ccaaactggc cttgaactcc   111180
tgacctcagg tgattcatcc gcctcggtct cccaaagtgt tgggattata ggcatgagcc   111240
accgtgtctg gcccctgttc agtgtatatc actaattttg ttttttatctc tagaagtttg  111300
atttaggtct tttaaaaatg tctccctgtg tttctgttta gctttgtgaa cacaattgta   111360
ataactgttt taatatcctt ctctgctagt tctaagatct tctaataact cccagttct    111420
tggtgttct cattggttga ttgatactcc tcgttttggg ttgtattttc ctgcctcttt    111480
gtatggctgc caattttttta ttggatgccc aaccttgtga attttacttt gttggatgct  111540
atatatttt gtgttcccat agatcttctt gagctttgtt ctgaggttag ttgagttaca    111600
tatagatggt ttactctttt gggtcttgct ttataatttg tcagatgggt tggagcagtg   111660
cttagtttag gactaatttt ttttttggac taattattcc tctttaggaa taattaggta   111720
ccatgcttag gaggcaagac catcctgagt actctaccta atgaaccaga aagtttgggt   111780
tttccagtcc gcctgctgag aacagtgact ttctagccct gtgtgagcgc tgagctctgc   111840
tccttctaat cctttccaat gcttctttcc ctggcctcag ggagttttct cacacacata   111900
tctctgctga gtactcgaga gggaccttcc ccagatctcc agagctctct ctgtcttgtt   111960
ttctcttctc tggtgctctg tcttatgaac tgtggctgtc ttggtctcct tagattctca   112020
gcacctcttc aattcagagg gttgcctgtc cctcctcctt gtgccacagc ctaggaactc   112080
tctcaaagca gcgagttggg gcagccatag ggctgactta gtctctcgtc tcccagggat   112140
cactgtcctt cattgctcat gtccagtgtc ttgaggactc tgggttttgt ctgttttgtt   112200
ttttggtttg ctttggttgt ctcaggcagg agggtaaacc cagtccctca ccctcattgt   112260
gctcagtagt ggaagtctca ctctattaca ttagatatta gtatttgtag cagagccctg   112320
gttccctggt acttggggag ctcttgaaag gccagaaaca gcatgctttc tcacctttc    112380
cagggcttca gtttctggtg cacatcaagc attccataca catttgttaa agtccttttgt  112440
tagacaagta gtgattcaca ggttctattt gtaattttt cagttaacat gtattgggta    112500
tctgctggga gctagtaaaa acaaaaagtg gtgtgtgaca aattcaattc tgacaagaac   112560
aaccttaaac acttagaata tactttgagc atatcagaat tttaaaaatg tgtggcccctt  112620
gagtatttga aaccaacaag aatctcattgc ttattagtag aggatatttt gttaaacaag  112680
tggagagaga ggcattttca gtctaattgg tgttggcttt tagcagctga tggaaaccag   112740
```

```
ttcgtgatta gccaggcagt ggtgaaacag gctgtgcatt ctgaatgcct aggtatctag    112800
gcattcagaa tggtggcgct cttttgagtta gcatcttctt ctttcttgat tcttttttt    112860 ttttttttga gatggacttt cgctcttgtt gcccaggtaa caactccagt gcaatggcgc    112920
catctcggct cactgtaacc tctgcctccc tggttcaagc gattctcctg cctcagcctc    112980
tcaagtagct gggattacag gtgtgcgcca ccacgcctgg ctaattttgt attttggta     113040 gagatggggt ttcactatat tggtcaggct ggtcttgaac tcctgacctc aagtgatgca    113100
cctgcctcga tctcccaaaa tgctgggatt acaggcgtga gccaccactc ccagcccctt    113160
cttgattctt gaaaaggaca ttgggtgctg tacatctcgt tatagatgtt gataaaaatg    113220
cttgtgagaa gagtaacatt aaggtagtta tttggtcatt tttgcagatt attttaagac    113280
aattctagga ctgatttgtg gtaaatcaca cattgctgta tcatagttgt gttcactgaa    113340
catattcagg ggctctacag atgcagggct cttagctgct tgcacactt ctgaattcct     113400 gccctgcgaa caggactgga tacctaatag acaacaggta cttgataaca gtttattgaa    113460
ttaatgagtg aatgaacaga tacataaatg catgaaagaa tggttgtaat gtatataact    113520
tggatttcaa acttttttac tgactgttca aaataagaaa ttgaaaactt tcctctgatt    113580
ttcctctact atttacacaa tttaaatgga agttatcttg taccttcaat ttctgtctag    113640
gattcgtaca ataacgggtc atctctgagt cgcttaatgt ctcacttgtc tttctacagt    113700
gtgttgaaga gatcctagga tacctgaaat cctgctttag tcgagaacca atgatggcaa    113760
ctgtttgtgt tcaacaagta agagcttcat tcttttcctc ttctgttaag acgttcgggt    113820
atgacagcaa aacgctgcta ctccttaaga ggcaggcgct gttggcataa tcagctggga    113880
ggattgtggg gtccagcgca gcacttttg gctcagtcca tgattgagcc aagaggccat     113940
ccttcccttc actccccagg aggacgaggt ctgtcactgt ggagggcaga ggacaccaga    114000
agctcctctg caacctcgct agttaacttc cagtccctcg gagtttctgt ttagaatgct    114060
caatctcatt tagaattgca aggaaaccca aaacgcctat ttaaggtaca aacagcactt    114120
catacaatat ctcatgaggt attaatagtg attcacagga agaatttcac gctgtgagtc    114180
tttgctaaca tatccagtta tttacagatg gatttgatat ttgtgtggga gattcttaaa    114240
agtgttgttc acgccacatt gttgatgcct cattttttc actgtagttg ttgaagactc     114300 tcttttggcac aaacttggcc tcccagtttg atggcttatc ttccaacccc agcaagtcac   114360
aaggccgagc acagcgcctt ggctcctcca gtgtgaggcc aggcttgtac cactactgct    114420
tcatggcccc gtacacccac ttcacccagg ccctcgctga cgccagcctg aggaacatgg    114480
tgcaggcgga gcaggagaac gacacctcgg ggtaacagtt gtggcaagaa tgctgtcgtt    114540
ggtgaaagca cgaaagagca agcaggaaat actttgtaaa agaataaaaa cgaaaatgt    114600 tagcgaacat cttctaatag tctgctgtat tcagagaact ctaggagata tatatggttg    114660
atgcaaagat gatttaaggc atagcccggc cttccaagaa gtgtgtggcc agtgagtgag    114720
atgggcttgg gacttacaca tctcagaggt gggggtagag gaggaggaac actgagtggg    114780
ctgagaagca gccagctctc attgccaaag tgtgtcagca aaccagaatg cagttcataa    114840
tgtccccacc cattcaaagc acaggacctg tagagtggtg tggcatgtgt tggtggcact    114900
tttcaggcct gtaacaagga tgaaagaaca gcttcatagc agcacagtag tgctggtgtt    114960
cagaggtgtg tgaaggccat agaagcatct tggatatatt accttgtgtt ttgtcagctt    115020
tatgactaga agtctctttt cacttaaatt tgttttttt ttttttgaga cggagtcttg     115080
```

```
ctctgtcgcc caggctggag tgcagtggtg caatctcagc tcactgcaag ctctgcatcc   115140
tgggttcatg ccattctcct gcctcagcct cccgagtagc tgggactaca ggcgcctgcc   115200
atcacgcctg gctaacttttt ttttgtattt ttagtagaga cggggtttca ccatgttagc   115260
caggatggtc tcgatctcct gacctcgtga tctgcccgtc ccggcctccc aaagtgctgg   115320
gattacaggc gtgagccacc gcgcccggcc tcttttcact taaatttatg tttgtgtttt   115380
taatgcctag tatacaggac ttcttaaatt gccttaagta tgaacaggta tttgagttgc   115440
taatctgtat agtagcaata atagaatccc ttgttttttcc ttttataaat ttagcgatta   115500
aatagctaca attaaaacac tagagtcagg agtcaaggaa aatacccatg ttccaggctg   115560
tatgttagtg atgtacttac tatatattgg agtttcagga gtaagtctgt ttcaatgctt   115620
tctgtaacca tttggggtat taataagcat gtgagtgtgt gcatgtttgg gttaatttca   115680
tatatgtttc ttagaaggga tatcattgat gtaaatattt taaaggcttg tcctccaaaa   115740
aaatcatgta atttcttcta aattactgat cttttaaatg accttcacct ttctctcaaa   115800
tctcacttaa gactgggctg agtagtcagt ttcctgtagc agaaaaaagc tcagacttga   115860
gtagccttct gcgagtgagg agacttgatg gctgtcaggc agctgtaaac tctaaataga   115920
gtgtcattat ctgaagaggg cgatgctgcc acactgagtg gcctttcaag ttgtttctca   115980
atctgacacg ttctgatcgt gtgaatgtga aattggtttg agcaggagta tatctgagtg   116040
cagaggagat tatttaaaga tattctcatt ctctgcttcc cttttattcc catttggcag   116100
atggtttgat gtcctccaga aagtgtctac ccagttgaag acaaacctca cgagtgtcac   116160
aaagaaccgt gcagataagg taatggtgc cgtttgtggc atgtgaactc aggcgtgtca   116220
gtgctagaga ggaaactgga gctgagactt tccaggtatt ttgcttgaag cttttagttg   116280
aaggcttact tatggattct ttctttcttt ttttctttt tatagaatgc tattcataat   116340
cacattcgtt tgtttgaacc tcttgttata aaagctttaa aacagtacac gactacaaca   116400
tgtgtgcagt tacagaagca ggttttagat ttgctggcgc agctggttca gttacgggtt   116460
aattactgtc ttctggattc agatcaggtt tgtcactttt atctttcatc catcataccct  116520 gttcctaatt tagtacaaat taccctaaaa gacactgaaa tctactttaa agaaatgtgg   116580
tctgcatgtt tccctcatca gttgctgctg cttatctttt tcatgcacct agctggtgca   116640
gaaggcctgg ggcatagcca gcctcagcaa gtcagcatcc ttgccccagc tccctggact   116700
caaggctaac ctggggttgg ctgttaggga tttccaaagg tttgtcccat ccacttgcct   116760
cccctccaaa ataagtttga atttaaattg tgagatacaa ttaagattta ttgtttgggg   116820 aacattttg caaaatctag agttagttta aacagattat caattattac cataattgat   116880
catctgcagt ttcaagctat ctaacaggtt cacttacctc tttaaaaagg aatggaattt   116940
agcaggacag taactgagac ccgtgctcct ggagtccatg tgggagctgt gtggctctgc   117000
acaagcattt gcacgcttcc cctcttgact gcattacctt cctcctatag ttgctgtggg   117060
caccagattc tggctagtcc tgtcccttca tgatgcacat tttcctcaag attcgtccca   117120
gttaaatcac tgcagatgaa actgcctttt catcgtcaaa atttaactgt cattttgag    117180 ccgtgatctt gggctacttt cttatgtggg gtaggaatat ttgtgagtta gaaatattac   117240
acttctctat ttccttctag acgtaaatct gttaatcctg tcagcactgt tactcacctg   117300
aaagggtctg tttccctagg agaactgagg gcactcggtc aacactgatt ttccacagtg   117360
ggtattgggg tggtatctgc ttgttttttt tgttgttgtt gtttgttttt ttttgttttt   117420
tttttgagat ggagtctcgc tctgtcaccc aggctggagt gcagggtgc gatctcggct    117480
```

```
cactgccagc tccgcctcag aggttcacgc cattctcctg cctcagcctc ccgagtagct 117540
gggactacag gcacccacca ctacgccagg ctaattttt gtattttag tagagacgag 117600 gtttcactgt gttagccagg atggtctcca tctcctgacc tcgtgatctg cccgcctcgg 117660
cctcccaaag tgctgggatg acaggcgtga gccaccgcgc ccggcctggg gtctgctttt 117720
aatgaaggag gcatcaaggg gtgggctttg cgttggcctg atgctttcat ctttctttca 117780
caaaacctgt ccgaagaaaa tccgtctaaa tgggccattg ctctcctcag gaaatagtca 117840
ttgggaactt cttttccttt cctttgacac taggaggctg actggggaga agccctggtc 117900
tatggctgtg ggcagcaggg gctgagagga gcaggctctc agggggggcac gggtacccca 117960 agggaagcca gagccctgat ttgttccatt ctagtaagaa caaagactgc tctggtttca 118020
tgtttgttct gattgccttt catcaaccgg tcccctttct cccagttctt aagattcagt 118080
acagtgacag ttttatgaac aagaatagaa cactagaaca gacaaaccat tgaactctat 118140
gctgataaag atttattgag ctcctgctgt atgtttgcat tctgcccaga ggctctgaga 118200
aaaccaggcc atatgctcca tgctttatcc atggaagctc cccgtcaggt tgggaaagct 118260
gacagctgca gggaatacag tgtgacacaa aactggctcc catgcagccc ttacgtgtcg 118320
cctctcagat ggttggggga cgaaggtcga ctcctttggg tatcttatta ctaaaccagt 118380
ttcagggaat ctgtgccacc ctatctgcca ttaacgtgaa cagatgagtc cccaaggtgt 118440
aattttgggt attgtctgat gtctcttgga atttattatt tgttttcca atgagatttc 118500 acctcagggt atagtaaagt tgttgagggg attcctggat gtgttctgca attatctagg 118560
ctgatttcag aatagagtta tgcttatagt caaatttatc agctgtcaag aattttattt 118620
aaaatttatg cagataagca ggaggaaaag aagcctggtt tttacatttt aatcctatta 118680
ttgatgtgaa attttatttt ccttcctgta ggtgtttatt ggctttgtat tgaaacagtt 118740
tgaatacatt gaagtgggcc agttcaggta atagcatttt attatttag atttttttct 118800 tcttcttgtg tacttacatg taatttaggt tattaagtga atgtttaaac tactgttagg 118860 cattttgct gttttctta aatggaaatc tgactaacat actgtgcatt tttgcttctc 118920
ttaaaaatta atgtatatct caagacttgt ttggaagtag ttatgtatct gaaaattcca 118980
tatgttgtca gtattcattg cacatttcaa agcatttaat tgtgttgaca gatggtggaa 119040
tgaaatcttg tggtggagca ctagttttta aatcttctta gagaaagcag ttttatataa 119100
tgttgtcttt agtaattatt atgcatttgt attctctgca gcttttctt gctagatgtt 119160 gaggtttaa tacttcttgc tagtccatta caggtttata attattaaaa gttaaaattc 119220
ttttagtacc taaatgctt aataaacatt gtaattagga aatttagtg cagaaggaaa 119280 gtgttcccag attccctggg gtctggaaac atagtgttta ttctaattac atgacacctc 119340
cactgtgttt tggggcaagt tactgttct cttttgagtt tcaatttctt caagagcaaa 119400
gaggcagagg agagctagga agatcgtagc tgctgtgccc ctgtgccgtc gggtgccttc 119460
tacctgctgc ctccgaacct ttacacatgt ccctgctctg cgcgagggca cagatgggat 119520
gcactgtggc agggtgggg ttagagtaga tcacggacac ctgttagctt gatgtgtgct 119580
tgctgtcaag gttgaatcat gaattatttt atgttgctta tattgatatg tatcttaatt 119640
ttaaaagaaa ggtctaaatg gatgttttg tttttaggga atcagaggca atcattccaa 119700
acatcttttt cttcttggta ttactatctt atgaacgcta tcattcaaaa cagatcattg 119760
gaattcctaa aatcattcag ctctgtgatg gcatcatggc cagtggaagg aaggctgtga 119820
```

-continued

```
cacatggtaa cgggacacac ctttcactgt cgtcttcggt gtcgtgatgt gcttggcagt   119880
gttcgttttc atatacccac tttgaacgtt gtcagtggca gccatgtgct tctcaggctc   119940
tgcatgtgtg tctgtgtatg tgaaggtact ggttagagac gtttcaaaag agaagagagc   120000
atattcttta ctctcagcaa tttgtaatct tctcagggaa aaaaattcaa gaaacagtaa   120060
gataacctaa ggtacagata gattctgaat ataaagttcc tgttcattca catgaaacgc   120120
taaaagttct tcacttgatc ttagccaaaa ggccaagaag cgatgcaaca ctaaaaattc   120180
ttaaatcgaa cttgccgtga attaaatttt gatctctcat ccagtggtat tggagatata   120240
gtttgacttg ggttcagggc tttctgtttt gcctgatgat tttgctggag cttaaataag   120300
gaacccagga gatggccagc tgtgcaagcc cccagcctgt ggaaggagct agtgtggttt   120360
tatgaatgag ttgcaaatct ttctttgagc tttttgaact gatcttccag cattgcccta   120420
ttgacccctc cctgactcct ttgctggaat ctgtaggctt ttgaactttg acagggacac   120480
atcctaagac ccttgcaaac tcccagatgt gagaatggca ctactactta gagtcttttc   120540
gactcagcgt gtgtgcagaa gagcatcaac cgggctgtgt tgcgaggcag ggccttggct   120600
gacctctcag tgtttacata gctaagccag ttagtgtttg ccacggcctc acaagggctt   120660
cagattcaca cagccaaagt atagattatt aaaggcatag gtgtttggtt tcctggactt   120720
ggagggtctt tggacagaaa atcagtaggc aaccacaccc agtactttgt gctgggaagc   120780
ttggtcatct gtgagagggt cagagagtat acccatgcgt gcatgccacc gaagggtcag   120840
tgagtattcc tgtgtgtgca tgtctcaggg ccggagagag tatgtgtcac tgagaggtca   120900
gagtgtttgt gtgtgtgtca aagagggttg cattgtgccc ttcactgagg ggtcagaggg   120960
tgcctcgcgt gtgtgtgtgt gtacgtgtgt gtgtgtcact gagggggtcag agtgtgcctg   121020
tgtgtgtgct tgtgtgtgcg tacatgtcac tgaggggtca gagtgtgcct ctgtgtgtgt   121080
gctcatgtgt gtgcatacgt gtcactgagg ggtcagagtg tgcctctgtg tgtgctcatt   121140
tgtgagcgta tgtgtcactg aggggtcag agtgtgcctc tgtgtgtgtg ctcatgtgtg   121200
agcgtatgtg tcactgaggg ggtcagagtg tgcctctgtg tgtgctca tgtgtgagcg   121260
tatgtgtcac tgaggggtca gtgttcctat gtgctcatga cattgagggt cagagtgtgc   121320
ctgtgtgcca atgaaaggca tttcttatat tttttatat gtggtcatag tagaccagtt   121380
aatttatttt gactcctgtg ttagaccaaa ataagacttg ggggaaagtc ccttatctat   121440
ctaatgacag agtgagttta cttaaaaaag cataataatc cagtggcttt gactaaatgt   121500
attatgtgga agtctttatt gtcttttcag atgaatcaag tagattattc ttgagaccag   121560
gaatgttgct gttttggtta tttggaaagt tttatcattt tcaaattgac ttttgaattt   121620
gagtcacctt ttttcagaag tggtgttaaa ttataggagc cctaggtttt ttttcttttt   121680
ttagaagtca tcacaaaatg atcagtgttc agaggaagag ctttgacctt ccacatggta   121740
taatgattga taaccttaat tcatctctta ccataaacca agtatgtgta agggttttct   121800
ttatttcttg aaagcatttt gtagatgttg agagcagttt tccaaatgta atttccatga   121860
aatgcctgat aagggtaccc ttttgtcccc acagccatac cggctctgca gcccatagtc   121920
cacgacctct ttgtattaag aggaacaaat aaagctgatg caggaaaaga gcttgaaacc   121980
caaaagagg tggtggtgtc aatgttactg agactcatcc agtaccatca ggtaagagga   122040
atgtatgttg gaactgtcgt ggatacttta ttgacccgtg cagatggaag gaagtgccat   122100
gtggtaacgc tcactgttaa ctgtgttact ttgaaccagg tttgggcttt ctggggcctg   122160
ggtagatgcc ggtgcagggg gatggggagg gaggcggggg gtgggggggt gtggtggagt   122220
```

```
tggggaggtg cagtggcagg aggtgttgtt ggtgtgtatc cttttttttt ttttgagatg    122280
gagtctctct ccgtcgccca ggctggagtg tggtggcacg atcttggctc attgcaagct    122340
ccacctcccg ggtttaagca attctcctgc ctccacctcc cgagtagctg ggattacagg    122400
catgcaccac catgcccagc aaatttttt tttgtatt ttagtagaga tggggtttca       122460
ccatgatggc caagctgttt cgaactcctg acctcaagtg atcctcctgc cttggcctcc    122520
caaagtgcta ggattacagg cgtgagccac catgcccagc ctggtgttta tctttaaagt    122580
gggcacagcc acaggagttc acctgactcc tggtctgaga gtcacgagat cgttcaagat    122640
agtgaggccc tcttttccaa aacgaggacc aaaaatcaat tgacagtgtt ggtcaagatg    122700
gtagaaacct taaaatgata gaaatctcaa ctctgaaata aaactttat ttgtatattt     122760 atttaccact attttgacat agggctaagg tcttttcctt tgagctgatt tctggttttg    122820
ttttcttaaa gtggcataag aattcaaaga cattttgagg aaggctgagt gcagaaatct    122880 ctcttttaa atgacttctc ctttctttta acttgcactg ttgtctagcc ctcacttatt     122940
ttgtcaattc tttttagctg tttgtctttg aatcttcata aagccatagc ttttctcata    123000
agaagcagca ctttctttgt tcattcatat tttaatgaac ccctgtagta tttaattaaa    123060
tacttaatgc ctaattaaat cacataattg caatgcaaaa gtacatgtat cataaagagg    123120
tctgaaaatg agcaactggc aagcaggtgg tggcaggcag agctgcttgg gtgggtgggt    123180
gtcatggaga ggagttcatc agccacatgt tcagtgagct ctggatatgt ctgtttagaa    123240
atgatcacta ataaacttgt gctcaaccat gtatacctct gggaagcagg tgctcttcag    123300
tagattgcct ctgcagagaa cacagaattg aagtgaatgt ccacaaaggc aatgagccac    123360
ctgcagaata gtttagtcaa ggctgtgttt gaagtttgcc aaagattaat atacatttga    123420
ttttcatgtt gtgccttttc tctgattgtg aaatattaca aattctatac aaataacaat    123480
gatggcaaat cctcctgagc aaagtgtgca ccttgtatgt gccctagagg aacttgtgtt    123540
tcgttctgat tcccctacat ttctcatgtc atagagtggg ggttgcatta gtgtcccct    123600 gtcctcgctg ggatcacatc tgtttggatc ctagagtctt ccagctgaac tgggacaagt    123660
ataacagacg gacacgtagg ggtggaaagg cgtctcttgg cagcagactt tctaattgtg    123720
cacgctctta taggtgttgg agatgttcat tcttgtcctg cagcagtgcc acaaggagaa    123780
tgaagacaag tggaagcgac tgtctcgaca gatagctgac atcatcctcc caatgttagc    123840
caaacagcag gtttgtcccc gcagccttgg cttgttgttg catagtgatg gtagcttaag    123900
gtccttgtga aaggtgggtg gctggaatca gctcttcctt cagtcctaat ctgtgccttg    123960
atagcagttc tccgtgctag tcatgggaca gctgacttca tttcttctca caatgccatc    124020
tcaggttggt attgcccacc tactttacag ggggatccc acagctccga gaggttatgg     124080
aggtgatcag gcagcacaca gctttagagt gctggggtga gggcgggcca aggctaactc    124140
taaagcccga acccttacct cctacactgc ctcctgcatt ctggtcaacc cagtgtttta    124200
tttggtggtt agattttgt ttttgttacc ttactgcttg taatttagca gttttcctt     124260 cctttccctt cctttccttt ccgacagggt ctcactctgt cacccaggct agagtgcagt    124320
cgtgtaatct cactgcaaca acctctgcct cccaggttca accaattctc ccacctcagc    124380
ctcctgagta gcaaggacca caggtgtgca ccactacgcc tggctagttt tttgtatttt    124440
tagtagagat gaggtctcgc tgtgttgccc aggctggttt taaactcctg ggcgcaagtg    124500
atccaccaac cttggcctgc caaagtgctg gcattacagg tgtgagccac ctcgcctggc    124560
```

```
ctattcatca ctaatcagaa tttctatgat caaatgacat gaatcattgt ttccacaact   124620
gcagtggaag gaaatggcct ggcagtgcca gtttcagaag cagcctgccc ccagtcaggc   124680
acaggccact gtgccccag tgtagcagca cctctgtagc tcacagagaa gggtggtggg    124740
gacctccttg aggcagctct gccagaaaat ctcatgagct gcctggcaca gcttgaggtt   124800 gcctttaag tggactcagc aaatacatgt ttgttcatct tgattataca caataaacaa    124860
ctactctgta tagtacgagt agtccgtggt ttttggcatt tgatttaaac ttagaggcat   124920
gtgatattga tgttactgcc ttcatgactg caccccatt ctgatttcat aatggaatgt     124980
tatcttgaga ccagttagac aacaggacag ggatcttggc ttctggtgag attgacagca   125040
gttttagtgt ggtcagggtc tccctgccta cagatggttt tagaatggtg ccctggaagc   125100
tttatcccat tcttttctgt gcgtaatctg agtagagtgg agatcgaagg cctgaataca   125160
tagtaaatac ctgacttaat atctgccgca atggaaattg tgtgatacaa catttatgaa   125220
acgcttagtg cagcacctgc caggtagctc accacaggtg catgttgcat tcagaagtag   125280
tgctagatac tatcctgtta ctggcagtgc atacatcagt gatcaaagca gattaaagaa   125340 agacccctg ccttcttgga gtgaagattt tgttgggatg cgggtaaggg gacagacaat    125400
agaaaagcaa gtgagtgaag tctataccat ggcggctgat caggaacacc gtacagaaga   125460
atccaggagg gaagagagtt aggtggtgtc tgcggtggga gtggcattgt tcagctggtg   125520
atgagaagaa gctttggtga tctggtgaca tttgagtgaa tttgcagaaa ggaaagatac   125580
aagcctagga gatacctggg gaaggaacat tccaggcaga gcaaatagca gtgcaaaggc   125640
cctggcgggg ggcggacatg ctgttagggt acaagcaatg agggtggagg agtggggcag   125700
ccatggggag ggaagggagt gaggcctggt ggggtgaggc cagtgtggag gagccttgag   125760
agggtttgcg ctgatgtggt gtaggtttta gcaggatcat tcttattcct gagttgaaa    125820 tagccttgag ggggaggtga gggcagagca gggccaccca tgtgagaccc ggcactggag   125880
tggaatggcc caagtcagca tcccttggca gcatgaaagc aaaaccagca aggtttgctg   125940
gtggcttaga tgtggcatgt gagagagagc agggctttgg gggtgatttc agggtgagga   126000
cagggtggct gtggacaagg tagggcagac attgggggca gcaggaggtc agagcctgtc   126060
tggatgtagc agttgagacc ccataggtgc ctaatgaggt gaggccagca tcaggtgtat   126120
gagcctggag ttgtcgagag actgtggggc aggggtcag catctgagat gtccactcac    126180
agtggaccca gactggctgg agaggaggag gagcttgaat accgagcctg ctgagtccca   126240
gctccaaggt caggtaggtg aggggagcca gtgctgggc aggggagta ggcaggtgtg      126300 gggttcctaa agccaagatt ttttttaagg cattttgtgc aggagggcga catctgctgt   126360
cagcaccttg gaacttggc ccaggttgg cagcaccgag ggcactgatg agtgcttttg      126420
gaggagcaaa gggagccaaa ccctaatggg aatgtgttcc tgaaaggaca ggagagagac   126480
ttgggaaaag gttttacttg aagagggaac ggagaaatag gcagtagcc agaggaggag     126540 aggagtcggc aatgggttaa gttggcagaa atgaaggcct gtttacgcac tgagggcaga   126600
agcaacaggg aggatcagtt catgacacag gagacacaaa tcgccgttgt ggtgttcaca   126660
gacatgggtt aggattggct gcatggatga cagagcactg tgggttctcc cagagttgct   126720
ggggaggagg cagagttggt gagcacaggc gagggtccag gatgcaggaa tcctggagct   126780
caagtcagtt gttcccttgt tgtaagatgt ggccagtgtt gtgagcttca catctgtgcc   126840
ttgaaaaaca ccacatctgt ttgcagagtt gtttactatg tatacacact cagtagaaac   126900
aaaaattgga aacagtcagt gcccaccatc aataagtaat ggttgaacac actgtggtat   126960
```

```
aagcttagac tatttagct tgggctattt tgcatgatta aaaatgttct ggccaggtgt   127020
ggtggctcat gcctgtaatc ccagcacttt gggaggccaa ggcaggcaga ttgcttgagc   127080
tcaggagttt gagaccagcc tgggcaacat ggtgaaaccc tgtctctact agaaatacaa   127140
aaagtagctg ggtgtggtgg tgtgcgcctg tagtcctggc taactcagga ggctgaggtg   127200
ggaggatcac ttgagcccat tcgtgcgcca ctgcactcct ggggcacaga gtgagactct   127260
gttagaaaga gagagagaga aagaagagag agggagggag gaaggaagga aggaaataaa   127320
tggaagaaat ggaagggagg aaggggaggg aggaaggaag aaaggaagtt cagccagttg   127380
ccttgggagt tctccattgc actgggttaa gtgagaagag cagagacgtt tatgattttt   127440
caaaacaact aaaacaaaac ctctgtgggt gagggggcaa ggatatggct ataggaacat   127500
ggggcagatt aagaaaggga tatacacaca ccacttagca tttgttacaa ctgttgtggg   127560
agggatggag tgcagaaaaa gaaaaaaaaa agtgcacacc atcccatgta tgtgtataca   127620
aagggacgct tggaagactg gtccccaaaa tgttggtaat gattgtgtca gggtgctgca   127680
gtgctagttg atttttttc acactttgt atatttgagt cttttacaga aagcatttat    127740
tatttatgta ataaaaatct aaatgacaag atttctgtta tgggaaaaat gtagctatac   127800
agtgttgttg taaaaatgtt tgcttggttc accactgaac ttaaaatgct tttaaatgag   127860
ggaaggtgac gatgagatga ttatgatgat ttgcccttga gttacatagc tggtgtacag   127920
gaagctgtcg tttcttttgg cttacgtaga aatgtttgtg gtgtctaatt ccacagatgc   127980
acattgactc tcatgaagcc cttggagtgt taaatacatt atttgagatt ttggccccctt  128040 cctccctccg tccggtagac atgcttttac ggagtatgtt cgtcactcca aacacaatgg   128100
tgagtctctc gcctggctca gcagatgaat ctggacggct tgttcaggct ctgattactg   128160
ggaccacccc cagaatgtct gagtcagtca gtttgggtag ggcttcttga gagtttgctt   128220 tttttttt tttttttttt ggtgtggggg tggtgcggaa cagagtctca ctctgtcgcc     128280
caggctggag tacagtgtca tgatctcggc tcactgcaag ctctgccttc cagcttcaca   128340
ccattctcct gcctcagcct cccgagttgc tgggactaca gcgcccacc accacgcccg    128400 gctaattttt ttgtattttt agtagagatg gggtttcacc gtgttagcca ggatggtctt   128460
gatctcctga cctcgtgacc cgcccatctc agcctcccaa agtgctggga ttacaggcgt   128520
gagccaccgc acccggcctt tttatttttt ttggagatgg agccttgctc tgtcacccag   128580
gctggagtac agtggcgcta cctcgactca ctgcaacctc cgcctccggg ttcaagcaa    128640 ttttcctgcc tcagcctccc gagtagctgg gactacaggt gcgtgccact gtgcccggct   128700 aatttttgt attttagta gagacggggt ttcactgtgt tagccaggat ggtcgcgatc     128760
tcctgacctt gtgatccgcc cgcctcggcc tccaaagtg ttgggattac aggtggctct    128820
cgcaccaagc caagagtttg cattttagc aaattcccag gtgaaactaa tgcctgcttt    128880
tctgggagca cactttggga ctcagtgata gagaggttta ttggtaggat agtaaaatag   128940 gagttattt ctttcacaaa attggcaatt gggggaaatt taatcttcct ttttcttca    129000 gctgtgactt atgtattatg tttattttag gcgtccgtga gcactgttca actgtggata   129060
tcgggaattc tggccatttt gagggttctg atttcccagt caactgaaga tattgttctt   129120
tctcgtattc aggagctctc cttctctccg tatttaatct cctgtacagt aattaatagg   129180
ttaagagatg gggacagtac ttcaacgcta gaagaacaca gtgaagggaa acaaataaag   129240
aatttgccag aagaaacatt ttcaaggtat gctttctatc tgagcctata actaacccat   129300
```

-continued

```
gcctttggg aagtcacgtg atgtttcaca gtcagtaagt ctggaataat acctggtctt    129360
gcttcacttc tgagttgggt aaagaagtct gtatcagtgt aattttctaa tccgtcctgc    129420
attatctatg gctcttggtt catacctgtc ttgaagttct gtcatgttct gtctcttgtc    129480
ctcagtagag atgctacagc agtggctcgc ctcaggcagg gcagggcagt ggggtggctg    129540
tcctgggggc aggcagtagg ggcacgctga cgtcagggaa gttgaaaccc aagagaagcc    129600
agtaaaagtg agtctcagat tgtcaccatg tgctggcagt tttacacgct gtcagtaata    129660
aaagtcttct ccctgcaggg cagcctgcct ccaataaata cgtgtagtat caaatcctgt    129720
cttccctcat aaattgtttg gaagctcccc aaggacagtg atgaggcact cgtaagtgct    129780
tgctgcctag atgggtccct ctccacctt gctagattct gagcattcac tgagttagag    129840
ctgcttctgc aaatgtgctg cttctgctaa gtggctgtga cttcatgcag ccttcacttg    129900
gtttgtcatc agtggagatg ccctgtgttg tcgaaggaga taagcccagt aagcctgctg    129960
ggcacctttt ggtttgcagg ttcagcaggc agcccatggc tttccctgtg tcgcattgaa    130020
gcagctggct aaaattgatg atacattaaa ttcctgtgac agatgatcag cttgtatttg    130080
tgtaatggtg tacagttcac aaagcttaaa aaaatgctac ctgccatttc atcctcagtg    130140
aggaaggtga tacacagaga gaccaagtga ctgtgtccac ggcgacggcg ctctgcattt    130200
cactttagcg gttaatgtac tctacctata tttttacttt atatttacca tatatctttt    130260
catgtatact tggcgtaagt gctttatagt agtcacctaa ttcactgtca tcttttttgt    130320
ttcttggaag gtttctatta caactggttg gtattctttt agaagacatt gttacaaaac    130380
agctgaaggt ggaaatgagt gagcagcaac atactttcta ttgccaggaa ctaggcacac    130440
tgctaatgtg tctgatccac atcttcaagt ctggtaggtg aatcacatta gtcttcctgg    130500
agtgtctcgt tccccattct gcactataca ctctcagagt gtaggagctg tgctgcccgt    130560
tagaaactct gccttgccca gtgtgccagt tgaaaatatt tgttgctgta agagtacacc    130620
tgataccatg tgacccagca gttccactct tgggtatata cccaaaagaa tggaaagcag    130680
ggtggtgaaa agatatttgc atgccagcat tcatagcagc attattcacg atagctaaaa    130740
tgtggaacca actgaagtgt ccctcgatgg atgaatggat aagcaaaatc tggtgtatat    130800
ttacagtgga atattattca gccttaaaaa aaggacattc tgacacatgc tacaacatgg    130860
gtgacccta aggacattat gctaaatgaa ataagccagt cacaaaagga caaatactat    130920
gtgattccac ttcatgagg gacctggagt agttaattca tagatataga aagtagaatg    130980
gtggttgcca ggggctgcag gggagggag ttattttac aagatgaaga gagttattct    131040
agaaatgaat ggtggtgatg gttgtataac attatgaatg tacttaatgc tactgaactg    131100
tacagttaaa aatagttaag aggaccaggt gtcatggctc atgcctgaaa tccaagcact    131160
ttgagaggcc aaggcaggag gattgcttga gccaaggagt ttgagaccag cctcagcaac    131220
atggtaggac cccatctgta caaacaaact agccggggat agtggtgtgc atgtggtccc    131280
agctactcag gagactgagg ctggaggatc gcttgagccc aggaggttaa gtctctagtg    131340
agatgtgttc atgccactgc actccagcct cggctataga gtaagaccct gcctcaaaaa    131400
aacaaaacaa aacaagacaa gagccaaaaa tggttaagat gggccaatca cagtggctta    131460
tgcctgtaat cccaacactt gggaggtca aggtaaaagg atcacttgaa gccaggagct    131520
tgggaccagc ctgagcaaca tatcgagacc cctatctcta caagaaaat caaaaactag    131580
ctagatatgg tgggcacatg cctgtagtcc cagctacttg ggaggctgag gtgggaggat    131640
ctcttgagct caggagttcg aggctgcagg gagctattat tgcactccag cctgggctac    131700
```

```
agaatgatac cctgcctctt attaaaaaaa aatccaaaaa aaaaaaaaag taaacctgag   131760
agcttcctcc tcctgtgtta aatttggagg ccaagatgtt tttgttactt ttacaaatga   131820
tcaaggacgg tgaaggttgg gcatggtagc tcacacctga aatcccagca ctttgggagg   131880
ctgaggcggg gtgatcgctt gagcttgaga ccagcctgga caacatagca agagacccca   131940
tctccacaaa aataaaaaaa taaaaaaaaa tagccaggag tagtggcatg agcctgagcc   132000
caggaggtca agctgtagtg agccatgatc atgccactgc actccagcct gggcgagatc   132060
gagaccatgt ctctagagaa agaaaatgac aaggacagtg aacccaagaa agtcataaga   132120
tgccagctgt gcagcaagca tggaaagcag ccagtccaaa ttaggacagt gtgttttcca   132180
agaagaacga tcgtttgtaa tgagaatgct ttgcttttaaa taaatgacta aatagctaga   132240
agcctagttc taggggatag gcacgtcttt cttctctcaa gaaaatagaa aggcaattct   132300
aatttctagt aacagcaaac agcattaagt catggtccaa atatgaggca aaccaaaatg   132360
tggcttgatt gttcagcagt tgatctgttg gaagcccttg atattaaaaa ggttctcctt   132420
taagcggctt aggagtcacg atcaaagacc tatagaaaga gatgccatcc ttctaggatc   132480
cttggctctc ttgggaacta gattcagata gtcataatgt aaatactgct tgagcttcct   132540
ttctttcttt cttctttct tttttttttt gagacagagt ttcactcttg ttgcccatcc   132600
tggagtgcaa tggtgccatc tcggctcacc gcaacctctg cctcccaggt tcaagcaatt   132660
ctcctgcctc agcctcccga gtagctggga ttacgggcat gcaccaccac gcctggctaa   132720 tttttttgtat ttttagtaga gacagggttt ctccatgttg aggctggtct cgaactcctg   132780
acctcaggtg atccacccgc ctcggcctcc caaagtgctg ggattacagg tgtgagccac   132840
cgcacccggc ccgagctttc attttttgaaa tcaatgtatg actgaaacac tgaagactta   132900
ctgacttaat tatggtttca gaacagaatg aaaatgtctt cggttctgat gaatataaaa   132960
ggaaaactaa ccaagttaat ttggcaagta gatggtagag atagaggtgg ggagtggaag   133020
gggaactaaa atcttcacct agcattgttg ggattatatg gttacatcat ctgaagttga   133080
cagaccaaaa tatagaggct tcagaggtct ccaaatagaa ctaaacatgt aattcagatt   133140
gttaggaggt agtataaatg agctaaatct catctttatt acggtagagt taatgggtga   133200
tgtctaaagt tgtctgaagt ctataaatca tgacaaatta tgatgtggtg attgtattca   133260
acagtctttc agttgcaggg ataaaacccc agtttaaact agagtaagag aaagaatgtg   133320
ttggtttaag ctcctggaaa gtgcaggcaa gggtagttgg taggactgca tctagtgttg   133380
taattctgtg gtctgcattg tatatttatg catctcagct ctgctttctt cttttcattt   133440
atataatttt taaattttat tttaaagata gggtctcact ttgtcgccta ggctgaagtg   133500
cagtggcatg aagtgcagtg cgaggctcac tctagcctcg aactcctggg ctctagagtt   133560
cttcctgcct cagccttcta agtagctgag acaataggca tgtaccaaca tgcctggata   133620
ggttttaaaa ttttttgta gaaatggaag tcttgctgtg ttgcccaggc gggtctttaa   133680
ctcttagctt caggcgatcc tcctgcctct gcctcccaaa atgctgaggt tataggtgtc   133740
acccaccacg cccagtctca tctctgcttc ctgtgttagt tttgttctct ggtgggctgt   133800
tttcacatga ccgaagatga cctctagcag gctgtgttct cagcccctca agtaggccta   133860
tgtgattggc cttgcatgag taatatgggt gaccataaac ccctgaatgc tctggtccac   133920
atgggccaaa tgggagactg gacagcattc cattgatgag gaggtggggc tggtctccgg   133980
gagtaaggga gaggagcaca tgcagtaact gatggtctgc tgcaagggat agcagcacag   134040
```

-continued

| | | | | |
|---|---|---|---|---|
|cagttagaat|tttggaggta|actaccagaa|ctgaaaacag|aaatgataac aagtagttgc 134100|
|cttaaaaagg|gatgggagca|gggtgctttt|gtgatcaaag|ctccttttctc ttactggatt 134160|
|tttgtacaca|ttttgcatac|atatcttaga|gtaaaagata|gcattttcag ccttggtcca 134220|
|tttgaggata|ctcttggcgt|ggcccgcctc|catgctagca|ggctctggtt gtgccaagtt 134280|
|cagttgagca|tcctggctct|tgcctgcacg|gaacttccag|tcagtgcgtc agtatcacaa 134340|
|gtcttgatat|ttcctatgaa|gaagaacagt|agtgcagtga|cagacgaaat gggtgggcag 134400|
|gcagaggcag|gatttctgag|ggagagaagt|agctagcttt|ttgcagagaa gagttccggc 134460|
|acccaagaga|gcagctgaga|gtacaggcag|gcaggcagga|tgccggtagg gcccggccgc 134520|
|acggcgccac|agaatcctgg|agaaaggggc|ctcttcatgg|cctctgcatt cagctgctgt 134580|
|caccctccgc|acaggccatg|gccaaaattt|aattttcata|gtggactcta gttttttgagc 134640|
|cttacttgct|attattgaaa|taattttctt|gtttctttt|aaagatcttc ggattatgct 134700|
|tcactgacca|ctgtaataag|tttaaagttg|agaaaatatg|gcttgttaat gaatgatagg 134760|
|tcaatttag|tatgttggtc|attttaatat|tttgccacca|gttggtttgg atttgatgcc 134820|
|aggaggagac|agcctcattt|ctaaggacta|gtcttgcctt|tgtgggataa gggtggtgtg 134880|
|ttctgtgtcc|ttctacatgt|ccgagcgatc|tctgtgcagc|tcaaatgtgg tcactgtctt 134940|
|attgcgctga|tttcctctcc|ttccatctca|caattgaggc|aaaatattgt tactgttgaa 135000|
|gtgttgtcca|ataggacttc|cagcagagac|aggatgtctg|cactgtctaa tttagttgcc 135060|
|tttagccaca|tgtggtgttc|tgtacctgaa|atgtggctgg|tctgattgga tagcttaatt 135120|
|tataatttta|tttaatttta|attaacttaa|atttaaacag|ctctgtgtgg atagtggctc 135180|
|ctgtatgaga|cagtgcaggt|ctgttgagaa|gcagctttac|tggtgggagt ggagggcttg 135240|
|gagagggcac|gtgggtttcc|tgctggtatc|ttttgacctt|attaatctg cccaacattt 135300|
|gcaagtaagt|tgtgtgtgtg|tgtatatata|aatgtgtgtt|tctgtcttct tgtttccttt 135360|
|gactgcattt|atttgaaaga|cactaggtgg|cagaattact|gtatttgatt ggtttcaaga 135420|
|taagagttga|ataattcat|ctcgtgtttt|tatataagta|aggtgtgttt agcatgtaaa 135480|
|attggtaata|tgtattcacg|tactgcttaa|acaaaggcta|tgaattccac ccataaaccg 135540|
|aaaatgaaga|cctttaaatt|tgtccatttc|aggcgtgggt|acttcttaaa taatacctgg 135600|
|ttcaggaact|agtcagaatg|gcacccttga|ctttttgttt|cctgcttttc ctcttgttgg 135660|
|gagaggaggg|tattcatccc|aaagtggttt|gcctatttca|cattccatct aggataagca 135720|
|gaatagccaa|gaaagatagc|tgtcctcctg|tttacaacat|tgggggtaac cagcatccct 135780|
|ctcttttggt|ccaagataga|ctggtttaga|aacagatgat|ggcaccagag gcccaggagg 135840|
|tggaaacatc|agctttgttt|gttgtccatg|tggctgaatt|agagctgtct ggccttgtag 135900|
|cctcaacacg|gccttccagc|tttgctcacc|gtgattttca|aggacacatc ttgtgctctt 135960|
|ccctgcctgc|catccagact|atacccagtc|agggtggcag|gagctgctgc cccttcctcc 136020|
|ctgagtcctg|gtcgtgggtg|gtggagatgt|gccatgacgc|tcacggaggc atgctcaccc 136080|
|cttcctctgt|ggcagagggg|atggctgcac|gacagctctt|ccctgtcctt tccaaagcgt 136140|
|ctgtggttcc|acttttggg|gcaaagcagg|aatactggaa|gagagagaaa gtggtccttt 136200|
|ctatagtaat|aaagttgaca|ttgattcaag|ttcatgcttg|gggaaaggac agggctacta 136260|
|acaattataa|tgctgggagc|aatggaattt|tctcatgggt|atgtggtagg tttaattta 136320|
|attatcccag|ttaattctta|gaactgctct|gtgaagtatt tccgcctttg tgcttaagtt 136380|
|ctaaaagatc|ctgtgccaaa|accaagaatg|aaaacccaag|cattctttct tgcccatcga 136440|

```
tctttctctc atcaggccac ttcttgggtt gatagtggtg agtgtagccg ctgccacttt   136500
cagaataccc accatgggcc ccagtcactg tgtggcgtgg agaagagatg gttctctctg   136560
tgtcatagct gaacaagccc agcccagaga ggtttctgcc ctaggagctc tcgatggtgg   136620
aattgggatg cgatcccaca tcctgcctgt tttgaaaaca gcattcttta tttccaattc   136680
ctgcttccat tgttcctttt aatatttctt tgtttagctc acaaaaacac ggcttgcgga   136740
gctgctgcgt gcagctgtag ctgtttctct gggtgcagcc tgcatccgcc ttcctgcccg   136800 cctccttttcc tgcactgcca tcgtggtctc cgggcacttg gtccctttct cttcccctga   136860 gtcccttttgg ctcccctgtg ccacccttgt gatccacagg ctctgccttc tttctgtctc   136920
agactgctgc tcatcactac tcgggaccct aggaagggag gttccaccga gaagcatctt   136980
ctcatctcag ccacgttctc agtgccactg ttgtctttgt taggtaatgg tagctactgt   137040
aacaaataaa ccaacatttc catggcttca caccagagaa ggttgtttct tggttttatg   137100
acaatgtatt gagggtgttc ttggttcacg gatggttttc ctccatgtgg gaattcgggg   137160
acccaggctc ctttccttct tttggttctg ttctccaggc cttcacatcc tctgtgtctg   137220
gttggggaca aggagaggga aggtaaagaa ggctttgtgg ccttggataa gtgacaggca   137280
tgcctttgct ggtgttctct cgtggtgaca ggtcacagcc ccaccctgta aaggggact    137340 gagagacgtc gtcctgctgc ttcccagcag cagcactgtg gtctctgatg tgttttctgt   137400
gaggataaaa acaggtgatt ccaggatgag gaaagtcagg gaaacccttg gaaggagggg   137460
accaggcggg tgtcaccatg ggattagtgg tggcttcaga atgagctgca gcgagtgcca   137520
tgccttctaa agcttttgct attctgatat gcccacacca tgcccagcag gtgtctgcct   137580
tgctctccgc agagagagtg atgaatcctt ctcatgagcc tctgtccagt tgttcctccc   137640
tccacctgga agggaccctg ggttcctcat aacatcccag cggaacaggg gaccttctat   137700
cctgtcccca agttcatcct catcctcctg ccggcttcct ggcccctctt atgtctgctt   137760
cctgacgcca catccttctg gattctctgg aattgaattt tgcctttgat gcttatttaa   137820
aaatatccat tgcaggccag gtgtggtggc tcacacctgt aatcctgtgc actttgggaa   137880
gccaaggtgg gcagattgct tgagcccagg agtttgagat tagcctgagc aacatgttga   137940
aatcctgttt ctatagaaaa tacaaaaatt agctgggcat ggtggcgcac acctatactc   138000
ccagctactc aggaacctga gacaggagga tcaattgagc cccggaggcc aaagctacag   138060
tgggctgtga tcgtgccact gtactccagt ctggtcaaac agagtgagac cctgtctgaa   138120
aaaaaaaaaa aaatccattg catacttcac cgtagcgaaa catgtatgtc ttacctttcc   138180
tttcctgcct gtagctgctc ttttacactt aacagccaca ctaagccagc cttaaatgaa   138240
aaacaaacca gcacttcctg tgccctcctg cttccttcat gaggggtccc tccctctgtg   138300
tacactccat tctcattgcc catggtggtt tgtttccctc ttgtttctca agccatggca   138360
gcctgcctct tgccctcttt actaaaaagg cctttgcaga ggctgcctgt gttctttctt   138420
tctaggtctc tctcatccta ggccctccag cttgattctg tggagctgcc ctcttgtcac   138480
tcagtagctt gtggggtctt ctctgtctag ccacttaatt gattgtgttc ctcgagttgc   138540
tgtccatggt ctctcgttac tgttttctct gtgtttctgc ctctctcctt ggccttggta   138600
ggtccatccc ctttgtgacc ttggctgttg ctctcatgga caactttctc ttgctggtcc   138660
ttgtagtcct ggcatccagc ttctcgacac gggacttgtc ctgccagtac ctcagacttg   138720
cacttaaaat tgaactagca ccactgtcac tctccagggc ctcttcttgt taattagatc   138780
```

```
attagggatg ttcagaatcc cagcatcata gtatgttcct cctcccgcta ccccaggaac   138840
cctaacctta cctcctcctc tctatctact aggaggtggc cctcagagtc cgtctcatct   138900
tccacctgaa cttccctaat aggctccagc agctgccacc ccggggctg agtacttcct    138960
ccatgccttg tgcagtgctg agcccttta c ctgggttctc ctgtttgctc cttattacag  139020
ccctgcgaac agatactgct cttaattcca tcttacacct aaggaagctg aggccccagg   139080
taaggtgcat ccaaggtcac ccaggtagta gacagtagag ccacgatctg aaccaggcag   139140
tctgattcag agcctgtgtt gacactcagc cacctagaac acagcttgga ttgtgggttt   139200
ctattacctg ttcaaaaccc ctacatcccg ggtctgtccc tgcacgtgct ctgtggcctg   139260
gctgcatctt ccttgaaggc agtgcatgcc tcttcactca gggggcccat gcaggaacag   139320
agggccccac agaaggatga ggccagtgca gaatgggctg gaggggacaa tgctgaccag   139380
gaagcaagtg tagagaaatc ccaggaaacc tggaggagcc agagacaagg cattagaact   139440
cctcgtcgtg acctggtctg cattctctga gtgtgctgct tctgttagct cgcttccttg   139500
gtctcaggtt atagtttaag gcattgtgga gccctaaaaa gcctgtactc tgttttacc    139560
tgttttagga ccctttcact ttggggatgt gttgattttt ttttttttt tttttttttt    139620
tttgagatag agtctcgctc cattgcccag gctagagtgc agtggcacga tcttggccac   139680
tgctgcccct gcctcctggg ttcaagcaat tcttgtgctc ccgcctccca aatacctggg   139740
attacaggca cccgccacca cactcggcca attttttgtat ttttagtgga cagggttt    139800
taccatgttg gtcaggctgg tctcgaactc ctgacctcaa gtgatctgcc caccttggcc   139860
tcccaaagtg ctgtgattat aggcgtgagc caccacaccc ggcctgaaat ttaaatcaga   139920
aataaaattt tgatcccaac agtgatgcca ggcagcccag atctggggga gagggtggcc   139980
ttggccagct gggcctttct ctgtttccca agtcttgctg cctctccctg ctgggctttg   140040
cagcctgtgc atgtctctgt gcctttgacc ttgtttatcc aaaggagagg atagaatgaa   140100
gtcatgattc ctggagccct gagaaggatg ctgtggagaa atttgccggt agaatctagc   140160
tgagtgtgtt gctgaggtgc cagcattgtg tgtggggagg ctgaccgctt ggcctgccta   140220
ggcccaggat gctccatggc cgggcacaga ggccacttgg ctgtcaggtg tcaggagcct   140280
gcagagggca cacagagcct ggaccgcagg ggggtcctgc tttctcacct ggcctccttc   140340
agcatttctg tccctcagtc cttagcaagc ccaggagctg ttgagtttgg caggtgccga   140400
gtgctgttcc tgcctgtgta gctgtggctc agtcctgtgg gggccccgct gtggcccgag   140460
tgcagtgatt cgaggcgctg agtgttccct gactccttct ccaggagctg tgttcagact   140520
ttcgcagctc ttggcttgga gctcctggag gcttggcat tgccgaccaa tgtggaggtc    140580
gacagtgaga gaggaggaat gctagctttc ttgaccagtc cattaaataa gtgggatatt   140640
ggccaggcac ggcggctcac gccttaatcc cagcactttg ggaggctgag gcgggtggat   140700
cacgagctca ggagttcaag accagcctgg ccaacatggt gaaacccct ctatactaaa    140760
aatacaaata ttagctgggc gtggtggcag gcgcctgtaa tcctagctac ttgggaggct   140820
gaggcaggag aacagcttga aaccggaagg tggagtttgc agtgagccaa gattgcgcca   140880
ctgcactcca acctgggcaa caagagcaaa actctatctc aaaaaaaaaa aaaaagtag    140940
gatatctgtt tctgcttaga aaaatcagaa ttttctaaat gccaggtgtt ctgaatacgt   141000
aagtatggga gacgactcag cctgtttcat ttttatgtaa aatcttcgcg tagccatgtg   141060
gcactggacc gagatgaaag caaagacatt tctccttaac tttgtttcta ggaatgttcc   141120
ggagaatcac agcagctgcc actaggctgt tccgcagtga tggctgtggc ggcagtttct   141180
```

```
acaccctgga cagcttgaac ttgcgggctc gttccatgat caccacccac ccggccctgg   141240
tgctgctctg gtgtcagata ctgctgcttg tcaaccacac cgactaccgc tggtgggcag   141300
aagtgcagca gaccccgaag taggttcata atgccccaca gcccagggcg ccagcccagc   141360
accctgtcct gagactccca gtaacctgag ctttggccac cgttaaagca ttttcatttt   141420
ccattttttg tgagggcttg tgaaatttct gctgcatatt aatattcctt tcatggacag   141480
catattattg ggacaaacat gcggtccagc taaaggcatt caaaatagca gttgctttct   141540
aaatgcgatt ttctttggca ggttctttga caccattgca tcttgtggga tatgcttgtc   141600
atgctctgtg gctcctacta agttctagtc cttaaattgg ttccatagcc agacatgttg   141660
caatgtctta acctcattat aaagtaaatg tggttctggt tatccttaga taatgaagta   141720
acagtgtagc aaatttcaaa acctcttgga aatgttattt taccattcaa aaaggcttac   141780
taaggttctc gttatgggtg gccctctttt tgcaaaaggt tttcaggctt aagctccatt   141840
tctaggtgct ccaacactcc attatttgta tatgtatgga aataaaagct gtgaccaccc   141900
ccaaccctgg cccccgccca gctgaatcct cagcacagta tttctggaag gctcaagatc   141960
ccacgctggg gaaaagaagt tctggagaca aagagggca ggtgctgccg tgcctctctg   142020
ctcagtatgg atactggacc ttgtgctgcc agggctccca gtagggccag ttcatggcac   142080
tcagctggaa agtccactgt tgggaggcat tcttaaccat ccactctgtg ccgtatgtag   142140
tggggtctgg tcattctgtt ggaggagaca gaccagtgac gacatttgaa atgcttggtg   142200
gatgtcttag gcctgttacg atgactgagc actgtggggg caggagacag aaagtcagtg   142260
tctcctagtt ctgtgctgct ttaacgtgca tagaaatcag ctgcggattc agcagatcac   142320
tccttttctg acagatgggc ctgcttactc tgatgttata tcagaaagct ctgaatctgg   142380
gaattgtgtc ccctgaattg gagtaacaga aatgcttaga tgatgagtgt ttaaaagaaa   142440
taaaccaaag gtaaatttag tttggaattc agcaagcgtc ttcattcagc cctctgaggg   142500
caaactacag cttttgtaa atgtaggtaa attctgtgac tgtttcgtga cccctctga   142560 tccagttttc ctttataacc ttctgtattg ttccttctat tatcctgaaa taacattaat   142620
agattaggct gggcgtggtg gctcatgcct ataatcccag caccttggga gccaaggcg   142680 ggcagatcac ctgaggccag gacttcgaga ccagcctggc caacatgatg aaatgctgtc   142740
tctactgaaa ataacaaaaa ttagccgagc atggtgacag gtgcctgtag tccctgctac   142800
tcagaaggct gaggcgggag aatcgcttga acctaggagg aaaaggttgc agtgagctga   142860
gatcgcgcca ctgcactcta gcctgggtga cagagtgaga ctccatctca aaaaaaaaaa   142920
aaaaaaaaaa aaattaatgg atcaatggat ttttaaccta ataattaaat ttcaaaaaat   142980
atcgttcttt aatggtaatg taaggtaaa attaagataa tatgtaacaa gcatgtgagt   143040
gtctaaggtg tccccgtggt ggaaggaaaa aataaatccc cataagtgtc caagatgccc   143100
atagagagca gagctgttct ggtttaaacc cctgctctta gcactgtgtt tttccagctg   143160
tgggtggtgg gggatgagta tcttttatt tccatgagat gagaaaaatg aattactaga   143220
agtgtgaaat acaaaacaca gctgctcttt ttttagccat agactcagca gccataaaat   143280
tgctgtatcc agttgcagaa attcctgctg cttactcttg accctctctc ggtttgtgtg   143340
catctcctct caggctggct cccagatggg agctggctcc aggcgacact gggtgctctg   143400
ctccaggagg tccttatgtg ggtcctgccc tagcctagcc cctctcttat ggactctgtc   143460
actgtgggtt tatgattcac tctcaatctg tcttacctct tggtgaactg ttagagtcct   143520
```

```
gcctatactt tggcgcttgt gggtgtgttg tggtacacat gatgtgttgg tcacttccca    143580
gctcatcttg ttctgagtca ccctagattt gggacattca ttcgccacca gtaccgggcg    143640
gtgtatggcc tgagatttgg gggggcttgt gctgctacaa attggggctg aatttgagtt    143700
gacagtggac cttctttatg tctactgctc atatttgaat tgcaaatact gcctcttctc    143760
tttcagaggc tcattaccct atagctgtat tattgcaaag tgcacaatta cagcttgagt    143820
gtaagtcaca ctgcgctggc aggacggccc actgagaaag gcacgtttc ctgttcgtta    143880 gttttcacat tgacacataa tttacaatac agtaaaatgt acttttctat caactgtagt    143940
cagtaacagc cccctcccc caaccacatc aagatataga ggagtgctgt cacttcaaac    144000
agttccctct tcctctgcca catcctgccc ctccccaggt ctaaccacca atccgtgctc    144060
tgtccctctg ttcagcccat tgcagaaggc catagaaata gaatctatag ctaggtgtg    144120 gtggctcatg cctgtaatcc cagtattttg agaggctgaa gtgggaggat gacttgaggc    144180
tgggagttca agactagcct gggctgccta gcaagacccc atctccagaa aaaaaaaatt    144240
taaaaattac aatcacgtcc ctgtagttca gctgcttggg aggctgaggc aggaggatca    144300
cttgagctca ggagttagag gttacagtga gctatgatcg tgccactgtg ctccagccta    144360
ggtgacacag caagacgttg tctctgggga aaaagaaag aaacggaacc acgcggtgtg    144420
cagccttctg agtctggccc ctttcggtga gcagtgtcta aagttctgtc gcgtgttgcc    144480
cacgcgtcgg tggctcgctc cttgcaactg ctgagcattg tatggctagg ctgtagtttg    144540
ttttcacttc accagttggg aaacagagaa aaggcacttt ttaaaaagtt taaatctgta    144600
gaattttggt tttaccagt tctcttctaa atcctgaggg attacaggaa aagttgttgt    144660
atttcagaat attcttagct tgatgtgacc tctgtccccg ttaaggccct ttgccgcaat    144720
gggaaggacg tcgctcggtc agaccctgaa ggtcagaggg gcagtttggg agtgtgtcaa    144780
cattttaact gtatggacta gagccaagag tctcaaggtt tataattccc acgtattcaa    144840
aaagaaaaaa acaataaagt gagaagtcag tgtagagtga aataacctgt gttagtgggg    144900
aagaagtgtt tttaaacagg atttccataa cgtataacat caacatgttt agagtggtga    144960
tgtttcattg ggaaacgaac agtaaaacat gaaagcaggg aggttttcat tctggcagtt    145020
ggcaactttc acggcagatg gagaatttca aaagcaattg ctcaattatc aaacatagcc    145080
agtgtgagtt ctgaaataaa ggtgctgatt gaatgtgcag cttatggtg gattttgcta    145140 ttcaggcaag cattttaatt ttctgcctgt taaattctgt tttctttagt ttttcatatg    145200
tggtttattg tagcttagga atagataact gagagtatat attacacata caacattctg    145260
atatggcaat atttaaaaca acttgtctgt tttagaacta gaattaaaca taatcatctt    145320
cagtattttg caaataagct cactgccatc cagaaacatt gtcaatgcat ctgttgctcc    145380
ttctagaaga cacagtctgt ccagcacaaa gttacttagt ccccagatgt ctggagaaga    145440
ggaggattct gacttggcag ccaaacttgg aatgtgcaat agagaaatag tacgaagagg    145500
ggctctcatt ctcttctgtg attatgtcgt aagtttgaaa tgcctgtaaa cggggttgag    145560
ggaggtgggg accaggagaa catcctgtgt agatgacact tgcatggacc ctctggaacc    145620
cagaccgccc ggtgtcctgc caagctccat cgaaactaaa tctagaatga atgtttactt    145680
ctgctgtgac atataattgg agaccaggcc tggccttcca gtcactggat tctaagttgg    145740
actgtgagag tttttgcagc tgactcattt atcaaatgcc cggctattgg ctcacgccta    145800
catgatgctg ggtatgtttg ttaatttgag ggaagcaatg gaataataat aactaatgat    145860
ttaaaaaaca aagtaagtgc attgactgta gtggggttct gattttaaat tttttttaaaa    145920
```

```
attaatacca ggagcagtgg cttatgccta aattccagca actcgagagg ctgaggtagg    145980
aagatcactt gagcccagga gtttgagaca agcctgggct atggtgtgag acacccatct    146040
ctaaaaaaat aaaaaataaa aaattatcca agtgtggtgg ctcgtgcctg taatcacagc    146100
tctttgagaa gctgagggcg gaggatggct tgagcctggg agttcgagac cagcctggca    146160
acacagagaa accctgcctc taccaaaaaa agaaagagag gaagaaagaa aaattagcct    146220
ggcgtggtgg tgcatgcctg tggtcccagc cacctgagag actgagaagg gaggattgct    146280
tgagcccaga agtttgaggc tgcagtgagc tgtgactgtg tcactgcact ccggcctggg    146340
tgacaaggcg agaccctgc tctaaaataa tttttttaag ttaatttgta gaaaggtgt    146400
tagatgttct ttgtcacatt ttatgatgga ttcctgttta aatgccgttc tctttaaaga    146460
aaaaaaaata acttgtggga gttttttaacc ataaaactag catcacatat ttaccatgga    146520
gaatttacaa aaaacaaat aaacggagga aaataaaacc tcctgtaatc atactactca    146580
gagataactt gctgttagat tttggtctag atttaatact ttttctatat ttatattaaa    146640
aatatttaaa acatatgcat ttctttgtca caaacatggt atcttataga tactactgtc    146700
acatagcaaa acagtgttaa atattctgaa tcagaaaagg aagccgactc tccaactgaa    146760
agaggtgtta tcctagagac ttttttctggt gatgacaatt tattaatagt cacttttgc    146820
tttactttct ctattgaagt agtttttcta ttttgttcta cttttaagga taatataatt    146880
tataatgctg ttttttcacag aaatataaga aaaagatac taattttata agttaataaa    146940
gtttgatcat cccaaatcca aaaatctgaa atccaaaatg ctccaaattc tgaagctttt    147000
tgagtgctga cattatgttc aaaggaaatg ttcattggaa ggtttcagat tttcggattt    147060
agggagctca acaaataagt ataatgcaca tatttcaaaa cctgaaaaaa atcctaaatt    147120
cagaatactt ctgatcccaa acatttcaga taagggttat tcaacctgta ctgtcagatg    147180
atcccaaatg aaaaatatta atcgttaacc aaatatcaag gaattgatca cattttacag    147240
tttctgccta ggattatgaa tcaagatgaa aaggctctgc atgtttaaaa atatatattt    147300
ttatttttctt ataaatctta aatatctaca cttaagattt atttgatatg tgggatccat    147360
tcatattttg gattcaacag ttctgtcaaa actgtgcag tgatagggga ttcttttttt    147420
cccactgaac tatcacaaaa ttggaaaaag agtaattgga gaaccccact ggcttagccg    147480
gcccgaagcc cgggagaggg caggcagtgc tgtggatggg gtcatcccag cgcaacgctg    147540
cccctgctac ctgcggatct cgctgaggcc tgcctttgtc ctttgaccct tggccatttg    147600
ttagtgtctc tgagagctgg actgctgtac cctacttccc cagggggcct aacttcacac    147660
agcctctgcc gcagtgcgtg gttggaggtg acggccttgg taaatcgagt ttcctacctc    147720
ctcaattatt tgtgctcata cactgtatat tttagtgag gttatatttt gggatgtgtt    147780
ttctccttct tacccttct ggcctttcta tggcattaat acctggtctc ttcttgtgta    147840
cttgaaaatg aatctctcat catatttttc cttagtgtca gaacctccat gactccgagc    147900
acttaacgtg gctcattgta aatcacattc aagatctgat cagcctttcc cacgagcctc    147960
cagtacagga cttcatcagt gccgttcatc ggaactctgc tgccagcggc ctgttcatcc    148020
aggcaattca gtctcgttgt gaaaaccttt caactgtacg tcttcatcct gccgactatt    148080
gccagttgca gttttccctg ccttaaaaat ggagtattga aattttttaac tttaatttct    148140
gatttgcaaa atagtcatct tttgttcttt tccttcttgc tgttagccaa ccatgctgaa    148200
gaaaactctt cagtgcttgg aggggatcca tctcagccag tcgggagctg tgctcacgct    148260
```

```
gtatgtggac aggcttctgt gcaccccttt ccgtgtgctg gctcgcatgg tcgacatcct 148320
tgcttgtcgc cgggtagaaa tgcttctggc tgcaaattta caggtattgg gaagagaaac 148380
cctgatattg atttatattg aaaatttagc aggccaagca aaacaggtgg ctggcttttt 148440
cctccgtaag tatggtcttg acatggtcac cgatagaaac atggaaacat ctgcaaactt 148500
gccgttactc gtgtgtccga tctgactgtt tcttgtattt ttttctagtc tgcccttact 148560
aggatgaact gtacacatca gttcatcctt tttaaatgag catgaggtta ttttgggttg 148620
ttaggtgtta caaacacact aatgtgtttt tgtctattag agcagcatgg cccagttgcc 148680
aatggaagaa ctcaacagaa tccaggaata ccttcagagc agcgggctcg ctcagaggta 148740
atgctggaaa cacaggtcgt ccttgtgtta ggacaaccca ggatataaag gatatagatt 148800
tgtacgggaa taaattcaca ggacaagaaa tcgatgtgcc ttataggtgg gtttactgca 148860
gaagtgccat aatagaacct tcctactttt aaaacaacca gatctcactt tctaaagagt 148920
aaaggatgac cggcaggatc acgtctgtga cgtgagtgga ggcagtttgc actcctggtg 148980
gctgtttgag aggtagcatt tagaatgcct gtattcactg tcctgtgatg agtgggaaaa 149040
taggttatca ggtttatctt agcaaaatca aagcatgtca tctaattgct aaacaagagt 149100
tggcaaatct gagagacatt actcaatcct ggcatgcag  gacttacatc tgcatcctgt 149160
tgccatttta tgtcttcaaa gcatttaatc atttagttgt gtttgcaaag tctttgagaa 149220
gcctttgtca gaaatcccta catctcctat gtgagtgtat ttccatgact gcagaataag 149280
ttaaacttttt acctttttcc ttcccttgcg gggcggggtg gggggcaggg attgtgtgtg 149340
tgagagggag agagagacag cagagaagga gaatataatt atcatgctgt gtactttgag 149400
ctgaaactgc aaaaaaggaa aaacacacaa aaattattat gcttttcagt cttttagagta 149460
ccttgtctat tatgcttttc agtcttttaga gtaccttgtt gatggtgttt ttaaatggga 149520
ttgggcacaa ttaggtggac agtttgggat gatttttcag tctgtagggc caagctcttt 149580
tgtaatttgc attatgaagt tgtcactctc atagcagatg gcgggagata aactattatt 149640
acttttttgac cctagactta gtcttcagtc cagatgaggg agattaaaag attataaata 149700
tcttgtgcca gatgaggtga ttttattttg aaatgaccat gaattcctat cagttgtctt 149760
actgggatat ttgatagtgg aatttgtgca tttgagtctt agatgatctg ttttacattt 149820
attaagaaag cctttattag ctttttatact gtgtattgcc tgttgcagtg tttgagtata 149880
aatgaaattt ctggaaaata ttaatggagt acaaactgtg atacttaaaa gtaaactagg 149940
gcctgcattt gtatcatgac ctgtttgagt attgatgaga agatagctgt gaagaaaaag 150000
gtttaaacaa gtgtattttc ctttaagaag ccactaatag tgcatctcct tagagtgtat 150060
atttctagaa tcctagtgtg cagagtttag actaagacta aaaaaaaaaa aaacaaatt 150120
atactgtaat ttcatttttta tttgtatttt agacaccaaa ggctctattc cctgctggac 150180
aggtttcgtc tctccaccat gcaagactca cttagtccct ctcctccagt ctcttcccac 150240
ccgctggacg gggatgggca cgtgtcactg gaaacagtga gtccggacaa agtaagtgtc 150300
cagcgtgtct gcatgggagg cacagggcgc tgagtgcctc tgtcacctgt ggcagataca 150360
gagagtgcag aggaggtgcc gtggacccaa ggagttctgg cgctcggctc ggctcagtga 150420
agctgtggtt agagacgtgg ggggccatca aggtctgagg gagccaagca gtgctgatgt 150480
gggaccctt tggtaggagt gtggggtgag tagttagtgg gtgaatcaag gaatagtcgg 150540
ccgtggcctc caggccctg actgcacagg ccttcaagca catgtcaatg ccgttagcct 150600
ccctccatct cctcatacct tctggccacc tgtgagttgc actgccactg ccagccattc 150660
```

```
tggtatgttg tcagcacctc cactgctcat acctcatggt tagggaccac ctggagcctt    150720
ggtagagcct tggtagagcc ttggtactct actttcctgg acaaagttca gcttatgaat    150780
atgaatttag atttcaaaaa ccagcagccc aagtataaga aagcgaaggt tcagtcctgc    150840
cttcttaggc tctattcgct aagcacctgc cctgccctgg ttgctgggga gagatgagta    150900
aagcagacaa cccaggagag gatggcaaag gggccgctaa cccttagtgg tttagctata    150960 tttgaaggc ctattggaag ttcaccaggt gaaggggag gctgtgaggg tgcccaggca    151020
ggtaacagaa gtccaaaggg gaaaacctgt ggtgtggtga gccgtatagc cacagcctgc    151080
cggccggcag ccctctcagc ctagtgcggt gttcccaagc actggcctag gcctgtagct    151140
ccagggatgt gaagtcccct tgaacgccgc ccatcatgtt ccccttatcc atttttttct    151200
tcccaggact ggtacgttca tcttgtcaaa tcccagtgtt ggaccaggtc agattctgca    151260
ctgctggaag gtgcagagct ggtgaatcgg attcctgctg aagatatgaa tgccttcatg    151320
atgaactcgg tacggggga gcagtggagg caaggaatcc tcagcttttc ttgtgacttc    151380
caagtgggat ttgtctcatc atcatgtgac ccacttgttg acaacacatg ttggggactc    151440
cagtctgggc agggacggga tgtcggagag actccactct gaatgggcc gggaagtggg    151500 gaggactcca tttcagatgg ggtcgggaca tgggggttat gctgatcgag acagaaaagc    151560
acattgtttc agccacatta gaatccacgg aggtgttgtt ttgaaatcca gctgccccca    151620
aggctgggtg tatggtttgg gatgagaact atctggcctc cactggagga acaaacacag    151680
gatgttatca tctaagctcc atggccaaga cagaatggaa gtcaaggttg cgtatttgcc    151740
gtagacttca acacagtgtc gtaatgcgtg acgtcaataa cttgtttcta gtgtcttgga    151800
agttgatctt tagtcgtaaa agagacccct ggatgcagcg agatttcctc tactcacacc    151860
tctgttagat gtagtgaggt tcttcacccc ccaaccccag atgtcagagg gcaccctgcg    151920
cagagctagg aggccatgca aagccttggt gtccctgtcc ctcacccgtg ggcaggtcct    151980
gtgagcagtg gggggccac ctcttgggta tggtgcagcc atgcccaag cagggcttct    152040 tctcagacct actaggacgg gagaaacctc ctggtgcttt agccctgcgt tgatatgcag    152100
caaatgggag ggaagtgggc acctgggagg acaaatgcct gtagaggccg ggagtgacgg    152160
caggtgttca tgaaaagaga ccttgtgggg agggcaacac aacagtgtgt tctgatgtac    152220
tgaagagctc aactgaaaac aacaggagaa ttagcccaaa atccatttac taaaattgtt    152280 tatcttttt ttttttttg agacaaagtc tcgctgttgt cccccaggct ggagtgcaat    152340
ggcgctatct tggctcactg caacctccgc ctcctgggtt catacgattc tcctgcctca    152400
gcctcccaaa tagctggtat taacaggcat gcaccaccac gcccggctaa ttttttgtatt    152460 tttagtagag acgggatttc accatgttgg ccaggctggt ctcaaactcc tgacctcagg    152520
tgatccgccc acctcggcct cccaaagtgc tgggattata ggcctgagcc accacgcccg    152580
gcctaaaatt gtttatctta agattcatgc agtgaaagct aacttactga gtgataaatt    152640
tgcttagtga tctgtttatt aggttttcca aatttgctaa ttgggctttg aacagctgta    152700
aaagttctga ctgtaaaaga aagcttcaac ttttggcatt catgatgctt ttctgagtat    152760
taaactaaga tagatgtttt acctgaagga tcggccacca atctttaaat ggctaaacaa    152820
aagggttgct aaaacataat ccaaattgac ataagaaata ccattttcc aaccaaaatt    152880 ttggcattca tatggctact tttacgtatt tcagctgcat ttgaacatct ttttcaaact    152940
ttagggtggt tggtgtatca ctgaggtctt ggatgacact ttagctttga ttttgttttt    153000
```

```
atgaattaaa attgtcatac caaaattttt atttcaagca aatccaagag cataaaaaat  153060
taaaatatta cttaaaatac taagagagaa cagatatata ttttactaag catatgttga  153120
atgaaattgt tcaaatattt ataacaggca tagagtagaa ttttcttaaa aatatttttg  153180
atggtatacc aatttgtatt ttctcagaaa catttgcctt attctttttt ctgttgtgtt  153240
tttcttacct gattgaaagc tcataatctg ttgttattgt ttgttaacct ttaatgctct  153300
gatttcagga gttcaaccta agcctgctag ctccatgctt aagcctaggg atgagtgaaa  153360
tttctggtgg ccagaagagt gcccttttg aagcagcccg tgaggtgact ctggcccgtg   153420
tgagcggcac cgtgcagcag ctccctgctg tccatcatgt cttccagccc gagctgcctg  153480
cagagccggc ggcctactgg agcaagttga atgatctgtt tggtaattaa aattaaaatt  153540
tatcttattt ttaaaaagca ttccagggcc agtatagtac tttgcaccaa gtaaatgtac  153600
aataaaggca gtggatctaa tacattgaaa gcgtttacag aggtagctaa agagcagcac  153660
gggtgtcctc ggctcagaat tcttcctgt gtgtttgcca ctttgccatt cattgacatg    153720
gtcatggaca tagggctcta agcccttgag gaaggctggg ccagacctca ggggagatgc  153780
agccccaaac cacgtgcagt cctgtggacg gatgtgtaga tgtgccactg aggaacaatg  153840
tcttgagctt tcatcagatt ctcagagaat tgcttgactg cctttcgaag ttgatgcatc  153900
tgtgctcacg tttgcaccca cccacgaggt ccttctgttt caggggatgc tgcactgtat  153960
cagtccctgc ccactctggc ccgggccctg cacagtacc tggtggtggt ctccaaactg    154020
cccagtcatt tgcaccttcc tcctgagaaa gagaaggaca ttgtgaaatt cgtggtggca  154080
acccttgagg taagaggcag ctcgggagct cagtgttgct gtggggaggg gcatggggc    154140
tgacactgaa gagggtaaag cagttttatt tgaaaagcaa gatctctgac cagtccagtc  154200
acttttccat ctcagcctgg cagtaagtct tgtcaccgtc aagttattgt agccatcctt  154260
caccctcacc tcgccactcc tcatggtggc ctgtgaggtc agccaggtcc ccttctcatc  154320
tgcacctacc atgttaggtg atcctaatt ttagagacat gaaaaataat catctggaag    154380
tactttatgt cttaagttgg cctggacatg tcagccaagg aatacttact tggtttgtgt  154440
tagtgcttgt aattcgcccc cagaatgtgt acacgttctg gatgcattaa agtctggcct  154500
gtatccttaa agggccatcg ctgtgctgcc tgccctcagc aaggacacac tttgcagacc  154560
cacagaggct ccgcctccac ctcacaccaa agaaagggag gagtccaaag ggcatcagtg  154620
ccattactca caaaatgata aatacaccct tattctgaac cacgtggagt catatggttt  154680
gtgatccctg tccttcaggt ttcagcttag tggggaagtg ggaaagtcag cgtgtgatca  154740
cagcacaggg tgattgctgc tgattatatt atgtgcctgc tgtatgcagg atgaaatact  154800
ttatatgcgt catcttattt gactctcaca accccctgtg agataggctc tgttactccc  154860
atttgacagg tgaggaaagc aaggcttaga gaatttcagt gacttgccca ggtcctctga  154920
gctaggaagt agccattctg gcatttgaac ccaaggcctg ctatccctag aacccacgct  154980
ctcaaattca acctatgaca gaggcaagcc ctggtgctgt gggagcccca aggaagagcc  155040
tctggcctgg tggccacgta gcccaggaga gatttctaca ggagcccaca gcgctgaagg  155100
agagagaggc agcagagtaa gggggctttg tggcagagag gggactggca ctttggggaa  155160
taggtgggtc aggactgaat gtaatggagc catgtcagag ctgtccttct ggaagggcaa  155220
ggcacctgg acgcgctgcc cctcagtgct ttggacggtt ccacaactgt gattcacacg    155280
gcttccccaa acgaaggtac acgagtgggc attctgtgac tcggtacttc cctttaggcc  155340
ctgtcctggc atttgatcca tgagcagatc ccgctgagtc tggatctcca ggcagggctg  155400
```

```
gactgctgct gcctggccct gcagctgcct ggcctctgga gcgtggtctc ctccacagag   155460
tttgtgaccc acgcctgctc cctcatctac tgtgtgcact tcatcctgga ggccggtgag   155520
tccccgtcca tgaacggtgg gttcctatca tagttcctgt ctgcttcacc atgttttat    155580 tttgtgctgc ctgtttgcca ggtactaagc taggaattgg ggatggagag gtagataaaa   155640
tatgcatcag gaagggctgg gccccatctc ttactctcca atatattgga gtctacactg   155700
gaatttaact ggaatttgct tttttagtca ttttatttag attttgaagt ttcagctttc   155760
atcaaaaata cctctaaact ttatgtctct gtgatctttg gtcttagctg ttttatgtat   155820
ttagtcttat atgatcataa gattaataac attacattca gaagattatt tgttttctgt   155880
cagagttaaa atgtttgttt ttatactgca ttgtaatatt aacgtactgt aaaataaaag   155940
tggcttgttc ttttcaagga acagtatcct caacaagggt cattagccac aattttaaa    156000 aaattggacg tcatagttta catgttagag ggcgttttga agctttgtat ttttaaatta   156060
aatgttatag agtgatgttt tcatgtttca taattgtttt catctgtgca tttgtagcca   156120
acttgaaaac aaagatccag ggattactac ttaaaagcca gacttcttgg aggttatagt   156180
gatgattttg atagtatctt gagccgtctc ataataacct cagggtgaga gatggccaac   156240
aggagacagt cgagggactt agaaatctga atgaaatctg aagttcaaat cttcagacat   156300
ataccactaa ccaagagatt ggtacctcag tctagtattg tctgtttgtc taaaattggt   156360
tctaaggaat ctaggctagt ctgtctatcc cttcaactt tgtgaggct gcacaaatgt     156420 aaaatgttga ataaaaagca ctgatggaag tgtgtagaaa ttcttctctt tgttctgttg   156480
taattttagt tgcagtgcag cctggagagc agcttcttag tccagaaaga aggacaaata   156540
ccccaaaagc catcagcgag gaggaggagg aagtagatcc aaacacacag agtaagtctc   156600
aggacccatt ttttcttac atgttgttcc tccaggactt aaaaatcatt cacagagacg     156660
tgcaccgcgg tgagtgtgga ctcctggaag cgcaccgtag ctccgctgtg tcctgctgct   156720
cctccctagc tgtcagggag gctgtagtcc attgctttgc cagctctttt gtttccgagt   156780 gaacaccta tccgtacaca tgcggctgtc tctgaccta cagaccagct gggatgccac      156840
tgggggagcg ctcccttccc cccgcacttc ccacactctg cagttattct gagatccttg   156900
agggcaggga acaggtttgt cttctttgtg ttctcagaaa ttaatgctcg gcctctggtc   156960
agcaagcaac aaccttttgt tgagtgataa tgaataaata aatgtttccc acatgagtat   157020
tcagtaacct cagtgtcagg ttcagccatc tgttttggtg gatatttaaa agaaaattcc   157080
gcttttccta cagaaaaaaa aaaaaatcca aatcccagtg atttaagcca gttatagact   157140
tagacatata ctacggcttt tcatgcactt tcctcccaat tctagagtag gtattttact   157200
aggaaaatgg tggcagtgcc tgttgggagg aagattcttt ggccaagtgt cttttgttct   157260
tgccagggcc cctaggctgc tggggtgctt cagcttcttt agcccagtgt ctggtgggga   157320
atggcccctg ttgcctgtcc cacagaggtg ggggtgcctc acctggagcc tgtccacaca   157380
ttttacacag cacgcttacc tggagcatca ggcatctttt ccatgctctg tggctcagga   157440
aacacgcctt tcaatcatg agtgcaccag tgcttttggg cttttctcc ccgcttttgt      157500 gcaatcctgg ttgtggatgg agttttcctg tctttagtct tctgcatagt acttttctct   157560
tctggttccc ggttcaaggt tttgtaatta gagaatgacc cagaagcaat ggcattttaa   157620
tgcacagcca aggacttctc tgaatttgta tctcaaacct ctgtgggtcc ttcaggcttc   157680
agtttgtgat ttcatgattt cttgttgcta cctaaggaat atgaaaacac ccacctccct   157740
```

```
actctgcatc ttccagccga gtggcacctc aggctgtgga tcctgtgctt ctgtggtgag 157800
gataagaata gtgccaaccg tgtggattga aatcaatcag ttaatccctc catgtaaagc 157860
acctggaacg gatgacagtc ttgttatgaa tactcaacaa atgctatcat gattttagt 157920
tagatttcca ttgctttaaa acagttgaga catcttggcg gtttgagtta gagcaacggg 157980
ccctgaagtg ggttctgttt gggtgaagat gattatgctt attccccatg gccctcttta 158040
ggcaagagtg ggaagctttc tttgtttttt taatcacctc gataggacgt tacttcttaa 158100
aggtcatcca ataaatatta ataggccggg cgcggtggct cacgcctgta atcccagcac 158160
tttgggaggc cgaggcgggc ggatcacgag gtcaggagat cgagaccatc ccagctaaaa 158220
cggtgaaacc ccgtctctac taaaaataca aaaaattagc cgggcgtagt ggcgggcgcc 158280
tgtagtccca gctacttggg aggctgaggc aggagaatgg cgtgaacccg ggaggcggag 158340
cttgcagtga gccgagatcc cgccactgca ctccagcctg ggcgacagag caagactccg 158400
tctcaaaaaa aaaaaaaaat attaataaag ccaactcgtt agcgtggggc ttaattgctt 158460
aagtccaatg agaagtcctt ctctatccta ggaagttgcc caaactgtag aatctcgtgg 158520
cctgtgggta atagccacgt aatacacact cactgcctca acaaatcata ttttagtagg 158580
tatgatattc tagactcaag acaccattct gtggatcttc ccaagggtgt gaagtgtcca 158640
cagcgtctgc cttgggagtt tccatgccca ccagaaccat gccccaagcc cctcaagcac 158700
tctgacctag gaaagccagt gaagcaagga tgacaacatg gcccttgat actagctgag 158760
ggacagacac aggtcctggg agaccagaga aagacgaggg gcagaggagg tgtcctaaag 158820
gaagtctgag gctgaggagc cacaggatgg cttccagctg tcacaggctg ctgctggcct 158880
tatcacagag agtgggccag agggctggga accaaggcca gagctcaggt tcaggaccat 158940
tccagcaatc ccagcagaaa atggggagaa ttgtatggta taggcggata tgaaggtaga 159000
atctgcaggc cttcagtggc caactcagag tctaagtgga ttccacagtt acagcttgag 159060
cagctggttg taggtcatgc tttctacact gggcatatag gatgtgtttt ttaaaaagtc 159120
ctctcttaac cgttgcttgt ttagatccta agtatatcac tgcagcctgt gagatggtgg 159180
cagaaatggt ggagtctctg cagtcggtgt tggccttggg tcataaaagg aatagcggcg 159240
tgccggcgtt tctcacgcca ttgctaagga acatcatcat cagcctggcc cgcctgcccc 159300
ttgtcaacag ctacacacgt gtgcccccac tggtgagtct gctcgttcct tgcagaaagac 159360
caagtacggt gaaaggcacc ggtaggccct gggctgggca cacgtgagag ggcgggacag 159420
aatccccgca gcccagaggc tgcctgctgt ggttctggtg cccactgtgg ttctggtgcc 159480
aggctgcttt cctcaggcac cacgtgtgga ggtcgctagt agaaatactg ggttttctaa 159540
aatgaactga ggccctacat ccctaagaga ttagtgttag acctgattct agagcaacta 159600
gaccactttg cttaatagca gaccagaaac cacacccct cgagtgagtg agatttttcct 159660
ttggagataa ttcatgtttt tctacacagt tttgcagttg tcttcagaat tggtttaaag 159720
taggtgttat tgccaggcgc agtagctcat gcctgtaatc ccagcacttt gggaagccaa 159780
ggtgggcgga tcacttgagg tcaggatttc gagaccagcc tggccaacat ggtgaaaccc 159840
catctctact aaaaatataa aaattagcca ggtgtggtgg tgtacgcctg taatcccagc 159900
tactcaggag actgagacag gagaatcgct tgaaccagg aggcgaaggt tgcagtaagc 159960
cgagatcgcg ccactgcact ctagcctggg caacagagca agactccgtc tcaaaaaaaa 160020
aaaaggtagg tgttattgat cagaaccctt gtttcagata acatgaggag cttagcttga 160080
ggagagtgag ggttgatgga gggggactga cttctgccca gtgaaatggc atcatctccc 160140
```

```
accagcccgc tgaaataaga tgatggggcc tgttccttag ggcctgcagc atcctcaggc   160200
aggaaagaaa ggccgacctg gcagggtgtg agccagcagg tgtaggtcag ggagaatgga   160260
gccaggtccc agggaagagg cttgtggctg cctgagaagg gtgcgtgcct gcctgtgtgt   160320
gtgtgtgcac gtgtgtgtat gtatgctgga gagtctaggg aggcttgctc caaggacgca   160380
gtattgtttg atcctgagag ataaggattc tgccgcaggg aatgaaggta ttccagatgg   160440
cgggcttatt ccgaagaaga ggccagtgcc tggcggtgct ggaagcagtt gcagaacagg   160500
gagttgtagg cttcctggg aagagagcag caggggtgct ggagaagcag gccacacttg   160560
ctgcatgggg ttgctctcgg ccccactctt ggtgcacagc gagtcactgt gggttcatta   160620
gcatctggtt atgagacagt aactgctcct ttggaggggc tcgtggagac catgcaggag   160680
ggcacggtct tgaggtcatg ccgtccagag cacacctgag gataggccag gacgggctgc   160740
acgctgtagg taaaattcct ccagcaagct cttcactggc attgaggagt ccctgagtg   160800 cggtcatctg gaaggcagct gtaacaggca ctgcagtctc tccctgggtg ggtaccagag   160860
aggagcatag gggagcataa ccgatttaaa gagagggctt tcctgtggtg aggtaagaga   160920
ttagctggtc attatcatag agccccctct gcctttgtgc agatgggctg tgggaatcct   160980
ggggttccgt tgggtccttt gtcacctcac tgaaggcatg taagctgagc tggccagacc   161040
gtgagctgat cctgccactt gaacagcatc aagcctgcct ctggattctt ctgtgcatgg   161100
cacttgtctg agcacctcac gcacagagaa ctggacttca gagtttacag aaataagctg   161160
tatggttcat tttcatgcct gcttgccaat aaacatatct gagctgaacc tcattgaacg   161220
cctgccttta ttctagcaca gcacctgctg tttgtgggcg aggggtgctg tctctaactc   161280
ctgcctgctt ctcccagcac tccctgagtg gggtgtgcca gcagcctcag gatgaggaca   161340
ggaagtggga gggcagagca gatttgggag ggccacttga tggggaagga agtcccagga   161400
agcagttgga gctgttttct gggggagaag gtgccagctc tgggacagtg ttggggtagt   161460
gaggagggag cccagtggag agaagtcggg cttcctgctt cctcacagta tgtctgtcct   161520
gactcaactc ggatgatgtc acttcctttt catcttctca ggtgtggaag cttggatggt   161580
cacccaaacc gggaggggat tttggcacag cattccctga gatcccgtg gagttcctcc   161640 aggaaaagga agtctttaag gagttcatct accgcatcaa cacactaggt actcttgggg   161700
cctctccttc aggtcaccat tgtcggacat ctaccgggag gaaatccaga gccccagta   161760 ctgggatctt ctcatttgac tccagaaaag atttaagcat gataataata caaacctatg   161820
tgaatacatt ttgcagtgtt ggcaaaactc cttttatact gagaaaatag atcccagttc   161880
ctgtgttttg tggcttgaat cccagctttg tgtattccgg gcttgtttga agtcaggaaa   161940
ggttcatgtg tagtggacaa cgtgagacca aattctgcct tagattttgc atttaggcta   162000
aacagtggca gcacttgtct cagaatgttt tcttgtgttc accagtctga tcctgttgtg   162060
tctcagtggt ccatttttctc atatgggaac aagcagacgg gagcagatgg agtcaggttt   162120
cttggcactc gccttcccca gagcctagag gcagcatggg gagaaagcag gcttggggct   162180
cagacagtcc tggtctgctt ccagccctcc tacctgagca gcgcagggca agtccgtcta   162240
acctctagag accctcagtt ttgtcatatg taaaatgggg gtcgtgtcta tttcatagaa   162300
ttgttgcaga tttagaaatt acatttctaa acaaatgtta ccccttattt ctaaataagt   162360
gtctaaatga ataagtcacc acttttgccc ctatttgatg gcaagaggtg tgatcttgtg   162420
gtgggactgt aatcagtcag ttctcagtga ctgtgccctg ctgtggtgtt tcctggaatg   162480
```

```
ttcctgtctt gtcctagaaa gtctggcagg ggcaccctga ctccactgtc cagtcctctc    162540
cccagtccct cgggcttctg cagatttgag gcttgtttgg atcccagaag gttgtggcag    162600
gagacacctt gcctctactt tccccttat aattcaatgt ccaaagagag ccctgagcag     162660
gtacctcacg ccagctgcct cacggagctc ctcctcttcc tggctgtgag gatcggtatc    162720
agtggcctcc tgctctctcc cccttgccta acacgagcac ctttgcttac ttgggtgccc    162780
ttgctcttga actgcccatc ggacgtgcgt gacccaagac tgtgccgcag tccttgcctt    162840
gtctgtgctc attttctttg ttcattttt tccctgtaac gtaaattgtt atatttgtct     162900
gtatctgtgt ctgaatcagt cctgcacgct ctccttctct ctgtctcttg ttctttcttt    162960
accccgttta tcacggggac cccgatgtcc attgctctag ttctcctgtc ctaagcaccc    163020
catcccgtct ctctggcctt accacaagtg gcgtggctgc ctcagacatc atgatgggga    163080
catgaagcac agctgtcaga acaactgtt cgttagatac actcgaatgc agctcatcaa     163140
tagggatgga gggtctgtcg gatgtatttt cactgaatcc ccgttcctac cttgatacac    163200
tcttttaat ctattcttct agacaggtca gaggaaccat tactttgact tttaaatttt     163260
tagcagcttt attgaggtag aattcacata ctacagattt cacccactct aagcggacag    163320
cttggtggcc attagtttta tccacagagt tgtgcagcca gctgcacagt ctcagggctg    163380
gactccaggg aagattttag cccatttagt gagtggggca gaagtggccc tggccctgca    163440
cgaggttgcc tgcatgggcg tccctgccct gtccctgtgt ctgctccact gggggttgac    163500
caggctgcca gggccgactt gggcctgtgc cacctgcctc tcatgtgtct cggacagtgc    163560
agccgatgtc tatacttcgg tttcctcaat gatgaaatgg aggggatagt gttccccgca    163620
tcatagaact gtgtgaggtt aagggactc actgcccttg gcgtggagcc ttctccaggg     163680
gccgtgctgt gtcggcgtag ctgtcagctc tccgttacag gcttgagaag ggttgacact    163740
ctctcatgta acatttatat ttctaggctg gaccagtcgt actcagtttg aagaaacttg    163800
ggccaccctc cttggtgtcc tggtgacgca gcccctcgtg atggagcagg aggagagccc    163860
accagaagta aggccacacc ctgtgctggt tggcacatgg gcagttatgg ccgcttgcag    163920
gcctttggtg gggaataaaa taaggcagca agctggtgtt cttttttct cttaccttat     163980
ttttgaaaga gtagctgaat ggtgtcttga ctgatattcc agagcaggga caaagcctgc    164040
tgaggtctgg gggctgcgat taccaatggc tggaatgcat tttattacgg tgcattccat    164100
gttaaggatc aatacgattg tgcccttct ggaaaatatc ttttagttta tcaatattca     164160
gaggagtgta ggttgaatta aaatgaaaag gcactttata aaggccatga gtagtacctg    164220
gtttcatttt tctaatgtct tgcagagatt ttatcaggct tcttgaagtg ttcacgtaca    164280
ttacgctaac acgatattaa taataactgt gctctggtac agcggagcca gcagaatggg    164340
aagttgtgga atgcaggccc ttgattctga tagaaggtgt ggtttgaact cacagaaatg    164400
acagtttgga gggtagacat atgtcacaag tcatcaagat tgtctttaaa ttcatgcata    164460
gaagctaaca gggtgtcata agcaaggcct gtaaaatgta tgagggaatt caaagataat    164520
ttattaaaaa gtaattcatg tttggagttt tgtgcccaaa ggagtccttg atttgaaaaa    164580
tgggcttttg cccatcagat tgtttcaggg cccgtgtgtg cggaggccct gccttgtgcc    164640
ccgtgagctc agcctgacag aaatcctttg gtagcactta aggctcctct tcctcccatt    164700
gaggcaggga agactctggg ttctgcaggc agaggtggtt gtgggtgtct tgctgctctt    164760
gttgacatgt gggctctcct tccaggaaga cacagagagg acccagatca acgtcctggc    164820
cgtgcaggcc atcacctcac tggtgctcag tgcaatgact gtgcctgtgg ccggcaaccc    164880
```

```
agctgtaagc tgcttggagc agcagccccg gaacaagcct ctgaaagctc tcgacaccag   164940
gtttgcttga gttcccacgt gtctctggga catagcaggt gctggggaca gtgggttccc   165000
cgctgaagcg tccagcagct tcaaccaggc cgttttcctt cattgctaga attgaaaaca   165060
ccgtccgtgt ggcctgtgca ggagatgcag acccaaaggt ggcctcctgg tcagtgagaa   165120
gctggaaacg tgacaggaac tgacgtgggg ttattgagca tttaggggaa gacgttagca   165180
gagcaggaat gagcaggcaa ctagtagaac acccacttaa gggctcacgg acaggtgctc   165240
acttaggaag tgagtttcat ttggtattac accaggttcc tttaggcaaa gcggagggaa   165300
agttctggtg tttttcactt gtaagatttt gaaggaaaca aaacactctt taccttttt    165360 ctaaaatgta ggtttgggag gaagctgagc attatcagag ggattgtgga gcaagagatt   165420
caagcaatgg tttcaaagag agagaatatt gccacccatc atttatatca ggcatgggat   165480
cctgtccctt ctctgtctcc ggctactaca ggtacctgag ggaaagggtg cggggagcg    165540 gttgtacttg ggctagaatg agagaagact ggcatgctca ccacaccagt gatgcgggaa   165600
gacctgagtg tggtctgagt tggaggctgt ggtgctaaat acgctgcccc tttcataagc   165660
aggagtctta gtcaggccca gggaggaagt aaaatctgga aatgaatgag aagcattctc   165720
tcctgccagt caagaaatga gaagcgaaag aattctcacg ggctgtaaga ccagcaggat   165780
ttaaaagttg aattagttgc ttatgttaag aactcaacca agttcatcta cacaagctga   165840
atctccagct tttcctaaga aaccatgtgt ggcagtggct gcagggcagg gcacagctgg   165900
gcctgagcac cccgctccct gcacctctcc cctccctggg ccctgcctgt cactgcccac   165960
tctcccacca agccttccgg ttgtgtgcct gccctatcac aggcatcgga gcttgtcacc   166020
tggtttaaaa gaagagagtt gtgtgggat ttgggatgca cgttttttcac tcaaaagtat   166080 tttagcgtag agctctgtga ttccgtagct atttaggagt ttaagcacct tgaaggcttt   166140
aattgcagaa agttctatgt ggacgtgcaa tgtgttatac gcagtgtcta tgagactcaa   166200
atgtttatta gggcgttgaa gtaaactgag cacttggagg gccatggatc cagccttcaa   166260
ggagctcata agtcaggagg acccaggagc aatgacctgt catagaaggc agaaaagagg   166320
ggcacagagg tgggtgggag gcatacacag gcagctcctg gagctccaag gggagcaagt   166380
gcttccaggg aagggggcgt ggaggcccct ttgaggagg caagttgatc tggggtctgg    166440
cagagggtta gctggggaca tttagcggga ggctggtgcc cggaattgg ggggatgccc     166500 agcagaaaga catgaggagg ctggcctggg gcgtgggggg gtgtgaaagg ttaagtgggg   166560
gcattatcct gctcccgctc ctgccggctg tatctggtca gcctgggcac cgaggtgggg   166620
ttctggaagg cactgttcac caaaatgctt atctgggtcc cccagagagc ttgcctgcct   166680
ggactgtcgg ctcgcctgca actgctgact cctaagcttt tgcagctcag cccacaacca   166740
gttcctattc acagaggtgg gagctgaggg gtgacaagtg actgctgcag tcttatttgt   166800
catagagaaa aagtgacaga gtccagcttg cccactggcc ctgccagctt aactggttat   166860
aaagtgacaa atccccaaga cccacagggc tctgcacaac ctgggccctc ctgccagtgg   166920
cggcgagggc aggtggctca cggctgggtg cctgtctggg caggagctgg gctggtatgg   166980
ggtgggcctg cggccctgcc cccctgtgca gatcaagact cagggtgctg gtgttcacag   167040
gtgccctcat cagccacgag aagctgctgc tacagatcaa ccccgagcgg gagctgggga   167100
gcatgagcta caaactcggc caggtcagtc tcgcgccccc gccgcctggc ctctgtccgt   167160
ttctgtcctc agactttggc gcttgacaca cccaggagaa aagctcagtg cactttttaa   167220
```

```
atgaaaggaa gttttccttt tttttaaaaa aaaatttaat gttcattgtt tttatctgtt    167280
ttattcctag gtcccgcaag cagaggaagc attagttttg tttttattta tgttctgtat    167340
tccagaaagt agttaagaga cctcacatgt agcgatagag atgtgtgtaa gagacagtga    167400
gagggcgtga cttggactta agcaaggacc gtgagacaca aaaaggggg tgaggacaga    167460 gtggagtcag ctgaaatgct caggaggaag tagacgccat gaagggccat ggtatggggg    167520
gccgcaggcg tggccgtgag tgtccctggg gccagctctt gggggctcc ctgagtgtcc    167580 ctgtccctgt ggccagttct gggtgggagc cccgtgtgca ggcagacagc tcggccactt    167640
cctagcaggt cacattggtc tgtgcttctg tttcctcctc agataagtga agggattcaa    167700
gggtctgggt gtggtggcta acacctgtaa tctataacat tttaggaggc tgaggcagga    167760
ggcttacctg agctcaggag gttgaggctg cagtgagcca tgattgcacc actgcactcc    167820
agcctgggca acagaccagt actctgtccc ttaaaaaaaa atgtaaacag aaacgtaggg    167880
ccatttgcat atgatggcac atggcgtgga gccctacagg tgtatgctgg gcggggcccg    167940
gctgtgctgg ccgacttgca ccttcctc accccggtg ctgtgtcttt cgctcaccgg    168000
gttcctgatt tagtgaaagc agttgtgcag gacagttctc tttgtagctt ttgtttctgt    168060
ggaaatgggt cagaatatgg tgtttagaaa cacttatgag ctctgagagt ttcctcttct    168120
gagttcctgg cctgcagcct tcacagcaga acccctgtga tgtcacaagc ctgtttctgt    168180
tccctgctct ctgcctgtac tgtcctgttt tgtgcctgcc ggtttcagtg acaggaagca    168240
gggagctact ggaccagcct gtattttct agacatagtt ggaaaaagaa gtcccactct    168300
tctgtccttt caccttgac agatgtttcc accccaagat aagtgaaaat gaccaatagg    168360
atgcactgta tttttcatga aagtgtttct gaagggcagg ctgagagtga gaggcctggg    168420
gctcactggg tgcctctggc cttgtcctgg gccagggac actggtctgt gcccgaggta    168480
ttccctatcc ccccaacccc gctgcatttg ccacatcct tcaatgtttg cgttgtgtcc    168540
agcgtccgca aaccaactgt catgggatca tactggggct gaagtacggt cccacccctg    168600
ccctgtctgg ggctgaagta cagtgccacc cctgccctgt ctggggctga aggacagtgc    168660 caccctgcc ctgtctgggg ctgaagtaca gtgccacccc tgccctgtct ggggctgaag    168720
gacagtgcca ccccttccct gtctggggct gaaggacagt gccacccctg ccctgtctgg    168780
ggctgaagga cagtgccacc cctgccctgt ctggggctga aggacagtgc cacccctgcc    168840
ctgtctgggg ctgaaggaca gtgccacccc tgccctgtct ggggctgaag gacagtgcca    168900 ccctgccct gtctggggct gaaggacagt gccacccctg ccctgtctgg ggctgaagga    168960
cagtgccacc cctgccctgt ctggggctga aggacagtgc caccctgcc ctgtctgggg    169020 ctgaaggaca gtgccacccc tgccctgtct ggggctgaag gacagtgcca ccctgccct    169080 gtctggggct gaaggacagt gccacccctg ccctgtctgg ggctgaagga cagtgccacc    169140
cctgccctgt ctggggctga aggacagtgc caccctgcc ctgtctgggg ctgaaggaca    169200
gtgccacccc tgccctgtct gggatgttta gcccctagat gccactggac tgagccgcta    169260
cttgcttttg ggaagagggg gtgggggtta ggggtctggg cgaggggagt gcagggctc    169320 ctccttggcc tgagagctgt tcatacagac tccctcgccca ctccctgcag ggtgctggt    169380 cccagggggg aaatggccct tggtgccaag aacgtgagtt ggggctagtg ccagtgatga    169440
tggagaacag cttttatgg gcacacagcc cacagcactg tgccaagtgc tcgaggcttc    169500
ccgagaacca ggcagaaagg aggacagtcg aggtgtgctg actgcgtggt ggctgcgtga    169560
tctagagcgc gggtcacaaa ggcgcgaggg agctctggcc ttgggtttac cgcaatgact    169620
```

```
gccagtgcgg gagactggaa aaggaatctc acgtattggt tccgtgtttt ggggactcca    169680
ttcagatgtc acttaggagt gaaagcatcc cttcgtagag cctctttctg tgtcaccctc    169740
ctcagctgct cctggggttg actggcccct gattcatgcc tttagcatgt gctggagctt    169800
cccagcagct gtccagcccc tgccccaccc tctctgtggg ctcccttgcc cgtaacctgg    169860
ggtgtctgaa cgaccttgc taaggggcag actgttagac ggtaggcatg tgctgagtcc     169920
cagtggccac acccacccac caggagcctg cactgtggc cgcagcactg agcagtgccc     169980
cgtttctgtg gcaggtgtcc atacactccg tgtggctggg aacagcatc acaccctga     170040
gggaggagga atgggacgag gaagaggagg aggaggccga cgcccctgca ccttcgtcac    170100
cacccacgtc tccagtcaac tccaggtttt ccaatggcct ttttcttttt aacagaaatt    170160
tgaaatttct tatcagtcat ttgatttgtt tgaggtgctt cttgaaatga gcctctcatc    170220
tcatgtactt ggaaaatacc catctcgcat attccacagg aaacaccggg ctggagttga    170280
catccactcc tgttcgcagt ttttgcttga gttgtacagc cgctggatcc tgccgtccag    170340
ctcagccagg aggaccccgg ccatcctgat cagtgaggtg gtcagatccg taagtgagcc    170400
ttcccattcc cctcacacct gcacgtgcca cacgcaccac acacgccaca caccccacac    170460
acacacaccg cccacacaca tgccacttgc acacacaccc ctcatgcatg caacacacac    170520
acaggccaca cgcaccatag acaccacaca cacatgccac atgcacacac atacacggca    170580
tgcaccatac acacaacaca cacagcacac atgccacaca cacgccac accacatgca     170640
ccacacacat gccacatgca cacacactcc acatgcatgc accacacaca cacacacaca   170700
ccacacacac cacatgcacc acaccacaca ggttacatgc acaacacaca cacatgccac    170760
gtgcacacac cccacacacc acatgtatgt gccacacaca gcacaaacc acacacatgc     170820
accacacaca tgccacatgt gcatgcacca gacacatggc acacactaca cacacgccac    170880
gtgcacacac cccacacaca tgtacgcacc acacacatgc cacacacaca tgcaccacac    170940
acatgccaca tgtacacaca tgtatataca caccccacac cacacacaca ccacttgcac    171000
accacgcaca cacaccacat gcgcacacac acaccacata cgccacatgt acacaccata    171060
cacacaccat acatgcacca cgtgtaccac gcacccacac agacacagca cacgcataca    171120
ccacacacac acgcacacat gcgtcccgca cagtaatgtc tcttgggtgt aagaacacga    171180
cttgccagta gtagcgttct ggatgcgttg cctggattct aacagcgcga ttctcccctt    171240
gccctcctgg ttttccacat ctccagcttc tagtggtctc agacttgttc accgagcgca    171300
accagtttga gctgatgtat gtgacgctga cagaactgcg aagggtgcac ccttcagaag    171360
acgagatcct cgctcagtac ctggtgcctg ccacctgcaa ggcagctgcc gtccttggga    171420
tggtaagtga caggtggcac agaggtttct gtgctgaagc cacggggggcc catctgcctt   171480
gggacctggt gttggccaga ggtgccgggt gcggctgcct ccttccaaga gttgacccga    171540
accggactcc acgcccacg tgagctgcag tgcttctcag atggagggg ttcagcgacg      171600
gtcagtgcca ttcacaggtc actgtgatgt gggttgtggc ggccaagcca tggtttgggg    171660
tcccgtatcc ctgggcttat gacatcattg tagtagccca tccccacaga accacggtgt    171720
gtggtggcgc tgaggcatcg tagatggtgg aaatgctact ggcttcccca tgctctgccc    171780
tgaggcctga ctgcctcact ccccttctca gttatgttcc aggcccccg agcttcctgg     171840
ctggacagct tctctcctgg gggccgtttt gtcacagtga ccctgtgttt ctagtcccaa    171900
atctgggtgc tatagtctct ttttagcgtg gtggttgtct tagtctttt tggctgctac     171960
```

```
cacaagttac cttagactgg gtaatttata aacagtggaa atttacttct caccgttctg   172020 gggctggaa gttttcatgg tcaaggtgcc agcagatttg gtgtgtgatg agggctgctc    172080
tctgcttcat agatggcatc ttctggctgg gtcctcacgg tggaaggagt gaacaagctc   172140
cctcaggcct tttagaaggg ccccaatcca caagggctct cccatcatga cctcatcacc   172200
tcccaaggcc ccaccttctt gtactgtggc actgcaaatt aggtgtcagt gtaggagttt   172260
caggagggat agaaacattc agaccatccc agcggtcaag tgttcatcct cttgagttcc   172320
tccttattct gcttctggtt tatcaggatt cagccagtgc agcatggtac ctgtattctg   172380
tggcacatca ccacatggta tttgccaagt atccatcacc tgcacacgtg aaatcattgc   172440
ccgtgggtcc cgacatctgg cgaagcatat tcaaggatgg cagaactgtc agagctggca   172500
cctctggttc cttgtcatgt ggcattacct agtaatccat tttatgatag caatggaaac   172560
tcatttcttc aacaaacacc tgagtggctg ccgtgtgcca gccgtctggg gcccttggtg   172620
agaatggcat ggtggtgccc atcagggcct gcctagcccg tgctctggac gggctcctgt   172680
gtgtcaggaa cgacaatgct gtcatgacgg tgaatgattt ttttttttgc catcactcca   172740
gccgctaaca tttgcggagc tcttcctccc gcaccccac ctgacaaggc caagggtgac    172800
cttggcccca ccctaggcgg ccaaggtcag aggttagctg gcttgtctgg gtcacacaaa   172860
atgcagcaga ggttgaggtg agcacatgtc cgtgacctgg agcctgactc cctctctgcg   172920
agtcttgact gctcttgcct agactctgtc ctccccgagc ccaaacgcca gtcatcttcc   172980
cttgtgggtg tccttcagcc tggtgccatg ctggtgactc agcagccgtc cagggagtgg   173040
aaacaattga gtgtgtgggt tccctgtgtg ggcatctctc ttcacggcga acaccctctg   173100
ggtgttgccc acacgatgtc aaagcggctc ttggaagggg tccttctcct ttgtgggaag   173160
tttcagctgc tgggctaact tgaattgtaa ctgtggtttt tgtgctcaggc ccagatcccc   173220 ctaggcaagt gttgtgccat cagtaatcaa atgagaaata atcattttga aaagcagatc   173280
ctaaggcagg atggtcatgg acactcactc ccagctcttt gtgcactcat gctttctgga   173340
agatggccat cctctgtgaa ggttttcagc gcgtcatgct tggtacccac gtatccagag   173400
catgtcgttt tgaggtattt gcccaccgtt gtgaaatccg tgccaccga gagcaggtcc    173460 tgatgtgggg cttcagaag tgggacctgg ggccgtacgc agtccttagg gaggggccgt    173520
gtggcgttgt gcgtgtgagg ggatagcaca gggtgaggtg gggccaag aaggaagtga     173580 cccacaaaga acagcctcct cttttggtcc ttgttcctgg gatggctggg agtggcttct   173640
gtgtcgtccg gccatttccc ctgcggagag gctcctacca ctgccgagaa cctcatcatt   173700
ccacaaaaac aagaggccgc ctggccatcc agcgctccat gggaattctg tgtccccata   173760
gtcttgggct gaaggagggt gacattcctt gctgacttct gcagggtct cctcactgtt    173820 aaagagcaga ttgaaagtga agaacgtggg ctaagtgttt aggtcgatat ttaaccctgc   173880
taggttttgg atactaagtg aaattgaggc cattttggtt gaagttgaca gaaaccacta   173940
tcagggatcc ccaagactac cccaggcttt tctagaaaga ctctcagcta agatgtgtta   174000
tggtaaaagc acacaaaaca aaatcagcaa agaaaattag caagggcaga ggcccatggg   174060
gcgatgtccc gaggacacca ggcttgagct tccagaatcc tctcccagcg gggtcgtgca   174120
ggacgcactt aactccccgc acagtgagcc gtgacagcgc gtgtgcagtg tcgtcgccag   174180
gaaagcacac tagagactcg gtgccagggt ttttactggg ggctgggcac atgggcaccc   174240
tctgcctgcc tcgtgcccag actctggact cccgagggaa aggcaagttc tcagcaccaa   174300
ccctggtgcc cacacaagca gctgagcaca gggagcccct cctcagtgag gatggtgggc   174360
```

```
accgtcccaa caccagccag gggccagcct tgcacacagg cctctcagga tggtctccgg    174420
cctgctgtgt agtctcttct gcacacaagc gtgagggcag cgcccccgcc tcggctgtgg    174480
ggaggagcca ctggacgtg agctctggtg gcatgcagca gcttttgtct gtgtgtgcct     174540
aggacaaggc cgtggcggag cctgtcagcc gcctgctgga gagcacgctc aggagcagcc    174600
acctgcccag caggggttgga gccctgcacg gcgtcctcta tgtgctggag tgcgacctgc   174660
tggacgacac tgccaagcag ctcatcccgg tcatcagcga ctatctcctc tccaacctga    174720
aagggatcgc ccagtgagtg ggagcctggc tggggctggg gcggggtct cagaatgagc     174780 tgtgaaggaa gcagcatcac cctctccaag tgcccaggct cctggccaga tggcaggcca    174840
ggtatcagtg ggaacccagg tgggtgccat ggctgaggtc agtgagacgc aagagcacag    174900
gtgcgtccta gaggcttcct cgggcacctc cagcgagctg gagctctcgc ctctgctgct    174960
gtctcatgtg gcgcttagca cactctccca cgtgcccatt cctgactctg ctctcgaggc   175020
catcggctct cattctctgc tcccagaacc ctgttattac ccaggctagc ctcctctctg   175080
caccttcccc gccctggccc agtacctccc tcttgtttcc actgtgattc cgacctcacc   175140
ttatcttaaa gctgctggac ggcaggttct gtacacacgt gtccttgaca aagcacggct   175200
ggtgccgcaa cccctcagcg agcaagtcaa gctcttcaca gcgatgtctt acaagcgcag   175260
agggctctgt gacaccctgg tctcaccgcc actcttccaa agtcgcagag ctttagcag   175320 agatgggccc agcctctctg agtcataggc ttctgcacac gggagctgtc tttagaggga   175380
gggtggaatt tcatcagcca cccacatggg ggagttgagg gcaagaatta ggagcaaaga   175440
tgggaagggg tctgggagga atggccagtg atccccttg acaagtgggc aggaaacggg    175500
ggctaggtca aagttgagtg gaagacctgg agggagacgg gaaggtctct gtaggcacag   175560
ttcagacagg agggaggtgt gagccagggc acatgccggt ggccgtctgg caggatttgg   175620
gacatgctgg agcagggaca gcggctcatc aggggccatt gccctcatcc aggccagagt   175680
gtcacaagcc cgtggggagg cccttctcgc ctgtcatcct tgctgggcag tgggtgctgt   175740
gctagcagga caggcggacg gctggcaact gtctctgcat ccctggagcc tggcataggg   175800
ccaagtcaca cggggcacag gcctgcaaat caggcacata tgttggtgca gtgacgtgat   175860 tttgggggc agccccagaa caggccccag acacaggcca aagccctgcc tgtgctggtg    175920
tgttgggctg ttctatggct cttgctgtgg gcatggagga ctcagggaag gagagttgag   175980
gtggtccagg agttgcgttt gggatgcaga gagcttgtgg catccaggta gaaatggtgc    176040
gtggggctga cctcagcacc atgggcagag gggccgtgtc acgtgcctcc gaggtggagg   176100
tgggaccacg tggtgacaga tatacgcatc actgggcacg ttttttgtggg tgttgggggg   176160 catcgtattg gctcctctgt tcacagtggc cactcattca gtccctggct accaggtcct   176220
cactgtgcca tggggaaggc cggcgctgtc ggggatcac agaaggcagc acgtcatgat    176280
ggcatgtgcc atgaaggaaa agcacagggc actcaggaag tagaggggac tggcctgggg   176340
tgtgggaatc tagggcctcg ttagggacag agagaggaa gtgtgtggtg gccagcatgg    176400
aggtggccac aggggaggct gagttaggcc gagagggcag ggcgttgggg aggtagacgg   176460
gctcagccac tcagggagtg gtcaagcaga ggctgaaggg tcaggccagg ttgcaggggc   176520 ctggggagc cactcagggt aggcgctccc gggagcccgc ctggcccata gctctacact    176580
cccgcgtggg gccggacatg ctgtgaagcc ctctccacgt tggatggggg tggctgagcc   176640
tggatgctgt ctcccgtttt cagctgcgtg aacattcaca gccagcagca cgtactggtc   176700
```

-continued

```
atgtgtgcca ctgcgtttta cctcattgag aactatcctc tggacgtagg gccggaattt   176760
tcagcatcaa taatacaggt gagtgggccc tggctgtctt cctctgcaca cggggagtgg   176820
gcttcccttc tctttttcctt gcaggatcat accagtgggc cagttttgac ttggtcggga   176880
ggaggcatga acacctgaga ctgtgcagcg attctttgac acagaggcct ttctccctgt   176940
gcagatgtgt ggggtgatgc tgtctggaag tgaggagtcc acccctcca tcatttacca    177000 ctgtgccctc agaggcctgg agcgcctcct gctctctgag cagctctccc gcctggatgc   177060
agaatcgctg gtcaagctga gtgtggacag agtgaacgtg cacagcccgc accgggccat   177120
ggcggctctg ggcctgatgc tcacctgcat gtacacaggt gagcatgtac acggtgccca   177180
taaggccagc ccaagtcctg ttcaagggag gcaggagcat gctcactcaa gggacctcga   177240
ctaggtgccc tctgatttca cacttctggt gttgccccaa gccggcccca tcaccttgca   177300
agaaaggctc tggagccccc agggctggag tacctggtca gggttgaccg tccctgtggt   177360
cactcatccc atgtggctga gctgggctgg gtcctgggca agcaagggc tgatatcacc    177420 tgctttcaga tctccaggga ctcactgac ccctgtgtac aaagcactgt ctacagagcc    177480
tattgggttg tatagaggta accttcgtac tgaacacttt tgttacagga aaggagaaag   177540
tcagtccggg tagaacttca gaccctaatc ctgcagcccc cgacagcgag tcagtgattg   177600
ttgctatgga gcgggtatct gttcttttg ataggtaaga agcgaagccc catccctcag    177660
ccgttagctt ccctagaact ttggcctgaa gctgtgcttt tgtgtgtgtc tgctgatccc   177720
ctggcgctgt tgctggagtc ctgccagtga ttccccacca cagcctgacc atgggctgcc   177780
ttggctcagg gttccactgg cgagctggtg gtccttggac cccagcactc aggtgtagcg   177840
ttgaccagtt ccaaggttgt cccagtgcct gcccatctct cctgagggct cagggacagt   177900
acctggcagt tgggggtgtg gcaggggggca ggaatgacca gcctctggga gggtgggggca  177960 gaagcctgta cagtgaggag gagctggctc agcctggctg cctatcgtga gagggggagcc  178020 cacggggctg tgggaggggg gccgtggtgc ctgtgagcag ggtgaggagc agcggcagga   178080
ggatgaaggt ggaacccaca catgcatctt tgagacccgt gtggtcagtg gcttctgccc   178140
cccaccaccc cccactgctg tgcgtgcata gaattggctt ccctcacctg ctctggaagt   178200
gggttaggag cttggtaggg cttttttctca aggacaaggg cccctgattt gctctcaggc   178260
ctcagtcctg gcgacatggt ggatctggag ccttgttgca ctgccttgcc tgtgctctcc   178320
aatcagggtg gccagtgggg agccatttgg cttttctcaa gagcatactc aggtggacct   178380
tgctccactg tttgaccaga tgaggcattc tgaacagcca agcctgtgct ggtctgtttt   178440
catgttgatt ttttttttc ttttcttttt gagatggagt ttttcccttg tcacccaggc    178500
tggagtgcaa tggtgtgatc tcggctcact gcaacctccg cctcccgggt tcaagtgatt   178560
ctcctgcctc agcctcccta gtagctggga ttacaggcac acaccaccat gcccagctaa   178620
tttttgtgtt tttagtagag acggggtttc accgtgttgg ctgggctggt ctcgaactcc   178680
tgaactcaag tgatccaccc tccttggcct cccaaagtgc tgggattgca ggcgtgagcc   178740
actgcgcccg gcccccatgt cgatttttaa atgcacctct gcatcgttct tcagtcccca   178800
tatgctcact gagcaccact gcgactggca gacgggcaca gggaggcgcc acgaccagtc   178860
ctggccttca aggggcttgt ggtctagtgg gcccaatgct aggtggcgag tgctccaaag   178920
agtgtggtgc acgccttccg cttgaccgct ctccagacgc cacagggagg cacctcgcag   178980
ctgaccacag atttctctct gtggagcagt gtcttcagag cggctgccat gccactgctg   179040
ggcgagggtc tgcgggcggg tagagccagg agcacctgtg aggaagtgca ctgccatttt   179100
```

```
cgtagctgct tcccgtgtgt ctcagttaca cacggctggc atgtgtgcac tgatgagacg   179160
ggaacgtgat ggttgctttt cagcactgaa agggatactg ctcaggggc gtgtttcagg    179220 atctggttag ggaagaagca gcgagagcac agatggggcc ctgtgtggta acaagaaaaa   179280
agtcctggtt gacaacagtg ccacgaagcg ttagaacaca tagggatgtt tgtggagcat   179340
ttgcatgtgg aaagcagcaa aaacataatg ggaacgggtt cttttgttat gattttaaa    179400 aatctctttt gtaacatcct tcccgctgcg ccgtttctgc atattccttt atgtagcttt   179460
caaactcctc ttaggagttc tggtccctac agggcgtggg agcccaggct ttacgtagct   179520
ttcaaactcc tcttaggagt tctggtccct acagggtgtg ggagcccagg gcctgtgccg   179580
agcagcctgc ctccacgagc tagacagagg aagggctggg gttttgcctt tttagtctca   179640
aaattcgtac tccagttgct taggctctga ctttccccac ttggaaagtc cctcacggcc   179700
gagggtccct cccagccctg atttcacatc ggcatttccc ccagtattag agccaaggcc   179760
ctccgcgggc aggtggggca gctgtgggag ctggtgccag tctctgacct gcgtccctcc   179820
tcccaggatc aggaaaggct ttccttgtga agccagagtg gtggccagga tcctgcccca   179880
gtttctagac gacttcttcc caccccagga catcatgaac aaagtcatcg gagagtttct   179940
gtccaaccag cagccatacc cccagttcat ggccaccgtg gtgtataagg tgaggttgca   180000
tgtgggatgg ggatggagtg ggaaagcctg gaggtggagt tgcctccgac ttcccagcag   180060
attcgccagc agagcccagc tcctccgctt taaagcagca atgcctctgg ccccaccccc   180120
acccccgcca cccaggcgca gcaggtgctt cccgtccccc cagccctgac actcaggcac   180180
ctgcttgctc cttgcaggtg tttcagactc tgcacagcac cgggcagtcg tccatggtcc   180240
gggactgggt catgctgtcc ctctccaact tcacgcagag gccccggtc gccatggcca    180300 cgtggagcct ctcctgcttc tttgtcagcg cgtccaccag cccgtgggtc gcggcgatgt   180360
atcctctctg gtccctggt gctggccccg tttcccttgt caacaccgag gctcatgttt    180420
catgataagg tttttgaaacc taacctttgc aaaaacccca cagatgccag ggtgacaggc   180480
cctcagcccc agggaagtaa aatgctgaca ggggtacaga aggagcacg tccagacatt     180540 tgctgaccag ggcctctcag aggggccggt gtatggcagg agggtcgcag ctgagggcc    180600 tttctgtgga gggcctgggt gaggggagcg agggtgggcg gtggtctctg cagacgtccc   180660
gcccactcgc gggctctgtg tggctgggct tctcctgaca ctgcttctca ttagctttgg   180720
tcattgtgcc tcgatcgccc tctcggggaa aggcttaagt aaagatccag ttcccacccc   180780
cagatgctgg ctgccaggag tttccctttc cacagccctt ccccaagaca gaccacaaga   180840
gcctccaagc agcacagttg tcctggtgct gacagcacag ccttgcccgg cgtgcctggc   180900
acggctctgc cctcactgca ttggagcagg ctagtggag ccagcggaa gcaccggcca    180960 ccagcgctgc acaggagcca ggccaggtga gtgctgccga gtgggtgccc tgcctgcagg   181020
gcatccagcc agccaagggt tgcaggaatg gaggtggagg cgctgatgca gctggaggca   181080
tccaggtggc ccttccgggg ctctgctcgc tctccaggct ccctggaccc ctttgtagac   181140
tgtttcagga gaggaactcc caggtgagga caggggaggca gcattcccct catttgccgg   181200 ccttttttcct taactcctgc accagcctcc cacatgtcat cagcaggatg ggcaagctgg   181260
agcaggtgga cgtgaacctt ttctgcctgg tcgccacaga cttctacaga caccagatag   181320
aggaggagct cgaccgcagg gccttccagt ctgtgcttga ggtggttgca gccccaggaa   181380
gcccatatca ccggctgctg acttgtttac gaaatgtcca caaggtcacc acctgctgag   181440
```

```
cgccatggtg ggagagactg tgaggcggca gctggggccg gagcctttgg aagtctgcgc    181500
ccttgtgccc tgcctccacc gagccagctt ggtccctatg ggcttccgca catgccgcgg    181560
gcggccaggc aacgtgcgtg tctctgccat gtggcagaag tgctctttgt ggcagtggcc    181620
aggcagggag tgtctgcagt cctggtgggg ctgagcctga ggccttccag aaagcaggag    181680
cagctgtgct gcaccccatg tgggtgacca ggtcctttct cctgatagtc acctgctggt    181740
tgttgccagg ttgcagctgc tcttgcatct gggccagaag tcctccctcc tgcaggctgg    181800
ctgttggccc ctctgctgtc ctgcagtaga aggtgccgtg agcaggcttt gggaacactg    181860
gcctgggtct ccctggtggg gtgtgcatgc cacgccccgt gtctggatgc acagatgcca    181920
tggcctgtgc tgggccagtg gctgggggtg ctagacaccc ggcaccattc tcccttctct    181980
ctttcttct caggatttaa aatttaatta tatcagtaaa gagattaatt ttaacgtaac       182040
tctttctatg cccgtgtaaa gtatgtgaat cgcaaggcct gtgctgcatg cgacagcgtc    182100
cggggtggtg gacagggccc ccggccacgc tccctctcct gtagccactg gcatagccct    182160
cctgagcacc cgctgacatt tccgttgtac atgttcctgt ttatgcattc acaaggtgac    182220
tgggatgtag agaggcgtta gtgggcaggt ggccacagca ggactgagga caggccccca    182280
ttatcctagg ggtgcgctca cctgcagccc ctcctcctcg ggcacagacg actgtcgttc    182340
tccacccacc agtcagggac agcagcctcc ctgtcactca gctgagaagg ccagccctcc    182400
ctggctgtga gcagcctcca ctgtgtccag agacatgggc ctcccactcc tgttccttgc    182460
tagccctggg gtggcgtctg cctaggagct ggctggcagg tgttgggacc tgctgctcca    182520
tggatgcatg cccctaagagt gtcactgagc tgtgttttgt ctgagcctct ctcggtcaac    182580
agcaaagctt ggtgtcttgg cactgttagt gacagagccc agcatccctt ctgcccccgt    182640
tccagctgac atcttgcacg gtgacccctt ttagtcagga gagtgcagat ctgtgctcat    182700
cggagactgc cccacggccc tgtcagagcc gccactccta tccccaggcc aggtccctgg    182760
accagcctcc tgtttgcagg cccagaggag ccaagtcatt aaaatggaag tggattctgg    182820
atggccgggc tgctgctgat gtaggagctg gatttgggag ctctgcttgc cgactggctg    182880
tgagacgagg caggggctct gcttcctcag ccctagaggc gagccaggca aggttggcga    182940
ctgtcatgtg gcttggtttg gtcatgcccg tcgatgtttt gggtattgaa tgtggtaagt    183000
ggaggaaatg ttggaactct gtgcaggtgc tgccttgaga cccccaagct tccacctgtc    183060
cctctcctat gtggcagctg gggagcagct gagatgtgga cttgtatgct gcccacatac    183120
gtgaggggga gctgaaaggg agccctcct ctgagcagcc tctgccaggc ctgtatgagg    183180
cttttcccac cagctcccaa cagaggcctc ccccagccag gaccacctcg tcctcgtggc    183240
ggggcagcag gagcggtaga aaggggtccg atgtttgagg aggcccttaa gggaagctac    183300
tgaattataa cacgtaagaa aatcaccatt ccgtattggt tgggggctcc tgtttctcat    183360
cctagctttt tcctgaaaag cccgctagaa ggtttgggaa cgaggggaaa gttctcagaa    183420
ctgttggctg ctccccaccc gcctcccgcc tccccgcag gttatgtcag cagctctgag    183480
acagcagtat cacaggccag atgttgttcc tggctagatg tttacatttg taagaaataa    183540
cactgtgaat gtaaaacaga gccattccct tggaatgcat atcgctgggc tcaacataga    183600
gtttgtcttc ctcttgttta cgacgtgatc taaaccagtc cttagcaagg ggctcagaac    183660
accccgctct ggcagtaggt gtcccccacc cccaaagacc tgcctgtgtg ctccggagat    183720
gaatatgagc tcattagtaa aaatgacttc acccacgcat atacataaag tatccatgca    183780
tgtgcatata gacacatcta taattttaca cacacacctc tcaagacgga gatgcatggc    183840
```

```
ctctaagagt gcccgtgtcg gttcttcctg gaagttgact ttccttagac ccgccaggtc 183900
aagttagccg cgtgacggac atccaggcgt gggacgtggt cagggcaggg ctcattcatt 183960
gcccactagg atcccactgg cgaagatggt ctccatatca gctctctgca gaagggagga 184020
agactttatc atgttcctaa aaatctgtgg caagcaccca tcgtattatc caaattttgt 184080
tgcaaatgtg attaatttgg ttgtcaagtt ttggggtgg gctgtgggga gattgctttt 184140
gttttcctgc tggtaatatc gggaaagatt ttaatgaaac cagggtagaa ttgtttggca 184200
atgcactgaa gcgtgtttct ttcccaaaat gtgcctccct tccgctgcgg gcccagctga 184260
gtctatgtag gtgatgtttc cagctgccaa gtgctctttg ttactgtcca ccctcatttc 184320
tgccagcgca tgtgtccttt caaggggaaa atgtgaagct gaacccctc cagacaccca 184380 gaatgtagca tctgagaagg ccctgtgccc taaaggacac ccctcgcccc catcttcatg 184440 gaggggtca tttcagagcc ctcggagcca atgaacagct cctcctcttg gagctgagat 184500
gagccccacg tggagctcgg gacgatagt agacagcaat aactcggtgt gtggccgcct 184560
ggcaggtgga acttcctccc gttgcggggt ggagtgaggt tagttctgtg tgtctggtgg 184620
gtggagtcag gcttctcttg ctacctgtga gcatccttcc cagcagacat cctcatcggg 184680
ctttgtccct cccccgcttc ctcccctctgc ggggaggacc cgggaccaca gctgctggcc 184740
agggtagact tggagctgtc ctccagaggg gtcacgtgta ggagtgagaa gaggaagat 184800 cttgagagct gctgagggac cttggagagc tcaggatggc tcagacgagg acactcgctt 184860
gccgggcctg ggcctcctgg gaaggaggga gctgctcaga atgccgcatg acaactgaag 184920
gcaacctgga aggttcaggg gccgctcttc ccccatgtgc ctgtcacgct ctggtgcagt 184980
caaaggaacg ccttcccctc agttgtttct aagagcagag tctcccgctg caatctgggt 185040
ggtaactgcc agccttggag gatcgtggcc aacgtggacc tgcctacgga gggtgggctc 185100
tgacccaagt ggggcctcct tgtccaggtc tcactgcttt gcaccgtggt cagagggact 185160
gtcagctgag cttgagctcc cctggagcca gcagggctgt gatgggcgag tcccggagcc 185220
ccacccagac ctgaatgctt ctgagagcaa agggaaggac tgacgagaga tgtatattta 185280
attttttaac tgctgcaaac attgtacatc caaattaaag gaaaaaaatg gaaaccatca 185340
gttgttgctg tgtgaggctt gctttgcttc atgagaacct agaccttgct gagctggagt 185400
cttaggaagc agtctcctaa gtgcttctcc agcaggggca gaaactgtcc caccagctaa 185460
catctggcat tatggagggt cccccaggca gctgccagca gggacaggcc ccgtgttttc 185520
tgtagccagg gatgaggaag tggccccagg gcatgggcct ggctgggtgc ttctgcaagg 185580
gccttcccaa accacagtac aggtggtctt cctgccctgc agatgggagc tgtgggagct 185640
gctggagctg ctggagcctt catggtcaag tgacatcata gcttatatg acatacacaa 185700 gcctcaggac ttggcccatg gcactgaagc aggtcatcag gcccagcaca gagactagag 185760
ctgtgttctc acaggcccca ccacccttcc acctccttgg ccattgacac ctgcgtccct 185820
ggcccagctg ctcccaggta accccaaag cagctggcac atcccacctc tggtgtggcc 185880
ggggctgctg tgtgtccgca gggcctgccc cgtctattct agcttgtttg tcctgtctga 185940
accagcgcct actccaagaa gcctctgctc agccagcgg ggatgcttct aagctccgga 186000
cgagcctctc ggaagccttg gtgattggtg gtgtagtcat cttgggatgc agatgtctta 186060
ccaacctgca agaacaaaaa ccctgtggct tcctctggtg cagggtattt agtcaatgtt 186120
tgctgaggtc ccgtctggtt ctggctaatt ggcagggggtc gtccacccat tctttccctg 186180
```

```
ctctgctgtc tgtgccagga gagacggggg ccagtcggcc aaggggccag ctcctgctgc  186240
ctgctcctct tgggcacgtg cgggggcccc ctttctctga gcaggatag ggatcagtct    186300
gccggaggga tgtggtggac aggcctaaag catttgggc ggggcatgcc acttgagctc    186360
cctaaatctg tctcctcata ggtgacaccg ctccagggcc ccccagtggc ctctcctttc   186420
agagctacct aaattctggt cacttcagag aaatggagca ccccttctc cctggtccag    186480
gtgtggacag cctggcacac tgagcacacc tggcatggct ggtaatttca gaaagaagag   186540
gggccgggt ccagtgggaa gcagcggtga acccctcgtg agtgggcttt gcagtccctc    186600
cccatgccac ggcagagctg ccctcaacac agccttcctc ttcctcatcg gagagcacac   186660
cctgtcccct tgccgagctg tgccctgtgc cttcggtggt atttgatttt ggctgctact   186720
ggctttgttg ggatctggaa gtcgcttccc ctgcgtggtg cgtggagcac tgtaagtcag   186780
atgagggaag tagccagggt gaggtgagta ccgggtggag ccgccactga agggactggg   186840
tagggggcc ttgcctctac atgatgtgac acagccaacc gaggacagag gaagcccgt    186900
tcctgggggt gtgggtgca cccctcaggg aagcctgcag tggggcctga ggaaaggcat    186960
cctccgcgag cccacgagtc tggtccatga gcaccgtgac agtgtctgtg ggtagaggtg   187020
gacccggcct tgtgtcatca ccaggacctc ttttgggaaa ccatgtggac atcgcttgcg   187080
ggtcccccag gctctgcagc cccagcagcc tggctgcctt ttgggcaagt ggcttgagcc   187140
acagaggacc cagtcctgtt gcagccacat cctctggggg ggcccgccag tgtggccggc   187200
tttctccacc ctacaccagg cctccaggtg tcctggtcgg gggtgtctgg gccctgggtg   187260
ggccctgtgg acctgtgagg tcagggtcag ggcatcactg gaggcagagg ctgaagttga   187320
tgggtctggg ttccccttgt gtgcacaggc ccctgccctc catgcttggt caggcagcta   187380
cccccaaaac tgctaggaca ggctggtcct gaggtggatc ctggcccctg taccctctgg   187440
acagcccacc cgcccaacct tctaccctgc cccagcggcg gcagtgttgg ccacatcctt   187500
cccctcctgg ccccaattgc tctggggaag tccaggctcc ggagcctgcc caggggcccc   187560
ccgtgatttg ggcccaggac tccacgtggt tctctgcctt cacccaagcc ctgaactcct   187620
cagctgccaa atccccaccc atctgcacag gctgtgctca ccactgctgc tcctggaagg   187680
tgcccctcag tgggacgccc acctcctctc tgggcttctg tgtttgggag ccctgctgcc   187740
cccacccttg gtcagtcccc atgtcctgct ggcctgtcag gcagggcaga aaatccaccc   187800
agaaatgctg agcaggatga gagtctagtt gggcccagcc tcattattta gaagggatgg   187860
aggcctaggg agcatgcttc tagcctgagc ccagcagggc cccgcccatg tcccaggtct   187920
gcaccaggga cagctcctgc cgaggcctga cctgccccctt ctccctcagg tgctgctggt   187980
tgaccagcct ctggccctag gagacccgt agcgactgag ggtccagca ggccatgcag     188040
ctttgccaag gtacgagccc ctccccagca ggggacagat gtggggaccc tcccaggcag   188100
gagcagctgg gtgcctggtg ctgccatctg ctgcctgcct ggttcttgtc ctcacattgg   188160
aggtcagtgt gagggctctg cctcgggaaa ggccatgag cttgccctgt ccagggcctc    188220
ccatgtgcac tgagcctggg aagagagggt tggagttgag ccttttaccc tgggaatgct   188280
gcctggagga tggtgcgggt gtggggtggc accctgccag gcaggccct gcctccctgc    188340
gcccactgga actcgggcag gcaggggtgt aggtgcctcc tctagagccg tccggtgggg   188400
gccccggca gtggtggtgg tgtccactgg ccagcagctg cccttcagc caggacagta    188460
ggcctgacgc tgtccccagc agctccaagg tggatttgtg gaaggggta gagggcacgt    188520
agaggcccca tgacctcccc agggttctgg gagggctgtg cccccttagc cagcaccatg   188580
```

```
ctgggtgata tagtcagatc ctgttacccc tgttgtggag gtgaggaaac aggttagtgg   188640
ggaggacatg actaaggtcc atgctgagtc gctagagctg cacccagaac cactgctggg   188700
accccatgcc tttctgctta ccccttgtgc cgggagatgc caagagatgc tgggagccag   188760
ccccacctct gcccttggag tcatggctac ggaaagggca ttcggaccgg tccctgacct   188820
caccggggag ggccgaaccc tgttcctgag gagccagggc ttcctagagg aggtaggcct   188880
tctagtcact ccttcatctg caggcactcc acagagctct ctgtgccagc ccccagcacg   188940
gagggctgac cttagtcgag tggagatgcc ccagtgccag gcagtaggga tgatgtctcc   189000
tgaggcccag atggaaggga ctggactagt ctcatgggc tgatggtggg gccaggcctt   189060
gaccagggac ccagtgtagg gggtgcagag acccctctga gttcctcaca catccctggg   189120
gccctcccca tacacttcct atcctgactg cgggcaagag ggagcccag ttcgccttcc    189180 ctatgctggg cacccacagt ggggctgggc accccgcca tgcccctgcc ctgtccttcc    189240
cctgagagcc tcggtcccac ctccaaggtg cctcagagga cagcaggggc agcgggcaga   189300
ggccgagatg cctcctcatt ccaggctcag ctgcccttct tggggcagcc cacacctgag   189360
agtctcctgc agttggtcag gcctgaggag ggcaggggg tgcctgctgt ccctctgctg    189420
accacagtgg catttagcct gggcaccgcg cccagcacag tccatgctgc acaggtgccg   189480
tgggctccac agagccctgc ctgacatgca tgtgttacgt ttcgggtgcc gatgcccttg   189540
ggcggcactt ctccgggcag aaccccagg ccaccgctcc ggttccggtt ccgctgcatc    189600
tggggctctc ggcaggctgt ggtcctccgg ccagcctggg ggcatctcag tccctcagcc   189660
ccacaggggc ctgccccgca gcctgggcct cgagcccgt ctccgcacgc tgtgccgaat    189720
ctggctgccc atcagctccc tgcgtaccca gactgtgccc tgccatgccc gtggctcttc   189780
ccaggagtgc cctgtggcct cccctggct tgctgggctg attccctcct gtgtctcaaa    189840
cagagctcac ctttgccatc actgctgtcc tcaccggccg gtgccagagg cccgtgtctg   189900
tgtaccctgt gtctgcacct ctgggcaggg cctggctctg accaacccgg gcttccagtg   189960
tccacagacc taaggcccag ggcgcctggg ggctggagca agagaagcaa aaggagccaa   190020 gggtggggt ttggggttct tgtgagggcc cagcccagg accccaggac caggacaccc     190080
aggagcccca gggcccagcc ccagttcaga aggcaggggc cttctgaggg agcttaaggg   190140
tcccacagcc caggaccccc accagggcca gtggccagcg ttgggggact cagcctcctc   190200
gtcgctcgtc ctctctgttt ctcccacctt ttgccccctt tctccttgcc tgttcccacc   190260
cgaggccccc tcttggcctg cgtgagccgg ggcggcactg aactgggggc cgatccgcct   190320
gggcggcggt gagaggcagg gccgggagcc gggccgctgg gtttgggcct ggcccgctcg   190380
ccgcaatatt gatggcccgt cagtgcagcc ctgattcctg tgctttcagt taaaaggttt   190440
ctgttgttgt agcttatgca gttgctctgt tgctatggaa acgtgacatc aaaatgacgt   190500
ttcccgttta aaagcttta actaaattcc tgcctgtcag atgtaggccc cattttgagc    190560
gtggagctgc cttcgagcga gcgtgagcgg cgcctcccgc ccatggtgcg tggggccggg   190620
ccggggccct cgctgagcgc gctctctcac cccacaggcg cctccggcat ggcggcggcc   190680
gaggggcccg gctacctcgt gtctccccag gcggagaagc accggcgggc ccgcaactgg   190740
acggacgccg agatgcgcgg cctcatgctg gtctgggagg agttcttcga cgagctcaag   190800
cagaccaagc gcaacgccaa ggtgtacgag aagatggcca gcaagctctt cgagatgacc   190860
ggcgagcgca ggctgggcga ggagatcaag atcaagatca ccaacatgac cttccagtac   190920
```

```
aggtgggcga gcgggcagtg tgggccccac caggacgggc gggcccgggc gtggcgggcc    190980
gctcctgact ttcttggagc tctgagtcgg gacgatgtgt gggtcgtggc ctgcctgtcg    191040
gtctcctctg gccgggtatg ggcagaaccc cacggggtga gacggggccc acggaaaccg    191100
tgtgtgcagc cttccattgg ggaagtgggg aaactgaggc ccagcaaggg caggaaacca    191160
gtctaagagc tgaggggtag caggggtggg gctggtgctg ggcagaggcc aggatggctc    191220
ccaggacgta tgggcggtct gggcactgtc cctcggaggc agcaacactc atggtggtgc    191280
ccactgacct cacaccctgc tcccccatag ggaggcggcg gctgccagtg ccctcccac     191340
caccaagctc ccaagctcag caggggtttc aggggcctac tgcgtcattg ggaaattga     191400
gactgcaagt gagaaggagg ctcagtgctc tgcgacttgg agcatccact gagcctctgc    191460
catgagccgg tgagccccac tggggctggc cctagggtca cggtgggta tttccagaaa     191520
tcaccaggtg aggtgcagga ccagccagcg catgggtggg gcttacggtg cgaagaagaa    191580
agaggtggag gcctgccctg gcccaggact cccagcgtgg gggctcccgg cctggcccca    191640
cctctgctcc tgctacatgg caggtgggcc cttcctgccc tggcaacctg cagggaaggc    191700
cggaggggac cacccagcca gggagatgtt ggcgtctagg aggggacagg tgtggtccca    191760
cacacccagc atcttaaagt gcgtgggtcc ccagcccatt aggacagggt cccgggtggg    191820
caggggtcat ggtggggtga aggtctcagg cacaggcaag gtcacaggtg cggtgagggt    191880
cttgcagggt gtgaaggtca taggtgtgcg gtgaaggtca caggtgtggg gtgatggttt    191940
tgggtgtggg gagggtcttg cacggagcga gggtggcagc aagagctgga agctgcaggg    192000
ggagaatggc agcagagagc acccggccct gtgggcggcc tggacagggc tgggcctggg    192060
gctgccggag agcctgtcag cttccaggat gggagtggcc tcactcagct gctccacctc    192120
cgggtcaggc aggtgagcct ggggcagaga ggctgagagc acctgagcca cttgtgggag    192180
aggccacccc cactgccccc ctcaggcgag gagccggcct ccagcacagc agaagggaac    192240
ccccagtccc cagccctagt gggagtgggg aagaggccca gcaaggcccc ggacagaccg    192300
ccagcctgtg aggtctccgc tttcagttgc gttgatttga tttttttctga gccttgaagg    192360
aggggtccgg ggcctggccc tgcccaaagg cccctaggca ggcccaaaag ccgggaccta    192420
gggtgctgag catgacggat gttgggtttg agcggctggc ttgcgacgtg agggctgagg    192480
tgtgagcctg ggtatcttca gaggttcggt ggacacaggc agctgcccgc ggccccactg    192540
ttcccgtggc ctcctagtcc tgctcaggca cctggtgagg aagggacgca gagggcagtg    192600
ggaggtggcc acgactgttc cagcaggctc ccctctgact caggaattca cgggcaccac    192660
ctccctggct ggctctggtt ggtgtctggc caggttattc attatttatg ctgaaagcct    192720
cttcagagtc ccaggggagg gtttctgtct ccattcctgg aggctgagag atgagggtgc    192780
agcagagtgg gggcctccac tccagaccct gcagtctggg ctggccaagg gctgcaccgg    192840
tgcactgcac gtcatggctg atgaagcact tccacaccgc agcccctcag agctgccaca    192900
gtcagcctta gttcaccgag ggggaagctg aggcccagag catgagaggg acttgcccag    192960
ggccacatag tccttagcag aggaagctgt ggctgggtga ctcgatcttt gtcctttttc    193020
tttatacccg cagtctcccc atagcagagg ctttctcttt ttttttcttt ttcttttttt    193080
ttttttaca agaactcttt atatattaag gctgttgggc tgaagaagcc tgagagggtg    193140
gctggttctg tggagcatgg tttgttgaag tacagtttgg gggcctccta cactgagaat    193200
aggccttttc tcgtttctcc aaagagtggg ctggctcaag tagggcagag agagaagcct    193260
ggggcagagg ttagggatgg gcacccagcg cctgccctca cacgctctgt gctggtgtct    193320
```

```
tcacagccac gtgccaccct gggcagcatc ccctgctcac catctggctg tgcctgtttg 193380
ctgggggcac ctcattcaga atccagctta ttgtttccaa cggccaatgg ccacaccctg 193440
gcaggtagca agagtaggag agaggagaca cccactccga gcacaggttg ggtttggagc 193500
ccggccttgg ggcactctgt cactcaaagg cagagtgggg agtgggcact gggccttagg 193560
aggtactggg tccagtgagg cagagatgcc cctgccccac ccccaccttg tggcttcttc 193620
cctggcctgg ccagagctgt ctggccgcca tgggccctg tgtctcctgc cttgacctcc 193680
cagagggcag ccgaggccca ggggaggcct ggggacttag cctctcaggg caggacctgt 193740
ctgcaggagt aggtgggtgc tgggggtccc agtggtaatg aggcatcagg cagtgtggga 193800
aggggcccat ccggcccacc ccagggcctc tgggcaggtt gcaggttgta gcgctggatc 193860
taggctcctg cccagactgt aggttcaacc aagaatggca tgggagccca gcctgctgtt 193920
tgctttatta aatctgccct gtagctgggg aggggctta ctttgatcat cactatgtca 193980
ttgatataaa aatagaggct cagagaggtg aatgaacctg cccaaagtca cacagcaaag 194040
tgtggagatg agatactgac tcagggctgt ggacactgaa gcctgtgctc taacgccagt 194100
ggctgtcgct ccctgaggca ttctctcccg aacaacacag ttattatatt acaaaatatt 194160
atcactatat ttatatatct tataatacct tattattaca ataaaacctt attactctac 194220
ctttcaaaat gaattattta aaaagcagta tttgctcatt gcagagagtc tagaaactat 194280
agaaaagcaa gggaaaagca ataggaccag ccccaaggtc ccagcatgca cagataacct 194340
tagtaatact gggacgtgtg cttcctttt aacatctgag cccgtgtagg tcctgaagcc 194400
cagcttcttt ctaagtccat tgtcatcttg accctggagc ctggccgatt ttgctgggga 194460
ggcccttgcc agccgagagc ggctcctgcc tgtgccggcg tggcgcgccc ctctgctgag 194520
gctgggcagg acagggctg ggccagctct gtttctcacc cttggctctt gtgtctctcg 194580
tttcaggaaa ttaaaatgca tgacagatag cgagtccgcc ccgcccgact ggccctatta 194640
cctagccatt gatgggattc tggccaaggt ccccgagtcc tgtgatggca aactgccgga 194700
cagccagccg ccggggccct ccacgtccca gaccgaggcg tccctgtcgc cgcccgctaa 194760
gtccacccct ctgtacttcc cgtataacca gtgctcctac gaaggccgct tcgaggatga 194820
tcgctccgac agctcctcca gcttactgtc ccttaagttc aggtagtgtg tctgcttgtc 194880
cttcccctgc cctggggtat ctcagccccc accatttaga gaaagggact gggagtggca 194940
aggccggcgg cggcggccac agtggttgca gaggccgtgg ctgcgggcag cgcctccagg 195000
gacaggcggc ctcagaccag ggagggcttt agtgtccaca ggcagaccga gtttgtctcc 195060
cagctccatc actttgagc tgcacggaaa gttccttgac ttctctggcc tcagtctccc 195120
tcctataaaa tgggggtaaa tcagtaccctt tctcagaggg tggctgggag catcacagga 195180
gagaagacgc agcatggggc ccggcacacg gagggagacc aagccccaga ccccagaatg 195240
cgccccctgg cctcccttag cccacacaga ccccaccctc acaggctagc tgccctctca 195300
gcactgggga gggtgtcggg ctgcacctca tcacgtgttg ccgtgggcat gacccgtccc 195360
ctctgccatc catcccacac ctcagacccg tcccgtgctg gccacgtgac tgtgcctgca 195420
agatgctcac agggcagccg ggagccaggc agcatgcagg acagacacct gcggggtggg 195480
cctggggagc ccagagaagg tgcttttgag gaggggacat ttgggtggg ctttcaaggt 195540
aaaatagaaa ttggccattt ggaggcaaga acaggaagat tgtggatttg agtcacagct 195600
tctcccctgc cctggtcttc aagtctttct gacaggaggt gtcagaaaag tatctttagt 195660
```

```
agagaaggcg tctccgagga gggtccctct catgccgggg gccgctgctt gactcaggat   195720
ttctcattga agacctgaga caaaaacgct tttgctggca gctagaagga accagcagga   195780
ggcctgagat ttgtggctgt tgttcccgtg gactgagccc agttctcaga ctcagctgcc   195840
tggggccttg cacaggactg gggcgtgggg gctgccctcc ctgatcaggc ccaaagcgcg   195900
gatctcacgc ccctgaggtt ggctgtaccc tctcagctca gagcagagtg tgggccaggg   195960
atgagcaggc actggagcag ggccctgggg tctgtgggtt ttggcagctc cctgcccttc   196020
agggaggtct gctgagacca cgggtggccc ctacccagc agcagagctc tcaggaggcg    196080
cccacagggc tggactgcct ttactcacca cctctaccag agctctgagg tcctggggag   196140
agagcccagg cctcttgtgg gccccacacc ctctaggtgc ctgtccttct gcctctctac   196200
caaggtgtgc cggccccatt tctaggccgc cgggagataa gggggctcac atctcaggcc   196260
cttccttctg ggacctcagt ttccccatct gcctaaggcc gggtgggggct ggtggtcttg   196320
gcttccctac aggggtcctg agtactctgc actacccagc accccccacc cctgccttca   196380
tctctccctg ggggtggtct ctccacccct ggccccaaac tggggctgag cccccacctg   196440
cccagtttgg tgggtgaagg gtgctccctg gcaggatatg cccctctgca gcccagaaca   196500
tcccacccctt tccagaccga aggggtgtgg attgtcctgg gacctggtc attggggtca    196560
tccgctagtc gcaaaggacg gcaatgcctg tggcctctct ttctttcttt ttcttttttt   196620
ttttttttga gacggagtct cgctcttgtg cagagagcag tggcgcgatc ttggctcact   196680
gcaacctccg cctcgtgggt tcaagcgatt ctcctgcctc agcctcccga gtagctggga   196740
ttacaggcac cgccacaac gcctggctaa ttttttgtatt tttagtagag atggggtttc    196800
accatgttgg ccaggctggt cttgaactcc tgacctcagg tgatccacct gcctctgcct   196860
cccaaagtgc tgggattaca ggcataagcc tccacacccg gccaccccctg ttactttctg   196920
tcaaaggcgg tgggttctgg cccctccttt gcacatggaa tatgagaccc tgagtaagtg   196980
acctgactcc ctggggcctc agtttcccca tttgcccagt aggattgtcg ggagggtccg   197040
gtgaggcccc tggtgtgccc aggctctgtg gccagcacgt ccacagccgg cactgtcctt   197100
ccaggtcgga ggagcggccg gtgaagaagc gcaaggtgca gagctgccac ctgcagaaga   197160
agcagctgcg gctgctggag gccatggtgg aggagcagcg ccggctgagc cgcgccgtgg   197220
aggagacctg ccgcgaggtg cgccgcgtgc tggaccagca gcacatcctg caggtgcaga   197280
gcctgcagct gcaggagcgc atgatgagtc tgctggagag gatcatcacc aagtccagcg   197340
tctaggccag caggcggcgg cggcggcggg gccgggcggc tggtggtact gctcaggcca   197400
cccagggcag gccactcagg ccaggcgggc aaggggggccg ccccgcgagc ggagaccgcc   197460
ttccacctgg cctctggcag gatgtccctt ctgaggggta ttttgaggaa ccccaggcc    197520
ctggggaccg tgaggctcca gtctccagca tgaatgccct tcctcggaca caggccaggg   197580
cctctggggt tcactccgag taagaacgtc ctagagccac tctccagtgt cgttactatc   197640
aatgatactt gacgtggctt tgatattaaa cgtatacttt ttcattcttg cctggaacgc   197700
acagtttgct gttgctggct tggtgaggat gccctgattg atggatcccg aaaatgaaag   197760
cagatgaaaa cgggttgggg caggctgag ctgggggagc tctctcctga agggaaccct    197820
gtgtcctccc tcaccaggac ctctgcgtct ctccttaaat ggcctctgac gcctgatgaa   197880
aaccccagcg accttccagg aggcttttat tcagctctgt ttggagcatc aggtgtttcc   197940
actgcctcct tagcaatgac actaataaaa gtcgtaacac ctgttcacat gcacagccct   198000
gttgagtgtt ctgggtgctg gagatatcat ggtggatgac acaaaggccc tggcctcttg   198060
```

```
gagcttatgc tcccatgcgg ggaagacaca tgggtcagta gagaaatggt tgcaggttgt  198120
gataagtgct ggaagggagg ggttggcctg aggacacgga ggcagacata cgtggagctg  198180
ggaacagtgg ccacacaggg aacggccagt gcgaaggccc agaggcagag gacactggag  198240
caagcccagg agcagctagg aggctggtgg ccagcagcca ggccacgaa gcccgtgcag  198300 cccgtgggga ggagtgttca tgcttttcaa gcttagtggg agtcttttgg ccagtgcagc  198360
tctgggtctg acatcggtgg gggacagagg ggtggtggag cggccacagc tgcaagctca  198420
cctcactgcc ggcccttcca ccagtttcaa actctttcta gaagctccag cttttcccaaa 198480 gctgaattct ctatgagcct ccttggccgg gactcgggcg tctggttgcc ctggctgcaa  198540
aggaggctgg ggccaggtgt gtttgagtca cctcctggaa ttaggcaagt tgctgcccaa  198600
atagaaggtt gttggcaggt gggtcagcag gtgaacagca tggtttgact cagggttcag  198660
aaaaatctcc ctctggctgc caagcgagca ggccgtggag acaggtgcag aggcaggtgt  198720
ggcagcagga tcctgccag gcagtgctgc agtcatcctg cgacaagcag cagcagctca  198780 tcctacccctc taggggtct tgaggtcagc caggcaagag agcagcttgg actccactgg  198840
gtgtgggacc agcctgtgga ccatggtggt gtggagggtg ccctcggcct gcctgtgtga  198900
aggagaggcc ggcgtgttct gtggagccca aggggagct gggcaagcag gattcacttc  198960
actctgaggg tcctggagct cccaccctcc tcagccatct ccccagagcc tgtgtgccga  199020
ggactcggcc catgttgctg tgggatgaga ggcagagtgt cgtgagggtg taaggagcgg  199080
cggcagtggt gggaggaggg agcagcagcc agcgctacgg tgccagtttc cagctgccag  199140
atgacgccgc tgaccctgtg gttgagaaga gatgcacaga gccagctctt gcaagccagt  199200
gtggctgcca tagcacctgc cgagaagcag aaggaagggt ggcccccagga ggacagagga  199260 tgcgggcaca tctgatgcgg gcctgagttt tgggagcttt tgctctagcc agtttccagc  199320
tccgggaccc acccgcctcg taggcaagac accacccaag aaatcatttg cttaacaaac  199380
acactgggct ccaactggac acctgtgcca ccctagatgc tgggaaccca gccatgacac  199440
aggcacctgc ccccagctgc tgaccactga ggctggctag cagctcccat ggggccagtg  199500
tggggttccc cagcctccta acagggagcc agtcacaagc cctcgagagg gaagggtgcc  199560
cgcggccctg gcaggaaggt taggctggac gctcccacaa gacataacag atggaggttc  199620
taaatgatgt agcaacttct tcaccctgaa actgctgtag agtcagccat gacgcaccgg  199680
tacttcagta actgccaggc atccgggaca gcacaccgcg agtcgctgct gtgcttgggt  199740
tagaagtggt ttggtctgtt ttcttctcgc cctctctaat cagagtcagt gattcatgcc  199800
cttccatcac cttagagaag gggcaggcgc tgcccgacct tctccaggct ggagcagcat  199860
cgcctcatgt cagcagaact cagctgtaga atatcgtggg gttggtgcct ttcatcagca  199920
gcatgtcctt aacaactttc tgatttcttc cttagttgtt ggtccattaa ggagaaaaaa  199980
aatgatctca gccattgcta aaatatttga taagattcag caaagcagca tgttaacatt  200040
gaaaactaga atcaggagcc aggcagatgt gcttgctttt cacctgtagt atttcatgtt  200100
gttttgacgt ttttagctaa tgcattaaga taaataaaca aaagccgggc acggtggttc  200160
acgcctgtaa tcccagcact ttgggaggct gaggcggag gatcctctga ggtcaggagt  200220
tcaagaccag cctgaccaac atggagaaac ctcgtcatta ctaaaaatac aaaattagct  200280
gggcgtggtg gtgcatgcct gtaatcccag ctacttggga ggctgaggca ggagaatcgc  200340
ttgaacccgg gaggcggagg ttgcagtgag ctgagattgc accactgcac tccagcctgg  200400
```

```
gtgacagtga aactcggtct caaaaaaaaa aaaaaattaa aaaaagataa ataaaataag 200460
caggataaga aatgaagaaa gtagagttac ctttgttttc agatttcatt tttgtatacc 200520
cagaaagcca aatgtacaaa agactgggag ctctttaaac cagcttaaac ttgttgaaaa 200580
tgaggatgaa gaaatatccc attcagagtt ggaatgaatt taacccagaa ggaacaggac 200640
ctctactgaa gagaactatg cagtcttact gaaaaatcta aataatacct gagcgctgga 200700
gaaacttcgc acactcctga aagctccaaa gtcaatgtca tcattttatt aatgtcattc 200760
caaacatagt ctcaataata tcacttcttg gttttgacat ggacgcgatg atgtttaaat 200820
tcatatgaaa aaagaacggg gccaaaagtc caaggccagt cagcgtgaga agaccgctcg 200880
gcctccctcg gagtcgggga gttggaaccg cagactgaga tcatgtggct gctggaggcc 200940
aggacgaacg tcgggaaatg gagactcctg cgttgctggt gggatgtggt gcagccgctt 201000
ccaggagcaa tttggtgtcc cgtcctaaag ctgaagaaac gcatttcctc tggtcagtgc 201060
cactcctaga caggccaccc tgcggcagcc gtcctcaaac tggtctgagg accctcaac 201120 gctcttaaaa atcattaaaa gtgggccagg tgcggtggct cacacctgta atcccagcac 201180
tttgggaggc caagacaggc ggatcacgag gtcaggacat tgagatcatc ctggctaaca 201240
cggtgaaacc ccgtctctac taaaaataca aaaaattagc cgggcgtggt ggcgggcgcc 201300
tgtagtccca gctacttggg aggctgagcc aggagaatgg cgtgaaccca ggaggtggag 201360
cttgcagtga gctgagatca ctccactgca ctccagcctg ggcagcagag cgagactctg 201420
tctcaaaaaa aaataataaa taaataaata aaaataaaat aaaataaaat tcattaaaag 201480
tgccaaagaa cttttgctta tgtgagttct aatgaccaat attaatacac attagaatat 201540
cttattagaa attaaacctg agacctttag aaaacatgta ttcatttcaa aatagcaata 201600
aacccatgac atattaacat aaataacaat tgtatgaaaa atatattttc caaacaaaa 201660 agttttcggg agaagtgtgg catagtttta catggtcgta aatctctggc ttaagagaag 201720
cccactggcc tctcagcagg ctctgggtcc gtccactttg ggggtgtttt ggttgtgaag 201780
tataggagtg aatggagaag ctcattctta cccagatgtg tatttgaaaa gaaaaggaac 201840
attttaataa cctttgcaaa taatcggtat attcttccgt gatcctattc caacactgga 201900
caggtggtgg tttgttttt tttttggag acggagtccc gctctgtcac tcaggctgga 201960
gtgcagtggc gcgatttcag ctcactgcaa gctccgcctc c                  202001
```

<210> SEQ ID NO 6
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 6
cctacaagag ct                                                      12

<210> SEQ ID NO 7
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 7
ggatgttctc ga                                                      12

```
<210> SEQ ID NO 8
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 8
agactttttc tggtgatgac aatttattaa                                        30

<210> SEQ ID NO 9
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 9
agactttttc tggtgatggc aatttattaa                                        30

<210> SEQ ID NO 10
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 10
taaattgtca tcacc                                                        15
```